(12) United States Patent
Holtzman et al.

(10) Patent No.: US 11,926,660 B2
(45) Date of Patent: *Mar. 12, 2024

(54) ANTI-ApoE ANTIBODIES

(71) Applicant: Washington University, St. Louis, MO (US)

(72) Inventors: David Holtzman, St. Louis, MO (US); Hong Jiang, St. Louis, MO (US); Thu Nga Bien-Ly, South San Francisco, CA (US); Mark S. Dennis, South San Francisco, CA (US); Jing Guo, South San Francisco, CA (US); Adam P. Silverman, South San Francisco, CA (US); Ryan J. Watts, South San Francisco, CA (US); Yin Zhang, South San Francisco, CA (US)

(73) Assignee: Washington University, St. Louis, MO (US)

( * ) Notice: Subject to any disclaimer, the term of this patent is extended or adjusted under 35 U.S.C. 154(b) by 132 days.

This patent is subject to a terminal disclaimer.

(21) Appl. No.: 17/410,686

(22) Filed: Aug. 24, 2021

(65) Prior Publication Data

US 2022/0411485 A1 Dec. 29, 2022

Related U.S. Application Data

(63) Continuation of application No. 16/345,637, filed as application No. PCT/US2017/058874 on Oct. 27, 2017, now Pat. No. 11,124,562.

(Continued)

(51) Int. Cl.
*C07K 16/28* (2006.01)
*A61K 9/00* (2006.01)
(Continued)

(52) U.S. Cl.
CPC ............ *C07K 16/18* (2013.01); *A61K 9/0019* (2013.01); *A61K 9/0085* (2013.01); *A61K 9/127* (2013.01);
(Continued)

(58) Field of Classification Search
CPC C07K 16/18; C07K 2317/33; C07K 2317/90; C07K 2317/92; A61P 25/28;
(Continued)

(56) References Cited

U.S. PATENT DOCUMENTS

| 4,741,900 A | 5/1988 | Alvarez et al. |
| 6,313,089 B1 | 11/2001 | Matthew et al. |

(Continued)

FOREIGN PATENT DOCUMENTS

| WO | 2003060158 A2 | 7/2003 |
| WO | 2012075422 A2 | 6/2012 |

(Continued)

OTHER PUBLICATIONS

Albert, M. et al., "The diagnosis of mild cognitive impairment due to Alzheimer's disease: Recommendations from the National Institute on Aging-Alzheimer's Association workgroups on diagnostic guidelines for Alzheimer's disease," NIH Public Access Author Manuscript, Mar. 25, 2012, pp. 1-17, published in final edited form as: Alzheimers Dement., May 2011, pp. 270-279, vol. 7, No. 3.

(Continued)

*Primary Examiner* — Aurora M Fontainhas
*Assistant Examiner* — Selam Berhane
(74) *Attorney, Agent, or Firm* — Polsinelli PC

(57) ABSTRACT

The present disclosure encompasses compositions and methods for effectively treating at least one symptom or sign of Aβ plaque or cerebral amyloid angiopathy (CAA) associated symptoms, or for decreasing amyloid plaque load or CAA load. The method comprises administering an effective (Continued)

amount of an anti-ApoE antibody to a mammalian subject, such as to a human.

8 Claims, 76 Drawing Sheets
(35 of 76 Drawing Sheet(s) Filed in Color)
Specification includes a Sequence Listing.

Related U.S. Application Data

(60) Provisional application No. 62/414,413, filed on Oct. 28, 2016, provisional application No. 62/533,336, filed on Jul. 17, 2017.

(51) Int. Cl.
| | |
|---|---|
| *A61K 9/127* | (2006.01) |
| *A61K 31/192* | (2006.01) |
| *A61K 39/00* | (2006.01) |
| *A61P 25/28* | (2006.01) |
| *C07K 16/18* | (2006.01) |

(52) U.S. Cl.
CPC ............ *A61K 31/192* (2013.01); *A61P 25/28* (2018.01); *A61K 2039/505* (2013.01); *C07K 2317/33* (2013.01); *C07K 2317/90* (2013.01); *C07K 2317/92* (2013.01)

(58) Field of Classification Search
CPC .... A61K 9/0019; A61K 9/0085; A61K 9/127; A61K 31/192; A61K 2039/505
See application file for complete search history.

(56) References Cited

U.S. PATENT DOCUMENTS

| | | | |
|---|---|---|---|
| 7,935,796 | B2 | 5/2011 | Lee et al. |
| 11,124,562 | B2* | 9/2021 | Holtzman .............. A61K 9/127 |
| 2003/0139362 | A1 | 7/2003 | Raber et al. |
| 2003/0186327 | A1 | 10/2003 | Babcock et al. |
| 2010/0061993 | A1 | 3/2010 | Nordstedt et al. |
| 2011/0158986 | A1 | 6/2011 | Holtzman et al. |
| 2012/0276099 | A1 | 11/2012 | Poppe |
| 2013/0017251 | A1 | 1/2013 | Huang et al. |
| 2014/0348843 | A1* | 11/2014 | Schenk .................. C07K 16/18 435/7.1 |
| 2014/0370619 | A1 | 12/2014 | Holtzman et al. |
| 2015/0118231 | A1 | 4/2015 | Michaelson |
| 2015/0140672 | A1 | 5/2015 | Bateman et al. |
| 2015/0254421 | A1 | 9/2015 | Bateman et al. |
| 2017/0218058 | A1 | 8/2017 | Rosenthal |

FOREIGN PATENT DOCUMENTS

| | | |
|---|---|---|
| WO | 2013168174 A1 | 11/2013 |
| WO | 2015187992 A2 | 12/2015 |
| WO | 2018081642 A1 | 5/2018 |

OTHER PUBLICATIONS

Almagro, J. et al., "Humanization of Antibodies," Front. Biosci., Jan. 2008, pp. 1619-1633, vol. 13.
Caldas, C. et al., "Humanization of the anti-CD18 antibody 6.7: an unexpected effect of a framework residue in binding to antigen," Mol. Immunol., 2003, pp. 941-952, vol. 39.
Chothia, C. et al., "Canonical Structures for the Hypervariable Regions of Immunoglobulins," J. Mol. Biol., 1987, pp. 901-917, vol. 196.
Clackson, T. et al., Making antibody fragments using phage display libraries, Nature, Aug. 1991, pp. 624-628, vol. 352.
Du, J. et al., "Molecular Basis of Recognition of Human Osteopontin by 23C3, A Potential Therapeutic Antibody for Treatment of Rheumatoid Arthritis," J. Mol. Biol., 2008, pp. 835-842, vol. 382.
Extended European Search Report dated Nov. 2, 2020 from related European Patent Application No. 17865058.6; 48 pgs.
Fagan, A. et al., "Inverse Relation between In Vivo Amyloid Imaging Load and Cerebrospinal Fluid AlphaBeta42 in Humans," Ann. Neurol., 2006, pp. 512-519, vol. 59.
GenBank Accession No. NM_000041, printed Sep. 3, 2019; 6 pgs.
Gerritse, K. et al., "Immunological discrimination between the human apolipoprotein E2(Arg158—Cys) and E3 isoforms," J. Lipid Res., 1992, pp. 273-280, vol. 33.
International Search Report and Written Opinion dated Apr. 5, 2018 from related PCT Patent Application No. PCT/US2017/058874; 17 pgs.
Klunk, W. et al., "Imaging Brain Amyloid in Alzheimer's Disease with Pittsburgh Compound-B," Ann. Neurol., 2004, pp. 306-319, vol. 55.
Liao, F. et al., "Anti-ApoE Antibody Given after Plaque Onset Decreases Abeta Accumulation and Improves Brain Function in a Mouse Model of Abeta Amyloidosis," J. Neurosci., May 21, 2014, pp. 7281-7292, vol. 34, No. 21.
Luz, I. et al., "An Anti-apoE4 Specific Monoclonal Antibody Counteracts the Pathological Effects of apoE4 In Vivo," Curr. Alzheimer Res., 2016, pp. 918-929, vol. 13.
McKhann, G. et al., "The diagnosis of dementia due to Alzheimer's disease: Recommendations from the National Institute on Aging-Alzheimer's Association workgroups on diagnostic guidelines for Alzheimer's disease," Alzheimer's & Dementia, 2011, pp. 263-269, vol. 7, No. 3.
NCBI Reference Sequence NC_000019.10, dated Jun. 14, 2019; 3 pgs.
NCBI Reference Sequence NP_000032.1, printed Sep. 3, 2019; 5 pgs.
Office Action dated Nov. 25, 2020 from related U.S. Appl. No. 16/345,637; 5 pgs.
Office Action dated Aug. 24, 2021 from related Japanese Patent Application No. 2019-523734; 5 pgs.
Ophir, G. et al., "Neutralization of apoE4 phenotypes with apoE4 specific antibodies," Neural Plasticity, 2003, p. 222, vol. 10, No. 3.
Pang, J. et al., "Potential implications of Apolipoprotein E in early brain injury after experimental subarachnoid hemorrhage: Involvement in the modulation of blood-brain barrier integrity," Oncotarget, 2016, pp. 56030-56044, vol. 7, No. 35.
Panka, D. et al., "Variable region framework differences result in decreased or increased affinity of variant anti-digoxin antibodies," Immunol., May 1988, pp. 3080-3084, vol. 85.
Partial Supplementary Search Report dated Jun. 8, 2020 from related European Patent Application No. 17865058.6; 31 pgs.
Portolano, S. et al., "Lack of promiscuity in autoantigen-specific H and L chain combinations as revealed by human H and L chain 'roulette'," J. Immunol., Feb. 1993, pp. 880-887, vol. 150, No. 3.
Sperling, R. et al., "Amyloid Related Imaging Abnormalities (ARIA) in Amyloid Modifying Therapeutic Trials: Recommendations from the Alzheimer's Association Research Roundtable Workgroup," NIH Public Access Author Manuscript, Jun. 26, 2013, pp. 1-34, published in final edited form as: Alzheimers Dement., Jul. 2011, pp. 367-385, vol. 7, No. 4.
Tokuda, T. et al., "Lipidation of apolipoprotein E influences its isoform-specific interaction with Alzheimer's amyloid beta peptides," Biochem. J., 2000, pp. 359-365, vol. 348.
UniProtKB Identifier P02649, printed Sep. 5, 2019; 35 pgs.
Xiang, J. et al., "Modification in Framework Region I Results in a Decreased Affinity of Chimeric ANTI-TAG72 Antibody," Mol. Immunol., 1991, pp. 141-148, vol. 28, No. 1/2.
Office Action dated Feb. 3, 2023 from related Australian Application No. 2017350947, 4 pages.
Office Action dated Jul. 6, 2023 from related Canacian Application No. 3,042,236, 3 pages.

* cited by examiner

| Antibody | Ka (1/Ms) | Kd (1/s) | Apparent KD (M) |
|---|---|---|---|
| HJ151 | 1.97E+04 | 0.00119 | 6.02E-08 |
| HJ153 | 6.62E+05 | 2.11E-04 | 3.19E-10 |
| HJ156 | 2.64E+04 | 0.00523 | 1.98E-07 |

HJ151B

HJ152B

HJ154B

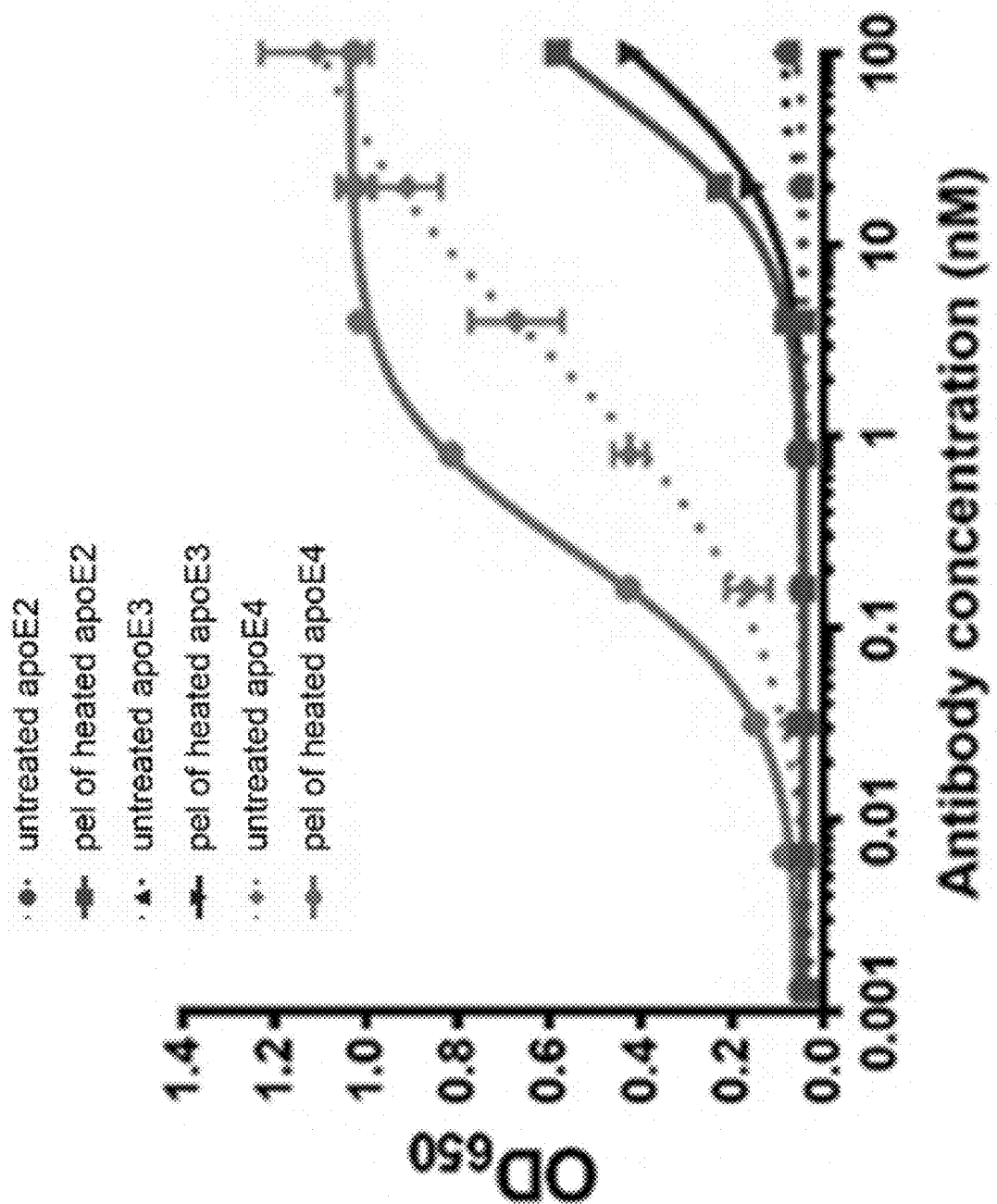

ANTI-ApoE ANTIBODIES

CROSS REFERENCE TO RELATED APPLICATIONS

This application is a continuation of U.S. application Ser. No. 16/345,637, filed Apr. 26, 2019, which is a national stage filing of PCT Application No. PCT/US2017/058874, filed Oct. 27, 2017, which claims priority to U.S. provisional application No. 62/414,413, filed Oct. 28, 2016, and U.S. provisional application No. 62/533,336 filed Jul. 17, 2017, each of which are hereby incorporated by reference in their entirety.

GOVERNMENTAL RIGHTS

This invention was made with government support under R01AG047644 awarded by the National Institutes of Health. The government has certain rights in the invention.

FIELD OF THE INVENTION

The invention relates to anti-ApoE antibodies and compositions thereof. The invention also relates to compositions and methods for delaying and/or preventing Aβ amyloidosis. The invention also relates to compositions and methods for delaying and/or preventing Aβ plaque associated symptoms and/or cerebral amyloid angiopathy (CAA) associated symptoms, such as those associated with Alzheimer's disease (AD) or CAA in a subject. In particular, the invention relates to modulating the concentration of amyloid-β (Aβ) in the brain of a subject.

REFERENCE TO SEQUENCE LISTING

A paper copy of the sequence listing and a computer readable form of the same sequence listing are appended below and herein incorporated by reference. The information recorded in computer readable form is identical to the written sequence listing, according to 37 C.F.R. 1.821(f).

BACKGROUND OF THE INVENTION

Alzheimer's disease (AD) is the most common cause of dementia and is an increasing public health problem. It is currently estimated to afflict over 5 million people in the United States, with an expected increase to 13 million by the year 2050. Alzheimer's disease leads to loss of memory, cognitive function, and ultimately loss of independence. It takes a heavy personal and financial toll on the subject and the family. Because of the severity and increasing prevalence of the disease in the population, it is urgent that better treatments be developed.

Cerebral amyloid angiopathy (CAA) occurs in about 90% of individuals who develop AD, as well as in some individuals independently of AD. CAA can lead to ischemic and hemorrhagic strokes causing severe disability or death. There are no current treatments for CAA.

Biochemical, genetic, and animal model evidence implicates amyloid-β (Aβ) as a pathogenic peptide in AD and in most cases of CAA. The neuropathologic and neurochemical hallmarks of AD include synaptic loss and selective neuronal death, a decrease in certain neurotransmitters, and the presence of abnormal proteinaceous deposits within neurons (neurofibrillary tangles) and in the extracellular space (cerebrovascular, diffuse, and neuritic plaques). The characteristic features of CAA include the buildup of fibrillar forms of Aβ in penetrating and leptomeningeal arterioles on the surface of the cerebral cortex. CAA can lead to ischemic or hemorrhagic stroke. The main constituent of the plaques seen in AD and CAA is Aβ, a 38-43 amino acid sequence peptide cleaved from the amyloid precursor protein (APP).

Throughout life, soluble Aβ is secreted primarily by neurons, but also other cell types. Excessive Aβ deposition may result from increased Aβ synthesis, e.g. as occurs in familial early-onset AD and in some cases of familial early onset CAA, decreased Aβ clearance in the brain, or increased Aβ fibrillogenesis. The lack of compelling evidence that Aβ over-production occurs in the more common late-onset forms of AD suggests that insufficient Aβ clearance may drive Aβ deposition and amyloid plaque formation and CAA as well.

The apolipoprotein E gene (ApoE) remains the most widely replicated genetic risk factor for late-onset AD and CAA, with carriers of the ε4 allele having a 3-15-fold greater risk as well as an earlier age of disease onset. ApoE4 carriers represent over 60% of the AD population whereas the ε2 allele is least represented in AD and may be protective in some populations. The human ApoE isoforms differ at amino acid position 112 or 158 (ε2 has Cys112, Cyst 58; ε3 has Cys112, Arg158; ε4 has Arg112, Arg158). Mouse ApoE and human ApoE share ~70% amino acid homology. The amino acid differences within human ApoE isoforms have effects on the structure and stability of the protein. For example, ApoE4 has a greater propensity towards an unstructured, molten globule state and is more likely to form aggregates, as compared to ApoE2 and ApoE3.

In the brain, ApoE is mainly produced by glia and predominantly functions to distribute cholesterol and lipids to neurons. The majority of ApoE in the CNS is found on HDL-like lipoprotein particles, and lipidation of ApoE is regulated by the ABCA1 and ABCG1 transporters. ABCA1 knockout mice crossed to transgenic AD mice produce ApoE that is poorly-lipidated and these mice have increased Aβ plaques. Conversely, the brains of AD transgenic mice overexpressing ABCA1 contain well-lipidated apoE lipoprotein particles and have reduced Aβ plaque deposition. Binding of ApoE to LDLR, LRP1, apoER2, and VLDLR, which are expressed on various neural cell types, enables the uptake of lipoprotein particles through receptor-mediated endocytosis, processing of the lipid cargo, and recycling of the unbound receptors. The amino acid difference at position 158 for ApoE2 confers decreased receptor binding to the LDLR and humans with the ε2/ε2 genotype have increased risk for type H hyperlipoproteinemia.

The deposition of Aβ plaques in AD patients is ApoE isoform-dependent (E4>E3>E2), the extent of interaction between ApoE and Aβ and the function of their interaction remains controversial. Strong evidence suggests the differential Aβ deposition is secondary to differences in apoE isoform-dependent Aβ clearance and aggregation. The clearance of Aβ monomers from the brains of AD transgenic mice is also ApoE isoform dependent (E2>E3>E4), and recent studies suggest ApoE4 may potentially hinder clearance by competing for binding to receptors that also function to clear Aβ. The extent of ApoE lipidation may also affect the formation of Ail oligomers with greater levels in ε4/ε4 AD patients than ε3/ε3. The present disclosure describes the discovery that anti-ApoE antibodies with certain characteristics provide a treatment for subjects with Aβ amyloidosis.

SUMMARY OF THE INVENTION

One aspect of the invention encompasses an isolated anti-ApoE antibody comprising (a) a light chain variable region comprising an L1 of SEQ ID NO: 86, an L2 of SEQ ID NO: 30, an L3 comprising SEQ ID NO: 88, or any combination thereof; and/or (b) a heavy chain variable region comprising an H1 comprising SEQ ID NO: 90, an H2 comprising SEQ ID NO: 92, an H3 comprising SEQ ID NO: 94, or any combination thereof. Compositions comprising the antibody, including but not limited to pharmaceutical compositions, are contemplated herein. In certain embodiments the antibody is a humanized antibody.

Another aspect of the invention encompasses an isolated anti-ApoE antibody comprising (a) a light chain variable region comprising an L1 of SEQ ID NO: 87, an L2 of SEQ ID NO: 30, an L3 comprising SEQ ID NO: 89, or any combination thereof; and/or (b) a heavy chain variable region comprising an H1 comprising SEQ ID NO: 91, an H2 comprising SEQ ID NO: 93, an H3 comprising SEQ ID NO: 95, or any combination thereof. Compositions comprising the antibody, including but not limited to pharmaceutical compositions, are contemplated herein. In certain embodiments the antibody is a humanized antibody.

Another aspect of the invention encompasses an isolated anti-ApoE antibody comprising (a) a light chain variable region comprising an L1 of SEQ ID NO: 78, an L2 of SEQ ID NO: 24, an L3 comprising SEQ ID NO: 25, or any combination thereof; and/or (b) a heavy chain variable region comprising an H1 comprising SEQ ID NO: 80, an H2 comprising SEQ ID NO: 82, an H3 comprising SEQ ID NO: 84, or any combination thereof. Compositions comprising the antibody, including but not limited to pharmaceutical compositions, are contemplated herein. In certain embodiments the antibody is a humanized antibody.

Another aspect of the invention encompasses an isolated anti-ApoE antibody comprising (a) a light chain variable region comprising an L1 of SEQ ID NO: 79, an L2 of SEQ ID NO: 24, an L3 comprising SEQ ID NO: 25, or any combination thereof; and/or (b) a heavy chain variable region comprising an H1 comprising SEQ ID NO: 81, an H2 comprising SEQ ID NO: 83, an H3 comprising SEQ ID NO: 86, or any combination thereof. Compositions comprising the antibody, including but not limited to pharmaceutical compositions, are contemplated herein. In certain embodiments the antibody is a humanized antibody.

Another aspect of the invention encompasses an isolated anti-ApoE antibody comprising (a) a light chain variable region comprising an L1 of SEQ ID NO: 105, an L2 of SEQ ID NO: 106, an L3 comprising SEQ ID NO: 107, or any combination thereof; and/or (b) a heavy chain variable region comprising an H1 comprising SEQ ID NO: 109, an H2 comprising SEQ ID NO: 111, an H3 comprising SEQ ID NO: 113, or any combination thereof. Compositions comprising the antibody, including but not limited to pharmaceutical compositions, are contemplated herein. In certain embodiments the antibody is a humanized antibody.

Another aspect of the invention encompasses an isolated anti-ApoE antibody comprising (a) a light chain variable region comprising an L1 of SEQ ID NO: 105, an L2 of SEQ ID NO: 106, an L3 comprising SEQ ID NO: 108, or any combination thereof; and/or (b) a heavy chain variable region comprising an H1 comprising SEQ ID NO: 110, an H2 comprising SEQ ID NO: 112, an H3 comprising SEQ ID NO: 114, or any combination thereof. Compositions comprising the antibody, including but not limited to pharmaceutical compositions, are contemplated herein. In certain embodiments the antibody is a humanized antibody.

Another aspect of the invention encompasses an isolated anti-ApoE antibody comprising (a) a light chain variable region comprising an L1 of SEQ ID NO: 23, an L2 of SEQ ID NO: 24, an L3 comprising SEQ ID NO: 25, or any combination thereof; and/or (b) a heavy chain variable region comprising an H1 comprising SEQ ID NO: 26, an H2 comprising SEQ ID NO: 27, an H3 comprising SEQ ID NO: 28, or any combination thereof. Compositions comprising the antibody, including but not limited to pharmaceutical compositions, are contemplated herein. In certain embodiments the antibody is a humanized antibody.

Another aspect of the invention encompasses an isolated anti-ApoE antibody comprising (a) a light chain variable region comprising an L1 of SEQ ID NO: 29, an L2 of SEQ ID NO: 30, an L3 comprising SEQ ID NO: 31, or any combination thereof; and/or (b) a heavy chain variable region comprising an H1 comprising SEQ ID NO: 32, an H2 comprising SEQ ID NO: 33, an H3 comprising SEQ ID NO: 34, or any combination thereof. Compositions comprising the antibody, including but not limited to pharmaceutical compositions, are contemplated herein. In certain embodiments the antibody is a humanized antibody.

Another aspect of the invention encompasses an isolated anti-ApoE antibody comprising (a) a light chain variable region comprising an L1 of SEQ ID NO: 47, an L2 of SEQ ID NO: 24, an L3 comprising SEQ ID NO: 25, or any combination thereof; and/or (b) a heavy chain variable region comprising an H1 comprising SEQ ID NO: 48, an H2 comprising SEQ ID NO: 49, an H3 comprising SEQ ID NO: 50, or any combination thereof. Compositions comprising the antibody, including but not limited to pharmaceutical compositions, are contemplated herein. In certain embodiments the antibody is a humanized antibody.

Another aspect of the invention encompasses an isolated anti-ApoE antibody comprising (a) a light chain variable region comprising an L1 of SEQ ID NO: 51, an L2 of SEQ ID NO: 24, an L3 comprising SEQ ID NO: 25, or any combination thereof; and/or (b) a heavy chain variable region comprising an H1 comprising SEQ ID NO: 52, an H2 comprising SEQ ID NO: 53, an H3 comprising SEQ ID NO: 54, or any combination thereof. Compositions comprising the antibody, including but not limited to pharmaceutical compositions, are contemplated herein. In certain embodiments the antibody is a humanized antibody.

Another aspect of the invention encompasses an isolated anti-ApoE antibody comprising (a) a light chain variable region comprising an L1 of SEQ ID NO: 55, an L2 of SEQ ID NO: 24, an L3 comprising SEQ ID NO: 25, or any combination thereof; and/or (b) a heavy chain variable region comprising an H1 comprising SEQ ID NO: 56, an H2 comprising SEQ ID NO: 57, an H3 comprising SEQ ID NO: 58, or any combination thereof. Compositions comprising the antibody, including but not limited to pharmaceutical compositions, are contemplated herein. In certain embodiments the antibody is a humanized antibody.

Another aspect of the invention encompasses an isolated anti-ApoE antibody comprising (a) a light chain variable region comprising an L1 of SEQ ID NO: 59, an L2 of SEQ ID NO: 24, an L3 comprising SEQ ID NO: 25, or any combination thereof; and/or (b) a heavy chain variable region comprising an H1 comprising SEQ ID NO: 60, an H2 comprising SEQ ID NO: 61, an H3 comprising SEQ ID NO: 62, or any combination thereof. Compositions comprising the antibody, including but not limited to pharmaceutical compositions, are contemplated herein. In certain embodiments the antibody is a humanized antibody.

Another aspect of the invention encompasses an isolated anti-ApoE antibody comprising (a) a light chain variable region comprising an L1 of SEQ ID NO: 63, an L2 of SEQ ID NO: 30, an L3 comprising SEQ ID NO: 64, or any combination thereof; and/or (b) a heavy chain variable region comprising an H1 comprising SEQ ID NO: 65, an H2 comprising SEQ ID NO: 66, an H3 comprising SEQ ID NO: 67, or any combination thereof. Compositions comprising the antibody, including but not limited to pharmaceutical compositions, are contemplated herein. In certain embodiments the antibody is a humanized antibody.

Another aspect of the invention encompasses an isolated anti-ApoE antibody comprising (a) a light chain variable region comprising an L1 of SEQ ID NO: 68, an L2 of SEQ ID NO: 24, an L3 comprising SEQ ID NO: 25, or any combination thereof; and/or (b) a heavy chain variable region comprising an H1 comprising SEQ ID NO: 69, an H2 comprising SEQ ID NO: 70, an H3 comprising SEQ ID NO: 71, or any combination thereof. Compositions comprising the antibody, including but not limited to pharmaceutical compositions, are contemplated herein. In certain embodiments the antibody is a humanized antibody.

Another aspect of the invention encompasses an isolated anti-ApoE antibody comprising (a) a light chain variable region comprising an L1 of SEQ ID NO: 72, an L2 of SEQ ID NO: 73, an L3 comprising SEQ ID NO: 74, or any combination thereof; and/or (b) a heavy chain variable region comprising an H1 comprising SEQ ID NO: 75, an H2 comprising SEQ ID NO: 76, an H3 comprising SEQ ID NO: 77, or any combination thereof. Compositions comprising the antibody, including but not limited to pharmaceutical compositions, are contemplated herein. In certain embodiments the antibody is a humanized antibody.

Another aspect of the invention encompasses an isolated anti-ApoE antibody comprising (a) a light chain variable region comprising an L1 of SEQ ID NO: 105, an L2 of SEQ ID NO: 106, an L3 comprising SEQ ID NO: 123, or any combination thereof; and/or (b) a heavy chain variable region comprising an H1 comprising SEQ ID NO: 124, an H2 comprising SEQ ID NO: 125, an H3 comprising SEQ ID NO: 126, or any combination thereof. Compositions comprising the antibody, including but not limited to pharmaceutical compositions, are contemplated herein. In certain embodiments the antibody is a humanized antibody.

Another aspect of the invention encompasses an isolated anti-ApoE antibody comprising (a) a light chain variable region comprising an L1 of SEQ ID NO: 99, an L2 of SEQ ID NO: 100, an L3 comprising SEQ ID NO: 101, or any combination thereof; and/or (b) a heavy chain variable region comprising an H1 comprising SEQ ID NO: 102, an H2 comprising SEQ ID NO: 103, an H3 comprising SEQ ID NO: 104, or any combination thereof. Compositions comprising the antibody, including but not limited to pharmaceutical compositions, are contemplated herein. In certain embodiments the antibody is a humanized antibody.

Another aspect of the invention encompasses an isolated anti-ApoE antibody comprising (a) a light chain variable region comprising an L1 of SEQ ID NO: 105, an L2 of SEQ ID NO: 106, an L3 comprising SEQ ID NO: 117, or any combination thereof; and/or (b) a heavy chain variable region comprising an H1 comprising SEQ ID NO: 118, an H2 comprising SEQ ID NO: 119, an H3 comprising SEQ ID NO: 120, or any combination thereof. Compositions comprising the antibody, including but not limited to pharmaceutical compositions, are contemplated herein. In certain embodiments the antibody is a humanized antibody.

Another aspect of the invention encompasses a method of improving a clinical sign of Aβ amyloidosis which comprises administering an effective amount of an anti-ApoE antibody to a living human subject. In another aspect, the invention encompasses a method of effectively treating at least one clinically detectable Aβ plaque associated symptom and/or CAA associated symptom which comprises administering an effective amount of an anti-ApoE antibody to a living human subject. In another aspect, the invention encompasses a method of treating Alzheimer's disease which comprises administering an effective amount of an anti-ApoE antibody to a living human subject. In another aspect, the invention encompasses a method of treating CAA which comprises administering an effective amount of an anti-ApoE antibody to a living human subject. In each of the above aspects, the anti-ApoE antibody may be an antibody described above.

Yet another aspect of the invention encompasses a pharmaceutical composition useful to treat at least one clinically detectable Aβ plaque associated symptom. The composition comprises a pharmaceutically effective amount of an anti-ApoE antibody adapted for administration to a living human subject. The anti-ApoE antibody may be an antibody described above. In an aspect, the medicinal composition is effectively administered to a living subject systemically.

Yet another aspect of the invention encompasses a pharmaceutical composition useful to treat at least one clinically detectable CAA associated symptom. The composition comprises a pharmaceutically effective amount of an anti-ApoE antibody adapted for administration to a living human subject. The anti-ApoE antibody may be an antibody described above. In an aspect, the pharmaceutical composition is effectively administered to a living subject systemically.

Yet another aspect of the invention encompasses a pharmaceutical composition useful to treat Alzheimer's disease. The composition comprises a pharmaceutically effective amount of an anti-ApoE antibody adapted for administration to a living human subject. The anti-ApoE antibody may be an antibody described above. In an aspect, the pharmaceutical composition is effectively administered to a living subject systemically.

Yet another aspect of the invention encompasses a pharmaceutical composition useful to treat CAA. The composition comprises a pharmaceutically effective amount of an anti-ApoE antibody adapted for administration to a living human subject. The anti-ApoE antibody may be an antibody described above. In an aspect, the pharmaceutical composition is effectively administered to a living subject systemically.

Still another aspect the invention encompasses a kit comprising a container containing a pharmaceutical composition comprising a pharmaceutically effective amount of an anti-ApoE antibody adapted for administration to a living human subject and any medical devices to be used for said administration. The anti-ApoE antibody may be an antibody described above.

Other aspects and iterations of the invention are detailed below.

BRIEF DESCRIPTION OF THE FIGURES

The application file contains at least one photograph executed in color. Copies of this patent application publication with color photographs will be provided by the Office upon request and payment of the necessary fee.

FIG. 5E-H are graphs depicting surface plasmon resonance profiles for various antibodies. Anti-ApoE antibodies were serially diluted 3-fold (starting at 100 nM for HJ153 (E), and 1000 nM for HJ151 (F), and HJ1156 (G)) for detection of binding to biotinylated-recombinant apoE4 captured on a streptavidin chip. Samples were injected at a flow rate of 30 μl/minute. (H) Apparent KD values of HJ151, HJ153 and HJ156 were calculated based on the SPR experiment.

Figure 1:
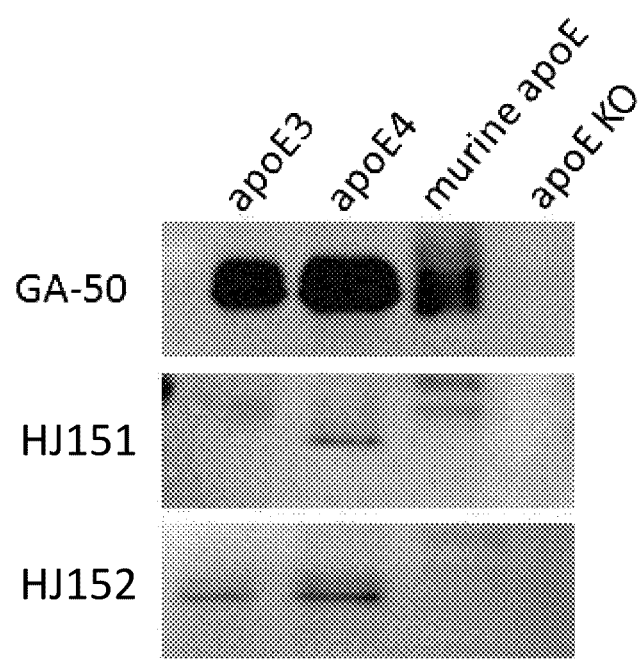
FIG. 1 depicts an image of a Western blot. The brain lysates from ApoE KO mice or mice expressing ApoE3, ApoE4 or murine ApoE were immunoblotted with GA-50, HJ151, or HJ152. The Western blot shows that HJ151 is ApoE4 specific and HJ152 recognizes both ApoE3 and ApoE4. GA-50 is a positive control.

Fibrillar Aβ plaque number, detected by X-34 staining, was quantified from cortex, n=10 per group. *p<0.05 compared to PBS and HJ16.6 groups.

FIG. 33A-F shows images of brain sections immunostained for Aβ with anti-Aβ antibody (HJ3.4-biotin). (A,D) Brain sections from non-treated, 2 month old mice before the development of Aβ plaques. (B,E) Brain sections from 3.5 month old mouse treated with PBS. (C,F) Brain sections from 3.5 month old mouse treated with negative control IgG (HJ16.6) at 50 mg/kg. Scale bar 300 μm, n=10 per group.

FIG. 34A-F shows images of brain sections immunostained for Aβ with anti-Aβ antibody (HJ3.4-biotin). (A,D) Brain sections from 3.5 month old mouse treated with HJ151 at 50 mg/kg. (B,E) Brain sections from 3.5 month old mouse treated with HJ155 at 50 mg/kg. (C,F) Brain sections from 3.5 month old mouse treated with HJ156 at 50 mg/kg. Scale bar 300 μm, n=10 per group.

FIG. 35A-F shows images of brain sections stained with X-34 dye that recognizes fibrillar plaques. (A,D) Brain sections from non-treated, 2 month old mice before the development of Aβ plaques. (B,E) Brain sections from 3.5 month old mouse treated with PBS. (C,F) Brain sections from 3.5 month old mouse treated with negative control IgG (HJ16.6) at 50 mg/kg. Scale bar 300 μm, n=10 per group.

FIG. 36A-F shows images of brain sections stained with X-34 dye that recognizes fibrillar plaques. (A,D) Brain sections from 3.5 month old mouse treated with HJ151 at 50 mg/kg. (B,E) Brain sections from 3.5 month old mouse treated with HJ155 at 50 mg/kg. (C,F) Brain sections from 3.5 month old mouse treated with HJ156 at 50 mg/kg. Scale bar 300 μm, n=10 per group.

FIG. 37A-F are graphs depicting the binding profile of HJ151, HJ153 and HJ156 with lipidated apoE. (A,B) ELISA following coating of plasma on plates. Plasma from apoE KO, APOE2, APOE3 and APOE4 mice was coated onto the plates. Chi153 and chi156 of different concentrations were loaded. The captured antibodies were detected with HRP-goat anti-human IgG antibody. (C,D) ELISA following coating of antibodies on plates. Plates were coated with HJ153 and HJ156. Plasma from mice with different genotypes was loaded. The captured ApoE was detected with HRP-goat-polyclonal anti-ApoE. (E) Plasma competition experiment was performed via ELISA format. Recombinant ApoE4 was coated onto the plates. HJ151 (50 nM), HJ153 (4 nM), and HJ156 (50 nM) pre-incubated with serially diluted plasma from APOE4 KI mice was loaded to the plates. The HJ15 antibodies bound to the plates were detected with HRP-Goat anti-mouse IgG antibodies. (F) Plasma antibody concentrations of HJ153, HJ156, or control IgG following IP injection into APOE4 KI or EKO mice. HJ156 was dosed at 2, 10 and 50 mg/kg and plasma samples collected by submandibular puncture. HJ153 was dosed at 10 mg/kg. Control murine IgG2a (msIgG2a) was anti-Her2 and dosed at 10 mg/kg. Quantification of dosed antibodies in plasma was by antigen capture ELISA using coated recombinant apoE4 to detect HJ153 or HJ156 with recombinant Her2 used to detect the control IgG. Peripheral clearance of HJ156 is similar to Control IgG with target mediated clearance observed by day 14. HJ153 exhibited high clearance and reached lower limits by 48 hours.

FIG. 38A-E are graphs depicting the binding of HJ151 and HJ156 with ApoE4 in the amyloid plaques in unfixed mouse brain sections and specificity for heat-induced aggregates of ApoE4. (A) Unfixed frozen brain sections from APPPS1/APOE4 or APPPS1/APOE KO mice were stained with anti-Aβ antibody HJ3.4, anti-ApoE antibodies HJ151 and HJ156. (Scale bar=400 μm). (B) Binding of HJ151, HJ153 and HJ156 to untreated recombinant ApoE4 (untreated) and ApoE4 that has been incubated at 40° C. for 24 hr (40 C). (C) Incubation of ApoE4 at 40° C. for 24 hour results in the formation of aggregates recovered in the pellet fraction after ultracentrifugation at 186,000 g for 1 hour. 1: untreated ApoE4. 2: ApoE4 that has been incubated at 40° C. for 24 hr. Supernatant (S) and pellet (P) from ultracentrifugation were resolved on SDS-PAGE and stained by Coomassie blue. (D) Binding of HJ156 to different preparations of ApoE4 loaded at the same concentration on the ELISA plate. Sup of untreated: Supernatant fraction of untreated ApoE4 from ultracentrifugation. Sup/Pel of 24 h 40 C: Supernatant/pellet fraction of ApoE4 incubated at 40° C. for 24 hour. (E) Binding of HJ156 to untreated and 40° C. incubated ApoE4 with and without denaturation by 1% SDS or 4M guanidine HCl.

FIG. 39A-D are images of HJ151, HJ156 and control antibody binding to human ApoE4 in living mouse brain. (A) Negative control IgG2ab (B) HJ151 and (C) HJ156 conjugated with Alexa 594 were applied directly onto the surface of the brain in living APPPS1-21/APOE4 mice that were 6 months of age and the binding of antibodies was observed under 2-photon microscopy. The amyloid was labeled using methoxy-X04. The middle panel is the higher power images of the area in the white frame of the top panel. Arrows indicate plaques. The bottom panel is the higher power images of the area in the yellow frame of the top panel. Arrows indicate CAA. (D) Control huIgG or chi156 at 50 mg/kg body weight (i.p.) were injected for one (0 hour) or two doses (0 and 48 hour) and APPPS1-21/APOE4 mice sacrificed at 48 hours after final injection. The antibodies in the brain were detected by biotinylated rabbit anti-human IgG followed by DAB. (Left panel: Bar=1 mm. right panel: high power image of the indicated areas in the left panel. Bar=300 μm)

Figure 40:
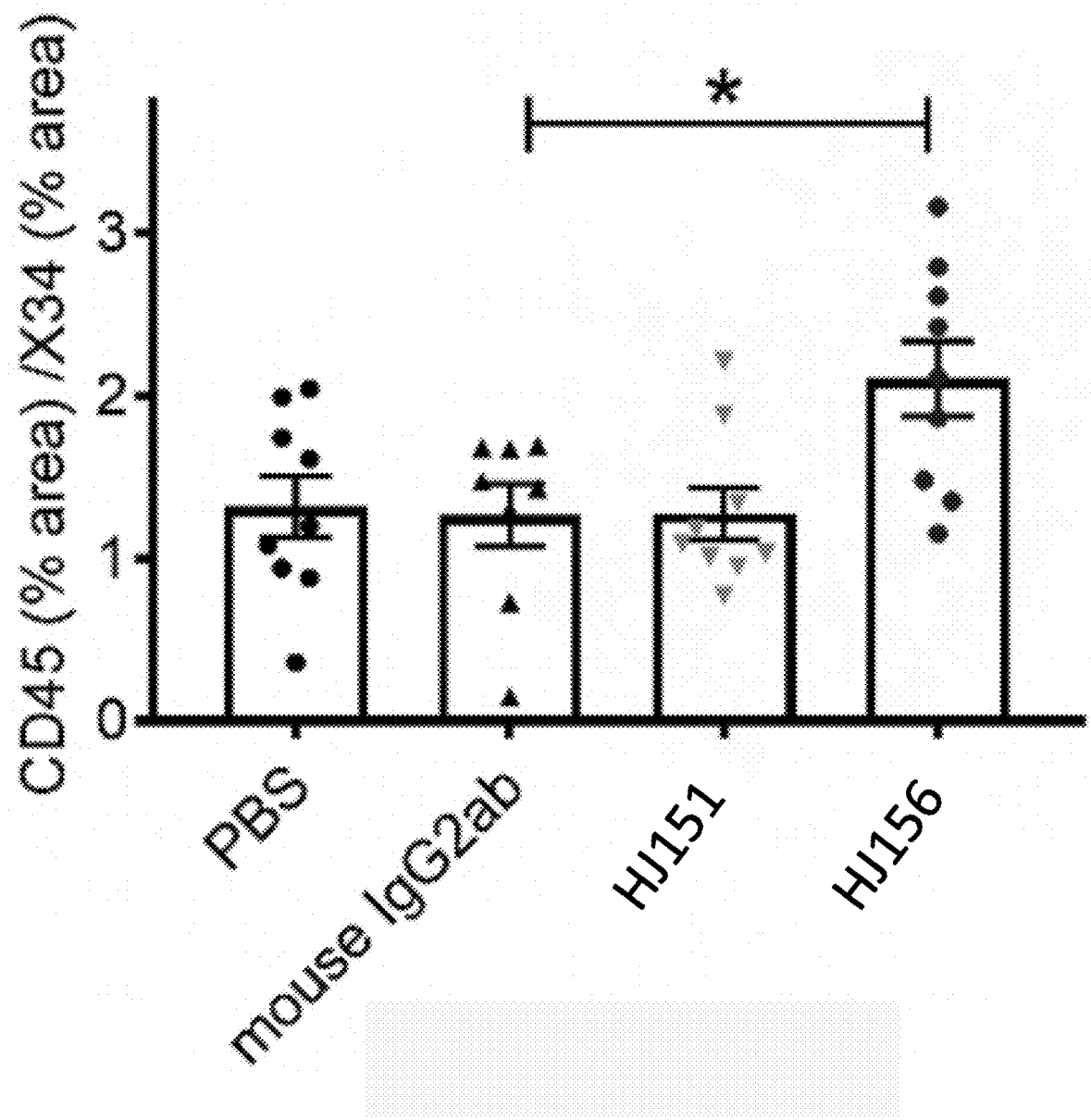

FIG. 40 depicts a graph showing that HJ156 activates microglia to facilitate plaque clearance. 4-month old APPPS1-21/APOE4 mice that already had existing plaques were administered a short-term treatment of HJ151 and HJ156 antibodies (4 doses by IP injection every 3 days). Stained sections were analyzed for CD45+ microglia area relative to the amount of fibrillar plaques. HJ151 had no effect on the amount of activated microglia. *p<0.05.

Figure 41:
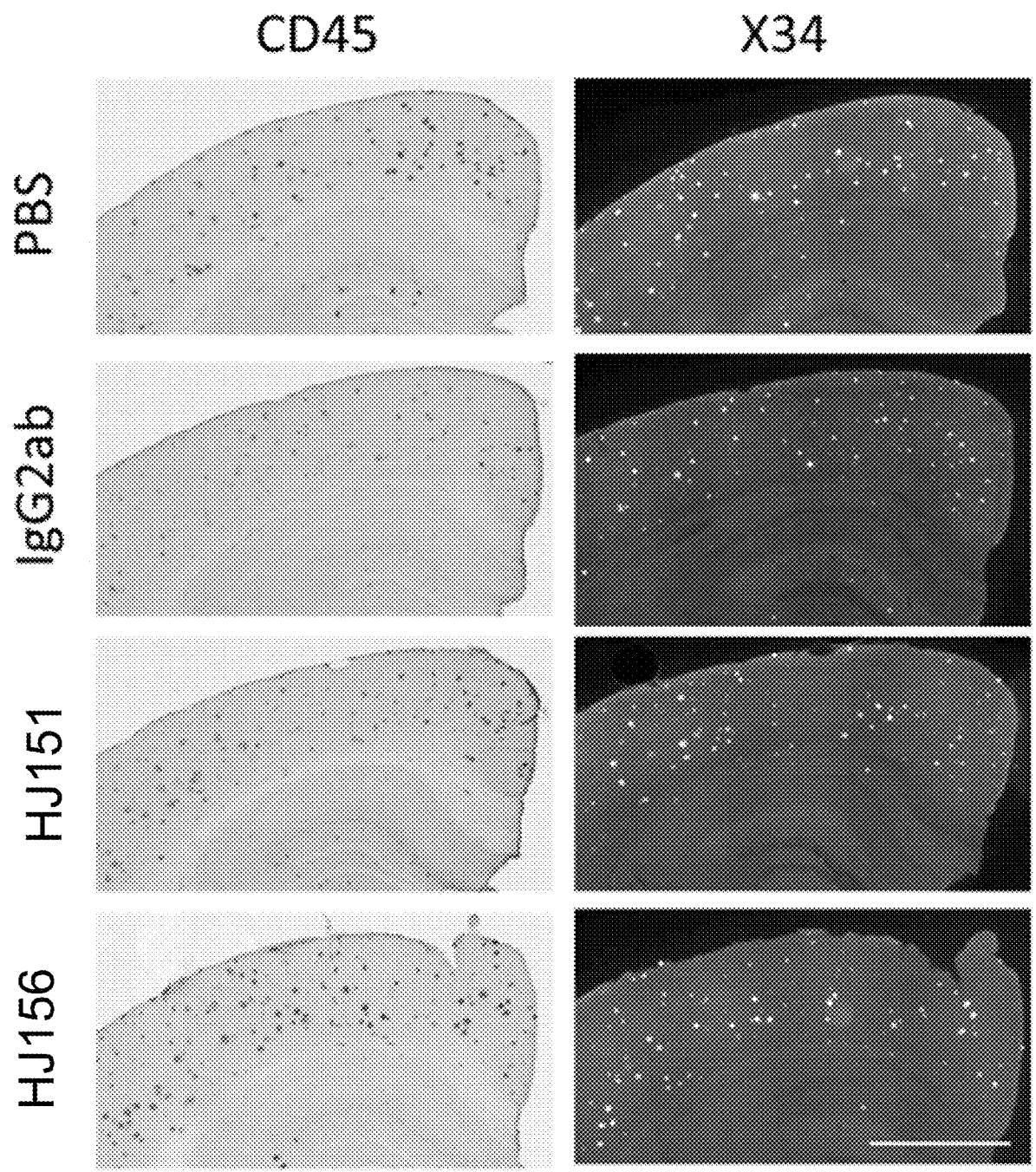

FIG. 41 depicts staining of microglia and plaques after acute immunization of HJ156. At the age of 4 months, the APPPS1/APOE4 mice received 4 IP injections of 50 mg/kg weight of antibodies every three days. The mice were sacrificed 24 hours after the final injection and the plaques were stained with X34 and the activated microglia was stained with CD45 (Bar=1 mm).

Figure 42A:
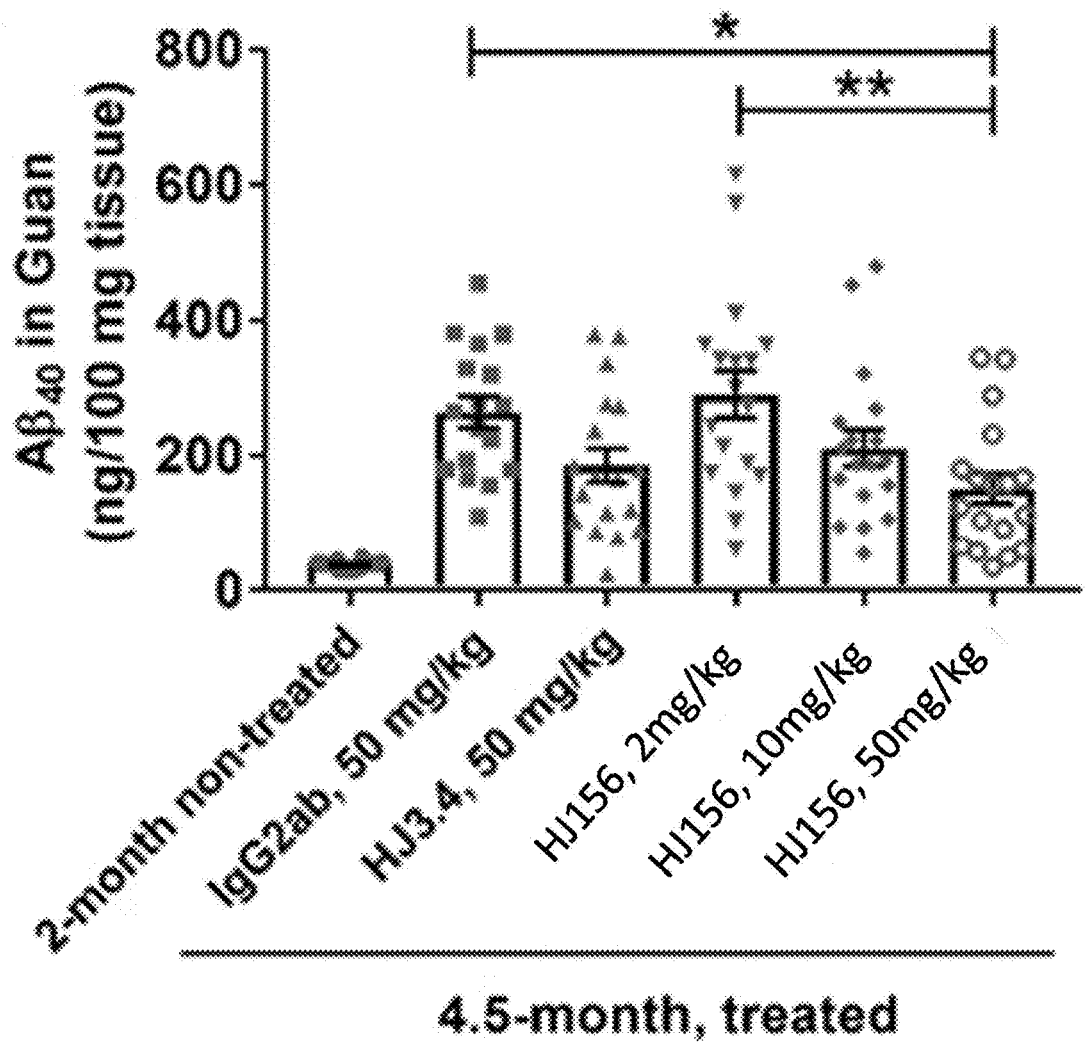
Figure 42B:
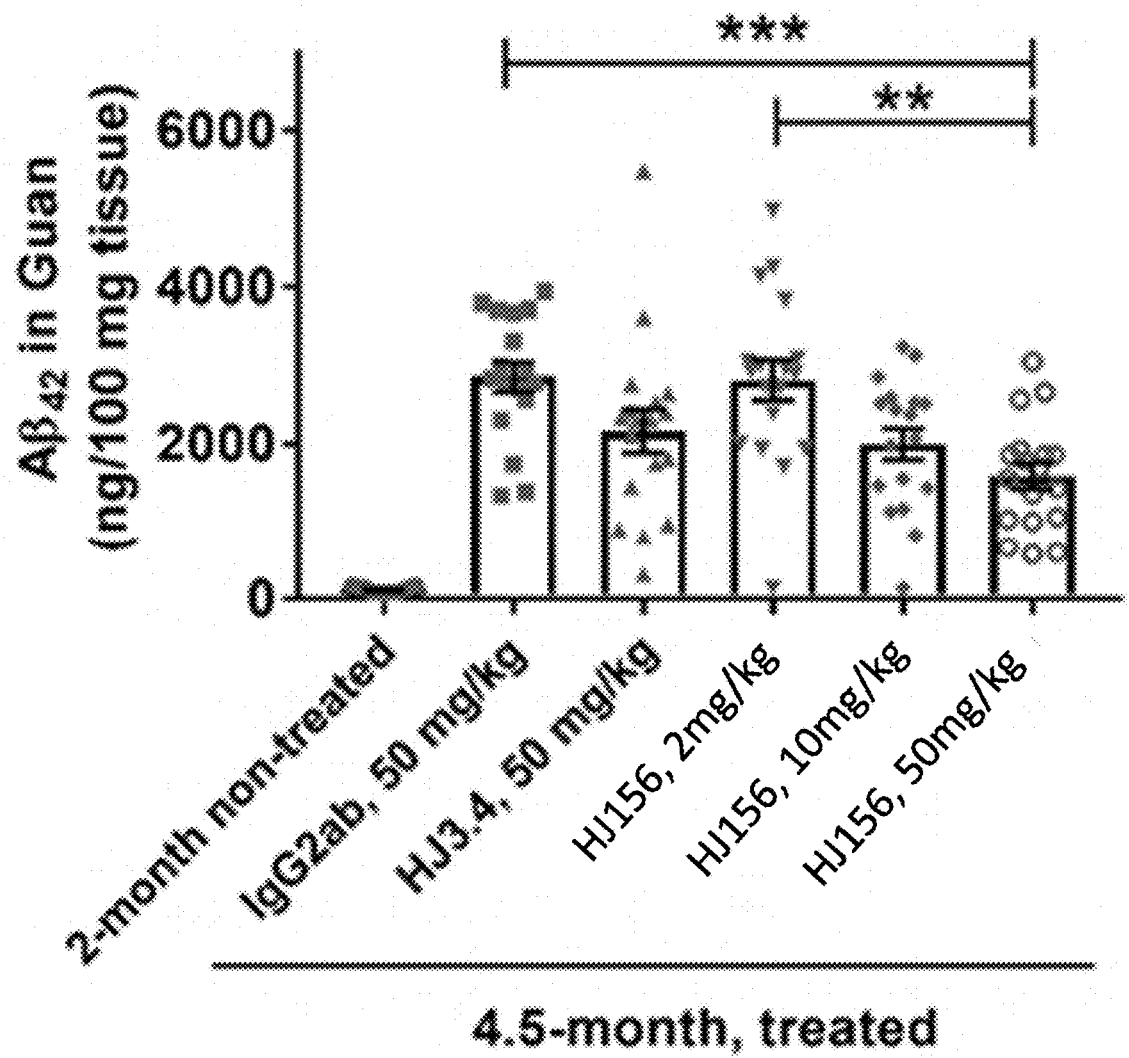

FIG. 42A-B graphically shows the results of a chronic dose-range efficacy study. Two-month-old APPPS1-21/APOE4 mice were IP injected with a weekly dose of IgG2ab (50 mg/kg), anti-Aβ HJ3.4 (50 mg/kg) or HJ156 (2, 10 and 50 mg/kg) for 12 doses (n=17-18/group, mixed gender). A group of 2 months old animals (n=12) were harvested to determine the baseline level of A. At the age of 4.5 months (3 days after the last dose), the mice were perfused with ice-cold PBS containing 0.3% heparin. The cerebral cortices were sequentially homogenized with cold PBS and 5 M guanidine buffer in the presence of 1× protease inhibitor mixture. (A) Aβ40 and (B) Aβ42 in the guanidine fraction were determined by ELISA. One-way ANOVA followed by Tukey post-test was performed to compare different groups. Data were expressed as mean±SEM. *p<0.05, p<0.01, *p<0.001.

Figure 43B:
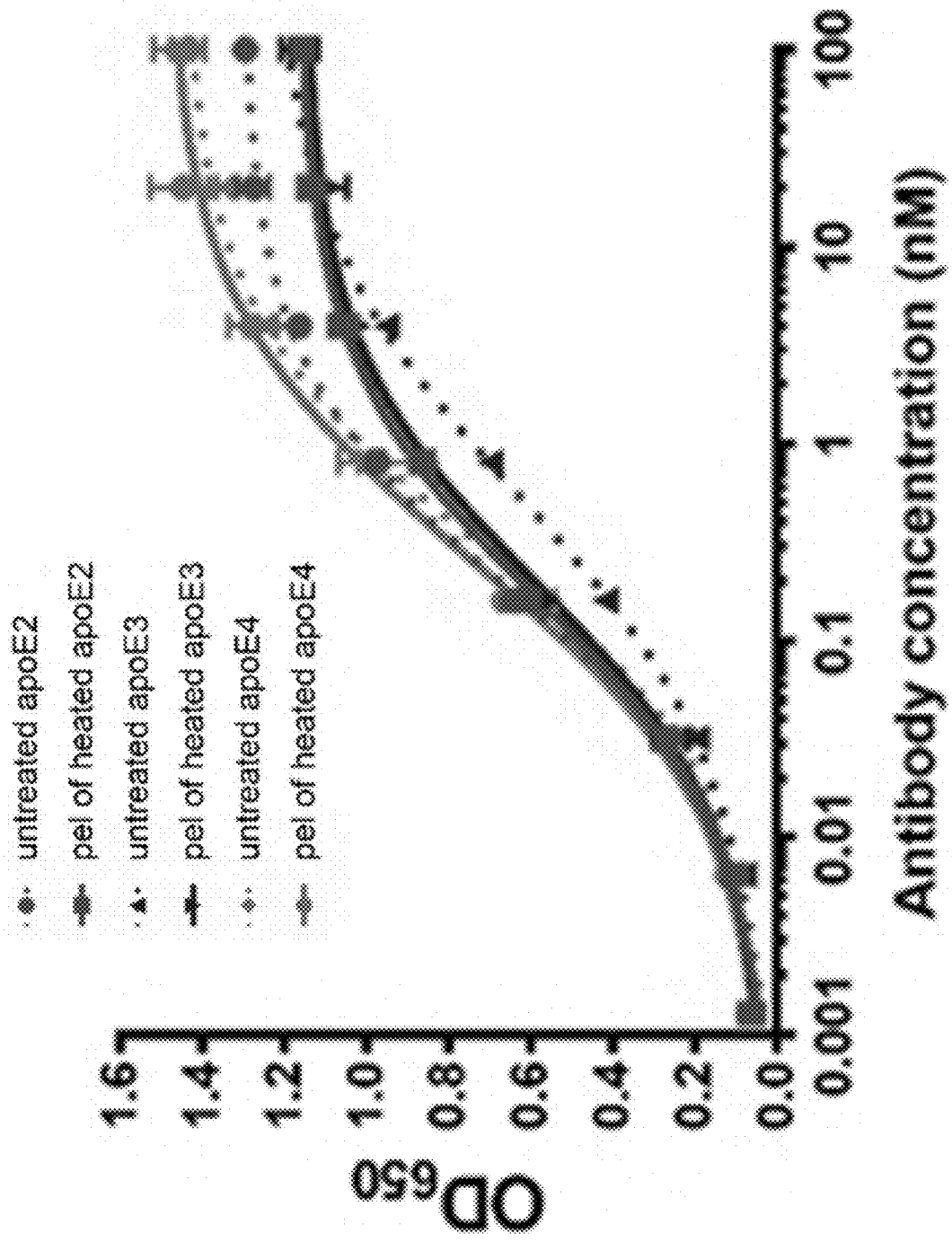
Figure 43C:
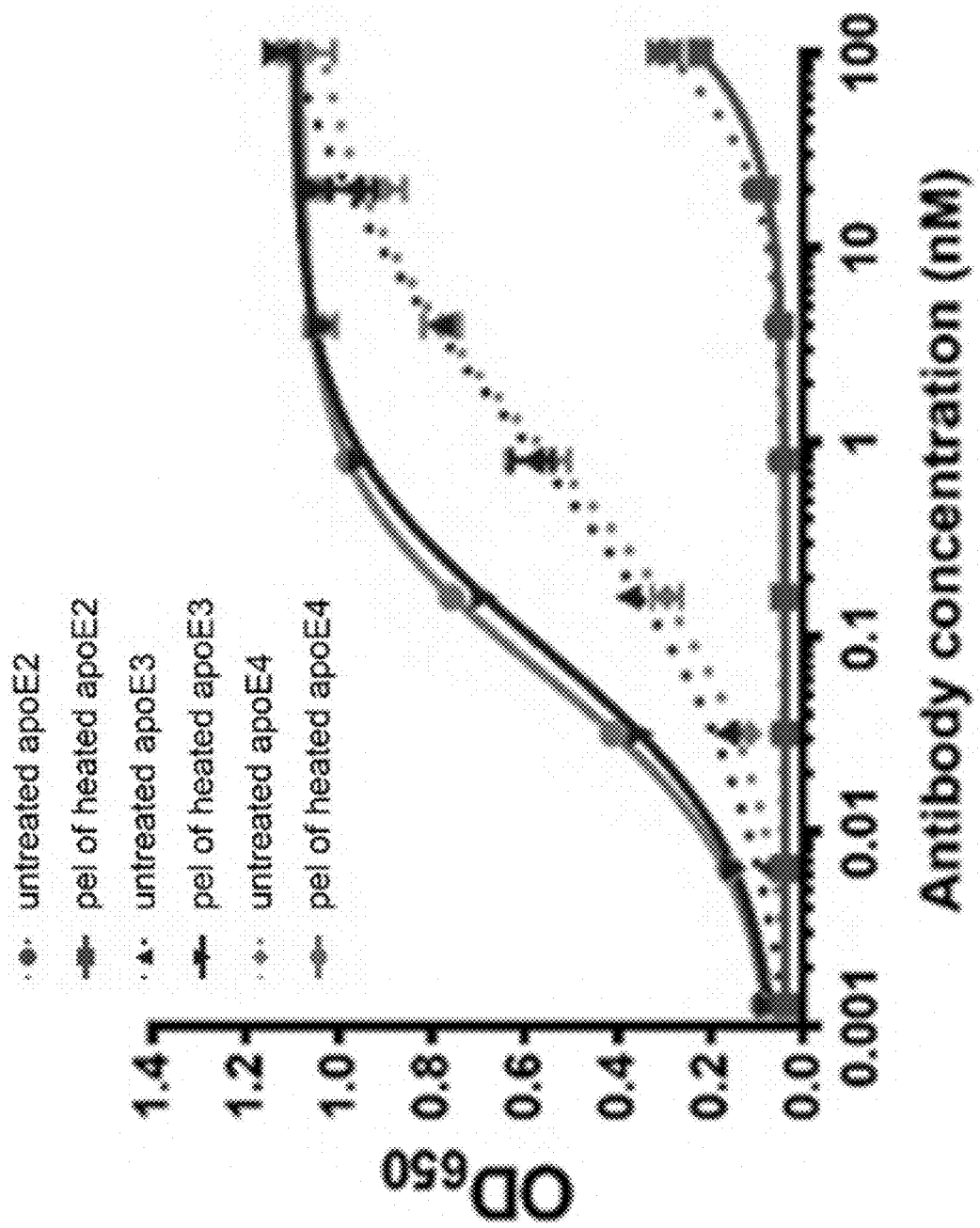

FIG. 43A-C graphically shows the binding of (A) HJ151, (B) HJ154, and (C) HJ156 antibodies to untreated recombinant and heat-induced aggregates of ApoE2, ApoE3, and ApoE4. The aggregated ApoE was induced by incubating ApoE at 1 mg/ml concentration at 40° C. for 24 hours. The aggregates then were recovered in the pellet fraction following ultracentrifugation at 186,000 g for 1 hour. For ELISA, the untreated ApoE or heat-induced aggregates of ApoE were coated directly to ELISA plates at 0.5 µg/ml overnight at 4° C. After three washes with PBS, the wells were blocked with 1% BSA-PBS for 1 hour at room temperature with shaking at 500 rpm. The blocked wells were washed once with PBS and subsequently loaded with antibodies at serial concentrations (starting at 100 nM with 5-fold dilutions thereafter). Bound antibodies were detected with HRP-labeled goat anti-mouse IgG (Jackson Immunoresearch) and visualized with TMB substrate at $OD_{650}$ (reaction stopped with BioFX stop solution). The results show that HJ151 only detected ApoE4 and had some preference for heat-treated ApoE4, HJ154 detected all three isoforms of ApoE and had no preference for conformation, and HJ156 detected both ApoE3 and ApoE4 and preferred heat treated ApoE.

DETAILED DESCRIPTION

Applicants have discovered anti-ApoE antibodies and methods of using the anti-ApoE antibodies to treat Aβ amyloidosis. The method comprises effectively administering to a living subject a therapeutically effective amount of an anti-ApoE antibody that (a) binds to human ApoE4 with a KD between about 0.1 pM to about 10 µM, or between about 0.1 pM to about 1 µM, (b) preferentially binds recombinant alipidated human ApoE4 as compared to ApoE4 derived from human plasma or human ApoE4 derived from plasma of a transgenic mouse expressing human ApoE4, and (c) binds to human ApoE in amyloid plaque in unfixed brain tissue. The present invention encompasses the discovery that anti-ApoE antibodies with these characteristics provide a treatment for subjects with Aβ amyloidosis including, but not limited to, subjects diagnosed with a disease characterized by brain Aβ plaques, subjects diagnosed with a disease characterized by vascular Aβ plaques in the brain, subjects diagnosed with Aβ plaque-associated symptoms, subjects diagnosed with CAA-associated symptoms, subjects with clinical signs of Aβ amyloidosis that may or may not have Aβ plaque associated symptoms and/or CAA associated symptoms, subjects diagnosed with Alzheimer's disease, and subjects diagnosed with CAA (collectively referred to, herein, as "subjects in need of treatment"). Methods for identifying clinical signs of Aβ amyloidosis in asymptomatic patients are known in the art and discussed below.

I. Definitions

The term "subject" refers to a human, or to a non-human animal expressing human ApoE.

The terms "treat," "treating," or "treatment" as used herein, refer to both therapeutic treatment and prophylactic or preventative measures, wherein the object is to prevent or slow down (lessen) an undesired physiological change or disease/disorder. Beneficial or desired clinical results include, but are not limited to, alleviation of symptoms, diminishment of extent of disease, stabilized (i.e., not worsening) state of disease, a delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the disease, condition, or disorder as well as those prone to have the disease, condition or disorder or those in which the disease, condition or disorder is to be prevented.

The term "Aβ" refers to peptides derived from a region in the carboxy terminus of a larger protein called amyloid precursor protein (APP). The gene encoding APP is located on chromosome 21. There are many forms of Aβ that may have toxic effects: Aβ peptides are typically 37-43 amino acid sequences long, though they can have truncations and modifications changing their overall size. They can be found in soluble and insoluble compartments, in monomeric, oligomeric and aggregated forms, intracellularly or extracellularly, and may be complexed with other proteins or molecules. The adverse or toxic effects of Aβ may be attributable to any or all of the above noted forms, as well as to others not described specifically. For example, two such Aβ isoforms include Aβ40 and Aβ42; with the Aβ42 isoform being particularly fibrillogenic or insoluble and associated with disease states.

"Aβ amyloidosis" is clinically defined as evidence of Aβ deposition in the brain or blood vessels of the brain, typically in the form of amyloid plaques or CAA. Diseases associated with Aβ amyloidosis include, but are not limited to, preclinical Alzheimer's disease, Alzheimer's disease (AD), cerebral amyloid angiopathy (CAA), Lewy body dementia, and inclusion body myositis. An "increased risk of developing a disease associated with Aβ amyloidosis" refers to a risk that is elevated over the expected risk given the subject's age, family history, genetic status and other known risk factors.

A "clinical sign of Aβ amyloidosis" refers to a measure of Aβ deposition known in the art. Clinical signs of Aβ amyloidosis may include, but are not limited to, Aβ deposition identified by amyloid imaging (e.g. PiB PET, fluorbetapir, or other imaging methods known in the art) or by decreased cerebrospinal fluid (CSF) Aβ42 or Aβ42/40 ratio. See, for example, Klunk W E et al. *Ann Neurol* 55(3) 2004, and Fagan A M et al. *Ann Neurol* 59(3) 2006, each hereby incorporated by reference in its entirety. Clinical signs of Aβ amyloidosis may also include measurements of the metabolism of Aβ, in particular measurements of Aβ42 metabolism alone or in comparison to measurements of the metabolism of other Aβ variants (e.g. Aβ37, Aβ38, Aβ39, Aβ40, and/or total Aβ), as described in U.S. patent Ser. Nos. 14/366,831, 14/523,148 and 14/747,453, each hereby incorporated by reference in its entirety. Additional methods are described in Albert et al. *Alzheimer's & Dementia* 2007 Vol. 7, pp. 170-179; McKhann et al., *Alzheimer's & Dementia* 2007 Vol. 7, pp. 263-269; and Sperling et al. *Alzheimer's & Dementia* 2007 Vol. 7, pp. 280-292, each hereby incorporated by reference in its entirety. Importantly, a subject with clinical signs of Aβ amyloidosis may or may not have symptoms associated with Aβ deposition. Yet subjects with clinical signs of Aβ amyloidosis are at an increased risk of developing a disease associated with Aβ amyloidosis.

An "Aβ plaque associated symptom" or a "CAA associated symptom" refers to any symptom caused by or associated with the formation of amyloid plaques or CAA, respectively, being composed of regularly ordered fibrillar aggregates called amyloid fibrils. Exemplary Aβ plaque associated symptoms may include, but are not limited to, neuronal degeneration, impaired cognitive function, impaired memory, altered behavior, emotional dysregulation, seizures, impaired nervous system structure or function, and an increased risk of development or worsening of Alzheimer's disease or CAA. Neuronal degeneration may include a change in structure of a neuron (including molecular changes such as intracellular accumulation of toxic proteins, protein aggregates, etc. and macro level changes such as change in shape or length of axons or dendrites, change in myelin sheath composition, loss of myelin sheath, etc.), a change in function of a neuron, a loss of function of a neuron, death of a neuron, or any combination thereof. Impaired cognitive function may include but is not limited to difficulties with memory, attention, concentration, language, abstract thought, creativity, executive function, planning, and organization. Altered behavior may include, but is not limited to, physical or verbal aggression, impulsivity, decreased inhibition, apathy, decreased initiation, changes in personality, abuse of alcohol, tobacco or drugs, and other addiction-related behaviors. Emotional dysregulation may include, but is not limited to, depression, anxiety, mania, irritability, and emotional incontinence. Seizures may include but are not limited to generalized tonic-clonic seizures, complex partial seizures, and non-epileptic, psychogenic seizures. Impaired nervous system structure or function may include, but is not limited to, hydrocephalus, Parkinsonism, sleep disorders, psychosis, impairment of balance and coordination. This may include motor impairments such as monoparesis, hemiparesis, tetraparesis, ataxia, ballismus and tremor. This also may include sensory loss or dysfunction including olfactory, tactile, gustatory, visual and auditory sensation. Furthermore, this may include autonomic nervous system impairments such as bowel and bladder dysfunction, sexual dysfunction, blood pressure and temperature dysregulation. Finally, this may include hormonal impairments attributable to dysfunction of the hypothalamus and pituitary gland such as deficiencies and dysregulation of growth hormone, thyroid stimulating hormone, lutenizing hormone, follicle stimulating hormone, gonadotropin releasing hormone, prolactin, and numerous other hormones and modulators.

"ApoE" (NP_000032.1, UniProtKB Identifier P02649) is an apolipoprotein expressed from the APOE gene mapped to chromosome 19 (for example, the nucleotide sequence identified as GenBank Accession Number NM_000041, or NCBI Reference Sequence: NC_000019.10), with three major polymorphic forms: ApoE2 (Cys112, Cys158), ApoE3 (Cys112, Arg158), and ApoE4 (Arg112, Arg158). Unless expressly stated otherwise, "ApoE" refers to "human ApoE," and includes functional fragments. "Recombinant ApoE" refers to ApoE encoded by a nucleic acid that has been introduced into a system (e.g. a prokaryotic cell, a eukaryotic cell, or a cell-free expression system) that supports expression of the nucleic acid and its translation into a protein. Methods for producing recombinant proteins are well-known in the art, and the production of recombinant ApoE disclosed herein is not limited to a particular system. Those of skill in the art will, however, appreciate that the choice of system can influence how "free from lipid" ApoE will be when recombinantly produced. As used herein, the term "alipidated ApoE" refers to ApoE recombinantly produced in a prokaryotic cell.

The term "antibody," as used herein, is used in the broadest sense and encompasses various antibody and antibody-like structures, including but not limited to full-length monoclonal, polyclonal, and multispecific (e.g., bispecific, trispecific, etc.) antibodies, as well as heavy chain antibodies and antibody fragments provided they exhibit the desired antigen-binding activity. The domain(s) of an antibody that is involved in binding an antigen is referred to as a "variable region" or "variable domain," and is described in further detail below. A single variable domain may be sufficient to confer antigen-binding specificity. Preferably, but not necessarily, antibodies useful in the discovery are produced recombinantly. Antibodies may or may not be glycosylated, though glycosylated antibodies may be preferred. An "isolated" antibody is one which has been separated from a component of its natural environment. In some embodiments, an antibody is purified to greater than 95% or 99% purity as determined by methods known in the art.

In addition to antibodies described herein, it may be possible to design an antibody mimetic or an aptamer using methods known in the art that functions substantially the same as an antibody of the invention. An "antibody mimetic" refers to a polypeptide or a protein that can specifically bind to an antigen but is not structurally related to an antibody. Antibody mimetics have a mass of about 3 kDa to about 20 kDa. Non-limiting examples of antibody mimetics are affibody molecules, affilins, affimers, alphabodies, anticalins, avimers, DARPins, and monobodies. Aptamers are a class of small nucleic acid ligands that are composed of RNA or single-stranded DNA oligonucleotides and have high specificity and affinity for their targets. Aptamers interact with and bind to their targets through structural recognition, a process similar to that of an antigen-antibody reaction. Aptamers have a lower molecular weight than antibodies, typically about 8-25 kDa.

The terms "full length antibody" and "intact antibody" may be used interchangeably, and refer to an antibody having a structure substantially similar to a native antibody structure or having heavy chains that contain an Fc region as defined herein. The basic structural unit of a native antibody comprises a tetramer. Each tetramer is composed of two identical pairs of polypeptide chains, each pair having one "light" chain (about 25 kDa) and one "heavy" chain (about 50-70 kDa). Light chains are classified as gamma, mu, alpha, and lambda. Heavy chains are classified as gamma, mu, alpha, delta, or epsilon, and define the antibody's isotype as IgG, IgM, IgA, IgD and IgE, respectively. The amino-terminal portion of each light and heavy chain includes a variable region of about 100 to 110 or more amino acid sequences primarily responsible for antigen recognition (VL and VH, respectively). The carboxy-terminal portion of each chain defines a constant region primarily responsible for effector function. Within light and heavy chains, the variable and constant regions are joined by a "J" region of about 12 or more amino acid sequences, with the heavy chain also including a "D" region of about 10 more amino acid sequences. Intact antibodies are properly cross-linked via disulfide bonds, as is known in the art.

The variable domains of the heavy chain and light chain of an antibody generally have similar structures, with each domain comprising four conserved framework regions (FRs) and three hypervariable regions (HVRs). (See, e.g., Kindt et al. *Kuby Immunology*, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

"Framework region" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence: FR1-HVR1-FR2-HVR2-FR3-HVR3-FR4. The FR domains of a heavy chain and a light chain may differ, as is known in the art.

The term "hypervariable region" or "HVR" as used herein refers to each of the regions of a variable domain which are hypervariable in sequence (also commonly referred to as "complementarity determining regions" or "CDR") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). As used herein, "an HVR derived from a variable region" refers to an HVR that has no more than two amino acid substitutions, as compared to the corresponding HVR from the original variable region. Exemplary HVRs herein include: (a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987)); (b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, MD (1991)); (c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), as defined below for various antibodies of this disclosure. Unless otherwise indicated, HVR residues and other residues in the variable domain (e.g., FR residues) are numbered herein according to Kabat et al., supra.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

A "variant Fc region" comprises an amino acid sequence that can differ from that of a native Fc region by virtue of one or more amino acid substitution(s) and/or by virtue of a modified glycosylation pattern, as compared to a native Fc region or to the Fc region of a parent polypeptide. In an example, a variant Fc region can have from about one to about ten amino acid substitutions, or from about one to about five amino acid substitutions in a native sequence Fc region or in the Fc region of the parent polypeptide. The variant Fc region herein may possess at least about 80% homology, at least about 90% homology, or at least about 95% homology with a native sequence Fc region and/or with an Fc region of a parent polypeptide.

An "antibody fragment" refers to a molecule other than an intact antibody that comprises a portion of an intact antibody that binds the antigen to which the intact antibody binds. Non-limiting examples of antibody fragments include but are not limited to Fv, Fab, Fab', Fab'-SH, F(ab')$_2$; single-chain forms of antibodies and higher order variants thereof; single-domain antibodies, and multispecific antibodies formed from antibody fragments.

Single-chain forms of antibodies, and their higher order forms, may include, but are not limited to, single-domain antibodies, single chain variant fragments (scFvs), divalent scFvs (di-scFvs), trivalent scFvs (tri-scFvs), tetravalent scFvs (tetra-scFvs), diabodies, and triabodies and tetrabodies. ScFv's are comprised of heavy and light chain variable regions connected by a linker. In most instances, but not all, the linker may be a peptide. A linker peptide is preferably from about 5 to 30 amino acids in length, or from about 10 to 25 amino acids in length. Typically, the linker allows for stabilization of the variable domains without interfering with the proper folding and creation of an active binding site. In preferred embodiments, a linker peptide is rich in glycine, as well as serine or threonine. ScFvs can be used to facilitate phage display or can be used for flow cytometry, immunohistochemistry, or as targeting domains. Methods of making and using scFvs are known in the art. ScFvs may also be conjugated to a human constant domain (e.g. a heavy constant domain is derived from an IgG domain, such as IgG1, IgG2, IgG3, or IgG4, or a heavy chain constant domain derived from IgA, IgM, or IgE). Diabodies, triabodies, and tetrabodies and higher order variants are typically created by varying the length of the linker peptide from zero to several amino acids. Alternatively, it is also well known in the art that multivalent binding antibody variants can be generated using self-assembling units linked to the variable domain.

A "single-domain antibody" refers to an antibody fragment consisting of a single, monomeric variable antibody domain.

Multispecific antibodies include bi-specific antibodies, tri-specific, or antibodies of four or more specificities. Multispecific antibodies may be created by combining the heavy and light chains of one antibody with the heavy and light chains of one or more other antibodies. These chains can be covalently linked.

"Monoclonal antibody" refers to an antibody that is derived from a single copy or clone, including e.g., any eukaryotic, prokaryotic, or phage clone. "Monoclonal antibody" is not limited to antibodies produced through hybridoma technology. Monoclonal antibodies can be produced using hybridoma techniques well known in the art, as well as recombinant technologies, phage display technologies, synthetic technologies or combinations of such technologies and other technologies readily known in the art. Furthermore, the monoclonal antibody may be labeled with a detectable label, immobilized on a solid phase and/or conjugated with a heterologous compound (e.g., an enzyme or toxin) according to methods known in the art.

A "heavy chain antibody" refers to an antibody that consists of two heavy chains. A heavy chain antibody may be an IgG-like antibody from camels, llamas, alpacas, sharks, etc., or an IgNAR from a cartilaginous fish.

A "humanized antibody" refers to a non-human antibody that has been modified to reduce the risk of the non-human antibody eliciting an immune response in humans following administration but retains similar binding specificity and affinity as the starting non-human antibody. A humanized antibody binds to the same or similar epitope as the non-human antibody. The term "humanized antibody" includes an antibody that is composed partially or fully of amino acid sequences derived from a human antibody germ line by altering the sequence of an antibody having non-human hypervariable regions ("HVR"). The simplest such alteration may consist simply of substituting the constant region of a human antibody for the murine constant region, thus resulting in a human/murine chimera which may have sufficiently low immunogenicity to be acceptable for pharmaceutical use. Preferably, the variable region of the antibody is also humanized by techniques that are by now well known in the art. For example, the framework regions of a variable region can be substituted by the corresponding human framework regions, while retaining one, several, or all six non-human HVRs. Some framework residues can be substituted with corresponding residues from a non-human VL domain or VH domain (e.g., the non-human antibody from which the HVR residues are derived), e.g., to restore or improve specificity or affinity of the humanized antibody. Substantially human framework regions have at least about 75% homology with a known human framework sequence (i.e. at least about 75%, at least about 80%, at least about 85%, at least about 90%, at least about 95%, or at least about 99% sequence identity). HVRs may also be randomly mutated such that binding activity and affinity for the antigen is maintained or enhanced in the context of fully human germline framework regions or framework regions that are substantially human. As mentioned above, it is sufficient for use in the methods of this discovery to employ an antibody fragment. Further, as used herein, the term "humanized antibody" refers to an antibody comprising a substantially human framework region, at least one HVR from a nonhuman antibody, and in which any constant region present is substantially human. Substantially human constant regions have at least about 90% with a known human constant sequence (i.e. about 90%, about 95%, or about 99% sequence identity). Hence, all parts of a humanized antibody, except possibly the HVRs, are substantially identical to corresponding pairs of one or more germline human immunoglobulin sequences.

If desired, the design of humanized immunoglobulins may be carried out as follows, or using similar methods familiar to those with skill in the art (for example, see Almagro, et al. Front. Biosci. 2008, 13(5):1619-33). A murine antibody variable region is aligned to the most similar human germ line sequences (e.g. by using BLAST or similar algorithm). The CDR residues from the murine antibody sequence are grafted into the similar human "acceptor" germline. Subsequently, one or more positions near the CDRs or within the framework (e.g., Vernier positions) may be reverted to the original murine amino acid in order to achieve a humanized antibody with similar binding affinity to the original murine antibody. Typically, several versions of humanized antibodies with different reversion mutations are generated and empirically tested for activity. The humanized antibody variant with properties most similar to the parent murine antibody and the fewest murine framework reversions is selected as the final humanized antibody candidate.

II. Anti-ApoE Antibody

Anti-ApoE antibodies disclosed herein can be described or specified in terms of the epitope(s) that they recognize or bind. The portion of a target polypeptide that specifically interacts with the antigen binding domain of an antibody is an "epitope." ApoE can comprise any number of epitopes, depending on the source of the protein (e.g. mouse, rat, cynomolgus monkey, human, etc.), isoform (e.g. ApoE2, ApoE3, ApoE4), conformational state of the isoform (e.g. fibrillar, aggregated, insoluble, soluble, monomeric, oligomeric, oxidized, post-translationally modified, etc.) and location of the isoform (e.g. intracellular, extracellular, complexed with other proteins or molecules in particle, in amyloid plaque, etc.). Furthermore, it should be noted that an "epitope" on ApoE can be a linear epitope or a conformational epitope, and in both instances can include non-polypeptide elements, e.g., an epitope can include a carbohydrate or lipid side chain. The term "affinity" refers to a measure of the strength of the binding of an individual epitope with an antibody's antigen binding site.

An "anti-ApoE antibody," as used herein, refers to an isolated antibody that binds to recombinant human ApoE4 or ApoE4 isolated from human brain with an affinity constant or affinity of interaction (KD) between about 0.1 pM to about 10 µM, preferably about 0.1 pM to about 1 µM, more preferably about 0.1 pM to about 100 nM. Methods for determining the affinity of an antibody for an antigen are known in the art, and further illustrated in the Examples. Anti-ApoE antibodies useful herein include those which are suitable for administration to a subject in a therapeutic amount.

Anti-ApoE antibodies disclosed herein can also be described or specified in terms of their cross-reactivity. The term "cross-reactivity" refers to the ability of an antibody, specific for one antigen, to react with a second antigen; a measure of relatedness between two different antigenic substances. Thus, an antibody is cross-reactive if it binds to an epitope other than the one that induced its formation. The cross-reactive epitope generally contains many of the same complementary structural features as the inducing epitope, and in some cases, can actually fit better than the original. For example, certain antibodies have some degree of cross-reactivity, in that they bind related, but non-identical epitopes, e.g., epitopes with at least about 85%, at least about 90%, or at least about 95% identity (as calculated using methods known in the art) to a reference epitope. An antibody can be said to have little or no cross-reactivity if it does not bind epitopes with less than about 95%, less than about 90%, or less than about 85% identity to a reference epitope. An antibody can be deemed "highly specific" for a certain epitope, if it does not bind any other analog, ortholog, or homolog of that epitope.

The epitope(s) to which anti-ApoE antibodies of this disclosure bind may be unique to ApoE4, may be common to ApoE4 and another ApoE isoform (e.g. ApoE2 and/or ApoE3), or may be an ApoE4 epitope that is related, but not identical, to an epitope in another isoform. In some embodiments, an anti-ApoE antibody does not preferentially bind to ApoE2, ApoE3, or ApoE4. In other embodiments, an anti-ApoE antibody preferentially binds to ApoE4, or preferentially binds to ApoE3 and ApoE4. An antibody that preferentially binds to an ApoE isoform binds to that isoform more readily than it would a different ApoE isoform. By "preferentially binds," it is meant that the antibody specifically binds to an epitope of a first antigen more readily than it would bind to another epitope of the first antigen or another epitope of a second antigen. In an example, an antibody can be considered to bind a first epitope preferentially if it binds the first epitope with an off rate (k(off)) that is less than the antibody's k(off) for the second epitope. In another example, an antibody can be considered to bind a first epitope preferentially if it binds said first epitope with a dissociation constant (KD) that is less than the antibody's KD for the second epitope. In another example an antibody can be considered to bind an ApoE isoform preferentially if the binding half maximal concentration ($EC_{50}$) of the antibody for that isoform is at least about 10-fold, 50-fold, or 100-fold less than $EC_{50}$ for the other isoforms as measured in an ELISA or similar assay. Alternatively, an antibody can be described as not preferentially binding ApoE2, ApoE3, or ApoE4 if the $EC_{50}$ for the antibody for each of the isoforms varies by less than 10-fold.

Another aspect of isolated, anti-ApoE antibodies of this disclosure is that they bind to human ApoE in amyloid plaque in unfixed brain tissue. "Unfixed brain tissue" refers to brain tissue that is not fixed with paraformaldehyde or other fixatives. An anti-ApoE antibody is described as "binding to human ApoE in amyloid plaques in unfixed brain tissue" when the staining pattern is consistent with binding to either Aβ in parenchymal brain amyloid plaques or Aβ in deposits around blood vessels in the brain in the form of CAA.

Another aspect of isolated, anti-ApoE antibodies of this disclosure is that they preferentially bind recombinant alipidated human ApoE4 as compared to ApoE4 derived from human plasma or human ApoE4 derived from plasma of a transgenic mouse expressing human ApoE4. Briefly, this can be measured by (a) coating recombinant alipidated human ApoE4 on an ELISA plate, (b) incubating an anti-ApoE antibody in the presence of varying dilutions of human plasma or plasma from a transgenic mouse expressing human ApoE4 (e.g., 20-fold to 1000-fold dilutions of plasma comprising about 1-5 μM ApoE) to produce a pre-incubated antibody-plasma mixture for each dilution, (c) adding the a pre-incubated antibody-plasma mixtures to the ELISA plate from (a) and allowing the mixtures to equilibrate with the coated recombinant alipidated ApoE4 on the plate, and (d) measuring binding of the anti-ApoE antibody in the mixtures to the recombinant alipidated ApoE4 coated on the plate. An antibody that preferentially binds recombinant alipidated ApoE4 will demonstrate similar binding to the plate at plasma dilutions between about 1000-fold up to about 20-fold (i.e., loss of binding signal no greater than 20%, or preferably no greater than 10%). Further details are provided in Example 13. In certain embodiments, an isolated, anti-ApoE antibody does not specifically bind to ApoE derived from plasma. Clearance (CL) is a pharmacokinetic parameter that describes the efficiency of irreversible elimination of a drug from systemic circulation, expressed as volume of blood/plasma/serum cleared of drug per unit time. An anti-ApoE antibody does not specifically bind to ApoE derived from plasma, for example, when it is administered to an animal expressing human ApoE and the clearance value of the antibody is less than 25 times that of an isotype control antibody (the amounts administered to the animal being similar for both antibodies). For example, see FIG. 37F and Example 19.

Another aspect of isolated, anti-ApoE antibodies of this disclosure is that they may or may not have a variant Fc region. For example, an Fc region can be modified to have increased or decreased affinity for an Fc receptor on a microglial cell and/or an altered glycosylation pattern.

Other aspects of anti-ApoE antibodies of this disclosure are described more thoroughly below.

(a) Anti-ApoE Antibodies that Preferentially Bind to ApoE3 and ApoE4: Group I

In another aspect, an anti-ApoE antibody has a heavy chain variable region comprising SEQ ID NO: 94. In some embodiments, the heavy chain variable region further comprises SEQ ID NO: 90 and/or SEQ ID NO: 92. In other embodiments, the heavy chain variable region further comprises SEQ ID NO: 91 and/or SEQ ID NO: 93. In certain of the above embodiments, the antibody has a light chain variable region comprising SEQ ID NO: 88 or SEQ ID NO: 89. The light chain variable region can further comprise (a) SEQ ID NO: 86 or SEQ ID NO: 87; and/or (b) SEQ ID NO: 30.

In another aspect, an anti-ApoE antibody has a heavy chain variable region comprising SEQ ID NO: 95. In some embodiments, the heavy chain variable region further comprises SEQ ID NO: 90 and/or SEQ ID NO: 92. In other embodiments, the heavy chain variable region further comprises SEQ ID NO: 91 and/or SEQ ID NO: 93. In certain of the above embodiments, the antibody has a light chain variable region comprising SEQ ID NO: 88 or SEQ ID NO: 89. The light chain variable region can further comprise (a) SEQ ID NO: 86 or SEQ ID NO: 87; and/or (b) SEQ ID NO: 30.

In another aspect, an anti-ApoE antibody is selected from Table A.

TABLE A

| | Group I antibodies | | | | | |
|---|---|---|---|---|---|---|
| | Light Chain HVR | | | Heavy Chain HVR | | |
| Antibody | L1 | L2 | L3 | H1 | H2 | H3 |
| 1 | SEQ ID NO: 86 | | | | | |
| 2 | SEQ ID NO: 86 | SEQ ID NO: 30 | | | | |
| 3 | SEQ ID NO: 86 | SEQ ID NO: 30 | SEQ ID NO: 88 | | | |
| 4 | | SEQ ID NO: 30 | | | | |
| 5 | | SEQ ID NO: 30 | SEQ ID NO: 88 | | | |
| 6 | | | SEQ ID NO: 88 | | | |
| 7 | SEQ ID NO: 86 | | SEQ ID NO: 88 | | | |
| 8 | | | | SEQ ID NO: 90 | | |
| 9 | | | | SEQ ID NO: 90 | SEQ ID NO: 92 | |
| 10 | | | | SEQ ID NO: 90 | SEQ ID NO: 92 | SEQ ID NO: 94 |
| 11 | | | | | SEQ ID NO: 92 | |
| 12 | | | | | SEQ ID NO: 92 | SEQ ID NO: 94 |
| 13 | | | | | | SEQ ID NO: 94 |
| 14 | | | | SEQ ID NO: 90 | | SEQ ID NO: 94 |
| 15 | SEQ ID NO: 86 | | | SEQ ID NO: 90 | | |
| 16 | SEQ ID NO: 86 | | | SEQ ID NO: 90 | SEQ ID NO: 92 | |
| 17 | SEQ ID NO: 86 | | | SEQ ID NO: 90 | SEQ ID NO: 92 | SEQ ID NO: 94 |
| 18 | SEQ ID NO: 86 | | | | SEQ ID NO: 92 | |
| 19 | SEQ ID NO: 86 | | | | SEQ ID NO: 92 | SEQ ID NO: 94 |
| 20 | SEQ ID NO: 86 | | | | | SEQ ID NO: 94 |
| 21 | SEQ ID NO: 86 | | | SEQ ID NO: 90 | | SEQ ID NO: 94 |
| 22 | SEQ ID NO: 86 | SEQ ID NO: 30 | | SEQ ID NO: 90 | | |

TABLE A-continued

| | Group I antibodies | | | | | |
|---|---|---|---|---|---|---|
| | Light Chain HVR | | | Heavy Chain HVR | | |
| Antibody | L1 | L2 | L3 | H1 | H2 | H3 |
| 23 | SEQ ID NO: 86 | SEQ ID NO: 30 | | SEQ ID NO: 90 | SEQ ID NO: 92 | |
| 24 | SEQ ID NO: 86 | SEQ ID NO: 30 | | SEQ ID NO: 90 | SEQ ID NO: 92 | SEQ ID NO: 94 |
| 25 | SEQ ID NO: 86 | SEQ ID NO: 30 | | | SEQ ID NO: 92 | |
| 26 | SEQ ID NO: 86 | SEQ ID NO: 30 | | | SEQ ID NO: 92 | SEQ ID NO: 94 |
| 27 | SEQ ID NO: 86 | SEQ ID NO: 30 | | | | SEQ ID NO: 94 |
| 28 | SEQ ID NO: 86 | SEQ ID NO: 30 | | SEQ ID NO: 90 | | SEQ ID NO: 94 |
| 29 | SEQ ID NO: 86 | SEQ ID NO: 30 | SEQ ID NO: 88 | SEQ ID NO: 90 | | |
| 30 | SEQ ID NO: 86 | SEQ ID NO: 30 | SEQ ID NO: 88 | SEQ ID NO: 90 | SEQ ID NO: 92 | |
| 31 | SEQ ID NO: 86 | SEQ ID NO: 30 | SEQ ID NO: 88 | SEQ ID NO: 90 | SEQ ID NO: 92 | SEQ ID NO: 94 |
| 32 | SEQ ID NO: 86 | SEQ ID NO: 30 | SEQ ID NO: 88 | | SEQ ID NO: 92 | |
| 33 | SEQ ID NO: 86 | SEQ ID NO: 30 | SEQ ID NO: 88 | | SEQ ID NO: 92 | SEQ ID NO: 94 |
| 34 | SEQ ID NO: 86 | SEQ ID NO: 30 | SEQ ID NO: 88 | SEQ ID NO: 90 | | SEQ ID NO: 94 |
| 35 | SEQ ID NO: 86 | SEQ ID NO: 30 | SEQ ID NO: 88 | | | SEQ ID NO: 94 |
| 36 | | SEQ ID NO: 30 | | SEQ ID NO: 90 | | |
| 37 | | SEQ ID NO: 30 | | SEQ ID NO: 90 | SEQ ID NO: 92 | |
| 38 | | SEQ ID NO: 30 | | SEQ ID NO: 90 | SEQ ID NO: 92 | SEQ ID NO: 94 |
| 39 | | SEQ ID NO: 30 | | | SEQ ID NO: 92 | |
| 40 | | SEQ ID NO: 30 | | | SEQ ID NO: 92 | SEQ ID NO: 94 |
| 41 | | SEQ ID NO: 30 | | | | SEQ ID NO: 94 |
| 42 | | SEQ ID NO: 30 | | SEQ ID NO: 90 | | SEQ ID NO: 94 |
| 43 | | SEQ ID NO: 30 | SEQ ID NO: 88 | SEQ ID NO: 90 | | |
| 44 | | SEQ ID NO: 30 | SEQ ID NO: 88 | SEQ ID NO: 90 | SEQ ID NO: 92 | |
| 45 | | SEQ ID NO: 30 | SEQ ID NO: 88 | SEQ ID NO: 90 | SEQ ID NO: 92 | SEQ ID NO: 94 |
| 46 | | SEQ ID NO: 30 | SEQ ID NO: 88 | | SEQ ID NO: 92 | |
| 47 | | SEQ ID NO: 30 | SEQ ID NO: 88 | | SEQ ID NO: 92 | SEQ ID NO: 94 |
| 48 | | SEQ ID NO: 30 | SEQ ID NO: 88 | | | SEQ ID NO: 94 |
| 49 | | SEQ ID NO: 30 | SEQ ID NO: 88 | SEQ ID NO: 90 | | SEQ ID NO: 94 |
| 50 | | | SEQ ID NO: 88 | SEQ ID NO: 90 | | |
| 51 | | | SEQ ID NO: 88 | SEQ ID NO: 90 | SEQ ID NO: 92 | |
| 52 | | | SEQ ID NO: 88 | SEQ ID NO: 90 | SEQ ID NO: 92 | SEQ ID NO: 94 |
| 53 | | | SEQ ID NO: 88 | | SEQ ID NO: 92 | |
| 54 | | | SEQ ID NO: 88 | | SEQ ID NO: 92 | SEQ ID NO: 94 |
| 55 | | | SEQ ID NO: 88 | | | SEQ ID NO: 94 |
| 56 | | | SEQ ID NO: 88 | SEQ ID NO: 90 | | SEQ ID NO: 94 |
| 57 | SEQ ID NO: 86 | | SEQ ID NO: 88 | SEQ ID NO: 90 | | |
| 58 | SEQ ID NO: 86 | | SEQ ID NO: 88 | SEQ ID NO: 90 | SEQ ID NO: 92 | |
| 59 | SEQ ID NO: 86 | | SEQ ID NO: 88 | SEQ ID NO: 90 | SEQ ID NO: 92 | SEQ ID NO: 94 |
| 60 | SEQ ID NO: 86 | | SEQ ID NO: 88 | | SEQ ID NO: 92 | |
| 61 | SEQ ID NO: 86 | | SEQ ID NO: 88 | | SEQ ID NO: 92 | SEQ ID NO: 94 |
| 62 | SEQ ID NO: 86 | | SEQ ID NO: 88 | | | SEQ ID NO: 94 |
| 63 | SEQ ID NO: 86 | | SEQ ID NO: 88 | SEQ ID NO: 90 | | SEQ ID NO: 94 |
| 64 | SEQ ID NO: 87 | | | | | |
| 65 | SEQ ID NO: 87 | SEQ ID NO: 30 | | | | |
| 66 | SEQ ID NO: 87 | SEQ ID NO: 30 | SEQ ID NO: 89 | | | |
| 67 | | SEQ ID NO: 30 | | | | |
| 68 | | SEQ ID NO: 30 | SEQ ID NO: 89 | | | |
| 69 | | | SEQ ID NO: 89 | | | |
| 70 | SEQ ID NO: 87 | | SEQ ID NO: 89 | | | |
| 71 | | | | SEQ ID NO: 91 | | |
| 72 | | | | SEQ ID NO: 91 | SEQ ID NO: 93 | |
| 73 | | | | SEQ ID NO: 91 | SEQ ID NO: 93 | SEQ ID NO: 95 |
| 74 | | | | | SEQ ID NO: 93 | |
| 75 | | | | | SEQ ID NO: 93 | SEQ ID NO: 95 |
| 76 | | | | | | SEQ ID NO: 95 |
| 77 | | | | SEQ ID NO: 91 | | SEQ ID NO: 95 |
| 78 | SEQ ID NO: 87 | | | SEQ ID NO: 91 | | |
| 79 | SEQ ID NO: 87 | | | SEQ ID NO: 91 | SEQ ID NO: 93 | |
| 80 | SEQ ID NO: 87 | | | SEQ ID NO: 91 | SEQ ID NO: 93 | SEQ ID NO: 95 |
| 81 | SEQ ID NO: 87 | | | | SEQ ID NO: 93 | |
| 82 | SEQ ID NO: 87 | | | | SEQ ID NO: 93 | SEQ ID NO: 95 |
| 83 | SEQ ID NO: 87 | | | | | SEQ ID NO: 95 |
| 84 | SEQ ID NO: 87 | | | SEQ ID NO: 91 | | SEQ ID NO: 95 |
| 85 | SEQ ID NO: 87 | SEQ ID NO: 30 | | SEQ ID NO: 91 | | |
| 86 | SEQ ID NO: 87 | SEQ ID NO: 30 | | SEQ ID NO: 91 | SEQ ID NO: 93 | |
| 87 | SEQ ID NO: 87 | SEQ ID NO: 30 | | SEQ ID NO: 91 | SEQ ID NO: 93 | SEQ ID NO: 95 |
| 88 | SEQ ID NO: 87 | SEQ ID NO: 30 | | | SEQ ID NO: 93 | |
| 89 | SEQ ID NO: 87 | SEQ ID NO: 30 | | | SEQ ID NO: 93 | SEQ ID NO: 95 |
| 90 | SEQ ID NO: 87 | SEQ ID NO: 30 | | | | SEQ ID NO: 95 |
| 91 | SEQ ID NO: 87 | SEQ ID NO: 30 | | SEQ ID NO: 91 | | SEQ ID NO: 95 |
| 92 | SEQ ID NO: 87 | SEQ ID NO: 30 | SEQ ID NO: 89 | SEQ ID NO: 91 | | |
| 93 | SEQ ID NO: 87 | SEQ ID NO: 30 | SEQ ID NO: 89 | SEQ ID NO: 91 | SEQ ID NO: 93 | |
| 94 | SEQ ID NO: 87 | SEQ ID NO: 30 | SEQ ID NO: 89 | SEQ ID NO: 91 | SEQ ID NO: 93 | SEQ ID NO: 95 |
| 95 | SEQ ID NO: 87 | SEQ ID NO: 30 | SEQ ID NO: 89 | | SEQ ID NO: 93 | |
| 96 | SEQ ID NO: 87 | SEQ ID NO: 30 | SEQ ID NO: 89 | | SEQ ID NO: 93 | SEQ ID NO: 95 |

TABLE A-continued

Group I antibodies

| | Light Chain HVR | | | Heavy Chain HVR | | |
| --- | --- | --- | --- | --- | --- | --- |
| Antibody | L1 | L2 | L3 | H1 | H2 | H3 |
| 97 | SEQ ID NO: 87 | SEQ ID NO: 30 | SEQ ID NO: 89 | | | SEQ ID NO: 95 |
| 98 | SEQ ID NO: 87 | SEQ ID NO: 30 | SEQ ID NO: 89 | SEQ ID NO: 91 | | SEQ ID NO: 95 |
| 99 | | SEQ ID NO: 30 | | SEQ ID NO: 91 | | |
| 100 | | SEQ ID NO: 30 | | SEQ ID NO: 91 | SEQ ID NO: 93 | |
| 101 | | SEQ ID NO: 30 | | SEQ ID NO: 91 | SEQ ID NO: 93 | SEQ ID NO: 95 |
| 102 | | SEQ ID NO: 30 | | | SEQ ID NO: 93 | |
| 103 | | SEQ ID NO: 30 | | | SEQ ID NO: 93 | SEQ ID NO: 95 |
| 104 | | SEQ ID NO: 30 | | | | SEQ ID NO: 95 |
| 105 | | SEQ ID NO: 30 | | SEQ ID NO: 91 | | SEQ ID NO: 95 |
| 106 | | SEQ ID NO: 30 | SEQ ID NO: 89 | SEQ ID NO: 91 | | |
| 107 | | SEQ ID NO: 30 | SEQ ID NO: 89 | SEQ ID NO: 91 | SEQ ID NO: 93 | |
| 108 | | SEQ ID NO: 30 | SEQ ID NO: 89 | SEQ ID NO: 91 | SEQ ID NO: 93 | SEQ ID NO: 95 |
| 109 | | SEQ ID NO: 30 | SEQ ID NO: 89 | | SEQ ID NO: 93 | |
| 110 | | SEQ ID NO: 30 | SEQ ID NO: 89 | | SEQ ID NO: 93 | SEQ ID NO: 95 |
| 111 | | SEQ ID NO: 30 | SEQ ID NO: 89 | | | SEQ ID NO: 95 |
| 112 | | SEQ ID NO: 30 | SEQ ID NO: 89 | SEQ ID NO: 91 | | SEQ ID NO: 95 |
| 113 | | | SEQ ID NO: 89 | SEQ ID NO: 91 | | |
| 114 | | | SEQ ID NO: 89 | SEQ ID NO: 91 | SEQ ID NO: 93 | |
| 115 | | | SEQ ID NO: 89 | SEQ ID NO: 91 | SEQ ID NO: 93 | SEQ ID NO: 95 |
| 116 | | | SEQ ID NO: 89 | | SEQ ID NO: 93 | |
| 117 | | | SEQ ID NO: 89 | | SEQ ID NO: 93 | SEQ ID NO: 95 |
| 118 | | | SEQ ID NO: 89 | | | SEQ ID NO: 95 |
| 119 | | | SEQ ID NO: 89 | SEQ ID NO: 91 | | SEQ ID NO: 95 |
| 120 | SEQ ID NO: 87 | | SEQ ID NO: 89 | SEQ ID NO: 91 | | |
| 121 | SEQ ID NO: 87 | | SEQ ID NO: 89 | SEQ ID NO: 91 | SEQ ID NO: 93 | |
| 122 | SEQ ID NO: 87 | | SEQ ID NO: 89 | SEQ ID NO: 91 | SEQ ID NO: 93 | SEQ ID NO: 95 |
| 123 | SEQ ID NO: 87 | | SEQ ID NO: 89 | | SEQ ID NO: 93 | |
| 124 | SEQ ID NO: 87 | | SEQ ID NO: 89 | | SEQ ID NO: 93 | SEQ ID NO: 95 |
| 125 | SEQ ID NO: 87 | | SEQ ID NO: 89 | | | SEQ ID NO: 95 |
| 126 | SEQ ID NO: 87 | | SEQ ID NO: 89 | SEQ ID NO: 91 | | SEQ ID NO: 95 |

In an exemplary embodiment, an anti-ApoE antibody of this group comprises a VL that has one or more HVRs derived from SEQ ID NO: 3 or a VH that has one or more HVRs derived from SEQ ID NO: 4. The HVR derived from SEQ ID NO: 3 may be L1, L2, L3, or any combination thereof. In certain embodiments, the VL may comprise an L1 of SEQ ID NO: 29, an L2 of SEQ ID NO: 30, an L3 of SEQ ID NO: 31, or any combination thereof (e.g. antibodies 1-7 in Table B). The HVR derived from SEQ ID NO: 4 may be H1, H2, H3, or any combination thereof. In certain embodiments, the VH may comprise an H1 of SEQ ID NO: 32, an H2 of SEQ ID NO: 33, an H3 of SEQ ID NO: 34, or any combination thereof (e.g. antibodies 8-14 in Table B). The antibody comprising one or more HVRs derived from SEQ ID NO: 4 may further comprise a light chain variable region (VL) comprising one or more HVRs derived from SEQ ID NO: 3. The HVR may be L1, L2, L3, or any combination thereof. In a preferred embodiment, the VL may comprise an L1 of SEQ ID NO: 29, an L2 of SEQ ID NO: 30, an L3 of SEQ ID NO: 31, or any combination thereof (e.g. antibodies 15-63 in Table B). In various embodiments above, the antibody may be a humanized antibody, or the antibody may have a VL with 90, 91, 92, 93, 94, 95, 96, 97, 98, 99, or 100% identity to SEQ ID NO: 3 and/or a VH with 90, 91, 92, 93, 94, 95, 96, 97, 98, 99 or 100% identity to SEQ ID NO: 4. In each of the above embodiments, the anti-ApoE antibody may optionally comprise one or more constant regions, or a portion of a constant region, that is substantially human (i.e. at least 90%, 95%, or 99% sequence identity with a known human framework sequence). The present disclosure also encompasses the corresponding nucleic acid sequences of SEQ ID NO: 3, 4, 29, 30, 31, 32, 33, and 34, which can readily be determined by one of skill in the art, and may be incorporated into a vector or other large DNA molecule, such as a chromosome, in order to express an antibody of the disclosure.

In another exemplary embodiment, an anti-ApoE antibody of this group comprises a VL that has one or more HVRs derived from SEQ ID NO: 17 or a VH that has one or more HVRs derived from SEQ ID NO: 18. The HVR derived from SEQ ID NO: 17 may be L1, L2, L3, or any combination thereof. In certain embodiments, the VL may comprise an L1 of SEQ ID NO: 63, an L2 of SEQ ID NO: 30, an L3 of SEQ ID NO: 64, or any combination thereof (e.g. antibodies 64-70 in Table B). The HVR derived from SEQ ID NO: 18 may be H1, H2, H3, or any combination thereof. In certain embodiments, the VH may comprise an H1 of SEQ ID NO: 65, an H2 of SEQ ID NO: 66, an H3 of SEQ ID NO: 67, or any combination thereof (e.g. antibodies 71-77 in Table B). The antibody comprising one or more HVRs derived from SEQ ID NO: 18 may further comprise a light chain variable region (VL) comprising one or more HVRs derived from SEQ ID NO: 17. The HVR may be L1, L2, L3, or any combination thereof. In a preferred embodiment, the VL may comprise an L1 of SEQ ID NO: 63, an L2 of SEQ ID NO: 30, an L3 of SEQ ID NO: 64, or any combination thereof (e.g. antibodies 78-126 in Table B). In various embodiments above, the antibody may be a humanized antibody, or the antibody may have a VL with 90, 91, 92, 93, 94, 95, 96, 97, 98, 99, or 100% identity to SEQ ID NO: 17 and/or a VH with 90, 91, 92, 93, 94, 95, 96, 97, 98, 99 or 100% identity to SEQ ID NO: 18. In each of the above embodiments, the anti-ApoE antibody may optionally comprise one or more constant regions, or a portion of a constant region, that is substantially human (i.e. at least 90%, 95%, or 99% sequence identity with a known human framework sequence). The present disclosure also encompasses the corresponding nucleic acid sequences of SEQ ID NO: 17, 18, 63, 30, 64, 65, 66, and 67, which can readily be determined by one of skill in the art, and may be incorporated into a vector or other large DNA molecule, such as a chromosome, in order to express an antibody of the disclosure.

In some embodiments, each of the exemplary antibodies described above may also contain a variant Fc region, including but not limited to a variant Fc region that is modified to alter the natural interaction with the microglia FcR.

In further embodiments, an isolated antibody of Group I recognizes an epitope listed in Tables 4-7, for example, as described for the exemplary antibody HJ152 or HJ1514.

TABLE B

Exemplary Group I Antibodies

| Antibody | Light Chain HVR | | | Heavy Chain HVR | | |
|---|---|---|---|---|---|---|
| | L1 | L2 | L3 | H1 | H2 | H3 |
| 1 | SEQ ID NO: 29 | | | | | |
| 2 | SEQ ID NO: 29 | SEQ ID NO: 30 | | | | |
| 3 | SEQ ID NO: 29 | SEQ ID NO: 30 | SEQ ID NO: 31 | | | |
| 4 | | SEQ ID NO: 30 | | | | |
| 5 | | SEQ ID NO: 30 | SEQ ID NO: 31 | | | |
| 6 | | | SEQ ID NO: 31 | | | |
| 7 | SEQ ID NO: 29 | | SEQ ID NO: 31 | | | |
| 8 | | | | SEQ ID NO: 32 | | |
| 9 | | | | SEQ ID NO: 32 | SEQ ID NO: 33 | |
| 10 | | | | SEQ ID NO: 32 | SEQ ID NO: 33 | SEQ ID NO: 34 |
| 11 | | | | | SEQ ID NO: 33 | |
| 12 | | | | | SEQ ID NO: 33 | SEQ ID NO: 34 |
| 13 | | | | | | SEQ ID NO: 34 |
| 14 | | | | SEQ ID NO: 32 | | SEQ ID NO: 34 |
| 15 | SEQ ID NO: 29 | | | SEQ ID NO: 32 | | |
| 16 | SEQ ID NO: 29 | | | SEQ ID NO: 32 | SEQ ID NO: 33 | |
| 17 | SEQ ID NO: 29 | | | SEQ ID NO: 32 | SEQ ID NO: 33 | SEQ ID NO: 34 |
| 18 | SEQ ID NO: 29 | | | | SEQ ID NO: 33 | |
| 19 | SEQ ID NO: 29 | | | | SEQ ID NO: 33 | SEQ ID NO: 34 |
| 20 | SEQ ID NO: 29 | | | | | SEQ ID NO: 34 |
| 21 | SEQ ID NO: 29 | | | SEQ ID NO: 32 | | SEQ ID NO: 34 |
| 22 | SEQ ID NO: 29 | SEQ ID NO: 30 | | SEQ ID NO: 32 | | |
| 23 | SEQ ID NO: 29 | SEQ ID NO: 30 | | SEQ ID NO: 32 | SEQ ID NO: 33 | |
| 24 | SEQ ID NO: 29 | SEQ ID NO: 30 | | SEQ ID NO: 32 | SEQ ID NO: 33 | SEQ ID NO: 34 |
| 25 | SEQ ID NO: 29 | SEQ ID NO: 30 | | | SEQ ID NO: 33 | |
| 26 | SEQ ID NO: 29 | SEQ ID NO: 30 | | | SEQ ID NO: 33 | SEQ ID NO: 34 |
| 27 | SEQ ID NO: 29 | SEQ ID NO: 30 | | | | SEQ ID NO: 34 |
| 28 | SEQ ID NO: 29 | SEQ ID NO: 30 | | SEQ ID NO: 32 | | SEQ ID NO: 34 |
| 29 | SEQ ID NO: 29 | SEQ ID NO: 30 | SEQ ID NO: 31 | SEQ ID NO: 32 | | |
| 30 | SEQ ID NO: 29 | SEQ ID NO: 30 | SEQ ID NO: 31 | SEQ ID NO: 32 | SEQ ID NO: 33 | |
| 31 | SEQ ID NO: 29 | SEQ ID NO: 30 | SEQ ID NO: 31 | SEQ ID NO: 32 | SEQ ID NO: 33 | SEQ ID NO: 34 |
| 32 | SEQ ID NO: 29 | SEQ ID NO: 30 | SEQ ID NO: 31 | | SEQ ID NO: 33 | |
| 33 | SEQ ID NO: 29 | SEQ ID NO: 30 | SEQ ID NO: 31 | | SEQ ID NO: 33 | SEQ ID NO: 34 |
| 34 | SEQ ID NO: 29 | SEQ ID NO: 30 | SEQ ID NO: 31 | SEQ ID NO: 32 | | SEQ ID NO: 34 |
| 35 | SEQ ID NO: 29 | SEQ ID NO: 30 | SEQ ID NO: 31 | | | SEQ ID NO: 34 |
| 36 | | SEQ ID NO: 30 | | SEQ ID NO: 32 | | |
| 37 | | SEQ ID NO: 30 | | SEQ ID NO: 32 | SEQ ID NO: 33 | |
| 38 | | SEQ ID NO: 30 | | SEQ ID NO: 32 | SEQ ID NO: 33 | SEQ ID NO: 34 |
| 39 | | SEQ ID NO: 30 | | | SEQ ID NO: 33 | |
| 40 | | SEQ ID NO: 30 | | | SEQ ID NO: 33 | SEQ ID NO: 34 |
| 41 | | SEQ ID NO: 30 | | | | SEQ ID NO: 34 |
| 42 | | SEQ ID NO: 30 | | SEQ ID NO: 32 | | SEQ ID NO: 34 |
| 43 | | SEQ ID NO: 30 | SEQ ID NO: 31 | SEQ ID NO: 32 | | |
| 44 | | SEQ ID NO: 30 | SEQ ID NO: 31 | SEQ ID NO: 32 | SEQ ID NO: 33 | |
| 45 | | SEQ ID NO: 30 | SEQ ID NO: 31 | SEQ ID NO: 32 | SEQ ID NO: 33 | SEQ ID NO: 34 |
| 46 | | SEQ ID NO: 30 | SEQ ID NO: 31 | | SEQ ID NO: 33 | |
| 47 | | SEQ ID NO: 30 | SEQ ID NO: 31 | | SEQ ID NO: 33 | SEQ ID NO: 34 |
| 48 | | SEQ ID NO: 30 | SEQ ID NO: 31 | | | SEQ ID NO: 34 |
| 49 | | SEQ ID NO: 30 | SEQ ID NO: 31 | SEQ ID NO: 32 | | SEQ ID NO: 34 |
| 50 | | | SEQ ID NO: 31 | SEQ ID NO: 32 | | |
| 51 | | | SEQ ID NO: 31 | SEQ ID NO: 32 | SEQ ID NO: 33 | |
| 52 | | | SEQ ID NO: 31 | SEQ ID NO: 32 | SEQ ID NO: 33 | SEQ ID NO: 34 |
| 53 | | | SEQ ID NO: 31 | | SEQ ID NO: 33 | |
| 54 | | | SEQ ID NO: 31 | | SEQ ID NO: 33 | SEQ ID NO: 34 |
| 55 | | | SEQ ID NO: 31 | | | SEQ ID NO: 34 |
| 56 | | | SEQ ID NO: 31 | SEQ ID NO: 32 | | SEQ ID NO: 34 |
| 57 | SEQ ID NO: 29 | | SEQ ID NO: 31 | SEQ ID NO: 32 | | |
| 58 | SEQ ID NO: 29 | | SEQ ID NO: 31 | SEQ ID NO: 32 | SEQ ID NO: 33 | |
| 59 | SEQ ID NO: 29 | | SEQ ID NO: 31 | SEQ ID NO: 32 | SEQ ID NO: 33 | SEQ ID NO: 34 |
| 60 | SEQ ID NO: 29 | | SEQ ID NO: 31 | | SEQ ID NO: 33 | |
| 61 | SEQ ID NO: 29 | | SEQ ID NO: 31 | | SEQ ID NO: 33 | SEQ ID NO: 34 |
| 62 | SEQ ID NO: 29 | | SEQ ID NO: 31 | | | SEQ ID NO: 34 |
| 63 | SEQ ID NO: 29 | | SEQ ID NO: 31 | SEQ ID NO: 32 | | SEQ ID NO: 34 |
| 64 | SEQ ID NO: 63 | | | | | |
| 65 | SEQ ID NO: 63 | SEQ ID NO: 30 | | | | |
| 66 | SEQ ID NO: 63 | SEQ ID NO: 30 | SEQ ID NO: 64 | | | |

TABLE B-continued

Exemplary Group I Antibodies

| Antibody | Light Chain HVR | | | Heavy Chain HVR | | |
|---|---|---|---|---|---|---|
| | L1 | L2 | L3 | H1 | H2 | H3 |
| 67 | | SEQ ID NO: 30 | | | | |
| 68 | | SEQ ID NO: 30 | SEQ ID NO: 64 | | | |
| 69 | | | SEQ ID NO: 64 | | | |
| 70 | SEQ ID NO: 63 | | SEQ ID NO: 64 | | | |
| 71 | | | | SEQ ID NO: 65 | | |
| 72 | | | | SEQ ID NO: 65 | SEQ ID NO: 66 | |
| 73 | | | | SEQ ID NO: 65 | SEQ ID NO: 66 | SEQ ID NO: 67 |
| 74 | | | | | SEQ ID NO: 66 | |
| 75 | | | | | SEQ ID NO: 66 | SEQ ID NO: 67 |
| 76 | | | | | | SEQ ID NO: 67 |
| 77 | | | | SEQ ID NO: 65 | | SEQ ID NO: 67 |
| 78 | SEQ ID NO: 63 | | | SEQ ID NO: 65 | | |
| 79 | SEQ ID NO: 63 | | | SEQ ID NO: 65 | SEQ ID NO: 66 | |
| 80 | SEQ ID NO: 63 | | | SEQ ID NO: 65 | SEQ ID NO: 66 | SEQ ID NO: 67 |
| 81 | SEQ ID NO: 63 | | | | SEQ ID NO: 66 | |
| 82 | SEQ ID NO: 63 | | | | SEQ ID NO: 66 | SEQ ID NO: 67 |
| 83 | SEQ ID NO: 63 | | | | | SEQ ID NO: 67 |
| 84 | SEQ ID NO: 63 | | | SEQ ID NO: 65 | | SEQ ID NO: 67 |
| 85 | SEQ ID NO: 63 | SEQ ID NO: 30 | | SEQ ID NO: 65 | | |
| 86 | SEQ ID NO: 63 | SEQ ID NO: 30 | | SEQ ID NO: 65 | SEQ ID NO: 66 | |
| 87 | SEQ ID NO: 63 | SEQ ID NO: 30 | | SEQ ID NO: 65 | SEQ ID NO: 66 | SEQ ID NO: 67 |
| 88 | SEQ ID NO: 63 | SEQ ID NO: 30 | | | SEQ ID NO: 66 | |
| 89 | SEQ ID NO: 63 | SEQ ID NO: 30 | | | SEQ ID NO: 66 | SEQ ID NO: 67 |
| 90 | SEQ ID NO: 63 | SEQ ID NO: 30 | | | | SEQ ID NO: 67 |
| 91 | SEQ ID NO: 63 | SEQ ID NO: 30 | | SEQ ID NO: 65 | | SEQ ID NO: 67 |
| 92 | SEQ ID NO: 63 | SEQ ID NO: 30 | SEQ ID NO: 64 | SEQ ID NO: 65 | | |
| 93 | SEQ ID NO: 63 | SEQ ID NO: 30 | SEQ ID NO: 64 | SEQ ID NO: 65 | SEQ ID NO: 66 | |
| 94 | SEQ ID NO: 63 | SEQ ID NO: 30 | SEQ ID NO: 64 | SEQ ID NO: 65 | SEQ ID NO: 66 | SEQ ID NO: 67 |
| 95 | SEQ ID NO: 63 | SEQ ID NO: 30 | SEQ ID NO: 64 | | SEQ ID NO: 66 | |
| 96 | SEQ ID NO: 63 | SEQ ID NO: 30 | SEQ ID NO: 64 | | SEQ ID NO: 66 | SEQ ID NO: 67 |
| 97 | SEQ ID NO: 63 | SEQ ID NO: 30 | SEQ ID NO: 64 | | | SEQ ID NO: 67 |
| 98 | SEQ ID NO: 63 | SEQ ID NO: 30 | SEQ ID NO: 64 | SEQ ID NO: 65 | | SEQ ID NO: 67 |
| 99 | | SEQ ID NO: 30 | | SEQ ID NO: 65 | | |
| 100 | | SEQ ID NO: 30 | | SEQ ID NO: 65 | SEQ ID NO: 66 | |
| 101 | | SEQ ID NO: 30 | | SEQ ID NO: 65 | SEQ ID NO: 66 | SEQ ID NO: 67 |
| 102 | | SEQ ID NO: 30 | | | SEQ ID NO: 66 | |
| 103 | | SEQ ID NO: 30 | | | SEQ ID NO: 66 | SEQ ID NO: 67 |
| 104 | | SEQ ID NO: 30 | | | | SEQ ID NO: 67 |
| 105 | | SEQ ID NO: 30 | | SEQ ID NO: 65 | | SEQ ID NO: 67 |
| 106 | | SEQ ID NO: 30 | SEQ ID NO: 64 | SEQ ID NO: 65 | | |
| 107 | | SEQ ID NO: 30 | SEQ ID NO: 64 | SEQ ID NO: 65 | SEQ ID NO: 66 | |
| 108 | | SEQ ID NO: 30 | SEQ ID NO: 64 | SEQ ID NO: 65 | SEQ ID NO: 66 | SEQ ID NO: 67 |
| 109 | | SEQ ID NO: 30 | SEQ ID NO: 64 | | SEQ ID NO: 66 | |
| 110 | | SEQ ID NO: 30 | SEQ ID NO: 64 | | SEQ ID NO: 66 | SEQ ID NO: 67 |
| 111 | | SEQ ID NO: 30 | SEQ ID NO: 64 | | | SEQ ID NO: 67 |
| 112 | | SEQ ID NO: 30 | SEQ ID NO: 64 | SEQ ID NO: 65 | | SEQ ID NO: 67 |
| 113 | | | SEQ ID NO: 64 | SEQ ID NO: 65 | | |
| 114 | | | SEQ ID NO: 64 | SEQ ID NO: 65 | SEQ ID NO: 66 | |
| 115 | | | SEQ ID NO: 64 | SEQ ID NO: 65 | SEQ ID NO: 66 | SEQ ID NO: 67 |
| 116 | | | SEQ ID NO: 64 | | SEQ ID NO: 66 | |
| 117 | | | SEQ ID NO: 64 | | SEQ ID NO: 66 | SEQ ID NO: 67 |
| 118 | | | SEQ ID NO: 64 | | | SEQ ID NO: 67 |
| 119 | | | SEQ ID NO: 64 | SEQ ID NO: 65 | | SEQ ID NO: 67 |
| 120 | SEQ ID NO: 63 | | SEQ ID NO: 64 | SEQ ID NO: 65 | | |
| 121 | SEQ ID NO: 63 | | SEQ ID NO: 64 | SEQ ID NO: 65 | SEQ ID NO: 66 | |
| 122 | SEQ ID NO: 63 | | SEQ ID NO: 64 | SEQ ID NO: 65 | SEQ ID NO: 66 | SEQ ID NO: 67 |
| 123 | SEQ ID NO: 63 | | SEQ ID NO: 64 | | SEQ ID NO: 66 | |
| 124 | SEQ ID NO: 63 | | SEQ ID NO: 64 | | SEQ ID NO: 66 | SEQ ID NO: 67 |
| 125 | SEQ ID NO: 63 | | SEQ ID NO: 64 | | | SEQ ID NO: 67 |
| 126 | SEQ ID NO: 63 | | SEQ ID NO: 64 | SEQ ID NO: 65 | | SEQ ID NO: 67 |

(b) Group II: Anti-ApoE Antibodies that Preferentially Bind to ApoE3 and ApoE4

In another aspect, an anti-ApoE antibody has a heavy chain variable region comprising SEQ ID NO: 84. In some embodiments, the heavy chain variable region further comprises SEQ ID NO: 80 and/or SEQ ID NO: 82. In other embodiments, the heavy chain variable region further comprises SEQ ID NO: 81 and/or SEQ ID NO: 83. In certain of the above embodiments, the antibody has a light chain variable region comprising SEQ ID NO: 25. The light chain variable region can further comprise (a) SEQ ID NO: 78 or SEQ ID NO: 79; and/or (b) SEQ ID NO: 24.

In another aspect, an anti-ApoE antibody has a heavy chain variable region comprising SEQ ID NO: 85. In some embodiments, the heavy chain variable region further comprises SEQ ID NO: 80 and/or SEQ ID NO: 82. In other embodiments, the heavy chain variable region further comprises SEQ ID NO: 81 and/or SEQ ID NO: 83. In certain of the above embodiments, the antibody has a light chain variable region comprising SEQ ID NO: 25. The light chain variable region can further comprise (a) SEQ ID NO: 78 or SEQ ID NO: 79; and/or (b) SEQ ID NO: 24.

In another aspect, an anti-ApoE antibody is selected from Table C.

TABLE C

Group II antibodies

| | Light Chain HVR | | | Heavy Chain HVR | | |
|---|---|---|---|---|---|---|
| Antibody | L1 | L2 | L3 | H1 | H2 | H3 |
| 1 | SEQ ID NO: 78 | | | | | |
| 2 | SEQ ID NO: 78 | SEQ ID NO: 24 | | | | |
| 3 | SEQ ID NO: 78 | SEQ ID NO: 24 | SEQ ID NO: 25 | | | |
| 4 | | SEQ ID NO: 24 | | | | |
| 5 | | SEQ ID NO: 24 | SEQ ID NO: 25 | | | |
| 6 | | | SEQ ID NO: 25 | | | |
| 7 | SEQ ID NO: 78 | | SEQ ID NO: 25 | | | |
| 8 | | | | SEQ ID NO: 80 | | |
| 9 | | | | SEQ ID NO: 80 | SEQ ID NO: 82 | |
| 10 | | | | SEQ ID NO: 80 | SEQ ID NO: 82 | SEQ ID NO: 84 |
| 11 | | | | | SEQ ID NO: 82 | |
| 12 | | | | | SEQ ID NO: 82 | SEQ ID NO: 84 |
| 13 | | | | | | SEQ ID NO: 84 |
| 14 | | | | SEQ ID NO: 80 | | SEQ ID NO: 84 |
| 15 | SEQ ID NO: 78 | | | SEQ ID NO: 80 | | |
| 16 | SEQ ID NO: 78 | | | SEQ ID NO: 80 | SEQ ID NO: 82 | |
| 17 | SEQ ID NO: 78 | | | SEQ ID NO: 80 | SEQ ID NO: 82 | SEQ ID NO: 84 |
| 18 | SEQ ID NO: 78 | | | | SEQ ID NO: 82 | |
| 19 | SEQ ID NO: 78 | | | | SEQ ID NO: 82 | SEQ ID NO: 84 |
| 20 | SEQ ID NO: 78 | | | | | SEQ ID NO: 84 |
| 21 | SEQ ID NO: 78 | | | SEQ ID NO: 80 | | SEQ ID NO: 84 |
| 22 | SEQ ID NO: 78 | SEQ ID NO: 24 | | SEQ ID NO: 80 | | |
| 23 | SEQ ID NO: 78 | SEQ ID NO: 24 | | SEQ ID NO: 80 | SEQ ID NO: 82 | |
| 24 | SEQ ID NO: 78 | SEQ ID NO: 24 | | SEQ ID NO: 80 | SEQ ID NO: 82 | SEQ ID NO: 84 |
| 25 | SEQ ID NO: 78 | SEQ ID NO: 24 | | | SEQ ID NO: 82 | |
| 26 | SEQ ID NO: 78 | SEQ ID NO: 24 | | | SEQ ID NO: 82 | SEQ ID NO: 84 |
| 27 | SEQ ID NO: 78 | SEQ ID NO: 24 | | | | SEQ ID NO: 84 |
| 28 | SEQ ID NO: 78 | SEQ ID NO: 24 | | SEQ ID NO: 80 | | SEQ ID NO: 84 |
| 29 | SEQ ID NO: 78 | | SEQ ID NO: 25 | SEQ ID NO: 80 | | |
| 30 | SEQ ID NO: 78 | SEQ ID NO: 24 | SEQ ID NO: 25 | SEQ ID NO: 80 | SEQ ID NO: 82 | |
| 31 | SEQ ID NO: 78 | SEQ ID NO: 24 | SEQ ID NO: 25 | SEQ ID NO: 80 | SEQ ID NO: 82 | SEQ ID NO: 84 |
| 32 | SEQ ID NO: 78 | SEQ ID NO: 24 | SEQ ID NO: 25 | | SEQ ID NO: 82 | |
| 33 | SEQ ID NO: 78 | SEQ ID NO: 24 | SEQ ID NO: 25 | | SEQ ID NO: 82 | SEQ ID NO: 84 |
| 34 | SEQ ID NO: 78 | SEQ ID NO: 24 | SEQ ID NO: 25 | SEQ ID NO: 80 | | SEQ ID NO: 84 |
| 35 | SEQ ID NO: 78 | SEQ ID NO: 24 | SEQ ID NO: 25 | | | SEQ ID NO: 84 |
| 36 | | SEQ ID NO: 24 | | SEQ ID NO: 80 | | |
| 37 | | SEQ ID NO: 24 | | SEQ ID NO: 80 | SEQ ID NO: 82 | |
| 38 | | SEQ ID NO: 24 | | SEQ ID NO: 80 | SEQ ID NO: 82 | SEQ ID NO: 84 |
| 39 | | SEQ ID NO: 24 | | | SEQ ID NO: 82 | |
| 40 | | SEQ ID NO: 24 | | | SEQ ID NO: 82 | SEQ ID NO: 84 |
| 41 | | SEQ ID NO: 24 | | | | SEQ ID NO: 84 |
| 42 | | SEQ ID NO: 24 | | SEQ ID NO: 80 | | SEQ ID NO: 84 |
| 43 | | SEQ ID NO: 24 | SEQ ID NO: 25 | SEQ ID NO: 80 | | |
| 44 | | SEQ ID NO: 24 | SEQ ID NO: 25 | SEQ ID NO: 80 | SEQ ID NO: 82 | |
| 45 | | SEQ ID NO: 24 | SEQ ID NO: 25 | SEQ ID NO: 80 | SEQ ID NO: 82 | SEQ ID NO: 84 |
| 46 | | SEQ ID NO: 24 | SEQ ID NO: 25 | | SEQ ID NO: 82 | |
| 47 | | SEQ ID NO: 24 | SEQ ID NO: 25 | | SEQ ID NO: 82 | SEQ ID NO: 84 |
| 48 | | SEQ ID NO: 24 | SEQ ID NO: 25 | | | SEQ ID NO: 84 |
| 49 | | SEQ ID NO: 24 | SEQ ID NO: 25 | SEQ ID NO: 80 | | SEQ ID NO: 84 |
| 50 | | | SEQ ID NO: 25 | SEQ ID NO: 80 | | |
| 51 | | | SEQ ID NO: 25 | SEQ ID NO: 80 | SEQ ID NO: 82 | |
| 52 | | | SEQ ID NO: 25 | SEQ ID NO: 80 | SEQ ID NO: 82 | SEQ ID NO: 84 |
| 53 | | | SEQ ID NO: 25 | | SEQ ID NO: 82 | |
| 54 | | | SEQ ID NO: 25 | | SEQ ID NO: 82 | SEQ ID NO: 84 |
| 55 | | | SEQ ID NO: 25 | | | SEQ ID NO: 84 |
| 56 | | | SEQ ID NO: 25 | SEQ ID NO: 80 | | SEQ ID NO: 84 |
| 57 | SEQ ID NO: 78 | | SEQ ID NO: 25 | SEQ ID NO: 80 | | |
| 58 | SEQ ID NO: 78 | | SEQ ID NO: 25 | SEQ ID NO: 80 | SEQ ID NO: 82 | |
| 59 | SEQ ID NO: 78 | | SEQ ID NO: 25 | SEQ ID NO: 80 | SEQ ID NO: 82 | SEQ ID NO: 84 |
| 60 | SEQ ID NO: 78 | | SEQ ID NO: 25 | | SEQ ID NO: 82 | |
| 61 | SEQ ID NO: 78 | | SEQ ID NO: 25 | | SEQ ID NO: 82 | SEQ ID NO: 84 |
| 62 | SEQ ID NO: 78 | | SEQ ID NO: 25 | | | SEQ ID NO: 84 |
| 63 | SEQ ID NO: 78 | | SEQ ID NO: 25 | SEQ ID NO: 80 | | SEQ ID NO: 84 |
| 64 | SEQ ID NO: 79 | | | | | |
| 65 | SEQ ID NO: 79 | SEQ ID NO: 24 | | | | |
| 66 | SEQ ID NO: 79 | SEQ ID NO: 24 | SEQ ID NO: 25 | | | |
| 67 | | SEQ ID NO: 24 | | | | |
| 68 | | SEQ ID NO: 24 | SEQ ID NO: 25 | | | |
| 69 | | | SEQ ID NO: 25 | | | |
| 70 | SEQ ID NO: 79 | | SEQ ID NO: 25 | | | |
| 71 | | | | SEQ ID NO: 81 | | |

TABLE C-continued

| | Group II antibodies | | | | | |
|---|---|---|---|---|---|---|
| | Light Chain HVR | | | Heavy Chain HVR | | |
| Antibody | L1 | L2 | L3 | H1 | H2 | H3 |
| 72 | | | | SEQ ID NO: 81 | SEQ ID NO: 83 | |
| 73 | | | | SEQ ID NO: 81 | SEQ ID NO: 83 | SEQ ID NO: 85 |
| 74 | | | | | SEQ ID NO: 83 | |
| 75 | | | | | SEQ ID NO: 83 | SEQ ID NO: 85 |
| 76 | | | | | | SEQ ID NO: 85 |
| 77 | | | | SEQ ID NO: 81 | | SEQ ID NO: 85 |
| 78 | SEQ ID NO: 79 | | | SEQ ID NO: 81 | | |
| 79 | SEQ ID NO: 79 | | | SEQ ID NO: 81 | SEQ ID NO: 83 | |
| 80 | SEQ ID NO: 79 | | | SEQ ID NO: 81 | SEQ ID NO: 83 | SEQ ID NO: 85 |
| 81 | SEQ ID NO: 79 | | | | SEQ ID NO: 83 | |
| 82 | SEQ ID NO: 79 | | | | SEQ ID NO: 83 | SEQ ID NO: 85 |
| 83 | SEQ ID NO: 79 | | | | | SEQ ID NO: 85 |
| 84 | SEQ ID NO: 79 | | | SEQ ID NO: 81 | | SEQ ID NO: 85 |
| 85 | SEQ ID NO: 79 | SEQ ID NO: 24 | | SEQ ID NO: 81 | | |
| 86 | SEQ ID NO: 79 | SEQ ID NO: 24 | | SEQ ID NO: 81 | SEQ ID NO: 83 | |
| 87 | SEQ ID NO: 79 | SEQ ID NO: 24 | | SEQ ID NO: 81 | SEQ ID NO: 83 | SEQ ID NO: 85 |
| 88 | SEQ ID NO: 79 | SEQ ID NO: 24 | | | SEQ ID NO: 83 | |
| 89 | SEQ ID NO: 79 | SEQ ID NO: 24 | | | SEQ ID NO: 83 | SEQ ID NO: 85 |
| 90 | SEQ ID NO: 79 | SEQ ID NO: 24 | | | | SEQ ID NO: 85 |
| 91 | SEQ ID NO: 79 | SEQ ID NO: 24 | | SEQ ID NO: 81 | | SEQ ID NO: 85 |
| 92 | SEQ ID NO: 79 | SEQ ID NO: 24 | SEQ ID NO: 25 | SEQ ID NO: 81 | | |
| 93 | SEQ ID NO: 79 | SEQ ID NO: 24 | SEQ ID NO: 25 | SEQ ID NO: 81 | SEQ ID NO: 83 | |
| 94 | SEQ ID NO: 79 | SEQ ID NO: 24 | SEQ ID NO: 25 | SEQ ID NO: 81 | SEQ ID NO: 83 | SEQ ID NO: 85 |
| 95 | SEQ ID NO: 79 | SEQ ID NO: 24 | SEQ ID NO: 25 | | SEQ ID NO: 83 | |
| 96 | SEQ ID NO: 79 | SEQ ID NO: 24 | SEQ ID NO: 25 | | SEQ ID NO: 83 | SEQ ID NO: 85 |
| 97 | SEQ ID NO: 79 | SEQ ID NO: 24 | SEQ ID NO: 25 | | | SEQ ID NO: 85 |
| 98 | SEQ ID NO: 79 | SEQ ID NO: 24 | SEQ ID NO: 25 | SEQ ID NO: 81 | | SEQ ID NO: 85 |
| 99 | | SEQ ID NO: 24 | | SEQ ID NO: 81 | | |
| 100 | | SEQ ID NO: 24 | | SEQ ID NO: 81 | SEQ ID NO: 83 | |
| 101 | | SEQ ID NO: 24 | | SEQ ID NO: 81 | SEQ ID NO: 83 | SEQ ID NO: 85 |
| 102 | | SEQ ID NO: 24 | | | SEQ ID NO: 83 | |
| 103 | | SEQ ID NO: 24 | | | SEQ ID NO: 83 | SEQ ID NO: 85 |
| 104 | | SEQ ID NO: 24 | | | | SEQ ID NO: 85 |
| 105 | | SEQ ID NO: 24 | | SEQ ID NO: 81 | | SEQ ID NO: 85 |
| 106 | | SEQ ID NO: 24 | SEQ ID NO: 25 | SEQ ID NO: 81 | | |
| 107 | | SEQ ID NO: 24 | SEQ ID NO: 25 | SEQ ID NO: 81 | SEQ ID NO: 83 | |
| 108 | | SEQ ID NO: 24 | SEQ ID NO: 25 | SEQ ID NO: 81 | SEQ ID NO: 83 | SEQ ID NO: 85 |
| 109 | | SEQ ID NO: 24 | SEQ ID NO: 25 | | SEQ ID NO: 83 | |
| 110 | | SEQ ID NO: 24 | SEQ ID NO: 25 | | SEQ ID NO: 83 | SEQ ID NO: 85 |
| 111 | | SEQ ID NO: 24 | SEQ ID NO: 25 | | | SEQ ID NO: 85 |
| 112 | | SEQ ID NO: 24 | SEQ ID NO: 25 | SEQ ID NO: 81 | | SEQ ID NO: 85 |
| 113 | | | SEQ ID NO: 25 | SEQ ID NO: 81 | | |
| 114 | | | SEQ ID NO: 25 | SEQ ID NO: 81 | SEQ ID NO: 83 | |
| 115 | | | SEQ ID NO: 25 | SEQ ID NO: 81 | SEQ ID NO: 83 | SEQ ID NO: 85 |
| 116 | | | SEQ ID NO: 25 | | SEQ ID NO: 83 | |
| 117 | | | SEQ ID NO: 25 | | SEQ ID NO: 83 | SEQ ID NO: 85 |
| 118 | | | SEQ ID NO: 25 | | | SEQ ID NO: 85 |
| 119 | | | SEQ ID NO: 25 | SEQ ID NO: 81 | | SEQ ID NO: 85 |
| 120 | SEQ ID NO: 79 | | SEQ ID NO: 25 | SEQ ID NO: 81 | | |
| 121 | SEQ ID NO: 79 | | SEQ ID NO: 25 | SEQ ID NO: 81 | SEQ ID NO: 83 | |
| 122 | SEQ ID NO: 79 | | SEQ ID NO: 25 | SEQ ID NO: 81 | SEQ ID NO: 83 | SEQ ID NO: 85 |
| 123 | SEQ ID NO: 79 | | SEQ ID NO: 25 | | SEQ ID NO: 83 | |
| 124 | SEQ ID NO: 79 | | SEQ ID NO: 25 | | SEQ ID NO: 83 | SEQ ID NO: 85 |
| 125 | SEQ ID NO: 79 | | SEQ ID NO: 25 | | | SEQ ID NO: 85 |
| 126 | SEQ ID NO: 79 | | SEQ ID NO: 25 | SEQ ID NO: 81 | | SEQ ID NO: 85 |

In an exemplary embodiment, an anti-ApoE antibody of this group comprises a VL that has one or more HVRs derived from SEQ ID NO: 9 or a VH that has one or more HVRs derived from SEQ ID NO: 10. The HVR derived from SEQ ID NO: 9 may be L1, L2, L3, or any combination thereof. In certain embodiments, the VL may comprise an L1 of SEQ ID NO: 47, an L2 of SEQ ID NO: 24, an L3 of SEQ ID NO: 25, or any combination thereof (e.g. antibodies 1-7 in Table D). The HVR derived from SEQ ID NO: 10 may be H1, H2, H3, or any combination thereof. In certain embodiments, the VH may comprise an H1 of SEQ ID NO: 48, an H2 of SEQ ID NO: 49, an H3 of SEQ ID NO: 50, or any combination thereof (e.g. antibodies 8-14 in Table D). The antibody comprising one or more HVRs derived from SEQ ID NO: 10 may further comprise a light chain variable region (VL) comprising one or more HVRs derived from SEQ ID NO: 9. The HVR may be L1, L2, L3, or any combination thereof. In a preferred embodiment, the VL may comprise an L1 of SEQ ID NO: 47, an L2 of SEQ ID NO: 24, an L3 of SEQ ID NO: 25, or any combination thereof (e.g. antibodies 15-63 in Table D). In various embodiments above, the antibody may be a humanized antibody, or the antibody may have a VL with 90, 91, 92, 93, 94, 95, 96, 97, 98, 99, or 100% identity to SEQ ID NO: 9 and/or a VH with 90, 91, 92, 93, 94, 95, 96, 97, 98, 99 or 100% identity to SEQ ID NO: 10. In each of the above embodiments, the anti-ApoE antibody may optionally comprise one or more constant regions, or a portion of a constant region, that is substantially human (i.e. at least 85%, 90%, 95%, or 99% sequence identity with a known human framework sequence). The present disclosure also encompasses the corresponding nucleic acid sequences of SEQ ID NO: 9, 10, 47, 24, 25, 48, 49, and 50, which can readily be determined by one of skill in the art, and may be incorporated into a vector or other large DNA molecule, such as a chromosome, in order to express an antibody of the disclosure.

In another exemplary embodiment, an anti-ApoE antibody of this group comprises a VL that has one or more HVRs derived from SEQ ID NO: 11 or a VH that has one or more HVRs derived from SEQ ID NO: 12. The HVR derived from SEQ ID NO: 11 may be L1, L2, L3, or any combination thereof. In certain embodiments, the VL may comprise an L1 of SEQ ID NO: 51, an L2 of SEQ ID NO: 24, an L3 of SEQ ID NO: 25, or any combination thereof (e.g. antibodies 64-70 in Table D). The HVR derived from SEQ ID NO: 12 may be H1, H2, H3, or any combination thereof. In certain embodiments, the VH may comprise an H1 of SEQ ID NO: 52, an H2 of SEQ ID NO: 53, an H3 of SEQ ID NO: 54, or any combination thereof (e.g. antibodies 71-77 in Table D). The antibody comprising one or more HVRs derived from SEQ ID NO: 12 may further comprise a light chain variable region (VL) comprising one or more HVRs derived from SEQ ID NO: 11. The HVR may be L1, L2, L3, or any combination thereof. In a preferred embodiment, the VL may comprise an L1 of SEQ ID NO: 51, an L2 of SEQ ID NO: 24, an L3 of SEQ ID NO: 25, or any combination thereof (e.g. antibodies 78-126 in Table D). In various embodiments above, the antibody may be a humanized antibody, or the antibody may have a VL with 90, 91, 92, 93, 94, 95, 96, 97, 98, 99, or 100% identity to SEQ ID NO: 11 and/or a VH with 90, 91, 92, 93, 94, 95, 96, 97, 98, 99 or 100% identity to SEQ ID NO: 12. In each of the above embodiments, the anti-ApoE antibody may optionally comprise one or more constant regions, or a portion of a constant region, that is substantially human (i.e. at least 85%, 90%, 95%, or 99% sequence identity with a known human framework sequence). The present disclosure also encompasses the corresponding nucleic acid sequences of SEQ ID NO: 11, 12, 51, 24, 25, 52, 53, and 54, which can readily be determined by one of skill in the art, and may be incorporated into a vector or other large DNA molecule, such as a chromosome, in order to express an antibody of the disclosure.

In another exemplary embodiment, an anti-ApoE antibody of this group comprises a VL that has one or more HVRs derived from SEQ ID NO: 13 or a VH that has one or more HVRs derived from SEQ ID NO: 14. The HVR derived from SEQ ID NO: 13 may be L1, L2, L3, or any combination thereof. In certain embodiments, the VL may comprise an L1 of SEQ ID NO: 55, an L2 of SEQ ID NO: 24, an L3 of SEQ ID NO: 25, or any combination thereof (e.g. antibodies 127-133 in Table D). The HVR derived from SEQ ID NO: 14 may be H1, H2, H3, or any combination thereof. In certain embodiments, the VH may comprise an H1 of SEQ ID NO: 56, an H2 of SEQ ID NO: 57, an H3 of SEQ ID NO: 58, or any combination thereof (e.g. antibodies 134-140 in Table D). The antibody comprising one or more HVRs derived from SEQ ID NO: 14 may further comprise a light chain variable region (VL) comprising one or more HVRs derived from SEQ ID NO: 13. The HVR may be L1, L2, L3, or any combination thereof. In a preferred embodiment, the VL may comprise an L1 of SEQ ID NO: 55, an L2 of SEQ ID NO: 24, an L3 of SEQ ID NO: 25, or any combination thereof (e.g. antibodies 141-189 in Table D). In various embodiments above, the antibody may be a humanized antibody, or the antibody may have a VL with 90, 91, 92, 93, 94, 95, 96, 97, 98, 99, or 100% identity to SEQ ID NO: 13 and/or a VH with 90, 91, 92, 93, 94, 95, 96, 97, 98, 99 or 100% identity to SEQ ID NO: 14. In each of the above embodiments, the anti-ApoE antibody may optionally comprise one or more constant regions, or a portion of a constant region, that is substantially human (i.e. at least 90%, 95%, or 99% sequence identity with a known human framework sequence). The present disclosure also encompasses the corresponding nucleic acid sequences of SEQ ID NO: 13, 14, 55, 24, 25, 56, 57, and 58, which can readily be determined by one of skill in the art, and may be incorporated into a vector or other large DNA molecule, such as a chromosome, in order to express an antibody of the disclosure.

In another exemplary embodiment, an anti-ApoE antibody of this group comprises a VL that has one or more HVRs derived from SEQ ID NO: 15 or a VH that has one or more HVRs derived from SEQ ID NO: 16. The HVR derived from SEQ ID NO: 15 may be L1, L2, L3, or any combination thereof. In certain embodiments, the VL may comprise an L1 of SEQ ID NO: 59, an L2 of SEQ ID NO: 24, an L3 of SEQ ID NO: 25, or any combination thereof (e.g. antibodies 190-196 in Table D). The HVR derived from SEQ ID NO: 16 may be H1, H2, H3, or any combination thereof. In certain embodiments, the VH may comprise an H1 of SEQ ID NO: 60, an H2 of SEQ ID NO: 61, an H3 of SEQ ID NO: 62, or any combination thereof (e.g. antibodies 197-203 in Table D). The antibody comprising one or more HVRs derived from SEQ ID NO: 16 may further comprise a light chain variable region (VL) comprising one or more HVRs derived from SEQ ID NO: 15. The HVR may be L1, L2, L3, or any combination thereof. In a preferred embodiment, the VL may comprise an L1 of SEQ ID NO: 59, an L2 of SEQ ID NO: 24, an L3 of SEQ ID NO: 25, or any combination thereof (e.g. antibodies 204-252 in Table D). In various embodiments above, the antibody may be a humanized antibody, or the antibody may have a VL with 90, 91, 92, 93, 94, 95, 96, 97, 98, 99, or 100% identity to SEQ ID NO: 15 and/or a VH with 90, 91, 92, 93, 94, 95, 96, 97, 98, 99 or 100% identity to SEQ ID NO: 16. In each of the above embodiments, the anti-ApoE antibody may optionally comprise one or more constant regions, or a portion of a constant region, that is substantially human (i.e. at least 90%, 95%, or 99% sequence identity with a known human framework sequence). The present disclosure also encompasses the corresponding nucleic acid sequences of SEQ ID NO: 15, 16, 59, 24, 25, 60, 61, and 62, which can readily be determined by one of skill in the art, and may be incorporated into a vector or other large DNA molecule, such as a chromosome, in order to express an antibody of the disclosure.

In another exemplary embodiment, an anti-ApoE antibody of this group comprises a VL that has one or more HVRs derived from SEQ ID NO: 19 or a VH that has one or more HVRs derived from SEQ ID NO: 20. The HVR derived from SEQ ID NO: 19 may be L1, L2, L3, or any combination thereof. In certain embodiments, the VL may comprise an L1 of SEQ ID NO: 68, an L2 of SEQ ID NO: 24, an L3 of SEQ ID NO: 25, or any combination thereof (e.g. antibodies 253-259 in Table D). The HVR derived from SEQ ID NO: 20 may be H1, H2, H3, or any combination thereof. In certain embodiments, the VH may comprise an H1 of SEQ ID NO: 69, an H2 of SEQ ID NO: 70, an H3 of SEQ ID NO: 71, or any combination thereof (e.g. antibodies 260-266 in Table D). The antibody comprising one or more HVRs derived from SEQ ID NO: 20 may further comprise a light chain variable region (VL) comprising one or more HVRs derived from SEQ ID NO: 19. The HVR may be L1, L2, L3, or any combination thereof. In a preferred embodiment, the VL may comprise an L1 of SEQ ID NO: 68, an L2 of SEQ ID NO: 24, an L3 of SEQ ID NO: 25, or any combination thereof (e.g. antibodies 267-315 in Table D). In various embodiments above, the antibody may be a humanized antibody, or the antibody may have a VL with 90, 91, 92, 93, 94, 95, 96, 97, 98, 99, or 100% identity to SEQ ID NO: 19 and/or a VH with 90, 91, 92, 93, 94, 95, 96, 97, 98, 99 or 100% identity to SEQ ID NO: 20. In each of the above embodiments, the anti-ApoE antibody may optionally comprise one or more constant regions, or a portion of a constant region, that is substantially human (i.e. at least 90%, 95%, or 99% sequence identity with a known human framework sequence). The present disclosure also encompasses the corresponding nucleic acid sequences of SEQ ID NO: 19, 20, 68, 24, 25, 69, 70, and 71, which can readily be determined by one of skill in the art, and may be incorporated into a vector or other large DNA molecule, such as a chromosome, in order to express an antibody of the disclosure.

In some embodiments, each of the exemplary antibodies described above may also contain a variant Fc region, including but not limited to a variant Fc region that is modified to alter the natural interaction with the microglia FcR.

In further embodiments, an isolated antibody of Group II recognizes an epitope listed in Tables 4-7, for example, as described for the exemplary antibody HJ155, HJ156, HJ159, HJ1513, or HJ1518.

TABLE D

Exemplary Group II Antibodies

| Antibody | Light Chain HVR | | | Heavy Chain HVR | | |
|---|---|---|---|---|---|---|
| | L1 | L2 | L3 | H1 | H2 | H3 |
| 1 | SEQ ID NO: 47 | | | | | |
| 2 | SEQ ID NO: 47 | SEQ ID NO: 24 | | | | |
| 3 | SEQ ID NO: 47 | SEQ ID NO: 24 | SEQ ID NO: 25 | | | |
| 4 | | SEQ ID NO: 24 | | | | |
| 5 | | SEQ ID NO: 24 | SEQ ID NO: 25 | | | |
| 6 | | | SEQ ID NO: 25 | | | |
| 7 | SEQ ID NO: 47 | | SEQ ID NO: 25 | | | |
| 8 | | | | SEQ ID NO: 48 | | |
| 9 | | | | SEQ ID NO: 48 | SEQ ID NO: 49 | |
| 10 | | | | SEQ ID NO: 48 | SEQ ID NO: 49 | SEQ ID NO: 50 |
| 11 | | | | | SEQ ID NO: 49 | |
| 12 | | | | | SEQ ID NO: 49 | SEQ ID NO: 50 |
| 13 | | | | | | SEQ ID NO: 50 |
| 14 | | | | SEQ ID NO: 48 | | SEQ ID NO: 50 |
| 15 | SEQ ID NO: 47 | | | SEQ ID NO: 48 | | |
| 16 | SEQ ID NO: 47 | | | SEQ ID NO: 48 | SEQ ID NO: 49 | |
| 17 | SEQ ID NO: 47 | | | SEQ ID NO: 48 | SEQ ID NO: 49 | SEQ ID NO: 50 |
| 18 | SEQ ID NO: 47 | | | | SEQ ID NO: 49 | |
| 19 | SEQ ID NO: 47 | | | | SEQ ID NO: 49 | SEQ ID NO: 50 |
| 20 | SEQ ID NO: 47 | | | | | SEQ ID NO: 50 |
| 21 | SEQ ID NO: 47 | | | SEQ ID NO: 48 | | SEQ ID NO: 50 |
| 22 | SEQ ID NO: 47 | SEQ ID NO: 24 | | SEQ ID NO: 48 | | |
| 23 | SEQ ID NO: 47 | SEQ ID NO: 24 | | SEQ ID NO: 48 | SEQ ID NO: 49 | |
| 24 | SEQ ID NO: 47 | SEQ ID NO: 24 | | SEQ ID NO: 48 | SEQ ID NO: 49 | SEQ ID NO: 50 |
| 25 | SEQ ID NO: 47 | SEQ ID NO: 24 | | | SEQ ID NO: 49 | |
| 26 | SEQ ID NO: 47 | SEQ ID NO: 24 | | | SEQ ID NO: 49 | SEQ ID NO: 50 |
| 27 | SEQ ID NO: 47 | SEQ ID NO: 24 | | | | SEQ ID NO: 50 |
| 28 | SEQ ID NO: 47 | SEQ ID NO: 24 | | SEQ ID NO: 48 | | SEQ ID NO: 50 |
| 29 | SEQ ID NO: 47 | SEQ ID NO: 24 | SEQ ID NO: 25 | SEQ ID NO: 48 | | |
| 30 | SEQ ID NO: 47 | SEQ ID NO: 24 | SEQ ID NO: 25 | SEQ ID NO: 48 | SEQ ID NO: 49 | |
| 31 | SEQ ID NO: 47 | SEQ ID NO: 24 | SEQ ID NO: 25 | SEQ ID NO: 48 | SEQ ID NO: 49 | SEQ ID NO: 50 |
| 32 | SEQ ID NO: 47 | SEQ ID NO: 24 | SEQ ID NO: 25 | | SEQ ID NO: 49 | |
| 33 | SEQ ID NO: 47 | SEQ ID NO: 24 | SEQ ID NO: 25 | | SEQ ID NO: 49 | SEQ ID NO: 50 |
| 34 | SEQ ID NO: 47 | SEQ ID NO: 24 | SEQ ID NO: 25 | SEQ ID NO: 48 | | SEQ ID NO: 50 |
| 35 | SEQ ID NO: 47 | SEQ ID NO: 24 | SEQ ID NO: 25 | | | SEQ ID NO: 50 |
| 36 | | SEQ ID NO: 24 | | SEQ ID NO: 48 | | |
| 37 | | SEQ ID NO: 24 | | SEQ ID NO: 48 | SEQ ID NO: 49 | |
| 38 | | SEQ ID NO: 24 | | SEQ ID NO: 48 | SEQ ID NO: 49 | SEQ ID NO: 50 |
| 39 | | SEQ ID NO: 24 | | | SEQ ID NO: 49 | |
| 40 | | SEQ ID NO: 24 | | | SEQ ID NO: 49 | SEQ ID NO: 50 |
| 41 | | SEQ ID NO: 24 | | | | SEQ ID NO: 50 |
| 42 | | SEQ ID NO: 24 | | SEQ ID NO: 48 | | SEQ ID NO: 50 |
| 43 | | SEQ ID NO: 24 | SEQ ID NO: 25 | SEQ ID NO: 48 | | |
| 44 | | SEQ ID NO: 24 | SEQ ID NO: 25 | SEQ ID NO: 48 | SEQ ID NO: 49 | |
| 45 | | SEQ ID NO: 24 | SEQ ID NO: 25 | SEQ ID NO: 48 | SEQ ID NO: 49 | SEQ ID NO: 50 |
| 46 | | SEQ ID NO: 24 | SEQ ID NO: 25 | | SEQ ID NO: 49 | |
| 47 | | SEQ ID NO: 24 | SEQ ID NO: 25 | | SEQ ID NO: 49 | SEQ ID NO: 50 |
| 48 | | SEQ ID NO: 24 | SEQ ID NO: 25 | | | SEQ ID NO: 50 |
| 49 | | SEQ ID NO: 24 | SEQ ID NO: 25 | SEQ ID NO: 48 | | SEQ ID NO: 50 |
| 50 | | | SEQ ID NO: 25 | SEQ ID NO: 48 | | |
| 51 | | | SEQ ID NO: 25 | SEQ ID NO: 48 | SEQ ID NO: 49 | |
| 52 | | | SEQ ID NO: 25 | SEQ ID NO: 48 | SEQ ID NO: 49 | SEQ ID NO: 50 |
| 53 | | | SEQ ID NO: 25 | | SEQ ID NO: 49 | |

TABLE D-continued

Exemplary Group II Antibodies

| | Light Chain HVR | | | Heavy Chain HVR | | |
|---|---|---|---|---|---|---|
| Antibody | L1 | L2 | L3 | H1 | H2 | H3 |
| 54 | | | SEQ ID NO: 25 | | SEQ ID NO: 49 | SEQ ID NO: 50 |
| 55 | | | SEQ ID NO: 25 | | | SEQ ID NO: 50 |
| 56 | | | SEQ ID NO: 25 | SEQ ID NO: 48 | | SEQ ID NO: 50 |
| 57 | SEQ ID NO: 47 | | SEQ ID NO: 25 | SEQ ID NO: 48 | | |
| 58 | SEQ ID NO: 47 | | SEQ ID NO: 25 | SEQ ID NO: 48 | SEQ ID NO: 49 | |
| 59 | SEQ ID NO: 47 | | SEQ ID NO: 25 | SEQ ID NO: 48 | SEQ ID NO: 49 | SEQ ID NO: 50 |
| 60 | SEQ ID NO: 47 | | SEQ ID NO: 25 | | SEQ ID NO: 49 | |
| 61 | SEQ ID NO: 47 | | SEQ ID NO: 25 | | SEQ ID NO: 49 | SEQ ID NO: 50 |
| 62 | SEQ ID NO: 47 | | SEQ ID NO: 25 | | | SEQ ID NO: 50 |
| 63 | SEQ ID NO: 47 | | SEQ ID NO: 25 | SEQ ID NO: 48 | | SEQ ID NO: 50 |
| 64 | SEQ ID NO: 51 | | | | | |
| 65 | SEQ ID NO: 51 | SEQ ID NO: 24 | | | | |
| 66 | SEQ ID NO: 51 | SEQ ID NO: 24 | SEQ ID NO: 25 | | | |
| 67 | | SEQ ID NO: 24 | | | | |
| 68 | | SEQ ID NO: 24 | SEQ ID NO: 25 | | | |
| 69 | | | SEQ ID NO: 25 | | | |
| 70 | SEQ ID NO: 51 | | SEQ ID NO: 25 | | | |
| 71 | | | | SEQ ID NO: 52 | | |
| 72 | | | | SEQ ID NO: 52 | SEQ ID NO: 53 | |
| 73 | | | | SEQ ID NO: 52 | SEQ ID NO: 53 | SEQ ID NO: 54 |
| 74 | | | | | SEQ ID NO: 53 | |
| 75 | | | | | SEQ ID NO: 53 | SEQ ID NO: 54 |
| 76 | | | | | | SEQ ID NO: 54 |
| 77 | | | | SEQ ID NO: 52 | | SEQ ID NO: 54 |
| 78 | SEQ ID NO: 51 | | | SEQ ID NO: 52 | | |
| 79 | SEQ ID NO: 51 | | | SEQ ID NO: 52 | SEQ ID NO: 53 | |
| 80 | SEQ ID NO: 51 | | | SEQ ID NO: 52 | SEQ ID NO: 53 | SEQ ID NO: 54 |
| 81 | SEQ ID NO: 51 | | | | SEQ ID NO: 53 | |
| 82 | SEQ ID NO: 51 | | | | SEQ ID NO: 53 | SEQ ID NO: 54 |
| 83 | SEQ ID NO: 51 | | | | | SEQ ID NO: 54 |
| 84 | SEQ ID NO: 51 | | | SEQ ID NO: 52 | | SEQ ID NO: 54 |
| 85 | SEQ ID NO: 51 | SEQ ID NO: 24 | | SEQ ID NO: 52 | | |
| 86 | SEQ ID NO: 51 | SEQ ID NO: 24 | | SEQ ID NO: 52 | SEQ ID NO: 53 | |
| 87 | SEQ ID NO: 51 | SEQ ID NO: 24 | | SEQ ID NO: 52 | SEQ ID NO: 53 | SEQ ID NO: 54 |
| 88 | SEQ ID NO: 51 | SEQ ID NO: 24 | | | SEQ ID NO: 53 | |
| 89 | SEQ ID NO: 51 | SEQ ID NO: 24 | | | SEQ ID NO: 53 | SEQ ID NO: 54 |
| 90 | SEQ ID NO: 51 | SEQ ID NO: 24 | | | | SEQ ID NO: 54 |
| 91 | SEQ ID NO: 51 | SEQ ID NO: 24 | | SEQ ID NO: 52 | | SEQ ID NO: 54 |
| 92 | SEQ ID NO: 51 | SEQ ID NO: 24 | SEQ ID NO: 25 | SEQ ID NO: 52 | | |
| 93 | SEQ ID NO: 51 | SEQ ID NO: 24 | SEQ ID NO: 25 | SEQ ID NO: 52 | SEQ ID NO: 53 | |
| 94 | SEQ ID NO: 51 | SEQ ID NO: 24 | SEQ ID NO: 25 | SEQ ID NO: 52 | SEQ ID NO: 53 | SEQ ID NO: 54 |
| 95 | SEQ ID NO: 51 | SEQ ID NO: 24 | SEQ ID NO: 25 | | SEQ ID NO: 53 | |
| 96 | SEQ ID NO: 51 | SEQ ID NO: 24 | SEQ ID NO: 25 | | SEQ ID NO: 53 | SEQ ID NO: 54 |
| 97 | SEQ ID NO: 51 | SEQ ID NO: 24 | SEQ ID NO: 25 | | | SEQ ID NO: 54 |
| 98 | SEQ ID NO: 51 | SEQ ID NO: 24 | SEQ ID NO: 25 | SEQ ID NO: 52 | | SEQ ID NO: 54 |
| 99 | | SEQ ID NO: 24 | | SEQ ID NO: 52 | | |
| 100 | | SEQ ID NO: 24 | | SEQ ID NO: 52 | SEQ ID NO: 53 | |
| 101 | | SEQ ID NO: 24 | | SEQ ID NO: 52 | SEQ ID NO: 53 | SEQ ID NO: 54 |
| 102 | | SEQ ID NO: 24 | | | SEQ ID NO: 53 | |
| 103 | | SEQ ID NO: 24 | | | SEQ ID NO: 53 | SEQ ID NO: 54 |
| 104 | | SEQ ID NO: 24 | | | | SEQ ID NO: 54 |
| 105 | | SEQ ID NO: 24 | | SEQ ID NO: 52 | | SEQ ID NO: 54 |
| 106 | | SEQ ID NO: 24 | SEQ ID NO: 25 | SEQ ID NO: 52 | | |
| 107 | | SEQ ID NO: 24 | SEQ ID NO: 25 | SEQ ID NO: 52 | SEQ ID NO: 53 | |
| 108 | | SEQ ID NO: 24 | SEQ ID NO: 25 | SEQ ID NO: 52 | SEQ ID NO: 53 | SEQ ID NO: 54 |
| 109 | | SEQ ID NO: 24 | SEQ ID NO: 25 | | SEQ ID NO: 53 | |
| 110 | | SEQ ID NO: 24 | SEQ ID NO: 25 | | SEQ ID NO: 53 | SEQ ID NO: 54 |
| 111 | | SEQ ID NO: 24 | SEQ ID NO: 25 | | | SEQ ID NO: 54 |
| 112 | | SEQ ID NO: 24 | SEQ ID NO: 25 | SEQ ID NO: 52 | | SEQ ID NO: 54 |
| 113 | | | SEQ ID NO: 25 | SEQ ID NO: 52 | | |
| 114 | | | SEQ ID NO: 25 | SEQ ID NO: 52 | SEQ ID NO: 53 | |
| 115 | | | SEQ ID NO: 25 | SEQ ID NO: 52 | SEQ ID NO: 53 | SEQ ID NO: 54 |
| 116 | | | SEQ ID NO: 25 | | SEQ ID NO: 53 | |
| 117 | | | SEQ ID NO: 25 | | SEQ ID NO: 53 | SEQ ID NO: 54 |
| 118 | | | SEQ ID NO: 25 | | | SEQ ID NO: 54 |
| 119 | | | SEQ ID NO: 25 | SEQ ID NO: 52 | | SEQ ID NO: 54 |
| 120 | SEQ ID NO: 51 | | SEQ ID NO: 25 | SEQ ID NO: 52 | | |
| 121 | SEQ ID NO: 51 | | SEQ ID NO: 25 | SEQ ID NO: 52 | SEQ ID NO: 53 | |
| 122 | SEQ ID NO: 51 | | SEQ ID NO: 25 | SEQ ID NO: 52 | SEQ ID NO: 53 | SEQ ID NO: 54 |
| 123 | SEQ ID NO: 51 | | SEQ ID NO: 25 | | SEQ ID NO: 53 | |
| 124 | SEQ ID NO: 51 | | SEQ ID NO: 25 | | SEQ ID NO: 53 | SEQ ID NO: 54 |
| 125 | SEQ ID NO: 51 | | SEQ ID NO: 25 | | | SEQ ID NO: 54 |
| 126 | SEQ ID NO: 51 | | SEQ ID NO: 25 | SEQ ID NO: 52 | | SEQ ID NO: 54 |
| 127 | SEQ ID NO: 55 | | | | | |

TABLE D-continued

Exemplary Group II Antibodies

| | Light Chain HVR | | | Heavy Chain HVR | | |
|---|---|---|---|---|---|---|
| Antibody | L1 | L2 | L3 | H1 | H2 | H3 |
| 128 | SEQ ID NO: 55 | SEQ ID NO: 24 | | | | |
| 219 | SEQ ID NO: 55 | SEQ ID NO: 24 | SEQ ID NO: 25 | | | |
| 130 | | SEQ ID NO: 24 | | | | |
| 131 | | SEQ ID NO: 24 | SEQ ID NO: 25 | | | |
| 132 | | | SEQ ID NO: 25 | | | |
| 133 | SEQ ID NO: 55 | | SEQ ID NO: 25 | | | |
| 134 | | | | SEQ ID NO: 56 | | |
| 135 | | | | SEQ ID NO: 56 | SEQ ID NO: 57 | |
| 136 | | | | SEQ ID NO: 56 | SEQ ID NO: 57 | SEQ ID NO: 58 |
| 137 | | | | | SEQ ID NO: 57 | |
| 138 | | | | | SEQ ID NO: 57 | SEQ ID NO: 58 |
| 139 | | | | | | SEQ ID NO: 58 |
| 140 | | | | SEQ ID NO: 56 | | SEQ ID NO: 58 |
| 141 | SEQ ID NO: 55 | | | SEQ ID NO: 56 | | |
| 142 | SEQ ID NO: 55 | | | SEQ ID NO: 56 | SEQ ID NO: 57 | |
| 143 | SEQ ID NO: 55 | | | SEQ ID NO: 56 | SEQ ID NO: 57 | SEQ ID NO: 58 |
| 144 | SEQ ID NO: 55 | | | | SEQ ID NO: 57 | |
| 145 | SEQ ID NO: 55 | | | | SEQ ID NO: 57 | SEQ ID NO: 58 |
| 146 | SEQ ID NO: 55 | | | | | SEQ ID NO: 58 |
| 147 | SEQ ID NO: 55 | | | SEQ ID NO: 56 | | SEQ ID NO: 58 |
| 148 | SEQ ID NO: 55 | SEQ ID NO: 24 | | SEQ ID NO: 56 | | |
| 149 | SEQ ID NO: 55 | SEQ ID NO: 24 | | SEQ ID NO: 56 | SEQ ID NO: 57 | |
| 150 | SEQ ID NO: 55 | SEQ ID NO: 24 | | SEQ ID NO: 56 | SEQ ID NO: 57 | SEQ ID NO: 58 |
| 151 | SEQ ID NO: 55 | SEQ ID NO: 24 | | | SEQ ID NO: 57 | |
| 152 | SEQ ID NO: 55 | SEQ ID NO: 24 | | | SEQ ID NO: 57 | SEQ ID NO: 58 |
| 153 | SEQ ID NO: 55 | SEQ ID NO: 24 | | | | SEQ ID NO: 58 |
| 154 | SEQ ID NO: 55 | SEQ ID NO: 24 | | SEQ ID NO: 56 | | SEQ ID NO: 58 |
| 155 | SEQ ID NO: 55 | SEQ ID NO: 24 | SEQ ID NO: 25 | SEQ ID NO: 56 | | |
| 156 | SEQ ID NO: 55 | SEQ ID NO: 24 | SEQ ID NO: 25 | SEQ ID NO: 56 | SEQ ID NO: 57 | |
| 157 | SEQ ID NO: 55 | SEQ ID NO: 24 | SEQ ID NO: 25 | SEQ ID NO: 56 | SEQ ID NO: 57 | SEQ ID NO: 58 |
| 158 | SEQ ID NO: 55 | SEQ ID NO: 24 | SEQ ID NO: 25 | | SEQ ID NO: 57 | |
| 159 | SEQ ID NO: 55 | SEQ ID NO: 24 | SEQ ID NO: 25 | | SEQ ID NO: 57 | SEQ ID NO: 58 |
| 160 | SEQ ID NO: 55 | SEQ ID NO: 24 | SEQ ID NO: 25 | SEQ ID NO: 56 | | SEQ ID NO: 58 |
| 161 | SEQ ID NO: 55 | SEQ ID NO: 24 | SEQ ID NO: 25 | | | SEQ ID NO: 58 |
| 162 | | SEQ ID NO: 24 | | SEQ ID NO: 56 | | |
| 163 | | SEQ ID NO: 24 | | SEQ ID NO: 56 | SEQ ID NO: 57 | |
| 164 | | SEQ ID NO: 24 | | SEQ ID NO: 56 | SEQ ID NO: 57 | SEQ ID NO: 58 |
| 165 | | SEQ ID NO: 24 | | | SEQ ID NO: 57 | |
| 166 | | SEQ ID NO: 24 | | | SEQ ID NO: 57 | SEQ ID NO: 58 |
| 167 | | SEQ ID NO: 24 | | | | SEQ ID NO: 58 |
| 168 | | SEQ ID NO: 24 | | SEQ ID NO: 56 | | SEQ ID NO: 58 |
| 169 | | SEQ ID NO: 24 | SEQ ID NO: 25 | SEQ ID NO: 56 | | |
| 170 | | SEQ ID NO: 24 | SEQ ID NO: 25 | SEQ ID NO: 56 | SEQ ID NO: 57 | |
| 171 | | SEQ ID NO: 24 | SEQ ID NO: 25 | SEQ ID NO: 56 | SEQ ID NO: 57 | SEQ ID NO: 58 |
| 172 | | SEQ ID NO: 24 | SEQ ID NO: 25 | | SEQ ID NO: 57 | |
| 173 | | SEQ ID NO: 24 | SEQ ID NO: 25 | | SEQ ID NO: 57 | SEQ ID NO: 58 |
| 174 | | SEQ ID NO: 24 | SEQ ID NO: 25 | | | SEQ ID NO: 58 |
| 175 | | SEQ ID NO: 24 | SEQ ID NO: 25 | SEQ ID NO: 56 | | SEQ ID NO: 58 |
| 176 | | | SEQ ID NO: 25 | SEQ ID NO: 56 | | |
| 177 | | | SEQ ID NO: 25 | SEQ ID NO: 56 | SEQ ID NO: 57 | |
| 178 | | | SEQ ID NO: 25 | SEQ ID NO: 56 | SEQ ID NO: 57 | SEQ ID NO: 58 |
| 179 | | | SEQ ID NO: 25 | | SEQ ID NO: 57 | |
| 180 | | | SEQ ID NO: 25 | | SEQ ID NO: 57 | SEQ ID NO: 58 |
| 181 | | | SEQ ID NO: 25 | | | SEQ ID NO: 58 |
| 182 | | | SEQ ID NO: 25 | SEQ ID NO: 56 | | SEQ ID NO: 58 |
| 183 | SEQ ID NO: 55 | | SEQ ID NO: 25 | SEQ ID NO: 56 | | |
| 184 | SEQ ID NO: 55 | | SEQ ID NO: 25 | SEQ ID NO: 56 | SEQ ID NO: 57 | |
| 185 | SEQ ID NO: 55 | | SEQ ID NO: 25 | SEQ ID NO: 56 | SEQ ID NO: 57 | SEQ ID NO: 58 |
| 186 | SEQ ID NO: 55 | | SEQ ID NO: 25 | | SEQ ID NO: 57 | |
| 187 | SEQ ID NO: 55 | | SEQ ID NO: 25 | | SEQ ID NO: 57 | SEQ ID NO: 58 |
| 188 | SEQ ID NO: 55 | | SEQ ID NO: 25 | | | SEQ ID NO: 58 |
| 189 | SEQ ID NO: 55 | | SEQ ID NO: 25 | SEQ ID NO: 56 | | SEQ ID NO: 58 |
| 190 | SEQ ID NO: 59 | | | | | |
| 191 | SEQ ID NO: 59 | SEQ ID NO: 24 | | | | |
| 192 | SEQ ID NO: 59 | SEQ ID NO: 24 | SEQ ID NO: 25 | | | |
| 193 | | SEQ ID NO: 24 | | | | |
| 194 | | SEQ ID NO: 24 | SEQ ID NO: 25 | | | |
| 195 | | | SEQ ID NO: 25 | | | |
| 196 | SEQ ID NO: 59 | | SEQ ID NO: 25 | | | |
| 197 | | | | SEQ ID NO: 60 | | |
| 198 | | | | SEQ ID NO: 60 | SEQ ID NO: 61 | |
| 199 | | | | SEQ ID NO: 60 | SEQ ID NO: 61 | SEQ ID NO: 62 |
| 200 | | | | | SEQ ID NO: 61 | |
| 201 | | | | | SEQ ID NO: 61 | SEQ ID NO: 62 |

TABLE D-continued

Exemplary Group II Antibodies

| | Light Chain HVR | | | Heavy Chain HVR | | |
|---|---|---|---|---|---|---|
| Antibody | L1 | L2 | L3 | H1 | H2 | H3 |
| 202 | | | | | | SEQ ID NO: 62 |
| 203 | | | | SEQ ID NO: 60 | | SEQ ID NO: 62 |
| 204 | SEQ ID NO: 59 | | | SEQ ID NO: 60 | | |
| 205 | SEQ ID NO: 59 | | | SEQ ID NO: 60 | SEQ ID NO: 61 | |
| 206 | SEQ ID NO: 59 | | | SEQ ID NO: 60 | SEQ ID NO: 61 | SEQ ID NO: 62 |
| 207 | SEQ ID NO: 59 | | | | SEQ ID NO: 61 | |
| 208 | SEQ ID NO: 59 | | | | SEQ ID NO: 61 | SEQ ID NO: 62 |
| 209 | SEQ ID NO: 59 | | | | | SEQ ID NO: 62 |
| 210 | SEQ ID NO: 59 | | | SEQ ID NO: 60 | | SEQ ID NO: 62 |
| 211 | SEQ ID NO: 59 | SEQ ID NO: 24 | | SEQ ID NO: 60 | | |
| 212 | SEQ ID NO: 59 | SEQ ID NO: 24 | | SEQ ID NO: 60 | SEQ ID NO: 61 | |
| 213 | SEQ ID NO: 59 | SEQ ID NO: 24 | | SEQ ID NO: 60 | SEQ ID NO: 61 | SEQ ID NO: 62 |
| 214 | SEQ ID NO: 59 | SEQ ID NO: 24 | | | SEQ ID NO: 61 | |
| 215 | SEQ ID NO: 59 | SEQ ID NO: 24 | | | SEQ ID NO: 61 | SEQ ID NO: 62 |
| 216 | SEQ ID NO: 59 | SEQ ID NO: 24 | | | | SEQ ID NO: 62 |
| 217 | SEQ ID NO: 59 | SEQ ID NO: 24 | | SEQ ID NO: 60 | | SEQ ID NO: 62 |
| 218 | SEQ ID NO: 59 | SEQ ID NO: 24 | SEQ ID NO: 25 | SEQ ID NO: 60 | | |
| 219 | SEQ ID NO: 59 | SEQ ID NO: 24 | SEQ ID NO: 25 | SEQ ID NO: 60 | SEQ ID NO: 61 | |
| 220 | SEQ ID NO: 59 | SEQ ID NO: 24 | SEQ ID NO: 25 | SEQ ID NO: 60 | SEQ ID NO: 61 | SEQ ID NO: 62 |
| 221 | SEQ ID NO: 59 | SEQ ID NO: 24 | SEQ ID NO: 25 | | SEQ ID NO: 61 | |
| 222 | SEQ ID NO: 59 | SEQ ID NO: 24 | SEQ ID NO: 25 | | SEQ ID NO: 61 | SEQ ID NO: 62 |
| 223 | SEQ ID NO: 59 | SEQ ID NO: 24 | SEQ ID NO: 25 | SEQ ID NO: 60 | | SEQ ID NO: 62 |
| 224 | SEQ ID NO: 59 | SEQ ID NO: 24 | SEQ ID NO: 25 | | | SEQ ID NO: 62 |
| 225 | | SEQ ID NO: 24 | | SEQ ID NO: 60 | | |
| 226 | | SEQ ID NO: 24 | | SEQ ID NO: 60 | SEQ ID NO: 61 | |
| 227 | | SEQ ID NO: 24 | | SEQ ID NO: 60 | SEQ ID NO: 61 | SEQ ID NO: 62 |
| 228 | | SEQ ID NO: 24 | | | SEQ ID NO: 61 | |
| 229 | | SEQ ID NO: 24 | | | SEQ ID NO: 61 | SEQ ID NO: 62 |
| 230 | | SEQ ID NO: 24 | | | | SEQ ID NO: 62 |
| 231 | | SEQ ID NO: 24 | | SEQ ID NO: 60 | | SEQ ID NO: 62 |
| 232 | | SEQ ID NO: 24 | SEQ ID NO: 25 | SEQ ID NO: 60 | | |
| 233 | | SEQ ID NO: 24 | SEQ ID NO: 25 | SEQ ID NO: 60 | SEQ ID NO: 61 | |
| 234 | | SEQ ID NO: 24 | SEQ ID NO: 25 | SEQ ID NO: 60 | SEQ ID NO: 61 | SEQ ID NO: 62 |
| 235 | | SEQ ID NO: 24 | SEQ ID NO: 25 | | SEQ ID NO: 61 | |
| 236 | | SEQ ID NO: 24 | SEQ ID NO: 25 | | SEQ ID NO: 61 | SEQ ID NO: 62 |
| 237 | | SEQ ID NO: 24 | SEQ ID NO: 25 | | | SEQ ID NO: 62 |
| 238 | | SEQ ID NO: 24 | SEQ ID NO: 25 | SEQ ID NO: 60 | | SEQ ID NO: 62 |
| 239 | | | SEQ ID NO: 25 | SEQ ID NO: 60 | | |
| 240 | | | SEQ ID NO: 25 | SEQ ID NO: 60 | SEQ ID NO: 61 | |
| 240 | | | SEQ ID NO: 25 | SEQ ID NO: 60 | SEQ ID NO: 61 | SEQ ID NO: 62 |
| 242 | | | SEQ ID NO: 25 | | SEQ ID NO: 61 | |
| 423 | | | SEQ ID NO: 25 | | SEQ ID NO: 61 | SEQ ID NO: 62 |
| 244 | | | SEQ ID NO: 25 | | | SEQ ID NO: 62 |
| 245 | | | SEQ ID NO: 25 | SEQ ID NO: 60 | | SEQ ID NO: 62 |
| 246 | SEQ ID NO: 59 | | SEQ ID NO: 25 | SEQ ID NO: 60 | | |
| 247 | SEQ ID NO: 59 | | SEQ ID NO: 25 | SEQ ID NO: 60 | SEQ ID NO: 61 | |
| 248 | SEQ ID NO: 59 | | SEQ ID NO: 25 | SEQ ID NO: 60 | SEQ ID NO: 61 | SEQ ID NO: 62 |
| 249 | SEQ ID NO: 59 | | SEQ ID NO: 25 | | SEQ ID NO: 61 | |
| 250 | SEQ ID NO: 59 | | SEQ ID NO: 25 | | SEQ ID NO: 61 | SEQ ID NO: 62 |
| 251 | SEQ ID NO: 59 | | SEQ ID NO: 25 | | | SEQ ID NO: 62 |
| 252 | SEQ ID NO: 59 | | SEQ ID NO: 25 | SEQ ID NO: 60 | | SEQ ID NO: 62 |
| 253 | SEQ ID NO: 68 | | | | | |
| 2454 | SEQ ID NO: 68 | SEQ ID NO: 24 | | | | |
| 255 | SEQ ID NO: 68 | SEQ ID NO: 24 | SEQ ID NO: 25 | | | |
| 256 | | SEQ ID NO: 24 | | | | |
| 257 | | SEQ ID NO: 24 | SEQ ID NO: 25 | | | |
| 258 | | | SEQ ID NO: 25 | | | |
| 259 | SEQ ID NO: 68 | | SEQ ID NO: 25 | | | |
| 260 | | | | SEQ ID NO: 69 | | |
| 261 | | | | SEQ ID NO: 69 | SEQ ID NO: 70 | |
| 262 | | | | SEQ ID NO: 69 | SEQ ID NO: 70 | SEQ ID NO: 71 |
| 263 | | | | | SEQ ID NO: 70 | |
| 264 | | | | | SEQ ID NO: 70 | SEQ ID NO: 71 |
| 265 | | | | | | SEQ ID NO: 71 |
| 266 | | | | SEQ ID NO: 69 | | SEQ ID NO: 71 |
| 267 | SEQ ID NO: 68 | | | SEQ ID NO: 69 | | |
| 268 | SEQ ID NO: 68 | | | SEQ ID NO: 69 | SEQ ID NO: 70 | |
| 269 | SEQ ID NO: 68 | | | SEQ ID NO: 69 | SEQ ID NO: 70 | SEQ ID NO: 71 |
| 270 | SEQ ID NO: 68 | | | | SEQ ID NO: 70 | |
| 271 | SEQ ID NO: 68 | | | | SEQ ID NO: 70 | SEQ ID NO: 71 |
| 272 | SEQ ID NO: 68 | | | | | SEQ ID NO: 71 |
| 273 | SEQ ID NO: 68 | | | SEQ ID NO: 69 | | SEQ ID NO: 71 |
| 274 | SEQ ID NO: 68 | SEQ ID NO: 24 | | SEQ ID NO: 69 | | |
| 275 | SEQ ID NO: 68 | SEQ ID NO: 24 | | SEQ ID NO: 69 | SEQ ID NO: 70 | |

TABLE D-continued

Exemplary Group II Antibodies

| Antibody | Light Chain HVR | | | Heavy Chain HVR | | |
|---|---|---|---|---|---|---|
| | L1 | L2 | L3 | H1 | H2 | H3 |
| 276 | SEQ ID NO: 68 | SEQ ID NO: 24 | | SEQ ID NO: 69 | SEQ ID NO: 70 | SEQ ID NO: 71 |
| 277 | SEQ ID NO: 68 | SEQ ID NO: 24 | | | SEQ ID NO: 70 | |
| 278 | SEQ ID NO: 68 | SEQ ID NO: 24 | | | SEQ ID NO: 70 | SEQ ID NO: 71 |
| 279 | SEQ ID NO: 68 | SEQ ID NO: 24 | | | | SEQ ID NO: 71 |
| 280 | SEQ ID NO: 68 | SEQ ID NO: 24 | | SEQ ID NO: 69 | | SEQ ID NO: 71 |
| 281 | SEQ ID NO: 68 | SEQ ID NO: 24 | SEQ ID NO: 25 | SEQ ID NO: 69 | | |
| 282 | SEQ ID NO: 68 | SEQ ID NO: 24 | SEQ ID NO: 25 | SEQ ID NO: 69 | SEQ ID NO: 70 | |
| 283 | SEQ ID NO: 68 | SEQ ID NO: 24 | SEQ ID NO: 25 | SEQ ID NO: 69 | SEQ ID NO: 70 | SEQ ID NO: 71 |
| 284 | SEQ ID NO: 68 | SEQ ID NO: 24 | SEQ ID NO: 25 | | SEQ ID NO: 70 | |
| 285 | SEQ ID NO: 68 | SEQ ID NO: 24 | SEQ ID NO: 25 | | SEQ ID NO: 70 | SEQ ID NO: 71 |
| 286 | SEQ ID NO: 68 | SEQ ID NO: 24 | SEQ ID NO: 25 | SEQ ID NO: 69 | | SEQ ID NO: 71 |
| 287 | SEQ ID NO: 68 | SEQ ID NO: 24 | SEQ ID NO: 25 | | | SEQ ID NO: 71 |
| 288 | | SEQ ID NO: 24 | | SEQ ID NO: 69 | | |
| 289 | | SEQ ID NO: 24 | | SEQ ID NO: 69 | SEQ ID NO: 70 | |
| 290 | | SEQ ID NO: 24 | | SEQ ID NO: 69 | SEQ ID NO: 70 | SEQ ID NO: 71 |
| 291 | | SEQ ID NO: 24 | | | SEQ ID NO: 70 | |
| 292 | | SEQ ID NO: 24 | | | SEQ ID NO: 70 | SEQ ID NO: 71 |
| 293 | | SEQ ID NO: 24 | | | | SEQ ID NO: 71 |
| 294 | | SEQ ID NO: 24 | | SEQ ID NO: 69 | | SEQ ID NO: 71 |
| 295 | | SEQ ID NO: 24 | SEQ ID NO: 25 | SEQ ID NO: 69 | | |
| 296 | | SEQ ID NO: 24 | SEQ ID NO: 25 | SEQ ID NO: 69 | SEQ ID NO: 70 | |
| 297 | | SEQ ID NO: 24 | SEQ ID NO: 25 | SEQ ID NO: 69 | SEQ ID NO: 70 | SEQ ID NO: 71 |
| 298 | | SEQ ID NO: 24 | SEQ ID NO: 25 | | SEQ ID NO: 70 | |
| 299 | | SEQ ID NO: 24 | SEQ ID NO: 25 | | SEQ ID NO: 70 | SEQ ID NO: 71 |
| 300 | | SEQ ID NO: 24 | SEQ ID NO: 25 | | | SEQ ID NO: 71 |
| 301 | | SEQ ID NO: 24 | SEQ ID NO: 25 | SEQ ID NO: 69 | | SEQ ID NO: 71 |
| 302 | | | SEQ ID NO: 25 | SEQ ID NO: 69 | | |
| 303 | | | SEQ ID NO: 25 | SEQ ID NO: 69 | SEQ ID NO: 70 | |
| 304 | | | SEQ ID NO: 25 | SEQ ID NO: 69 | SEQ ID NO: 70 | SEQ ID NO: 71 |
| 305 | | | SEQ ID NO: 25 | | SEQ ID NO: 70 | |
| 306 | | | SEQ ID NO: 25 | | SEQ ID NO: 70 | SEQ ID NO: 71 |
| 307 | | | SEQ ID NO: 25 | | | SEQ ID NO: 71 |
| 308 | | | SEQ ID NO: 25 | SEQ ID NO: 69 | | SEQ ID NO: 71 |
| 309 | SEQ ID NO: 68 | | SEQ ID NO: 25 | SEQ ID NO: 69 | | |
| 310 | SEQ ID NO: 68 | | SEQ ID NO: 25 | SEQ ID NO: 69 | SEQ ID NO: 70 | |
| 311 | SEQ ID NO: 68 | | SEQ ID NO: 25 | SEQ ID NO: 69 | SEQ ID NO: 70 | SEQ ID NO: 71 |
| 312 | SEQ ID NO: 68 | | SEQ ID NO: 25 | | SEQ ID NO: 70 | |
| 313 | SEQ ID NO: 68 | | SEQ ID NO: 25 | | SEQ ID NO: 70 | SEQ ID NO: 71 |
| 314 | SEQ ID NO: 68 | | SEQ ID NO: 25 | | | SEQ ID NO: 71 |
| 315 | SEQ ID NO: 68 | | SEQ ID NO: 25 | SEQ ID NO: 69 | | SEQ ID NO: 71 |

(c) Group III: Anti-ApoE Antibodies that do not Preferentially Bind ApoE4, ApoE3 or ApoE2

In another aspect, an anti-ApoE antibody has a heavy chain variable region comprising SEQ ID NO: 113. In some embodiments, the heavy chain variable region further comprises SEQ ID NO: 109 and/or SEQ ID NO: 111. In other embodiments, the heavy chain variable region further comprises SEQ ID NO: 110 and/or SEQ ID NO: 112. In certain of the above embodiments, the antibody has a light chain variable region comprising SEQ ID NO: 107. The light chain variable region can further comprise (a) SEQ ID NO: 105; and/or (b) SEQ ID NO: 106.

In another aspect, an anti-ApoE antibody has a heavy chain variable region comprising SEQ ID NO: 114. In some embodiments, the heavy chain variable region further comprises SEQ ID NO: 109 and/or SEQ ID NO: 111. In other embodiments, the heavy chain variable region further comprises SEQ ID NO: 110 and/or SEQ ID NO: 112. In certain of the above embodiments, the antibody has a light chain variable region comprising SEQ ID NO: 108. The light chain variable region can further comprise (a) SEQ ID NO: 105; and/or (b) SEQ ID NO: 106.

In another aspect, an anti-ApoE antibody is selected from Table E.

TABLE E

Group III Antibodies

| Antibody | Light Chain HVR | | | Heavy Chain HVR | | |
|---|---|---|---|---|---|---|
| | L1 | L2 | L3 | H1 | H2 | H3 |
| 1 | SEQ ID NO: 105 | | | | | |
| 2 | SEQ ID NO: 105 | SEQ ID NO: 106 | | | | |
| 3 | SEQ ID NO: 105 | SEQ ID NO: 106 | SEQ ID NO: 107 | | | |
| 4 | | SEQ ID NO: 106 | | | | |
| 5 | | SEQ ID NO: 106 | SEQ ID NO: 107 | | | |
| 6 | | | SEQ ID NO: 107 | | | |
| 7 | SEQ ID NO: 105 | | SEQ ID NO: 107 | | | |

TABLE E-continued

Group III Antibodies

| | Light Chain HVR | | | Heavy Chain HVR | | |
|---|---|---|---|---|---|---|
| Antibody | L1 | L2 | L3 | H1 | H2 | H3 |
| 8 | | | | SEQ ID NO: 109 | | |
| 9 | | | | SEQ ID NO: 109 | SEQ ID NO: 111 | |
| 10 | | | | SEQ ID NO: 109 | SEQ ID NO: 111 | SEQ ID NO: 113 |
| 11 | | | | | SEQ ID NO: 111 | |
| 12 | | | | | SEQ ID NO: 111 | SEQ ID NO: 113 |
| 13 | | | | | | SEQ ID NO: 113 |
| 14 | | | | SEQ ID NO: 109 | | SEQ ID NO: 113 |
| 15 | SEQ ID NO: 105 | | | SEQ ID NO: 109 | | |
| 16 | SEQ ID NO: 105 | | | SEQ ID NO: 109 | SEQ ID NO: 111 | |
| 17 | SEQ ID NO: 105 | | | SEQ ID NO: 109 | SEQ ID NO: 111 | SEQ ID NO: 113 |
| 18 | SEQ ID NO: 105 | | | | SEQ ID NO: 111 | |
| 19 | SEQ ID NO: 105 | | | | SEQ ID NO: 111 | SEQ ID NO: 113 |
| 20 | SEQ ID NO: 105 | | | | | SEQ ID NO: 113 |
| 21 | SEQ ID NO: 105 | | | SEQ ID NO: 109 | | SEQ ID NO: 113 |
| 22 | SEQ ID NO: 105 | SEQ ID NO: 106 | | SEQ ID NO: 109 | | |
| 23 | SEQ ID NO: 105 | SEQ ID NO: 106 | | SEQ ID NO: 109 | SEQ ID NO: 111 | |
| 24 | SEQ ID NO: 105 | SEQ ID NO: 106 | | SEQ ID NO: 109 | SEQ ID NO: 111 | SEQ ID NO: 113 |
| 25 | SEQ ID NO: 105 | SEQ ID NO: 106 | | | SEQ ID NO: 111 | |
| 26 | SEQ ID NO: 105 | SEQ ID NO: 106 | | | SEQ ID NO: 111 | SEQ ID NO: 113 |
| 27 | SEQ ID NO: 105 | SEQ ID NO: 106 | | | | SEQ ID NO: 113 |
| 28 | SEQ ID NO: 105 | SEQ ID NO: 106 | | SEQ ID NO: 109 | | SEQ ID NO: 113 |
| 29 | SEQ ID NO: 105 | SEQ ID NO: 106 | SEQ ID NO: 107 | SEQ ID NO: 109 | | |
| 30 | SEQ ID NO: 105 | SEQ ID NO: 106 | SEQ ID NO: 107 | SEQ ID NO: 109 | SEQ ID NO: 111 | |
| 31 | SEQ ID NO: 105 | SEQ ID NO: 106 | SEQ ID NO: 107 | SEQ ID NO: 109 | SEQ ID NO: 111 | SEQ ID NO: 113 |
| 32 | SEQ ID NO: 105 | SEQ ID NO: 106 | SEQ ID NO: 107 | | SEQ ID NO: 111 | |
| 33 | SEQ ID NO: 105 | SEQ ID NO: 106 | SEQ ID NO: 107 | | SEQ ID NO: 111 | SEQ ID NO: 113 |
| 34 | SEQ ID NO: 105 | SEQ ID NO: 106 | SEQ ID NO: 107 | SEQ ID NO: 109 | | SEQ ID NO: 113 |
| 35 | SEQ ID NO: 105 | SEQ ID NO: 106 | SEQ ID NO: 107 | | | SEQ ID NO: 113 |
| 36 | | SEQ ID NO: 106 | | SEQ ID NO: 109 | | |
| 37 | | SEQ ID NO: 106 | | SEQ ID NO: 109 | SEQ ID NO: 111 | |
| 38 | | SEQ ID NO: 106 | | SEQ ID NO: 109 | SEQ ID NO: 111 | SEQ ID NO: 113 |
| 39 | | SEQ ID NO: 106 | | | SEQ ID NO: 111 | |
| 40 | | SEQ ID NO: 106 | | | SEQ ID NO: 111 | SEQ ID NO: 113 |
| 41 | | SEQ ID NO: 106 | | | | SEQ ID NO: 113 |
| 42 | | SEQ ID NO: 106 | | SEQ ID NO: 109 | | SEQ ID NO: 113 |
| 43 | | SEQ ID NO: 106 | SEQ ID NO: 107 | SEQ ID NO: 109 | | |
| 44 | | SEQ ID NO: 106 | SEQ ID NO: 107 | SEQ ID NO: 109 | SEQ ID NO: 111 | |
| 45 | | SEQ ID NO: 106 | SEQ ID NO: 107 | SEQ ID NO: 109 | SEQ ID NO: 111 | SEQ ID NO: 113 |
| 46 | | SEQ ID NO: 106 | SEQ ID NO: 107 | | SEQ ID NO: 111 | |
| 47 | | SEQ ID NO: 106 | SEQ ID NO: 107 | | SEQ ID NO: 111 | SEQ ID NO: 113 |
| 48 | | SEQ ID NO: 106 | SEQ ID NO: 107 | | | SEQ ID NO: 113 |
| 49 | | SEQ ID NO: 106 | SEQ ID NO: 107 | SEQ ID NO: 109 | | SEQ ID NO: 113 |
| 50 | | | SEQ ID NO: 107 | SEQ ID NO: 109 | | |
| 51 | | | SEQ ID NO: 107 | SEQ ID NO: 109 | SEQ ID NO: 111 | |
| 52 | | | SEQ ID NO: 107 | SEQ ID NO: 109 | SEQ ID NO: 111 | SEQ ID NO: 113 |
| 53 | | | SEQ ID NO: 107 | | SEQ ID NO: 111 | |
| 54 | | | SEQ ID NO: 107 | | SEQ ID NO: 111 | SEQ ID NO: 113 |
| 55 | | | SEQ ID NO: 107 | | | SEQ ID NO: 113 |
| 56 | | | SEQ ID NO: 107 | SEQ ID NO: 109 | | SEQ ID NO: 113 |
| 57 | SEQ ID NO: 105 | | SEQ ID NO: 107 | SEQ ID NO: 109 | | |
| 58 | SEQ ID NO: 105 | | SEQ ID NO: 107 | SEQ ID NO: 109 | SEQ ID NO: 111 | |
| 59 | SEQ ID NO: 105 | | SEQ ID NO: 107 | SEQ ID NO: 109 | SEQ ID NO: 111 | SEQ ID NO: 113 |
| 60 | SEQ ID NO: 105 | | SEQ ID NO: 107 | | SEQ ID NO: 111 | |
| 61 | SEQ ID NO: 105 | | SEQ ID NO: 107 | | SEQ ID NO: 111 | SEQ ID NO: 113 |
| 62 | SEQ ID NO: 105 | | SEQ ID NO: 107 | | | SEQ ID NO: 113 |
| 63 | SEQ ID NO: 105 | | SEQ ID NO: 107 | SEQ ID NO: 109 | | SEQ ID NO: 113 |
| 64 | SEQ ID NO: 105 | | | | | |
| 65 | SEQ ID NO: 105 | SEQ ID NO: 106 | | | | |
| 66 | SEQ ID NO: 105 | SEQ ID NO: 106 | SEQ ID NO: 108 | | | |
| 67 | | SEQ ID NO: 106 | | | | |
| 68 | | SEQ ID NO: 106 | SEQ ID NO: 108 | | | |
| 69 | | | SEQ ID NO: 108 | | | |
| 70 | SEQ ID NO: 105 | | SEQ ID NO: 108 | | | |
| 71 | | | | SEQ ID NO: 110 | | |
| 72 | | | | SEQ ID NO: 110 | SEQ ID NO: 112 | |
| 73 | | | | SEQ ID NO: 110 | SEQ ID NO: 112 | SEQ ID NO: 114 |
| 74 | | | | | SEQ ID NO: 112 | |
| 75 | | | | | SEQ ID NO: 112 | SEQ ID NO: 114 |
| 76 | | | | | | SEQ ID NO: 114 |
| 77 | | | | SEQ ID NO: 110 | | SEQ ID NO: 114 |
| 78 | SEQ ID NO: 105 | | | SEQ ID NO: 110 | | |
| 79 | SEQ ID NO: 105 | | | SEQ ID NO: 110 | SEQ ID NO: 112 | |
| 80 | SEQ ID NO: 105 | | | SEQ ID NO: 110 | SEQ ID NO: 112 | SEQ ID NO: 114 |
| 81 | SEQ ID NO: 105 | | | | SEQ ID NO: 112 | |

TABLE E-continued

Group III Antibodies

| | Light Chain HVR | | | Heavy Chain HVR | | |
|---|---|---|---|---|---|---|
| Antibody | L1 | L2 | L3 | H1 | H2 | H3 |
| 82 | SEQ ID NO: 105 | | | | SEQ ID NO: 112 | SEQ ID NO: 114 |
| 83 | SEQ ID NO: 105 | | | | | SEQ ID NO: 114 |
| 84 | SEQ ID NO: 105 | | | SEQ ID NO: 110 | | SEQ ID NO: 114 |
| 85 | SEQ ID NO: 105 | SEQ ID NO: 106 | | SEQ ID NO: 110 | | |
| 86 | SEQ ID NO: 105 | SEQ ID NO: 106 | | SEQ ID NO: 110 | SEQ ID NO: 112 | |
| 87 | SEQ ID NO: 105 | SEQ ID NO: 106 | | SEQ ID NO: 110 | SEQ ID NO: 112 | SEQ ID NO: 114 |
| 88 | SEQ ID NO: 105 | SEQ ID NO: 106 | | | SEQ ID NO: 112 | |
| 89 | SEQ ID NO: 105 | SEQ ID NO: 106 | | | SEQ ID NO: 112 | SEQ ID NO: 114 |
| 90 | SEQ ID NO: 105 | SEQ ID NO: 106 | | | | SEQ ID NO: 114 |
| 91 | SEQ ID NO: 105 | SEQ ID NO: 106 | | SEQ ID NO: 110 | | SEQ ID NO: 114 |
| 92 | SEQ ID NO: 105 | SEQ ID NO: 106 | SEQ ID NO: 108 | SEQ ID NO: 110 | | |
| 93 | SEQ ID NO: 105 | SEQ ID NO: 106 | SEQ ID NO: 108 | SEQ ID NO: 110 | SEQ ID NO: 112 | |
| 94 | SEQ ID NO: 105 | SEQ ID NO: 106 | SEQ ID NO: 108 | SEQ ID NO: 110 | SEQ ID NO: 112 | SEQ ID NO: 114 |
| 95 | SEQ ID NO: 105 | SEQ ID NO: 106 | SEQ ID NO: 108 | | SEQ ID NO: 112 | |
| 96 | SEQ ID NO: 105 | SEQ ID NO: 106 | SEQ ID NO: 108 | | SEQ ID NO: 112 | SEQ ID NO: 114 |
| 97 | SEQ ID NO: 105 | SEQ ID NO: 106 | SEQ ID NO: 108 | | | SEQ ID NO: 114 |
| 98 | SEQ ID NO: 105 | SEQ ID NO: 106 | SEQ ID NO: 108 | SEQ ID NO: 110 | | SEQ ID NO: 114 |
| 99 | | SEQ ID NO: 106 | | SEQ ID NO: 110 | | |
| 100 | | SEQ ID NO: 106 | | SEQ ID NO: 110 | SEQ ID NO: 112 | |
| 101 | | SEQ ID NO: 106 | | SEQ ID NO: 110 | SEQ ID NO: 112 | SEQ ID NO: 114 |
| 102 | | SEQ ID NO: 106 | | | SEQ ID NO: 112 | |
| 103 | | SEQ ID NO: 106 | | | SEQ ID NO: 112 | SEQ ID NO: 114 |
| 104 | | SEQ ID NO: 106 | | | | SEQ ID NO: 114 |
| 105 | | SEQ ID NO: 106 | | SEQ ID NO: 110 | | SEQ ID NO: 114 |
| 106 | | SEQ ID NO: 106 | SEQ ID NO: 108 | SEQ ID NO: 110 | | |
| 107 | | SEQ ID NO: 106 | SEQ ID NO: 108 | SEQ ID NO: 110 | SEQ ID NO: 112 | |
| 108 | | SEQ ID NO: 106 | SEQ ID NO: 108 | SEQ ID NO: 110 | SEQ ID NO: 112 | SEQ ID NO: 114 |
| 109 | | SEQ ID NO: 106 | SEQ ID NO: 108 | | SEQ ID NO: 112 | |
| 110 | | SEQ ID NO: 106 | SEQ ID NO: 108 | | SEQ ID NO: 112 | SEQ ID NO: 114 |
| 111 | | SEQ ID NO: 106 | SEQ ID NO: 108 | | | SEQ ID NO: 114 |
| 112 | | SEQ ID NO: 106 | SEQ ID NO: 108 | SEQ ID NO: 110 | | SEQ ID NO: 114 |
| 113 | | | SEQ ID NO: 108 | SEQ ID NO: 110 | | |
| 114 | | | SEQ ID NO: 108 | SEQ ID NO: 110 | SEQ ID NO: 112 | |
| 115 | | | SEQ ID NO: 108 | SEQ ID NO: 110 | SEQ ID NO: 112 | SEQ ID NO: 114 |
| 116 | | | SEQ ID NO: 108 | | SEQ ID NO: 112 | |
| 117 | | | SEQ ID NO: 108 | | SEQ ID NO: 112 | SEQ ID NO: 114 |
| 118 | | | SEQ ID NO: 108 | | | SEQ ID NO: 114 |
| 119 | | | SEQ ID NO: 108 | SEQ ID NO: 110 | | SEQ ID NO: 114 |
| 120 | SEQ ID NO: 105 | | SEQ ID NO: 108 | SEQ ID NO: 110 | | |
| 121 | SEQ ID NO: 105 | | SEQ ID NO: 108 | SEQ ID NO: 110 | SEQ ID NO: 112 | |
| 122 | SEQ ID NO: 105 | | SEQ ID NO: 108 | SEQ ID NO: 110 | SEQ ID NO: 112 | SEQ ID NO: 114 |
| 123 | SEQ ID NO: 105 | | SEQ ID NO: 108 | | SEQ ID NO: 112 | |
| 124 | SEQ ID NO: 105 | | SEQ ID NO: 108 | | SEQ ID NO: 112 | SEQ ID NO: 114 |
| 125 | SEQ ID NO: 105 | | SEQ ID NO: 108 | | | SEQ ID NO: 114 |
| 126 | SEQ ID NO: 105 | | SEQ ID NO: 108 | SEQ ID NO: 110 | | SEQ ID NO: 114 |

In an exemplary embodiment, an anti-ApoE antibody of this group comprises a VL that has one or more HVRs derived from SEQ ID NO: 115 or a VH that has one or more HVRs derived from SEQ ID NO: 116. The HVR derived from SEQ ID NO: 115 may be L1, L2, L3, or any combination thereof. In certain embodiments, the VL may comprise an L1 of SEQ ID NO: 105, an L2 of SEQ ID NO: 106, an L3 of SEQ ID NO: 117, or any combination thereof (e.g. antibodies 1-7 in Table F). The HVR derived from SEQ ID NO: 116 may be H1, H2, H3, or any combination thereof. In certain embodiments, the VH may comprise an H1 of SEQ ID NO: 118, an H2 of SEQ ID NO: 119, an H3 of SEQ ID NO: 120, or any combination thereof (e.g. antibodies 8-14 in Table F). The antibody comprising one or more HVRs derived from SEQ ID NO: 116 may further comprise a light chain variable region (VL) comprising one or more HVRs derived from SEQ ID NO: 115. The HVR may be L1, L2, L3, or any combination thereof. In a preferred embodiment, the VL may comprise an L1 of SEQ ID NO: 105, an L2 of SEQ ID NO: 106, an L3 of SEQ ID NO: 117, or any combination thereof (e.g. antibodies 15-63 in Table F). In various embodiments above, the antibody may be a humanized antibody, or the antibody may have a VL with 90, 91, 92, 93, 94, 95, 96, 97, 98, 99, or 100% identity to SEQ ID NO: 115 and/or a VH with 90, 91, 92, 93, 94, 95, 96, 97, 98, 99 or 100% identity to SEQ ID NO: 116. In each of the above embodiments, the anti-ApoE antibody may optionally comprise one or more constant regions, or a portion of a constant region, that is substantially human (i.e. at least 85%, 90%, 95%, or 99% sequence identity with a known human framework sequence). The present disclosure also encompasses the corresponding nucleic acid sequences of SEQ ID NO: 115, 116, 105, 106, 117, 118, 119, and 120, which can readily be determined by one of skill in the art, and may be incorporated into a vector or other large DNA molecule, such as a chromosome, in order to express an antibody of the disclosure.

In another exemplary embodiment, an anti-ApoE antibody of this group comprises a VL that has one or more HVRs derived from SEQ ID NO: 121 or a VH that has one or more HVRs derived from SEQ ID NO: 122. The HVR derived from SEQ ID NO: 121 may be L1, L2, L3, or any combination thereof. In certain embodiments, the VL may comprise an L1 of SEQ ID NO: 105, an L2 of SEQ ID NO:

106, an L3 of SEQ ID NO: 123, or any combination thereof (e.g. antibodies 64-70 in Table F). The HVR derived from SEQ ID NO: 122 may be H1, H2, H3, or any combination thereof. In certain embodiments, the VH may comprise an H1 of SEQ ID NO: 124, an H2 of SEQ ID NO: 125, an H3 of SEQ ID NO: 126, or any combination thereof (e.g. antibodies 71-77 in Table F). The antibody comprising one or more HVRs derived from SEQ ID NO: 122 may further comprise a light chain variable region (VL) comprising one or more HVRs derived from SEQ ID NO: 121. The HVR may be L1, L2, L3, or any combination thereof. In a preferred embodiment, the VL may comprise an L1 of SEQ ID NO: 105, an L2 of SEQ ID NO: 106, an L3 of SEQ ID NO: 123, or any combination thereof (e.g. antibodies 78-126 in Table F). In various embodiments above, the antibody may be a humanized antibody, or the antibody may have a VL with 90, 91, 92, 93, 94, 95, 96, 97, 98, 99, or 100% identity to SEQ ID NO: 121 and/or a VH with 90, 91, 92, 93, 94, 95, 96, 97, 98, 99 or 100% identity to SEQ ID NO: 122. In each of the above embodiments, the anti-ApoE antibody may optionally comprise one or more constant regions, or a portion of a constant region, that is substantially human (i.e. at least 85%, 90%, 95%, or 99% sequence identity with a known human framework sequence). The present disclosure also encompasses the corresponding nucleic acid sequences of SEQ ID NO: 121, 122, 105, 106, 123, 124, 125, and 126, which can readily be determined by one of skill in the art, and may be incorporated into a vector or other large DNA molecule, such as a chromosome, in order to express an antibody of the disclosure.

In some embodiments, each of the exemplary antibodies described above may also contain a variant Fc region, including but not limited to a variant Fc region that is modified to alter the natural interaction with the microglia FcR.

In further embodiments, an isolated antibody of Group III recognizes an epitope listed in Tables 4-7.

TABLE F

Exemplary Group III Antibodies

| Antibody | Light Chain HVR | | | Heavy Chain HVR | | |
|---|---|---|---|---|---|---|
| | L1 | L2 | L3 | H1 | H2 | H3 |
| 1 | SEQ ID NO: 105 | | | | | |
| 2 | SEQ ID NO: 105 | SEQ ID NO: 106 | | | | |
| 3 | SEQ ID NO: 105 | SEQ ID NO: 106 | SEQ ID NO: 117 | | | |
| 4 | | SEQ ID NO: 106 | | | | |
| 5 | | SEQ ID NO: 106 | SEQ ID NO: 117 | | | |
| 6 | | | SEQ ID NO: 117 | | | |
| 7 | SEQ ID NO: 105 | | SEQ ID NO: 117 | | | |
| 8 | | | | SEQ ID NO: 118 | | |
| 9 | | | | SEQ ID NO: 118 | SEQ ID NO: 119 | |
| 10 | | | | SEQ ID NO: 118 | SEQ ID NO: 119 | SEQ ID NO: 120 |
| 11 | | | | | SEQ ID NO: 119 | |
| 12 | | | | | SEQ ID NO: 119 | SEQ ID NO: 120 |
| 13 | | | | | | SEQ ID NO: 120 |
| 14 | | | | SEQ ID NO: 118 | | SEQ ID NO: 120 |
| 15 | SEQ ID NO: 105 | | | SEQ ID NO: 118 | | |
| 16 | SEQ ID NO: 105 | | | SEQ ID NO: 118 | SEQ ID NO: 119 | |
| 17 | SEQ ID NO: 105 | | | SEQ ID NO: 118 | SEQ ID NO: 119 | SEQ ID NO: 120 |
| 18 | SEQ ID NO: 105 | | | | SEQ ID NO: 119 | |
| 19 | SEQ ID NO: 105 | | | | SEQ ID NO: 119 | SEQ ID NO: 120 |
| 20 | SEQ ID NO: 105 | | | | | SEQ ID NO: 120 |
| 21 | SEQ ID NO: 105 | | | SEQ ID NO: 118 | | SEQ ID NO: 120 |
| 22 | SEQ ID NO: 105 | SEQ ID NO: 106 | | SEQ ID NO: 118 | | |
| 23 | SEQ ID NO: 105 | SEQ ID NO: 106 | | SEQ ID NO: 118 | SEQ ID NO: 119 | |
| 24 | SEQ ID NO: 105 | SEQ ID NO: 106 | | SEQ ID NO: 118 | SEQ ID NO: 119 | SEQ ID NO: 120 |
| 25 | SEQ ID NO: 105 | SEQ ID NO: 106 | | | SEQ ID NO: 119 | |
| 26 | SEQ ID NO: 105 | SEQ ID NO: 106 | | | SEQ ID NO: 119 | SEQ ID NO: 120 |
| 27 | SEQ ID NO: 105 | SEQ ID NO: 106 | | | | SEQ ID NO: 120 |
| 28 | SEQ ID NO: 105 | SEQ ID NO: 106 | | SEQ ID NO: 118 | | SEQ ID NO: 120 |
| 29 | SEQ ID NO: 105 | SEQ ID NO: 106 | SEQ ID NO: 117 | SEQ ID NO: 118 | | |
| 30 | SEQ ID NO: 105 | SEQ ID NO: 106 | SEQ ID NO: 117 | SEQ ID NO: 118 | SEQ ID NO: 119 | |
| 31 | SEQ ID NO: 105 | SEQ ID NO: 106 | SEQ ID NO: 117 | SEQ ID NO: 118 | SEQ ID NO: 119 | SEQ ID NO: 120 |
| 32 | SEQ ID NO: 105 | SEQ ID NO: 106 | SEQ ID NO: 117 | | SEQ ID NO: 119 | |
| 33 | SEQ ID NO: 105 | SEQ ID NO: 106 | SEQ ID NO: 117 | | SEQ ID NO: 119 | SEQ ID NO: 120 |
| 34 | SEQ ID NO: 105 | SEQ ID NO: 106 | SEQ ID NO: 117 | SEQ ID NO: 118 | | SEQ ID NO: 120 |
| 35 | SEQ ID NO: 105 | SEQ ID NO: 106 | SEQ ID NO: 117 | | | SEQ ID NO: 120 |
| 36 | | SEQ ID NO: 106 | | SEQ ID NO: 118 | | |
| 37 | | SEQ ID NO: 106 | | SEQ ID NO: 118 | SEQ ID NO: 119 | |
| 38 | | SEQ ID NO: 106 | | SEQ ID NO: 118 | SEQ ID NO: 119 | SEQ ID NO: 120 |
| 39 | | SEQ ID NO: 106 | | | SEQ ID NO: 119 | |
| 40 | | SEQ ID NO: 106 | | | SEQ ID NO: 119 | SEQ ID NO: 120 |
| 41 | | SEQ ID NO: 106 | | | | SEQ ID NO: 120 |
| 42 | | SEQ ID NO: 106 | | SEQ ID NO: 118 | | SEQ ID NO: 120 |
| 43 | | SEQ ID NO: 106 | SEQ ID NO: 117 | SEQ ID NO: 118 | | |
| 44 | | SEQ ID NO: 106 | SEQ ID NO: 117 | SEQ ID NO: 118 | SEQ ID NO: 119 | |
| 45 | | SEQ ID NO: 106 | SEQ ID NO: 117 | SEQ ID NO: 118 | SEQ ID NO: 119 | SEQ ID NO: 120 |
| 46 | | SEQ ID NO: 106 | SEQ ID NO: 117 | | SEQ ID NO: 119 | |
| 47 | | SEQ ID NO: 106 | SEQ ID NO: 117 | | SEQ ID NO: 119 | SEQ ID NO: 120 |
| 48 | | SEQ ID NO: 106 | SEQ ID NO: 117 | | | SEQ ID NO: 120 |
| 49 | | SEQ ID NO: 106 | SEQ ID NO: 117 | SEQ ID NO: 118 | | SEQ ID NO: 120 |
| 50 | | | SEQ ID NO: 117 | SEQ ID NO: 118 | | |

TABLE F-continued

Exemplary Group III Antibodies

| | Light Chain HVR | | | Heavy Chain HVR | | |
|---|---|---|---|---|---|---|
| Antibody | L1 | L2 | L3 | H1 | H2 | H3 |
| 51 | | | SEQ ID NO: 117 | SEQ ID NO: 118 | SEQ ID NO: 119 | |
| 52 | | | SEQ ID NO: 117 | SEQ ID NO: 118 | SEQ ID NO: 119 | SEQ ID NO: 120 |
| 53 | | | SEQ ID NO: 117 | | SEQ ID NO: 119 | |
| 54 | | | SEQ ID NO: 117 | | SEQ ID NO: 119 | SEQ ID NO: 120 |
| 55 | | | SEQ ID NO: 117 | | | SEQ ID NO: 120 |
| 56 | | | SEQ ID NO: 117 | SEQ ID NO: 118 | | SEQ ID NO: 120 |
| 57 | SEQ ID NO: 105 | | SEQ ID NO: 117 | SEQ ID NO: 118 | | |
| 58 | SEQ ID NO: 105 | | SEQ ID NO: 117 | SEQ ID NO: 118 | SEQ ID NO: 119 | |
| 59 | SEQ ID NO: 105 | | SEQ ID NO: 117 | SEQ ID NO: 118 | SEQ ID NO: 119 | SEQ ID NO: 120 |
| 60 | SEQ ID NO: 105 | | SEQ ID NO: 117 | | SEQ ID NO: 119 | |
| 61 | SEQ ID NO: 105 | | SEQ ID NO: 117 | | SEQ ID NO: 119 | SEQ ID NO: 120 |
| 62 | SEQ ID NO: 105 | | SEQ ID NO: 117 | | | SEQ ID NO: 120 |
| 63 | SEQ ID NO: 105 | | SEQ ID NO: 117 | SEQ ID NO: 118 | | SEQ ID NO: 120 |
| 64 | SEQ ID NO: 105 | | | | | |
| 65 | SEQ ID NO: 105 | SEQ ID NO: 106 | | | | |
| 66 | SEQ ID NO: 105 | SEQ ID NO: 106 | SEQ ID NO: 123 | | | |
| 67 | | SEQ ID NO: 106 | | | | |
| 68 | | SEQ ID NO: 106 | SEQ ID NO: 123 | | | |
| 69 | | | SEQ ID NO: 123 | | | |
| 70 | SEQ ID NO: 105 | | SEQ ID NO: 123 | | | |
| 71 | | | | SEQ ID NO: 124 | | |
| 72 | | | | SEQ ID NO: 124 | SEQ ID NO: 125 | |
| 73 | | | | SEQ ID NO: 124 | SEQ ID NO: 125 | SEQ ID NO: 126 |
| 74 | | | | | SEQ ID NO: 125 | |
| 75 | | | | | SEQ ID NO: 125 | SEQ ID NO: 126 |
| 76 | | | | | | SEQ ID NO: 126 |
| 77 | | | | SEQ ID NO: 124 | | SEQ ID NO: 126 |
| 78 | SEQ ID NO: 105 | | | SEQ ID NO: 124 | | |
| 79 | SEQ ID NO: 105 | | | SEQ ID NO: 124 | SEQ ID NO: 125 | |
| 80 | SEQ ID NO: 105 | | | SEQ ID NO: 124 | SEQ ID NO: 125 | SEQ ID NO: 126 |
| 81 | SEQ ID NO: 105 | | | | SEQ ID NO: 125 | |
| 82 | SEQ ID NO: 105 | | | | SEQ ID NO: 125 | SEQ ID NO: 126 |
| 83 | SEQ ID NO: 105 | | | | | SEQ ID NO: 126 |
| 84 | SEQ ID NO: 105 | | | SEQ ID NO: 124 | | SEQ ID NO: 126 |
| 85 | SEQ ID NO: 105 | SEQ ID NO: 106 | | SEQ ID NO: 124 | | |
| 86 | SEQ ID NO: 105 | SEQ ID NO: 106 | | SEQ ID NO: 124 | SEQ ID NO: 125 | |
| 87 | SEQ ID NO: 105 | SEQ ID NO: 106 | | SEQ ID NO: 124 | SEQ ID NO: 125 | SEQ ID NO: 126 |
| 88 | SEQ ID NO: 105 | SEQ ID NO: 106 | | | SEQ ID NO: 125 | |
| 89 | SEQ ID NO: 105 | SEQ ID NO: 106 | | | SEQ ID NO: 125 | SEQ ID NO: 126 |
| 90 | SEQ ID NO: 105 | SEQ ID NO: 106 | | | | SEQ ID NO: 126 |
| 91 | SEQ ID NO: 105 | SEQ ID NO: 106 | | SEQ ID NO: 124 | | SEQ ID NO: 126 |
| 92 | SEQ ID NO: 105 | SEQ ID NO: 106 | SEQ ID NO: 123 | SEQ ID NO: 124 | | |
| 93 | SEQ ID NO: 105 | SEQ ID NO: 106 | SEQ ID NO: 123 | SEQ ID NO: 124 | SEQ ID NO: 125 | |
| 94 | SEQ ID NO: 105 | SEQ ID NO: 106 | SEQ ID NO: 123 | SEQ ID NO: 124 | SEQ ID NO: 125 | SEQ ID NO: 126 |
| 95 | SEQ ID NO: 105 | SEQ ID NO: 106 | SEQ ID NO: 123 | | SEQ ID NO: 125 | |
| 96 | SEQ ID NO: 105 | SEQ ID NO: 106 | SEQ ID NO: 123 | | SEQ ID NO: 125 | SEQ ID NO: 126 |
| 97 | SEQ ID NO: 105 | SEQ ID NO: 106 | SEQ ID NO: 123 | | | SEQ ID NO: 126 |
| 98 | SEQ ID NO: 105 | SEQ ID NO: 106 | SEQ ID NO: 123 | SEQ ID NO: 124 | | SEQ ID NO: 126 |
| 99 | | SEQ ID NO: 106 | | SEQ ID NO: 124 | | |
| 100 | | SEQ ID NO: 106 | | SEQ ID NO: 124 | SEQ ID NO: 125 | |
| 101 | | SEQ ID NO: 106 | | SEQ ID NO: 124 | SEQ ID NO: 125 | SEQ ID NO: 126 |
| 102 | | SEQ ID NO: 106 | | | SEQ ID NO: 125 | |
| 103 | | SEQ ID NO: 106 | | | SEQ ID NO: 125 | SEQ ID NO: 126 |
| 104 | | SEQ ID NO: 106 | | | | SEQ ID NO: 126 |
| 105 | | SEQ ID NO: 106 | | SEQ ID NO: 124 | | SEQ ID NO: 126 |
| 106 | | SEQ ID NO: 106 | SEQ ID NO: 123 | SEQ ID NO: 124 | | |
| 107 | | SEQ ID NO: 106 | SEQ ID NO: 123 | SEQ ID NO: 124 | SEQ ID NO: 125 | |
| 108 | | SEQ ID NO: 106 | SEQ ID NO: 123 | SEQ ID NO: 124 | SEQ ID NO: 125 | SEQ ID NO: 126 |
| 109 | | SEQ ID NO: 106 | SEQ ID NO: 123 | | SEQ ID NO: 125 | |
| 110 | | SEQ ID NO: 106 | SEQ ID NO: 123 | | SEQ ID NO: 125 | SEQ ID NO: 126 |
| 111 | | SEQ ID NO: 106 | SEQ ID NO: 123 | | | SEQ ID NO: 126 |
| 112 | | SEQ ID NO: 106 | SEQ ID NO: 123 | SEQ ID NO: 124 | | SEQ ID NO: 126 |
| 113 | | | SEQ ID NO: 123 | SEQ ID NO: 124 | | |
| 114 | | | SEQ ID NO: 123 | SEQ ID NO: 124 | SEQ ID NO: 125 | |
| 115 | | | SEQ ID NO: 123 | SEQ ID NO: 124 | SEQ ID NO: 125 | SEQ ID NO: 126 |
| 116 | | | SEQ ID NO: 123 | | SEQ ID NO: 125 | |
| 117 | | | SEQ ID NO: 123 | | SEQ ID NO: 125 | SEQ ID NO: 126 |
| 118 | | | SEQ ID NO: 123 | | | SEQ ID NO: 126 |
| 119 | | | SEQ ID NO: 123 | SEQ ID NO: 124 | | SEQ ID NO: 126 |
| 120 | SEQ ID NO: 105 | | SEQ ID NO: 123 | SEQ ID NO: 124 | | |
| 121 | SEQ ID NO: 105 | | SEQ ID NO: 123 | SEQ ID NO: 124 | SEQ ID NO: 125 | |

TABLE F-continued

Exemplary Group III Antibodies

| Antibody | Light Chain HVR | | | Heavy Chain HVR | | |
|---|---|---|---|---|---|---|
| | L1 | L2 | L3 | H1 | H2 | H3 |
| 122 | SEQ ID NO: 105 | | SEQ ID NO: 123 | SEQ ID NO: 124 | SEQ ID NO: 125 | SEQ ID NO: 126 |
| 123 | SEQ ID NO: 105 | | SEQ ID NO: 123 | | SEQ ID NO: 125 | |
| 124 | SEQ ID NO: 105 | | SEQ ID NO: 123 | | SEQ ID NO: 125 | SEQ ID NO: 126 |
| 125 | SEQ ID NO: 105 | | SEQ ID NO: 123 | | | SEQ ID NO: 126 |
| 126 | SEQ ID NO: 105 | | SEQ ID NO: 123 | SEQ ID NO: 124 | | SEQ ID NO: 126 |

(d) Anti-ApoE Antibodies that Preferentially Bind to ApoE4 Over ApoE3 or ApoE2

In exemplary embodiment, an anti-ApoE antibody of this group comprises a VL that has one or more HVRs derived from SEQ ID NO: 1 or a VH that has one or more HVRs derived from SEQ ID NO: 2. The HVR derived from SEQ ID NO: 1 may be L1, L2, L3, or any combination thereof. In certain embodiments, the VL may comprise an L1 of SEQ ID NO: 23, an L2 of SEQ ID NO: 24, an L3 of SEQ ID NO: 96, or any combination thereof (e.g. antibodies 1-7 in Table G). The HVR derived from SEQ ID NO: 2 may be H1, H2, H3, or any combination thereof. In certain embodiments, the VH may comprise an H1 of SEQ ID NO: 26, an H2 of SEQ ID NO: 27, an H3 of SEQ ID NO: 28, or any combination thereof (e.g. antibodies 8-14 in Table G). The antibody comprising one or more HVRs derived from SEQ ID NO: 2 may further comprise a light chain variable region (VL) comprising one or more HVRs derived from SEQ ID NO: 1. The HVR may be L1, L2, L3, or any combination thereof. In a preferred embodiment, the VL may comprise an L1 of SEQ ID NO: 23, an L2 of SEQ ID NO: 24, an L3 of SEQ ID NO: 96, or any combination thereof (e.g. antibodies 15-63 in Table G). In various embodiments above, the antibody may be a humanized antibody, or the antibody may have a VL with 90, 91, 92, 93, 94, 95, 96, 97, 98, 99, or 100% identity to SEQ ID NO: 1 and/or a VH with 90, 91, 92, 93, 94, 95, 96, 97, 98, 99 or 100% identity to SEQ ID NO: 2. In each of the above embodiments, the anti-ApoE antibody may optionally comprise one or more constant regions, or a portion of a constant region, that is substantially human (i.e. at least 90%, 95%, or 99% sequence identity with a known human framework sequence). The present disclosure also encompasses the corresponding nucleic acid sequences of SEQ ID NO: 1, 2, 23, 24, 96, 26, 27, and 28, which can readily be determined by one of skill in the art, and may be incorporated into a vector or other large DNA molecule, such as a chromosome, in order to express an antibody of the disclosure.

In some embodiments, each of the exemplary antibodies described above may also contain a variant Fc region, including but not limited to a variant Fc region that is modified to alter the natural interaction with the microglia FcR.

In further embodiments, an isolated antibody of Group IV recognizes an epitope listed in Tables 4-7, for example, as described for the exemplary antibody HJ151.

TABLE G

Exemplary Antibodies

| Antibody | Light Chain HVR | | | Heavy Chain HVR | | |
|---|---|---|---|---|---|---|
| | L1 | L2 | L3 | H1 | H2 | H3 |
| 1 | SEQ ID NO: 23 | | | | | |
| 2 | SEQ ID NO: 23 | SEQ ID NO: 24 | | | | |
| 3 | SEQ ID NO: 23 | SEQ ID NO: 24 | SEQ ID NO: 96 | | | |
| 4 | | SEQ ID NO: 24 | | | | |
| 5 | | SEQ ID NO: 24 | SEQ ID NO: 96 | | | |
| 6 | | | SEQ ID NO: 96 | | | |
| 7 | SEQ ID NO: 23 | | SEQ ID NO: 96 | | | |
| 8 | | | | SEQ ID NO: 26 | | |
| 9 | | | | SEQ ID NO: 26 | SEQ ID NO: 27 | |
| 10 | | | | SEQ ID NO: 26 | SEQ ID NO: 27 | SEQ ID NO: 28 |
| 11 | | | | | SEQ ID NO: 27 | |
| 12 | | | | | SEQ ID NO: 27 | SEQ ID NO: 28 |
| 13 | | | | | | SEQ ID NO: 28 |
| 14 | | | | SEQ ID NO: 26 | | SEQ ID NO: 28 |
| 15 | SEQ ID NO: 23 | | | SEQ ID NO: 26 | | |
| 16 | SEQ ID NO: 23 | | | SEQ ID NO: 26 | SEQ ID NO: 27 | |
| 17 | SEQ ID NO: 23 | | | SEQ ID NO: 26 | SEQ ID NO: 27 | SEQ ID NO: 28 |
| 18 | SEQ ID NO: 23 | | | | SEQ ID NO: 27 | |
| 19 | SEQ ID NO: 23 | | | | SEQ ID NO: 27 | SEQ ID NO: 28 |
| 20 | SEQ ID NO: 23 | | | | | SEQ ID NO: 28 |
| 21 | SEQ ID NO: 23 | | | SEQ ID NO: 26 | | SEQ ID NO: 28 |
| 22 | SEQ ID NO: 23 | SEQ ID NO: 24 | | SEQ ID NO: 26 | | |
| 23 | SEQ ID NO: 23 | SEQ ID NO: 24 | | SEQ ID NO: 26 | SEQ ID NO: 27 | |
| 24 | SEQ ID NO: 23 | SEQ ID NO: 24 | | SEQ ID NO: 26 | SEQ ID NO: 27 | SEQ ID NO: 28 |
| 25 | SEQ ID NO: 23 | SEQ ID NO: 24 | | | SEQ ID NO: 27 | |
| 26 | SEQ ID NO: 23 | SEQ ID NO: 24 | | | SEQ ID NO: 27 | SEQ ID NO: 28 |
| 27 | SEQ ID NO: 23 | SEQ ID NO: 24 | | | | SEQ ID NO: 28 |
| 28 | SEQ ID NO: 23 | SEQ ID NO: 24 | | SEQ ID NO: 26 | | SEQ ID NO: 28 |

TABLE G-continued

Exemplary Antibodies

| | Light Chain HVR | | | Heavy Chain HVR | | |
|---|---|---|---|---|---|---|
| Antibody | L1 | L2 | L3 | H1 | H2 | H3 |
| 29 | SEQ ID NO: 23 | SEQ ID NO: 24 | SEQ ID NO: 96 | SEQ ID NO: 26 | | |
| 30 | SEQ ID NO: 23 | SEQ ID NO: 24 | SEQ ID NO: 96 | SEQ ID NO: 26 | SEQ ID NO: 27 | |
| 31 | SEQ ID NO: 23 | SEQ ID NO: 24 | SEQ ID NO: 96 | SEQ ID NO: 26 | SEQ ID NO: 27 | SEQ ID NO: 28 |
| 32 | SEQ ID NO: 23 | SEQ ID NO: 24 | SEQ ID NO: 96 | | SEQ ID NO: 27 | |
| 33 | SEQ ID NO: 23 | SEQ ID NO: 24 | SEQ ID NO: 96 | | SEQ ID NO: 27 | SEQ ID NO: 28 |
| 34 | SEQ ID NO: 23 | SEQ ID NO: 24 | SEQ ID NO: 96 | SEQ ID NO: 26 | | SEQ ID NO: 28 |
| 35 | SEQ ID NO: 23 | SEQ ID NO: 24 | SEQ ID NO: 96 | | | SEQ ID NO: 28 |
| 36 | | SEQ ID NO: 24 | | SEQ ID NO: 26 | | |
| 37 | | SEQ ID NO: 24 | | SEQ ID NO: 26 | SEQ ID NO: 27 | |
| 38 | | SEQ ID NO: 24 | | SEQ ID NO: 26 | SEQ ID NO: 27 | SEQ ID NO: 28 |
| 39 | | SEQ ID NO: 24 | | | SEQ ID NO: 27 | |
| 40 | | SEQ ID NO: 24 | | | SEQ ID NO: 27 | SEQ ID NO: 28 |
| 41 | | SEQ ID NO: 24 | | | | SEQ ID NO: 28 |
| 42 | | SEQ ID NO: 24 | | SEQ ID NO: 26 | | SEQ ID NO: 28 |
| 43 | | SEQ ID NO: 24 | SEQ ID NO: 96 | SEQ ID NO: 26 | | |
| 44 | | SEQ ID NO: 24 | SEQ ID NO: 96 | SEQ ID NO: 26 | SEQ ID NO: 27 | |
| 45 | | SEQ ID NO: 24 | SEQ ID NO: 96 | SEQ ID NO: 26 | SEQ ID NO: 27 | SEQ ID NO: 28 |
| 46 | | SEQ ID NO: 24 | SEQ ID NO: 96 | | SEQ ID NO: 27 | |
| 47 | | SEQ ID NO: 24 | SEQ ID NO: 96 | | SEQ ID NO: 27 | SEQ ID NO: 28 |
| 48 | | SEQ ID NO: 24 | SEQ ID NO: 96 | | | SEQ ID NO: 28 |
| 49 | | SEQ ID NO: 24 | SEQ ID NO: 96 | SEQ ID NO: 26 | | SEQ ID NO: 28 |
| 50 | | | SEQ ID NO: 96 | SEQ ID NO: 26 | | |
| 51 | | | SEQ ID NO: 96 | SEQ ID NO: 26 | SEQ ID NO: 27 | |
| 52 | | | SEQ ID NO: 96 | SEQ ID NO: 26 | SEQ ID NO: 27 | SEQ ID NO: 28 |
| 53 | | | SEQ ID NO: 96 | | SEQ ID NO: 27 | |
| 54 | | | SEQ ID NO: 96 | | SEQ ID NO: 27 | SEQ ID NO: 28 |
| 55 | | | SEQ ID NO: 96 | | | SEQ ID NO: 28 |
| 56 | | | SEQ ID NO: 96 | SEQ ID NO: 26 | | SEQ ID NO: 28 |
| 57 | SEQ ID NO: 23 | | SEQ ID NO: 96 | SEQ ID NO: 26 | | |
| 58 | SEQ ID NO: 23 | | SEQ ID NO: 96 | SEQ ID NO: 26 | SEQ ID NO: 27 | |
| 59 | SEQ ID NO: 23 | | SEQ ID NO: 96 | SEQ ID NO: 26 | SEQ ID NO: 27 | SEQ ID NO: 28 |
| 60 | SEQ ID NO: 23 | | SEQ ID NO: 96 | | SEQ ID NO: 27 | |
| 61 | SEQ ID NO: 23 | | SEQ ID NO: 96 | | SEQ ID NO: 27 | SEQ ID NO: 28 |
| 62 | SEQ ID NO: 23 | | SEQ ID NO: 96 | | | SEQ ID NO: 28 |
| 63 | SEQ ID NO: 23 | | SEQ ID NO: 96 | SEQ ID NO: 26 | | SEQ ID NO: 28 |

(e) Additional Anti-ApoE Antibodies that do not Preferentially Bind to ApoE2, ApoE3 or ApoE4

In an exemplary embodiment, an anti-ApoE antibody of this group comprises a VL that has one or more HVRs derived from SEQ ID NO: 21 or a VH that has one or more HVRs derived from SEQ ID NO: 22. The HVR derived from SEQ ID NO: 21 may be L1, L2, L3, or any combination thereof. In certain embodiments, the VL may comprise an L1 of SEQ ID NO: 72, an L2 of SEQ ID NO: 73, an L3 of SEQ ID NO: 74, or any combination thereof (e.g. antibodies 1-7 in Table H). The HVR derived from SEQ ID NO: 22 may be H1, H2, H3, or any combination thereof. In certain embodiments, the VH may comprise an H1 of SEQ ID NO: 75, an H2 of SEQ ID NO: 76, an H3 of SEQ ID NO: 77, or any combination thereof (e.g. antibodies 8-14 in Table H). The antibody comprising one or more HVRs derived from SEQ ID NO: 22 may further comprise a light chain variable region (VL) comprising one or more HVRs derived from SEQ ID NO: 21. The HVR may be L1, L2, L3, or any combination thereof. In a preferred embodiment, the VL may comprise an L1 of SEQ ID NO: 72, an L2 of SEQ ID NO: 73, an L3 of SEQ ID NO: 74, or any combination thereof (e.g. antibodies 15-63 in Table H). In various embodiments above, the antibody may be a humanized antibody, or the antibody may have a VL with 90, 91, 92, 93, 94, 95, 96, 97, 98, 99, or 100% identity to SEQ ID NO: 21 and/or a VH with 90, 91, 92, 93, 94, 95, 96, 97, 98, 99 or 100% identity to SEQ ID NO: 22. In each of the above embodiments, the anti-ApoE antibody may optionally comprise one or more constant regions, or a portion of a constant region, that is substantially human (i.e. at least 90%, 95%, or 99% sequence identity with a known human framework sequence). The present disclosure also encompasses the corresponding nucleic acid sequences of SEQ ID NO: 21, 22, 72, 73, 74, 75, 76, and 77, which can readily be determined by one of skill in the art, and may be incorporated into a vector or other large DNA molecule, such as a chromosome, in order to express an antibody of the disclosure.

In an exemplary embodiment, an anti-ApoE antibody of this group comprises a VL that has one or more HVRs derived from SEQ ID NO: 97 or a VH that has one or more HVRs derived from SEQ ID NO: 98. The HVR derived from SEQ ID NO: 97 may be L1, L2, L3, or any combination thereof. In certain embodiments, the VL may comprise an L1 of SEQ ID NO: 99, an L2 of SEQ ID NO: 100, an L3 of SEQ ID NO: 101, or any combination thereof (e.g. antibodies 64-70 in Table H). The HVR derived from SEQ ID NO: 98 may be H1, H2, H3, or any combination thereof. In certain embodiments, the VH may comprise an H1 of SEQ ID NO: 102, an H2 of SEQ ID NO: 103, an H3 of SEQ ID NO: 104, or any combination thereof (e.g. antibodies 71-77 in Table H). The antibody comprising one or more HVRs derived from SEQ ID NO: 98 may further comprise a light chain variable region (VL) comprising one or more HVRs derived from SEQ ID NO: 97. The HVR may be L1, L2, L3, or any combination thereof. In a preferred embodiment, the VL may comprise an L1 of SEQ ID NO: 99, an L2 of SEQ ID NO: 100, an L3 of SEQ ID NO: 101, or any combination thereof (e.g. antibodies 78-126 in Table H). In various embodiments above, the antibody may be a humanized antibody, or the antibody may have a VL with 90, 91, 92, 93, 94, 95, 96, 97, 98, 99, or 100% identity to SEQ ID NO: 97 and/or a VH with 90, 91, 92, 93, 94, 95, 96, 97, 98, 99 or 100% identity to SEQ ID NO: 98. In each of the above embodiments, the anti-ApoE antibody may optionally comprise one or more constant regions, or a portion of a constant region, that is substantially human (i.e. at least 90%, 95%, or 99% sequence identity with a known human framework sequence). The present disclosure also encompasses the corresponding nucleic acid sequences of SEQ ID NO: 97, 98, 99, 100, 101, 102, 103, and 104, which can readily be determined by one of skill in the art, and may be incorporated into a vector or other large DNA molecule, such as a chromosome, in order to express an antibody of the disclosure.

In some embodiments, each of the exemplary antibodies described above may also contain a variant Fc region, including but not limited to a variant Fc region that is modified to alter the natural interaction with the microglia FcR.

In further embodiments, an isolated antibody of Group V recognizes an epitope listed in Tables 4-7, for example, as described for the exemplary antibody HJ1526.

TABLE H

Exemplary Antibodies

| Antibody | Light Chain HVR | | | Heavy Chain HVR | | |
|---|---|---|---|---|---|---|
| | L1 | L2 | L3 | H1 | H2 | H3 |
| 1 | SEQ ID NO: 72 | | | | | |
| 2 | SEQ ID NO: 72 | SEQ ID NO: 73 | | | | |
| 3 | SEQ ID NO: 72 | SEQ ID NO: 73 | SEQ ID NO: 74 | | | |
| 4 | | SEQ ID NO: 73 | | | | |
| 5 | | SEQ ID NO: 73 | SEQ ID NO: 74 | | | |
| 6 | | | SEQ ID NO: 74 | | | |
| 7 | SEQ ID NO: 72 | | SEQ ID NO: 74 | | | |
| 8 | | | | SEQ ID NO: 75 | | |
| 9 | | | | SEQ ID NO: 75 | SEQ ID NO: 76 | |
| 10 | | | | SEQ ID NO: 75 | SEQ ID NO: 76 | SEQ ID NO: 77 |
| 11 | | | | | SEQ ID NO: 76 | |
| 12 | | | | | SEQ ID NO: 76 | SEQ ID NO: 77 |
| 13 | | | | | | SEQ ID NO: 77 |
| 14 | | | | SEQ ID NO: 75 | | SEQ ID NO: 77 |
| 15 | SEQ ID NO: 72 | | | SEQ ID NO: 75 | | |
| 16 | SEQ ID NO: 72 | | | SEQ ID NO: 75 | SEQ ID NO: 76 | |
| 17 | SEQ ID NO: 72 | | | SEQ ID NO: 75 | SEQ ID NO: 76 | SEQ ID NO: 77 |
| 18 | SEQ ID NO: 72 | | | | SEQ ID NO: 76 | |
| 19 | SEQ ID NO: 72 | | | | SEQ ID NO: 76 | SEQ ID NO: 77 |
| 20 | SEQ ID NO: 72 | | | | | SEQ ID NO: 77 |
| 21 | SEQ ID NO: 72 | | | SEQ ID NO: 75 | | SEQ ID NO: 77 |
| 22 | SEQ ID NO: 72 | SEQ ID NO: 73 | | SEQ ID NO: 75 | | |
| 23 | SEQ ID NO: 72 | SEQ ID NO: 73 | | SEQ ID NO: 75 | SEQ ID NO: 76 | |
| 24 | SEQ ID NO: 72 | SEQ ID NO: 73 | | SEQ ID NO: 75 | SEQ ID NO: 76 | SEQ ID NO: 77 |
| 25 | SEQ ID NO: 72 | SEQ ID NO: 73 | | | SEQ ID NO: 76 | |
| 26 | SEQ ID NO: 72 | SEQ ID NO: 73 | | | SEQ ID NO: 76 | SEQ ID NO: 77 |
| 27 | SEQ ID NO: 72 | SEQ ID NO: 73 | | | | SEQ ID NO: 77 |
| 28 | SEQ ID NO: 72 | SEQ ID NO: 73 | | SEQ ID NO: 75 | | SEQ ID NO: 77 |
| 29 | SEQ ID NO: 72 | SEQ ID NO: 73 | SEQ ID NO: 74 | SEQ ID NO: 75 | | |
| 30 | SEQ ID NO: 72 | SEQ ID NO: 73 | SEQ ID NO: 74 | SEQ ID NO: 75 | SEQ ID NO: 76 | |
| 31 | SEQ ID NO: 72 | SEQ ID NO: 73 | SEQ ID NO: 74 | SEQ ID NO: 75 | SEQ ID NO: 76 | SEQ ID NO: 77 |
| 32 | SEQ ID NO: 72 | SEQ ID NO: 73 | SEQ ID NO: 74 | | SEQ ID NO: 76 | |
| 33 | SEQ ID NO: 72 | SEQ ID NO: 73 | SEQ ID NO: 74 | | SEQ ID NO: 76 | SEQ ID NO: 77 |
| 34 | SEQ ID NO: 72 | SEQ ID NO: 73 | SEQ ID NO: 74 | SEQ ID NO: 75 | | SEQ ID NO: 77 |
| 35 | SEQ ID NO: 72 | SEQ ID NO: 73 | SEQ ID NO: 74 | | | SEQ ID NO: 77 |
| 36 | | SEQ ID NO: 73 | | SEQ ID NO: 75 | | |
| 37 | | SEQ ID NO: 73 | | SEQ ID NO: 75 | SEQ ID NO: 76 | |
| 38 | | SEQ ID NO: 73 | | SEQ ID NO: 75 | SEQ ID NO: 76 | SEQ ID NO: 77 |
| 39 | | SEQ ID NO: 73 | | | SEQ ID NO: 76 | |
| 40 | | SEQ ID NO: 73 | | | SEQ ID NO: 76 | SEQ ID NO: 77 |
| 41 | | SEQ ID NO: 73 | | | | SEQ ID NO: 77 |
| 42 | | SEQ ID NO: 73 | | SEQ ID NO: 75 | | SEQ ID NO: 77 |
| 43 | | SEQ ID NO: 73 | SEQ ID NO: 74 | SEQ ID NO: 75 | | |
| 44 | | SEQ ID NO: 73 | SEQ ID NO: 74 | SEQ ID NO: 75 | SEQ ID NO: 76 | |
| 45 | | SEQ ID NO: 73 | SEQ ID NO: 74 | SEQ ID NO: 75 | SEQ ID NO: 76 | SEQ ID NO: 77 |
| 46 | | SEQ ID NO: 73 | SEQ ID NO: 74 | | SEQ ID NO: 76 | |
| 47 | | SEQ ID NO: 73 | SEQ ID NO: 74 | | SEQ ID NO: 76 | SEQ ID NO: 77 |
| 48 | | SEQ ID NO: 73 | SEQ ID NO: 74 | | | SEQ ID NO: 77 |
| 49 | | SEQ ID NO: 73 | SEQ ID NO: 74 | SEQ ID NO: 75 | | SEQ ID NO: 77 |
| 50 | | | SEQ ID NO: 74 | SEQ ID NO: 75 | | |
| 51 | | | SEQ ID NO: 74 | SEQ ID NO: 75 | SEQ ID NO: 76 | |
| 52 | | | SEQ ID NO: 74 | SEQ ID NO: 75 | SEQ ID NO: 76 | SEQ ID NO: 77 |
| 53 | | | SEQ ID NO: 74 | | SEQ ID NO: 76 | |
| 54 | | | SEQ ID NO: 74 | | SEQ ID NO: 76 | SEQ ID NO: 77 |
| 55 | | | SEQ ID NO: 74 | | | SEQ ID NO: 77 |
| 56 | | | SEQ ID NO: 74 | SEQ ID NO: 75 | | SEQ ID NO: 77 |
| 57 | SEQ ID NO: 72 | | SEQ ID NO: 74 | SEQ ID NO: 75 | | |
| 58 | SEQ ID NO: 72 | | SEQ ID NO: 74 | SEQ ID NO: 75 | SEQ ID NO: 76 | |

TABLE H-continued

Exemplary Antibodies

| | Light Chain HVR | | | Heavy Chain HVR | | |
|---|---|---|---|---|---|---|
| Antibody | L1 | L2 | L3 | H1 | H2 | H3 |
| 59 | SEQ ID NO: 72 | | SEQ ID NO: 74 | SEQ ID NO: 75 | SEQ ID NO: 76 | SEQ ID NO: 77 |
| 60 | SEQ ID NO: 72 | | SEQ ID NO: 74 | SEQ ID NO: 75 | SEQ ID NO: 76 | |
| 61 | SEQ ID NO: 72 | | SEQ ID NO: 74 | | SEQ ID NO: 76 | SEQ ID NO: 77 |
| 62 | SEQ ID NO: 72 | | SEQ ID NO: 74 | | | SEQ ID NO: 77 |
| 63 | SEQ ID NO: 72 | | SEQ ID NO: 74 | SEQ ID NO: 75 | | SEQ ID NO: 77 |
| 64 | SEQ ID NO: 99 | | | | | |
| 65 | SEQ ID NO: 99 | SEQ ID NO: 100 | | | | |
| 66 | SEQ ID NO: 99 | SEQ ID NO: 100 | SEQ ID NO: 101 | | | |
| 67 | | SEQ ID NO: 100 | | | | |
| 68 | | SEQ ID NO: 100 | SEQ ID NO: 101 | | | |
| 69 | | | SEQ ID NO: 101 | | | |
| 70 | SEQ ID NO: 99 | | SEQ ID NO: 101 | | | |
| 71 | | | | SEQ ID NO: 102 | | |
| 72 | | | | SEQ ID NO: 102 | SEQ ID NO: 103 | |
| 73 | | | | SEQ ID NO: 102 | SEQ ID NO: 103 | SEQ ID NO: 104 |
| 74 | | | | | SEQ ID NO: 103 | |
| 75 | | | | | SEQ ID NO: 103 | SEQ ID NO: 104 |
| 76 | | | | | | SEQ ID NO: 104 |
| 77 | | | | SEQ ID NO: 102 | | SEQ ID NO: 104 |
| 78 | SEQ ID NO: 99 | | | SEQ ID NO: 102 | | |
| 79 | SEQ ID NO: 99 | | | SEQ ID NO: 102 | SEQ ID NO: 103 | |
| 80 | SEQ ID NO: 99 | | | SEQ ID NO: 102 | SEQ ID NO: 103 | SEQ ID NO: 104 |
| 81 | SEQ ID NO: 99 | | | | SEQ ID NO: 103 | |
| 82 | SEQ ID NO: 99 | | | | SEQ ID NO: 103 | SEQ ID NO: 104 |
| 83 | SEQ ID NO: 99 | | | | | SEQ ID NO: 104 |
| 84 | SEQ ID NO: 99 | | | SEQ ID NO: 102 | | SEQ ID NO: 104 |
| 85 | SEQ ID NO: 99 | SEQ ID NO: 100 | | SEQ ID NO: 102 | | |
| 86 | SEQ ID NO: 99 | SEQ ID NO: 100 | | SEQ ID NO: 102 | SEQ ID NO: 103 | |
| 87 | SEQ ID NO: 99 | SEQ ID NO: 100 | | SEQ ID NO: 102 | SEQ ID NO: 103 | SEQ ID NO: 104 |
| 88 | SEQ ID NO: 99 | SEQ ID NO: 100 | | | SEQ ID NO: 103 | |
| 89 | SEQ ID NO: 99 | SEQ ID NO: 100 | | | SEQ ID NO: 103 | SEQ ID NO: 104 |
| 90 | SEQ ID NO: 99 | SEQ ID NO: 100 | | | | SEQ ID NO: 104 |
| 91 | SEQ ID NO: 99 | SEQ ID NO: 100 | | SEQ ID NO: 102 | | SEQ ID NO: 104 |
| 92 | SEQ ID NO: 99 | SEQ ID NO: 100 | SEQ ID NO: 101 | SEQ ID NO: 102 | | |
| 93 | SEQ ID NO: 99 | SEQ ID NO: 100 | SEQ ID NO: 101 | SEQ ID NO: 102 | SEQ ID NO: 103 | |
| 94 | SEQ ID NO: 99 | SEQ ID NO: 100 | SEQ ID NO: 101 | SEQ ID NO: 102 | SEQ ID NO: 103 | SEQ ID NO: 104 |
| 95 | SEQ ID NO: 99 | SEQ ID NO: 100 | SEQ ID NO: 101 | | SEQ ID NO: 103 | |
| 96 | SEQ ID NO: 99 | SEQ ID NO: 100 | SEQ ID NO: 101 | | SEQ ID NO: 103 | SEQ ID NO: 104 |
| 97 | SEQ ID NO: 99 | SEQ ID NO: 100 | SEQ ID NO: 101 | SEQ ID NO: 102 | | SEQ ID NO: 104 |
| 98 | SEQ ID NO: 99 | SEQ ID NO: 100 | SEQ ID NO: 101 | | | SEQ ID NO: 104 |
| 99 | | SEQ ID NO: 100 | | SEQ ID NO: 102 | | |
| 100 | | SEQ ID NO: 100 | | SEQ ID NO: 102 | SEQ ID NO: 103 | |
| 101 | | SEQ ID NO: 100 | | SEQ ID NO: 102 | SEQ ID NO: 103 | SEQ ID NO: 104 |
| 102 | | SEQ ID NO: 100 | | | SEQ ID NO: 103 | |
| 103 | | SEQ ID NO: 100 | | | SEQ ID NO: 103 | SEQ ID NO: 104 |
| 104 | | SEQ ID NO: 100 | | | | SEQ ID NO: 104 |
| 105 | | SEQ ID NO: 100 | | SEQ ID NO: 102 | | SEQ ID NO: 104 |
| 106 | | SEQ ID NO: 100 | SEQ ID NO: 101 | SEQ ID NO: 102 | | |
| 107 | | SEQ ID NO: 100 | SEQ ID NO: 101 | SEQ ID NO: 102 | SEQ ID NO: 103 | |
| 108 | | SEQ ID NO: 100 | SEQ ID NO: 101 | SEQ ID NO: 102 | SEQ ID NO: 103 | SEQ ID NO: 104 |
| 109 | | SEQ ID NO: 100 | SEQ ID NO: 101 | | SEQ ID NO: 103 | |
| 110 | | SEQ ID NO: 100 | SEQ ID NO: 101 | | SEQ ID NO: 103 | SEQ ID NO: 104 |
| 111 | | SEQ ID NO: 100 | SEQ ID NO: 101 | | | SEQ ID NO: 104 |
| 112 | | SEQ ID NO: 100 | SEQ ID NO: 101 | SEQ ID NO: 102 | | SEQ ID NO: 104 |
| 113 | | | SEQ ID NO: 101 | SEQ ID NO: 102 | | |
| 114 | | | SEQ ID NO: 101 | SEQ ID NO: 102 | SEQ ID NO: 103 | |
| 115 | | | SEQ ID NO: 101 | SEQ ID NO: 102 | SEQ ID NO: 103 | SEQ ID NO: 104 |
| 116 | | | SEQ ID NO: 101 | | SEQ ID NO: 103 | |
| 117 | | | SEQ ID NO: 101 | | SEQ ID NO: 103 | SEQ ID NO: 104 |
| 118 | | | SEQ ID NO: 101 | | | SEQ ID NO: 104 |
| 119 | | | SEQ ID NO: 101 | SEQ ID NO: 102 | | SEQ ID NO: 104 |
| 120 | SEQ ID NO: 99 | | SEQ ID NO: 101 | SEQ ID NO: 102 | | |
| 121 | SEQ ID NO: 99 | | SEQ ID NO: 101 | SEQ ID NO: 102 | SEQ ID NO: 103 | |
| 122 | SEQ ID NO: 99 | | SEQ ID NO: 101 | SEQ ID NO: 102 | SEQ ID NO: 103 | SEQ ID NO: 104 |
| 123 | SEQ ID NO: 99 | | SEQ ID NO: 101 | | SEQ ID NO: 103 | |
| 124 | SEQ ID NO: 99 | | SEQ ID NO: 101 | | SEQ ID NO: 103 | SEQ ID NO: 104 |
| 125 | SEQ ID NO: 99 | | SEQ ID NO: 101 | | | SEQ ID NO: 104 |
| 126 | SEQ ID NO: 99 | | SEQ ID NO: 101 | SEQ ID NO: 102 | | SEQ ID NO: 104 |

(f) Group V

In another aspect, an anti-ApoE antibody competitively inhibits binding of a reference antibody to its epitope. An antibody is said to competitively inhibit binding of a reference antibody to a given epitope if the antibody preferentially binds to that epitope to the extent that it blocks binding of the reference antibody to the epitope by at least 50%, at least 60%, at least 70%, at least 80%, or at least 90%. Competitive inhibition can be determined by any method known in the art, for example, competition ELISA assays. In some embodiments, an anti-ApoE antibody competitively inhibits HJ152 and/or HJ1514 binding to human ApoE. In other embodiments, an anti-ApoE antibody competitively inhibits HJ155, HJ156, HJ159, HJ1513 and/or HJ1518 binding to human ApoE. In still other embodiments, an anti-ApoE antibody competitively inhibits HJ151 binding to human ApoE. In yet other embodiments, an anti-ApoE antibody competitively inhibits HJ1526 binding to human ApoE. In an alternative embodiment, an anti-ApoE antibody competitively inhibits HJ158 binding to human ApoE. In a different embodiment, an anti-ApoE antibody competitively inhibits HJ1531 and/or HJ1536 binding to human ApoE.

III. Treatment Methods

The present disclosure provides a method of treating Aβ amyloidosis, the method comprising administering a therapeutically effective amount of an anti-ApoE antibody to a subject in need thereof. The present disclosure also provides a method of treating a subject diagnosed with a disease characterized by brain Aβ plaques, the method comprising administering a therapeutically effective amount of an anti-ApoE antibody to the subject. The present disclosure also provides a method of treating a subject diagnosed with a disease characterized by vascular Aβ plaques in the brain, the method comprising administering a therapeutically effective amount of an anti-ApoE antibody to the subject. The present disclosure also provides a method of preventing the progression of a disease characterized by Aβ plaques in the brain, the method comprising administering a therapeutically effective amount of an anti-ApoE antibody to a subject in need thereof. The present disclosure also provides a method of treating a subject diagnosed with Alzheimer's disease, the method comprising administering a therapeutically effective amount of an anti-ApoE antibody to the subject. The present disclosure also provides a method of treating a subject diagnosed with CAA, the method comprising administering a therapeutically effective amount of an anti-ApoE antibody to the subject. Suitable anti-ApoE antibodies are described in Section II. In embodiments where the subject is a human, the anti-ApoE antibody is adapted for administration to a living human subject (e.g. humanized).

In one embodiment, the disclosure provides a method of preventing the progression, or slowing the rate of progression, of a disease characterized by Aβ plaques in the brain. The method comprises administering a therapeutically effective amount of an anti-ApoE antibody to a subject in need thereof. Suitable anti-ApoE antibodies include those disclosed herein. Progression of a disease characterized by Aβ plaques in the brain can be evaluated by methods known in the art and described herein, including a worsening of a clinical sign of Aβ amyloidosis, an Aβ plaque associated symptom, or a CAA associated symptom. In exemplary embodiments, the clinical sign is amyloid plaque load.

In another embodiment, the disclosure provides a method for improving a clinical sign of Aβ amyloidosis. The method comprises administering a therapeutically effective amount of an anti-ApoE antibody to a subject in need thereof. Suitable anti-ApoE antibodies include those disclosed herein. Non-limiting examples of improved clinical signs of Aβ amyloidosis may include a decrease in amyloid plaque load, stabilization of amyloid plaque load (i.e. no further increase), an increase in CSF Aβ42 concentration, an increase in CSF Aβ42/Aβ40 ratio, a decreased Aβ42/Aβ40 peak time ratio as measured by stable isotope labeling kinetics (e.g. such that is closer to 1), a decreased Aβ42/Aβ40 FTR ratio as measured by stable isotope labeling kinetics (e.g. such that is closer to 1), and a change in the ratio of the relative labeling Aβ42 to the relative labeling of Aβ40 (or another Aβ peptide) after stable isotope labeling such that the ratio is closer to 1. In each of the above embodiments, the improvement (i.e. the change) in the clinical sign is at least statistically significant. In certain embodiments, the change may be at least 1, 2, 3, 4, 5, 6, 7, 8, 9, 10, 11, 12, 13, 14, 15, 16, 17, 18, 19, or 20% compared to untreated or negative control treated subjects. In some embodiments, the change may be at least 20, 25, 30, 35, 40, 45, 50, 55, 60, 65, 70, 75, 80, 85, 90, or 95% compared to untreated or negative control treated subjects. In other embodiments, the change may be at least 100, 125, 150, 200, 250, 300, 350, 400, or 450% compared to untreated or negative control treated subjects.

In another embodiment, the disclosure provides a method for decreasing amyloid plaque load in the brain of a subject. The method comprises administering a therapeutically effective amount of an anti-ApoE antibody to a subject. Suitable anti-ApoE antibodies include those disclosed herein. A method of the invention may decrease the amyloid plaque load in the hippocampus of a subject and/or decrease the amyloid plaque load in the brain cortex of a subject. In each of the above embodiments, the amyloid plaque load may be decreased by at least 1, 2, 3, 4, 5, 6, 7, 8, 9, 10, 11, 12, 13, 14, 15, 16, 17, 18, 19, or 20% compared to untreated or negative control treated subjects. In some embodiments, the amyloid plaque load may be decreased by at least 20, 25, 30, 35, 40, 45, 50, 55, 60, 65, 70, 75, 80, 85, 90, or 95% compared to untreated or negative control treated subjects. In other embodiments, the amyloid plaque load may be decreased by at least 100, 125, 150, 200, 250, 300, 350, 400, or 450% compared to untreated or negative control treated subjects.

In another embodiment, the disclosure provides a method for decreasing CAA load in the brain of a subject. The method comprises administering a therapeutically effective amount of an anti-ApoE antibody to a subject with fibrillar forms of Aβ in penetrating and/or leptomeningeal arterioles on the surface of the cerebral cortex. Suitable anti-ApoE antibodies include those disclosed herein. A method of the invention may decrease CAA load in the penetrating and/or leptomeningeal arterioles on the surface of the cerebral cortex of a subject. In each of the above embodiments, CAA load may be decreased by at least 1, 2, 3, 4, 5, 6, 7, 8, 9, 10, 11, 12, 13, 14, 15, 16, 17, 18, 19, or 20% compared to untreated or negative control treated subjects. In some embodiments, the amyloid plaque load may be decreased by at least 20, 25, 30, 35, 40, 45, 50, 55, 60, 65, 70, 75, 80, 85, 90, or 95% compared to untreated or negative control treated subjects. In other embodiments, the amyloid plaque load may be decreased by at least 100, 125, 150, 200, 250, 300, 350, 400, or 450% compared to untreated or negative control treated subjects.

Another embodiment includes a method of reducing insoluble $A\beta_{42}$ levels in the brain of a subject in need thereof. The method comprises administering a therapeutically effective amount of an anti-ApoE antibody to the subject. In one example, the method further comprises reducing insoluble Aβ$_{40}$ levels in the brain of the subject. In another example, the method comprises selectively reducing insoluble Aβ40 levels, reducing insoluble Aβ42 levels, or a combination thereof compared to soluble Aβ40, Aβ42 levels, or a combination thereof in the brain of a subject.

The level of Aβ can be assessed by any suitable method known in the art comprising, e.g., analyzing Aβ by one or more techniques chosen from Western blot, immunoprecipitation, enzyme-linked immunosorbent assay (ELISA), radioimmunoassay (RIA), fluorescent activated cell sorting (FACS), two-dimensional gel electrophoresis, mass spectroscopy (MS), matrix-assisted laser desorption/ionization-time of flight-MS (MALDI-TOF), surface-enhanced laser desorption ionization-time of flight (SEMI-TOE), high performance liquid Chromatography (HPLC), fast protein liquid chromatography (FPLC), multidimensional liquid chromatography (LC) followed by tandem mass spectrometry (MS/MS), and laser densitometry. In vivo imaging of Aβ is particularly suited for evaluating amyloid plaque load. Non-limiting examples of in vivo imaging methods include positron emission tomography (PET), single photon emission tomography (SPECT), near infrared (NIR) optical imaging or magnetic resonance imaging (MRI). Suitable imaging agents are also known in the art (e.g. PIB).

In another embodiment, the disclosure provides a method for improving an Aβ plaque associated symptom and/or a CAA associated symptom in a subject. The method comprises administering a therapeutically effective amount of an anti-ApoE antibody that specifically binds ApoE to a subject with at least one Aβ plaque associated symptom and/or at least one CAA associated symptom. Suitable anti-ApoE antibodies include those disclosed herein. Non-limiting examples of improved Aβ plaque associated symptoms are identified above. In certain embodiments, improved Aβ plaque associated symptoms may include reduced neuronal degeneration, impaired cognitive function, altered behavior, emotional dysregulation, and/or seizures. In each of the above embodiments, the improvement (i.e. the change) in the symptom is at least statistically significant. In certain embodiments, the change may be at least 1, 2, 3, 4, 5, 6, 7, 8, 9, 10, 11, 12, 13, 14, 15, 16, 17, 18, 19, or 20% compared to untreated or negative control treated subjects. In some embodiments, the change may be at least 20, 25, 30, 35, 40, 45, 50, 55, 60, 65, 70, 75, 80, 85, 90, or 95% compared to untreated or negative control treated subjects. In other embodiments, the change may be at least 100, 125, 150, 200, 250, 300, 350, 400, or 450% compared to untreated or negative control treated subjects.

For each of the above embodiments, suitable anti-ApoE antibodies are described in Section II. In certain embodiments, an anti-ApoE antibody is (a) selected from an antibody listed in Tables A-H, (b) is an anti-ApoE antibody that competitively inhibits HJ152 and/or HJ1514 binding to human ApoE, or (c) is an anti-ApoE antibody that competitively inhibits HJ155, HJ156, HJ159, HJ1513 and/or HJ1518 binding to human ApoE. In certain embodiments, an anti-ApoE antibody is selected from an antibody listed in Tables A-B, or is an anti-ApoE antibody that competitively inhibits HJ152 and/or HJ1514 binding to human ApoE. In certain embodiments, an anti-ApoE antibody is selected from an antibody listed in Tables C-D, or is an anti-ApoE antibody that competitively inhibits HJ155, HJ156, HJ159, HJ1513 and/or HJ1518 binding to human ApoE. In certain embodiments, an anti-ApoE antibody is selected from an antibody listed in Tables E-F, or is an anti-ApoE antibody that competitively inhibits HJ1531, and/or HJ1536 binding to human ApoE. In certain embodiments, an anti-ApoE antibody is selected from an antibody listed in Table G, or is an anti-ApoE antibody that competitively inhibits HJ151 binding to human ApoE. In certain embodiments, an anti-ApoE antibody is selected from an antibody listed in Table H, or is an anti-ApoE antibody that competitively inhibits HJ158 or HJ1526 binding to human ApoE.

Anti-ApoE antibody disclosed herein can also be conjugated to therapeutic agents, prodrugs, peptides, proteins, enzymes, viruses, biological response modifiers, pharmaceutical agents, or PEG. In certain embodiments, therapeutic agent may be a drug, a radioisotope, a lectin, or a toxin. Conjugates that are immunotoxins have been widely described in the art. The toxins can be coupled to the antibodies by conventional coupling techniques or immunotoxins containing protein toxin portions can be produced as fusion proteins. In using radioisotopically conjugated anti-ApoE antibodies for immunotherapy, certain isotopes can be chosen depending on such factors as leukocyte distribution as well as stability and emission. Depending on the autoimmune response, some emitters can be used. In general, α and β particle emitting radioisotopes are utilized in immunotherapy. In certain embodiments, short range, high energy α emitters such as $^{212}$Bi can be used. Examples of radioisotopes which can be bound to the anti-ApoE antibodies disclosed herein for therapeutic purposes include, but are not limited to $^{123}$I, $^{124}$I, $^{125}$I, $^{131}$I, $^{89}$Zr, $^{90}$Y, $^{67}$Cu, $^{64}$Cu, $^{111}$In, $^{212}$Bi, $^{212}$At, $^{211}$Pb, $^{47}$SC, $^{109}$Pd, and $^{188}$Re. Other therapeutic agents which can be coupled to the anti-ApoE antibodies, as well as ex vivo and in vivo therapeutic protocols, are known, or can be easily ascertained, by those of ordinary skill in the art.

Administration of an anti-ApoE antibody, or a composition comprising an anti-ApoE antibody, is performed using standard effective techniques, include peripherally (i.e. not by administration into the central nervous system) or locally to the central nervous system. Peripheral administration includes but is not limited to intravenous, intraperitoneal, subcutaneous, pulmonary, transdermal, intramuscular, intranasal, buccal, sublingual, or suppository administration. Local administration, including directly into the central nervous system (CNS) includes but is not limited to via a lumbar, intraventricular or intraparenchymal catheter or using a surgically implanted controlled release formulation.

Pharmaceutical compositions for effective administration are deliberately designed to be appropriate for the selected mode of administration, and pharmaceutically acceptable excipients such as compatible dispersing agents, buffers, surfactants, preservatives, solubilizing agents, isotonicity agents, stabilizing agents and the like are used as appropriate. Remington's Pharmaceutical Sciences, Mack Publishing Co., Easton Pa., 16Ed ISBN: 0-912734-04-3, latest edition, incorporated herein by reference in its entirety, provides a compendium of formulation techniques as are generally known to practitioners. It may be particularly useful to alter the solubility characteristics of the antibodies useful in this discovery, making them more lipophilic, for example, by encapsulating them in liposomes or by blocking polar groups.

The concentration of antibody in formulations to be administered is an effective amount and ranges from as low as about 0.1% by weight to as much as about 15 or about 20% by weight and will be selected primarily based on fluid volumes, viscosities, and so forth, in accordance with the particular mode of administration selected if desired. A typical composition for injection to a living subject could be made up to contain 1 mL sterile buffered water of phosphate buffered saline and about 1-1000 mg of any one of or a combination of the antibodies disclosed herein. The formulation could be sterile filtered after making the formulation, or otherwise made microbiologically acceptable. A typical composition for intravenous infusion could have volumes between 1-250 mL of fluid, such as sterile Ringer's solution, and 1-100 mg per ml, or more in anti-ApoE antibody concentration. Anti-ApoE antibodies disclosed herein can be frozen or lyophilized for storage and reconstituted in a suitable sterile carrier prior to use. Lyophilization and reconstitution may lead to varying degrees of antibody activity loss (e.g. with conventional immune globulins, IgM antibodies tend to have greater activity loss than IgG antibodies). Dosages administered are effective dosages and may have to be adjusted to compensate. The pH of the formulations generally pharmaceutical grade quality, will be selected to balance antibody stability (chemical and physical) and comfort to the subject when administered. Generally, a pH between 4 and 8 is tolerated. Doses will vary from individual to individual based on size, weight, and other physiobiological characteristics of the individual receiving the successful administration.

As used herein, the term "therapeutically effective amount" means an amount of a substance (e.g. an anti-ApoE antibody) that leads to measurable and beneficial effects for the subject administered the substance, i.e., significant efficacy. The therapeutically effective amount or dose of compound administered according to this discovery will be determined using standard clinical techniques and may be by influenced by the circumstances surrounding the case, including the antibody administered, the route of administration, and the status of the symptoms being treated, among other considerations. A typical dose may contain from about 0.01 mg/kg to about 100 mg/kg of an anti-ApoE antibody described herein. Doses can range from about 0.05 mg/kg to about 50 mg/kg, more preferably from about 0.1 mg/kg to about 25 mg/kg. The frequency of dosing may be daily or once, twice, three times or more per week or per month, as needed as to effectively treat the symptoms.

The timing of administration of the treatment relative to the disease itself and duration of treatment will be determined by the circumstances surrounding the case. Duration of treatment could range from a single dose administered on a one-time basis to a life-long course of therapeutic treatments.

Although the foregoing methods appear the most convenient and most appropriate and effective for administration of proteins such as humanized antibodies, by suitable adaptation, other effective techniques for administration, such as intraventricular administration, transdermal administration and oral administration may be employed provided proper formulation is utilized herein. In addition, a person skilled in the art can use a polynucleotide of the invention encoding any one of the above-described antibodies instead of the proteinaceous material itself. For example, In addition, it may be desirable to employ controlled release formulations using biodegradable films and matrices, or osmotic mini-pumps, or delivery systems based on dextran beads, alginate, or collagen.

IV. Diagnosing or Tracking Methods

The present disclosure also provides anti-ApoE antibodies conjugated to a detectable signal (i.e. a measurable substance, or a substance that generates a measurable signal). Non-limiting examples include various enzymes, prosthetic groups, fluorescent materials, luminescent materials, bioluminescent materials, radioactive materials, positron emitting metals using various positron emission tomographies, and nonradioactive paramagnetic metal ions. See, e.g., U.S. Pat. No. 4,741,900 for metal ions which can be conjugated to antibodies for use as diagnostics according to the disclosure. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}$I, $^{131}$I, $^{111}$In or $^{99}$Tc. The signal generated by the agent can be measured, for example, by single-photon emission computed tomography (SPECT) or positron emission tomography (PET).

Anti-ApoE antibodies conjugated to a detectable signal may be used diagnostically to, for example, monitor the development or progression of a neurodegenerative disease as part of a clinical testing procedure to, e.g., determine the efficacy of a given treatment and/or prevention regimen. The patient's treatment can be adjusted based on the level of neurodegenerative disease progression.

In some embodiments, a method of assessing disease progression in a subject being treated for a neurodegenerative disease characterized by brain amyloid plaques or a neurodegenerative disease characterized by vascular amyloid plaques in the brain is provided, the method comprising: (a) administering an anti-ApoE antibody disclosed herein that is labeled with an agent that generates a measurable signal as described herein (i.e. "labeled anti-ApoE antibody"), wherein the signal is measured in the patient following the administration; (b) administering the labeled anti-ApoE or antigen-binding fragment thereof at one or more time intervals following the administration of (a), wherein the signal is measured in the patient following the administration; and (c) assessing disease progression in the patient based on a change in the signal measured in the patient at the one or more time intervals following administration of (a); wherein an increase in the signal indicates progression of the neurodegenerative disease in the patient. In certain embodiments, the subject is being treated with the same anti-ApoE antibody, but in an unlabeled form. In certain embodiments, the subject is being treated with an anti-ApoE antibody that competitively inhibits the labeled anti-ApoE antibody binding to human ApoE. In certain embodiments, the subject is being treated with an anti-ApoE antibody that does not competitively inhibit the labeled anti-ApoE antibody binding to human ApoE. In certain embodiments, the subject is being treated with other drugs known in the art.

In other embodiments, a method of assessing disease progression in a subject being treated for a neurodegenerative disease characterized by brain amyloid plaques or a neurodegenerative disease characterized by vascular amyloid plaques in the brain is provided, the method comprising: (a) administering an anti-ApoE antibody disclosed herein that is labeled with an agent that generates a measurable signal as described herein (i.e. "labeled anti-ApoE antibody"), wherein the signal is measured in the patient following the administration; (b) assessing the disease state in the subject upon review of a comparison of the signal measured in the subject to the signal measured following administration of the labeled antibody or antigen-binding fragment thereof to one or more control subjects; wherein an increase in the signal generated in the patient relative to the control subject correlates with an increase in brain amyloid plaques; and (c) treating the patient with a therapy appropriate for the patient's disease state. A "control subject(s)," refers to any normal healthy subject (or a pool of subjects), a subject or subjects with different degrees of disease, or even the actual test subject at an earlier stage of disease. In certain embodiments, the therapy is the same anti-ApoE antibody, but in an unlabeled form. In certain embodiments, the therapy is an anti-ApoE antibody that competitively inhibits the labeled anti-ApoE antibody binding to human ApoE. In certain embodiments, the therapy is an anti-ApoE antibody that does not competitively inhibit the labeled anti-ApoE antibody binding to human ApoE. In certain embodiments, the therapy is with an anti-Aβ antibody, an anti-tau antibody, a gamma-secretase inhibitor, a beta-secretase inhibitor, a cholinesterase inhibitor, an NMDA receptor antagonist, or other drugs known in the art.

The present disclosure also provides the use of the anti-ApoE antibodies disclosed herein for measuring the amount of brain amyloid plaques in a test subject, assessing disease progression in a patient being treated for a neurodegenerative disease or treating a neurodegenerative disease characterized by brain amyloid plaques in a patient in need of treatment.

V. Pharmaceutical Compositions

The present disclosure encompasses pharmaceutical compositions comprising an anti-ApoE antibody disclosed in Section II, so as to facilitate administration and promote stability of the active agent. For example, an anti-ApoE antibody of this disclosure may be admixed with at least one pharmaceutically acceptable carrier or excipient resulting in a pharmaceutical composition which is capably and effectively administered (given) to a living subject, such as to a suitable subject (i.e. "a subject in need of treatment" or "a subject in need thereof"). Methods of preparing and administering anti-ApoE antibodies disclosed herein to a subject in need thereof are well known to or are readily determined by those skilled in the art. The route of administration of an anti-ApoE antibody can be, for example, peripheral, oral, parenteral, by inhalation or topical.

Pharmaceutical compositions for effective administration are deliberately designed to be appropriate for the selected mode of administration, and pharmaceutically acceptable excipients such as compatible carriers, dispersing agents, buffers, surfactants, preservatives, solubilizing agents, isotonicity agents, stabilizing agents and the like are used as appropriate.

Non-limiting examples of pharmaceutically acceptable carriers, include physiological saline, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, wool fat or oa combination thereof.

Prevention of the action of microorganisms can be achieved by various antibacterial and antifungal agents, for example, parabens, chlorobutanol, phenol, ascorbic acid, thimerosal and the like. In many cases, isotonic agents can be included, for example, sugars, polyalcohols, such as mannitol, sorbitol, or sodium chloride in the composition.

Prolonged absorption of the injectable compositions can be brought about by including in the composition an agent which delays absorption, for example, aluminum monostearate and gelatin.

Compositions disclosed herein can be frozen or lyophilized for storage and reconstituted in a suitable sterile carrier prior to use.

In some embodiments, anti-ApoE antibodies may be formulated for parenteral administration. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives can also be present such as, for example, antimicrobials, anti-oxidants, chelating agents, and inert gases and the like. Parenteral formulations can be a single bolus dose, an infusion or a loading bolus dose followed with a maintenance dose. These compositions can be administered at specific fixed or variable intervals, e.g., once a day, or on an "as needed" basis.

Certain pharmaceutical compositions, as disclosed herein, can be orally administered in an acceptable dosage form including, e.g., capsules, tablets, aqueous suspensions or solutions. Certain pharmaceutical compositions also can be administered by nasal aerosol or inhalation. Such compositions can be prepared as solutions in saline, employing benzyl alcohol or other suitable preservatives, absorption promoters to enhance bioavailability, and/or other conventional solubilizing or dispersing agents.

The amount of an anti-ApoE antibody to be combined with the carrier materials to produce a single dosage form will vary depending upon the host treated and the particular mode of administration. The composition can be administered as a single dose, multiple doses or over an established period of time in an infusion. Dosage regimens also can be adjusted to provide the optimum desired response (e.g., a therapeutic or prophylactic response).

The following examples are included to demonstrate preferred embodiments of the invention. It should be appreciated by those of skill in the art that the techniques disclosed in the examples that follow represent techniques discovered by the inventors to function well in the practice of the invention. Those of skill in the art should, however, in light of the present disclosure, appreciate that many changes can be made in the specific embodiments that are disclosed and still obtain a like or similar result without departing from the spirit and scope of the invention, therefore all matter set forth or shown in the accompanying examples and drawings is to be interpreted as illustrative and not in a limiting sense

EXAMPLES

The following examples illustrate various iterations of the invention.

Example 1

Murine monoclonal antibodies to ApoE were generated and sequenced. Briefly, to generate the antibodies, human recombinant ApoE4 protein (299 amino acids) was injected intraperitoneally (IP) into a wildtype mouse on a B6C3 background. 100 µg of antigen (in 200 µl PBS+200 µl complete Freund's adjuvant) was injected on day 0, day 14 and day 28. A last boost of 50 µg of antigen in PBS was injected IP 3 days before fusion of myeloma cells with spleen cells of the mice. Serum was tested by direct ELISA to ApoE4 on day 21 and day 35. If titer was over 1:10,000, myeloma cells were then fused with mouse spleen cells per standard protocol, followed by isolation of hybridoma clones.

TABLE 1

| Antibody | Light chain variable region | Heavy chain variable region |
|---|---|---|
| HJ151 | SEQ ID NO: 1 | SEQ ID NO: 2 |
| HJ152 | SEQ ID NO: 3 | SEQ ID NO: 4 |
| HJ153 | SEQ ID NO: 5 | SEQ ID NO: 6 |
| HJ154 | SEQ ID NO: 7 | SEQ ID NO: 8 |
| HJ155 | SEQ ID NO: 9 | SEQ ID NO: 10 |
| HJ156 | SEQ ID NO: 11 | SEQ ID NO: 12 |
| HJ158 | SEQ ID NO: 97 | SEQ ID NO: 98 |
| HJ159 | SEQ ID NO: 13 | SEQ ID NO: 14 |
| HJ1513 | SEQ ID NO: 15 | SEQ ID NO: 16 |
| HJ1514 | SEQ ID NO: 17 | SEQ ID NO: 18 |
| HJ1518 | SEQ ID NO: 19 | SEQ ID NO: 20 |
| HJ1526 | SEQ ID NO: 21 | SEQ ID NO: 22 |
| HJ1531 | SEQ ID NO: 115 | SEQ ID NO: 116 |
| HJ1536 | SEQ ID NO: 121 | SEQ ID NO: 122 |

Example 2

Figure 2:
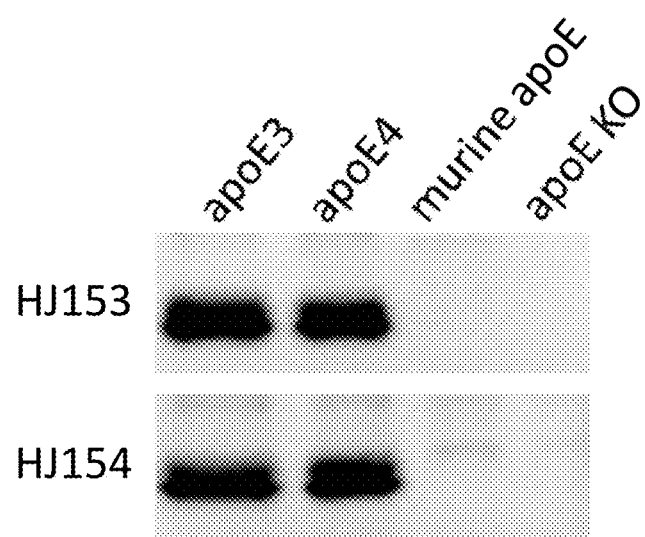
FIG. 2 depicts an image of a Western blot. The brain lysates from ApoE KO mice or mice expressing ApoE3, ApoE4 or murine ApoE were immunoblotted with HJ153 or HJ154. The Western blot shows that HJ153 and HJ154 recognize both ApoE3 and ApoE4.

Brain lysates from apoE KO mice or mice expressing human apoE3, human apoE4 or murine apoE were immunoblotted with HJ151, HJ152, HJ153, and HJ154. A commercial apoE antibody GA-50 was used as a positive control. FIG. 1 and FIG. 2 show that, by Western blot, HJ152, HJ153, and HJ154 recognize both ApoE3 and ApoE4, and HJ151 is ApoE4 specific.

Example 3

Figure 3:
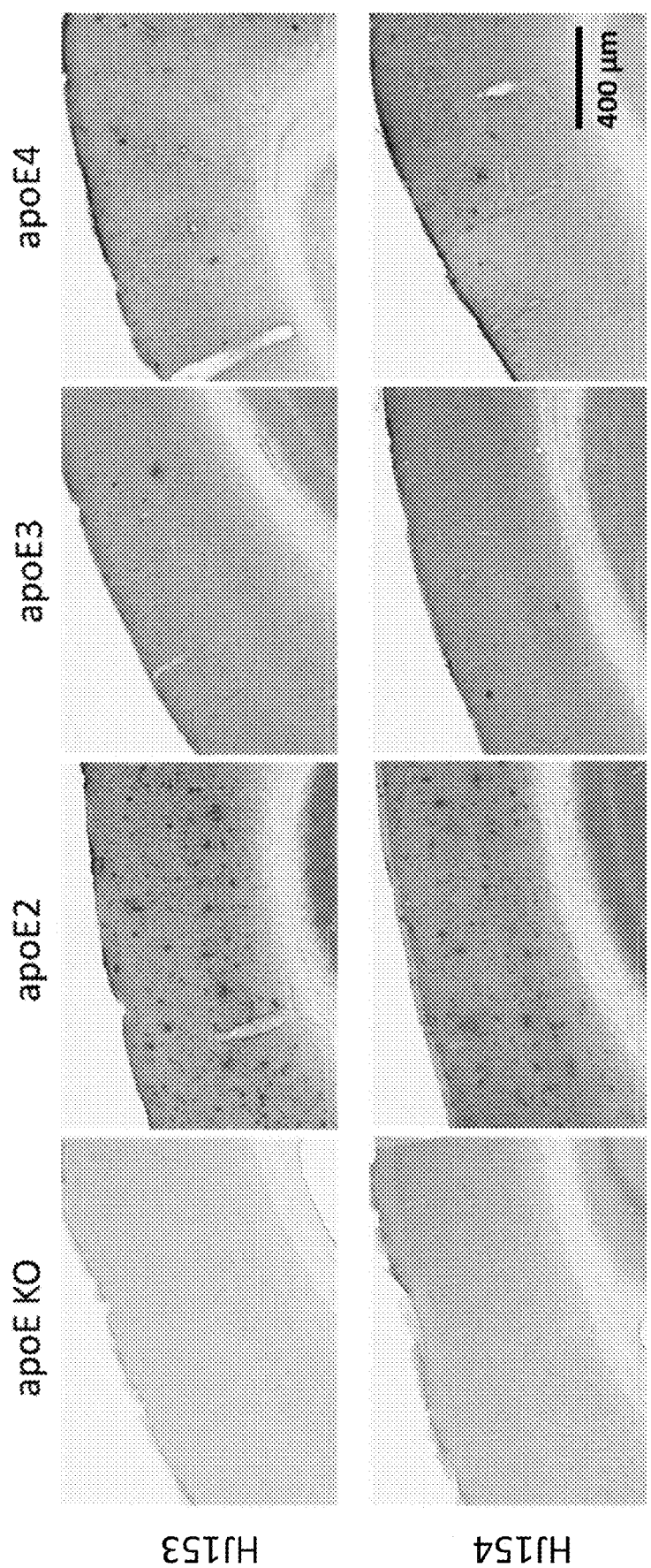
FIG. 3 depicts images of brain tissue from 5XFAD APP transgenic mice expressing different human ApoE isoforms and stained using biotinylated HJ153 or HJ154 antibodies. The figure shows these two antibodies stain ApoE in the neuropil, in astrocytes, and in amyloid plaques if plaques are present. Brain tissue from ApoE KO mouse was used as negative control.

Brain tissue from 5XFAD APP transgenic mice expressing different human ApoE isoforms were stained using biotinylated HJ153 and HJ154. Brain tissue from ApoE KO mouse was used as negative control. As shown in FIG. 3, HJ153 and HJ154 stain ApoE in the neuropil, in astrocytes, and in amyloid plaques, if plaques are present.

Example 4

Figure 4:
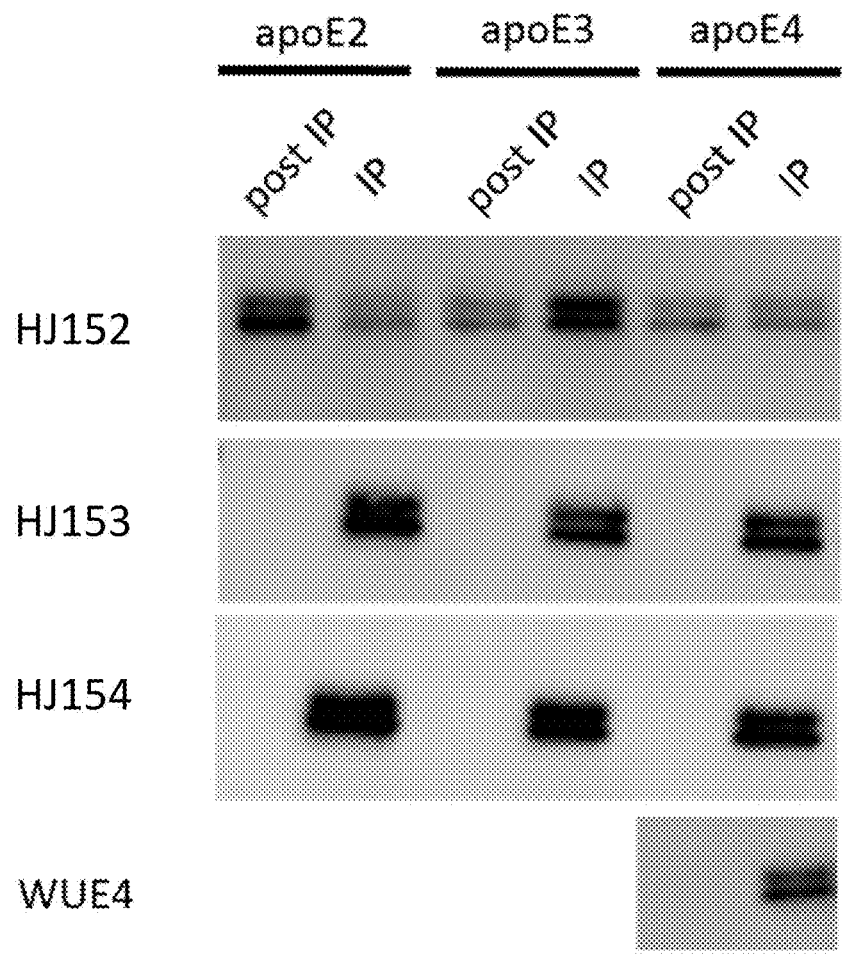
FIG. 4 depicts images of several immunoblots. Samples containing ApoE2, ApoE3 or ApoE4 were immunoprecipitated using HJ152, HJ153 or HJ154. Materials immunoprecipitated with anti-ApoE antibodies (labeled as IP) and the solution after immunoprecipitation (labeled as post IP) were immunoblotted after running an SDS-PAGE gel and transfer to nitrocellulose membrane using GA-50, a commercial anti-ApoE antibody. WUE4, a monoclonal antibody against human ApoE, was used as a positive control. The results showed that HJ152 was able to immunoprecipitate some of the ApoE from the samples while there was still some ApoE remaining in the post IP product. HJ153 and HJ154 were able to immunoprecipitate all ApoE from the samples.

Phosphate buffered saline brain cortical tissue lysates containing ApoE2, ApoE3 or ApoE4 were immunoprecipitated using HJ152, HJ153 and HJ154. Materials immunoprecipitated with the antibodies (labeled as IP) and the solution after immunoprecipitation were immunoblotted after running an SDS-PAGE gel and transfer to nitrocellulose membrane using commercial apoE antibody GA-50. WUE4, a monoclonal antibody against human apoE, was used as a positive control. As shown in FIG. 4, HJ152 is able to immunoprecipitate some of the apoE from the samples, though there is still some apoE remaining in the sample after immunoprecipitation (compare IP vs. post IP, respectively). FIG. 4 also shows that HJ153 and HJ154 are able to immunoprecipitate all ApoE from the samples.

Example 5

Figure 5A:
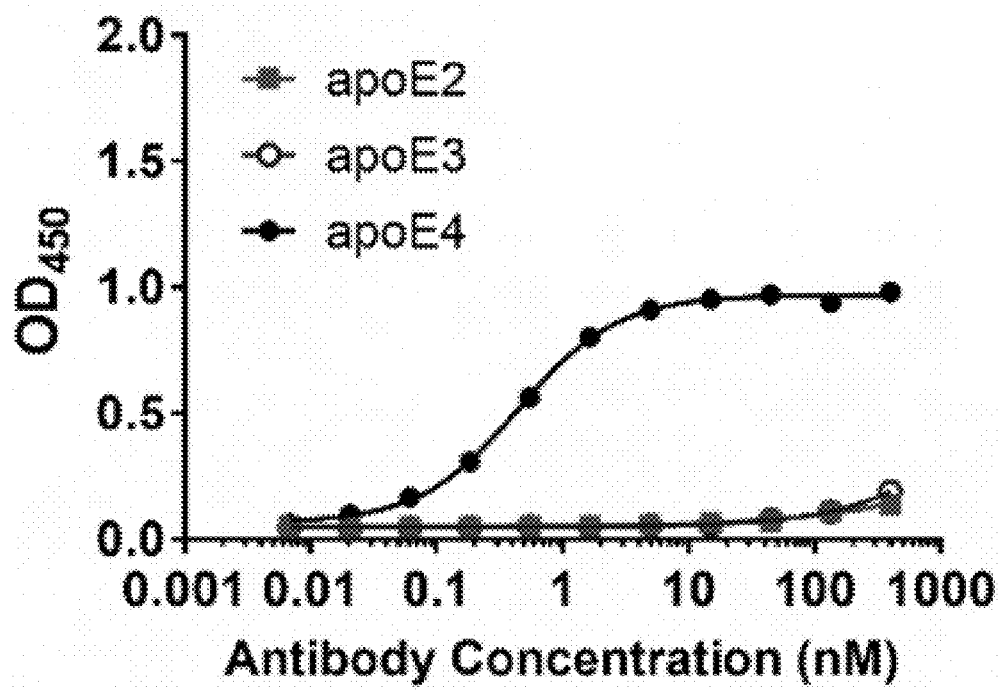
FIG. 5A-H depicts graphs showing aspects of various antibodies. Specifically, FIG. 5A-D graphically shows the results of an ELISA using various antibodies. ELISA plates were coated with 0.5 μg/ml of recombinant apoE2 (square), apoE3 (open circle), or apoE4 (closed circle). Then different concentrations of (A) HJ151, (B) HJ153, (C) HJ154, or (D) HJ156 were loaded on the plates. Horse-radish peroxidase labeled goat anti-mouse secondary antibodies were used to detect binding. The results show that HJ153 and HJ154 bind ApoE2, ApoE3 and ApoE4 as detected in the ELISA. HJ151 is specific for ApoE4 and HJ156 binds only ApoE3 and ApoE4.
Figure 5B:
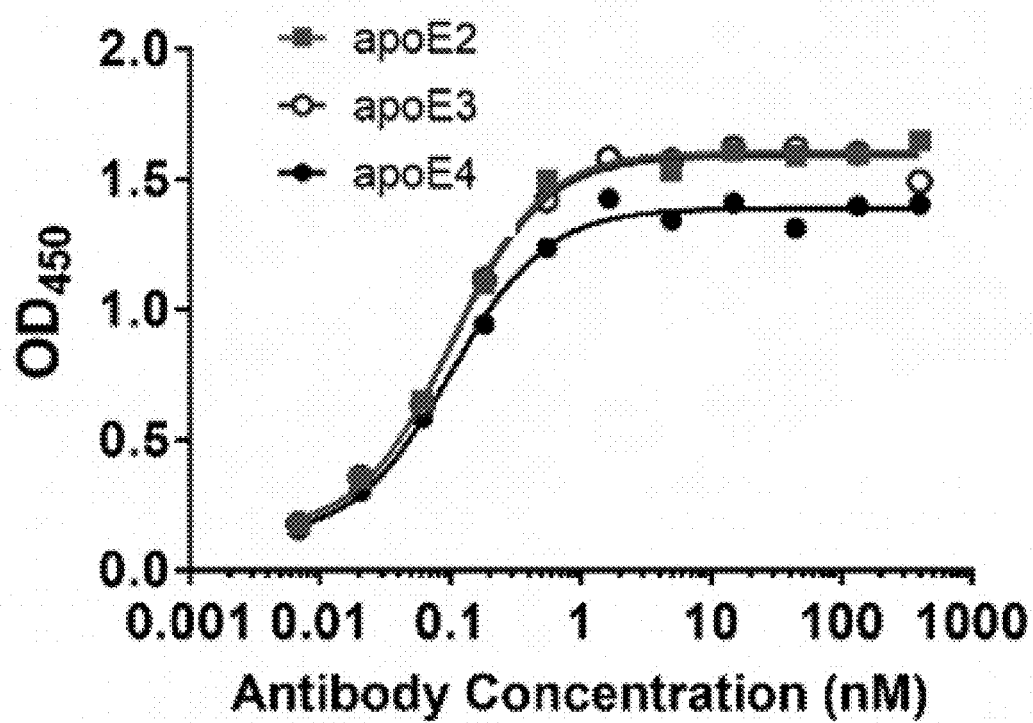
Figure 5C:
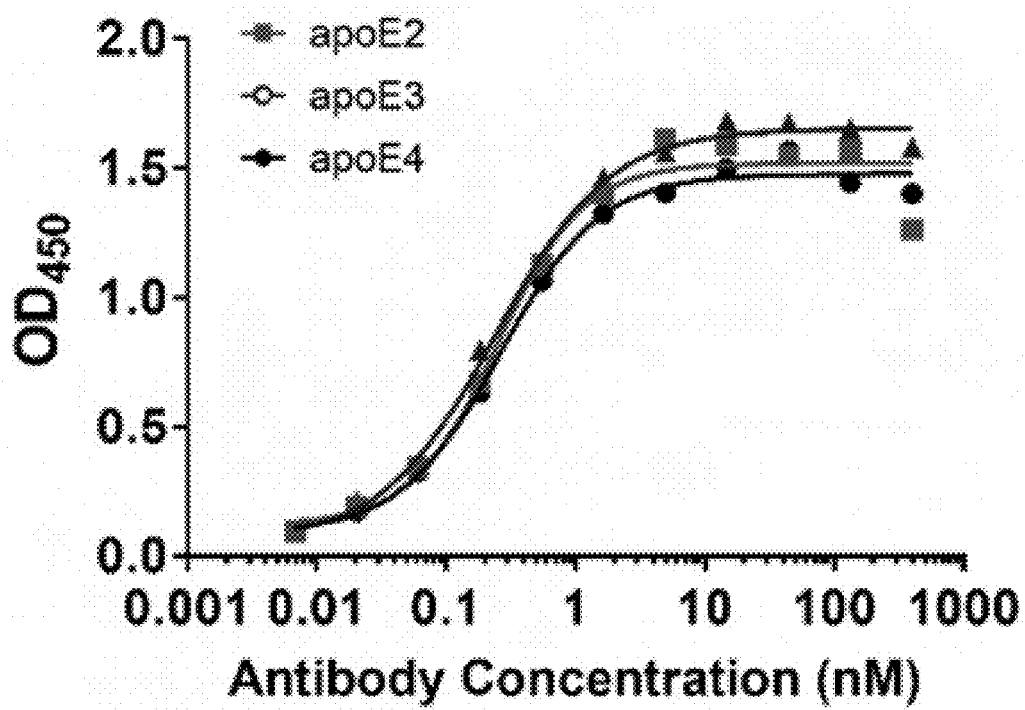
Figure 5D:
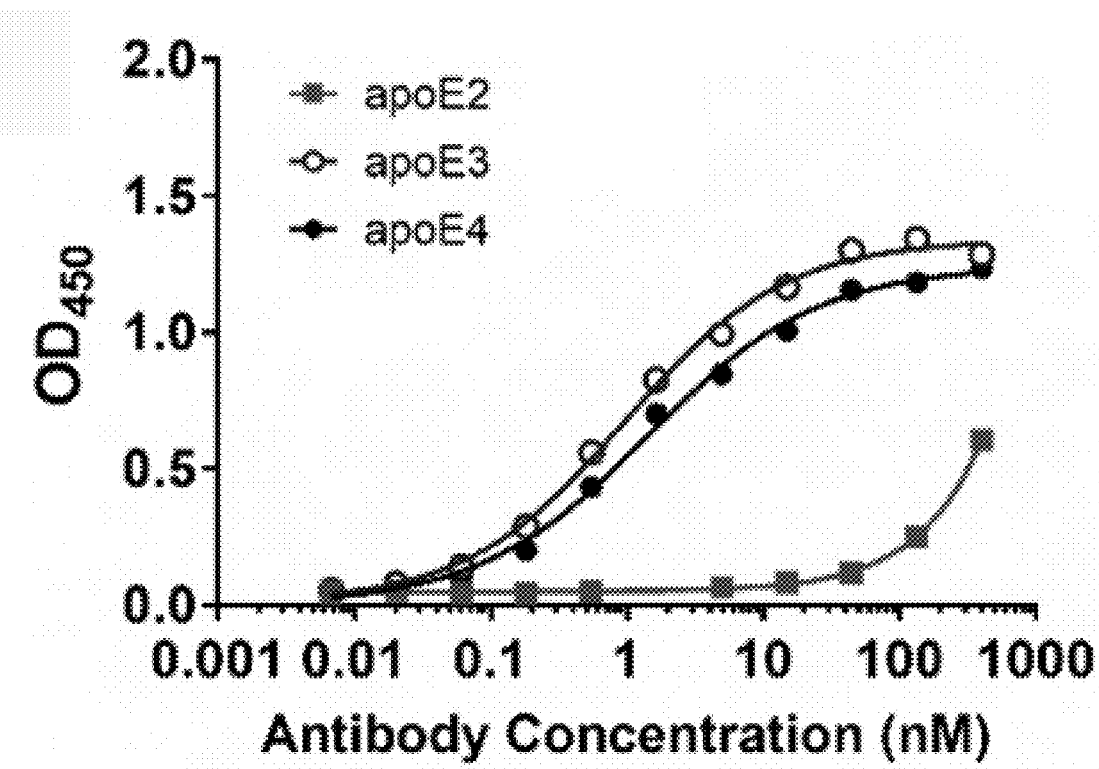
Figure 5E:
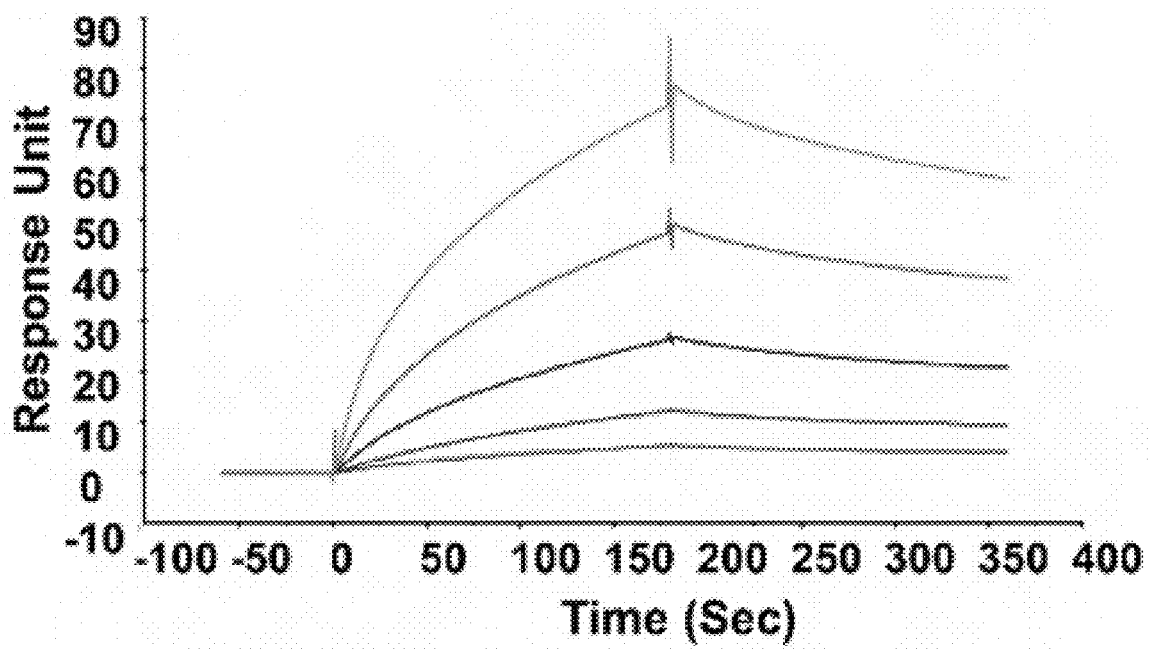
Figure 5F:
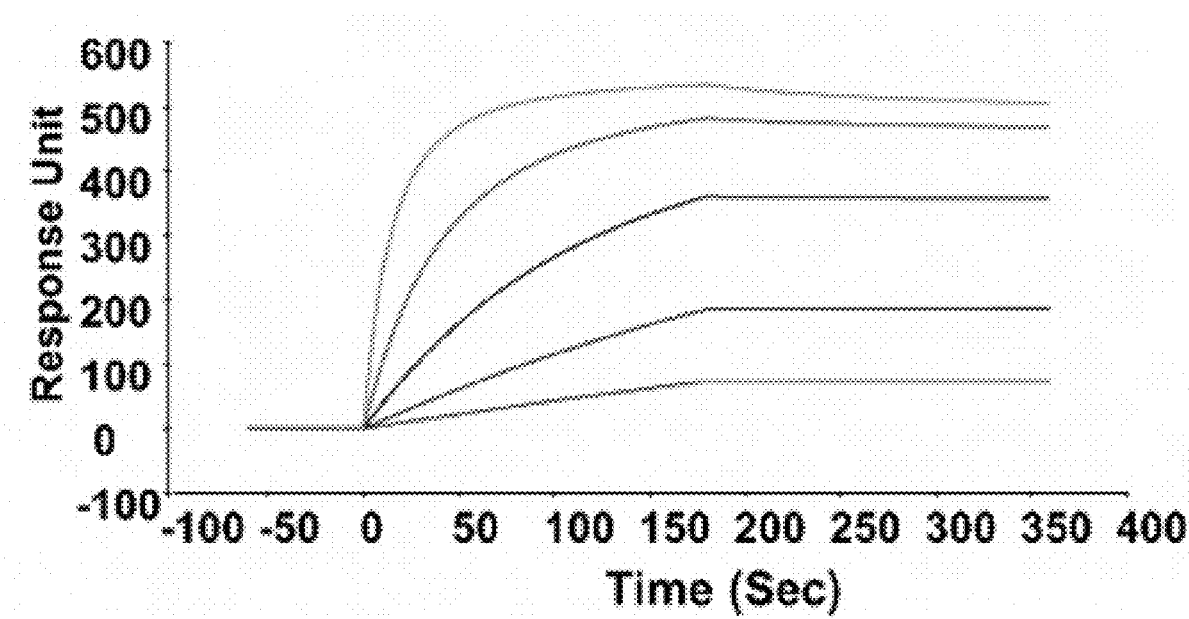
Figures 5G, 5H:
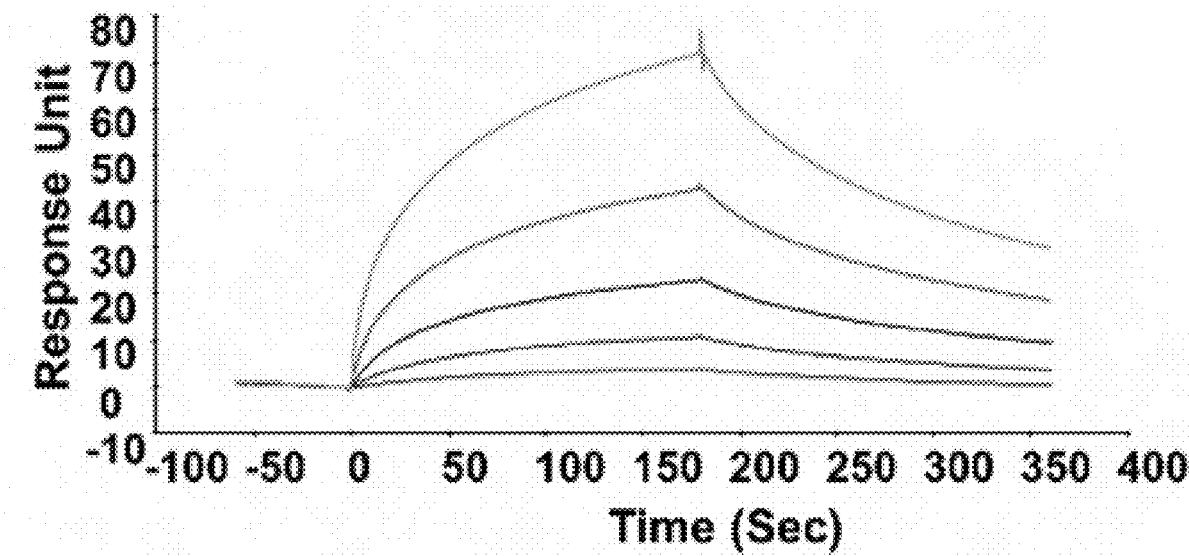

ELISA plates were coated with 0.5 µg/ml of recombinant apoE2, apoE3, or apoE4. Then different concentrations of HJ151 (FIG. 5A), HJ153 (FIG. 5B), HJ154 (FIG. 5C), or HJ156 (FIG. 5D) were loaded on the plates. Horse-radish peroxidase labeled goat anti-mouse secondary antibodies were used to detect binding. FIG. 5A-D shows that HJ153 and HJ154 bind ApoE2, ApoE3 and ApoE4 as detected in the ELISA. HJ151 is specific for ApoE4 and HJ156 binds only ApoE3 and ApoE4. Surface plasmon resonance profiles for various antibodies was also performed. Anti-ApoE antibodies were serially diluted 3-fold (starting at 100 nM for HJ153 (FIG. 5F), and 1000 nM for HJ151 (FIG. 5E), and HJ156 (FIG. 5G) for detection of binding to biotinylated-recombinant apoE4 captured on a streptavidin chip. Samples were injected at a flow rate of 30 µl/minute. FIG. 5H shows apparent KD values of HJ151, HJ153 and HJ156 which were calculated based on the SPR experiment.

Example 6

APP/PS1-21 E4/E4 mice received continuous intracerebroventricular (ICV) infusion of PBS (negative control), mouse IgG2 (negative control), HJ5.1 (anti-Aβ antibody, positive control), or an anti-apoE antibody (HJ151, HJ154, or HJ156), beginning at 2 months of age (n=10-12/group). Anti-ApoE antibody or control antibody (2 mg/ml) was filled into a subcutaneous osmotic minipump (Alzet, model 2006) and infused through a surgically implanted catheter into the left lateral cerebral ventricle (bregma −0.4 mm, 1.0 mm lateral to midline, 2.5 mm below the skull), infusing fluid at the speed of 1.2 µl/min for 6 weeks.

Figure 6:
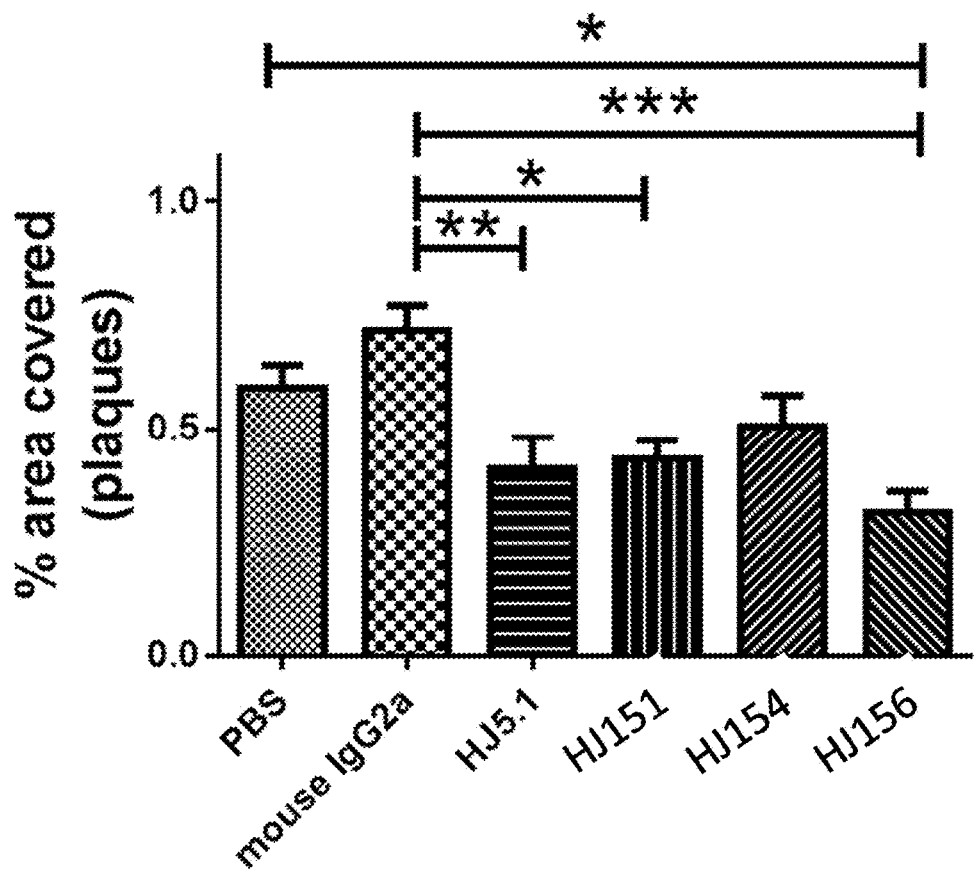
FIG. 6 depicts a graph showing some anti-ApoE antibodies decrease Aβ plaques in APP/PS1-21 E4/E4 mice after ICV infusion. APP/PS1-21 E4/E4 mice received continuous intracerebroventricular (ICV) infusion of PBS (negative control), mouse IgG2ab (negative control), HJ5.1 (anti-Aβ antibody, positive control), or anti-apoE antibody (HJ151, HJ154, and HJ156) beginning at 2 months of age. Anti-ApoE antibody or control antibody (2 mg/ml) was filled into a subcutaneous osmotic minipump (Alzet, model 2006) and infused through a surgically implanted catheter into the left lateral cerebral ventricle (bregma −0.4 mm, 1.0 mm lateral to midline, 2.5 mm below the skull), infusing fluid at the speed of 1.2 μl/min for 6 weeks. At the age of 3.5-months, the mice were perfused and the sections were stained for Aβ plaques using anti-Aβ antibody HJ3.4B. The percent of area covered by plaques in the cerebral cortex dorsal to hippocampus was quantified. One-way ANOVA followed by Tukey post-test was used to analyze the data (*, $p<0.05$; , $p<0.01$; *, $p<0.001$; n=10-12/group).
Figure 7:
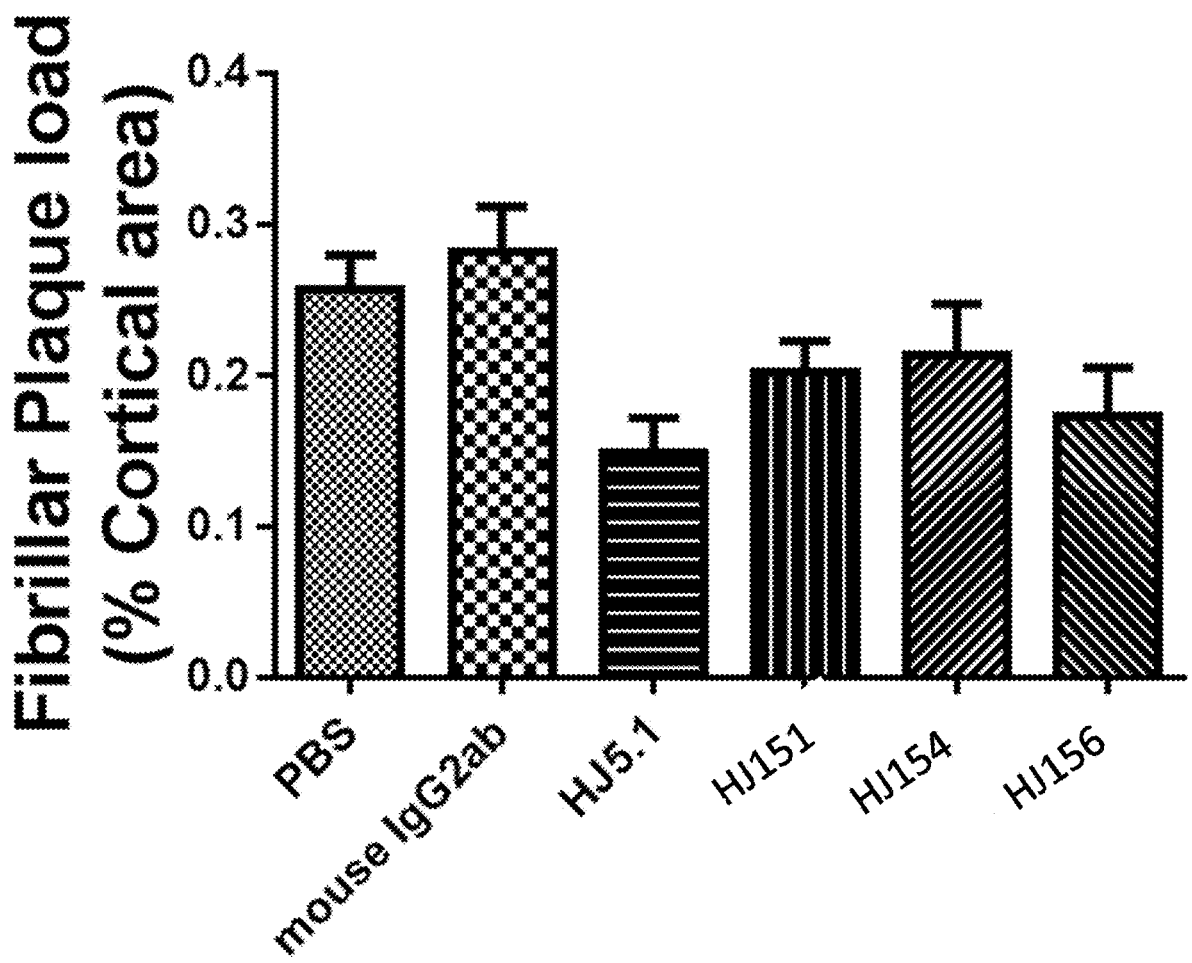
FIG. 7 depicts a graph showing some anti-ApoE antibodies decrease fibrillar plaque load after ICV infusion in APP/PS1-21 E4/E4 mice. APP/PS1-21 E4/E4 mice received continuous intracerebroventricular (ICV) infusion of PBS (negative control), mouse IgG2ab (negative control), HJ5.1 (anti-Aβ antibody, positive control), or anti-apoE antibody (HJ151, HJ154, and HJ156) from 2 months of age. Anti-apoE antibody or control antibody (2 mg/ml) was filled into a subcutaneous osmotic minipump (Alzet, model 2006) and infused through a surgically implanted catheter into the left lateral cerebral ventricle (bregma −0.4 mm, 1.0 mm lateral to midline, 2.5 mm below the skull) at the speed of 1.2 μl/min for 6 weeks. At the age of 3.5-months, the mice were perfused and the brain sections were stained for fibrillar plaques using Thioflavine S. The area covered by plaques in the cerebral cortex dorsal to hippocampus was quantified. One-way ANOVA followed by Tukey post-test was used to analyze the data (*, $p<0.05$; n=10-12/group).
Figure 8A:
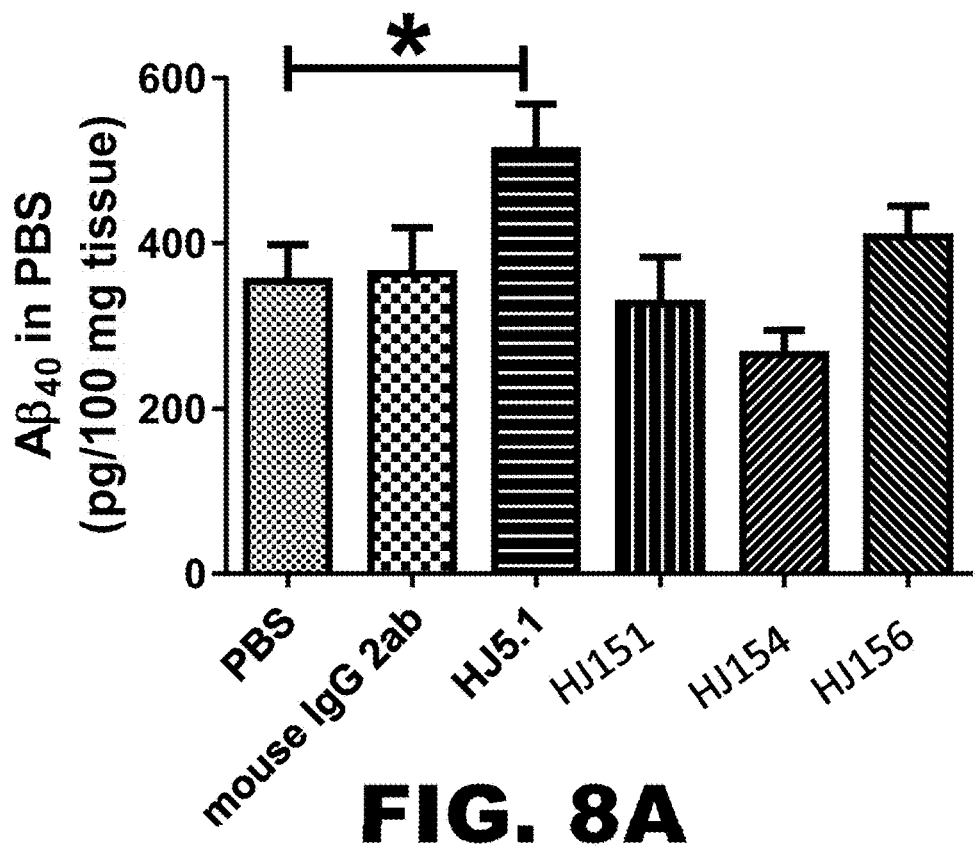
FIG. 8A-F depicts graphs showing that anti-ApoE antibodies decrease insoluble Aβ42 in APP/PS1-21 E4/E4 mice after ICV infusion. APP/PS1-21 E4/E4 mice received continuous intracerebroventricular (ICV) infusion of PBS (negative control), mouse IgG2ab (negative control), HJ5.1 (anti-Aβ antibody, positive control), or anti-apoE antibody (HJ151, HJ154, and HJ156) from 2 months of age. Anti-apoE antibody or control antibody (2 mg/ml) was filled into a subcutaneous osmotic minipump (Alzet, model 2006) and infused through a surgically implanted catheter into the left lateral cerebral ventricle (bregma −0.4 mm, 1.0 mm lateral to midline, 2.5 mm below the skull) at the speed of 1.2 μl/min for 6 weeks (n=10-12/group). At the age of 3.5-months, the mice were perfused and the cortical tissue was homogenized in PBS, Triton and 5M Guanidine sequentially. The Aβ levels in soluble (A, D) and insoluble (B, C, E, F) fractions were measured (Aβ40 data shown in A-C, Aβ42 data shown in D-F). Student's t-test was used for data analysis. Anti-apoE antibodies reduced $A\beta_{42}$ levels in different fractions (*, $p<0.05$; **, $p<0.01$).
Figure 8B:
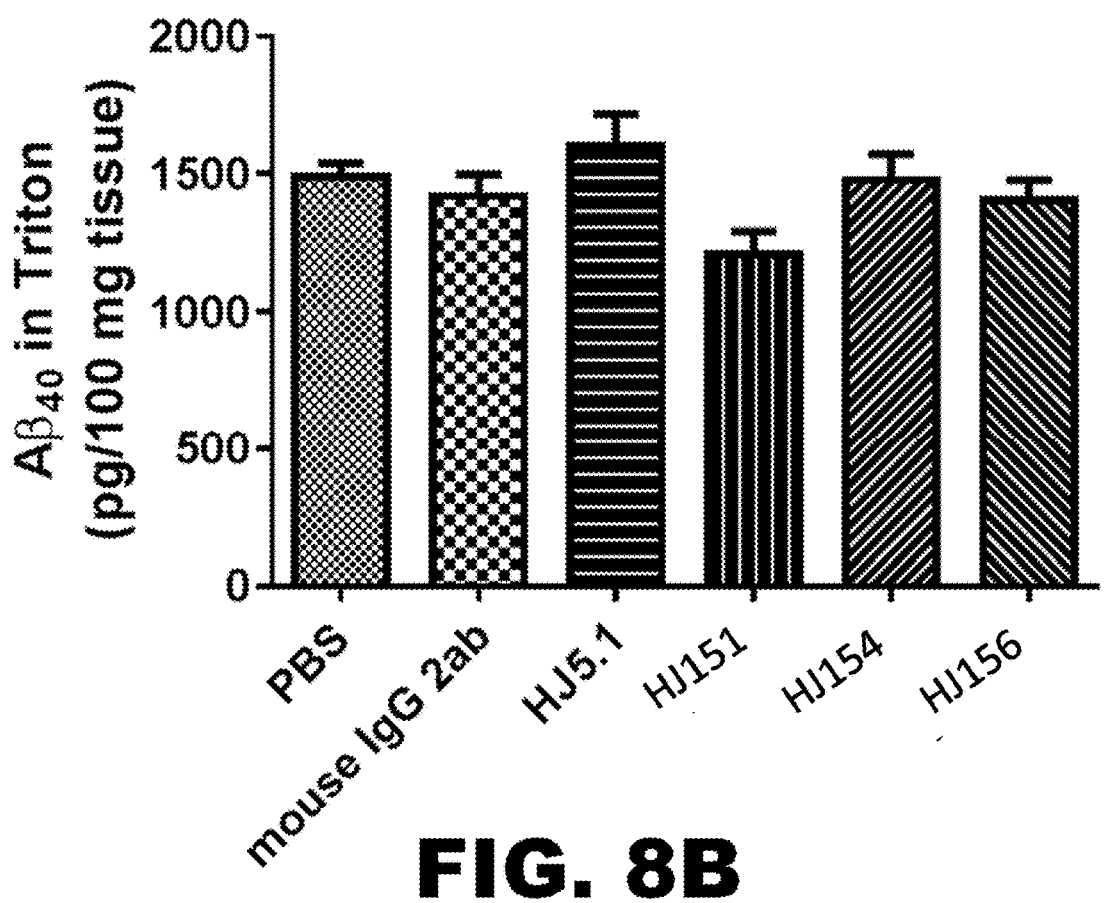
Figure 8C:
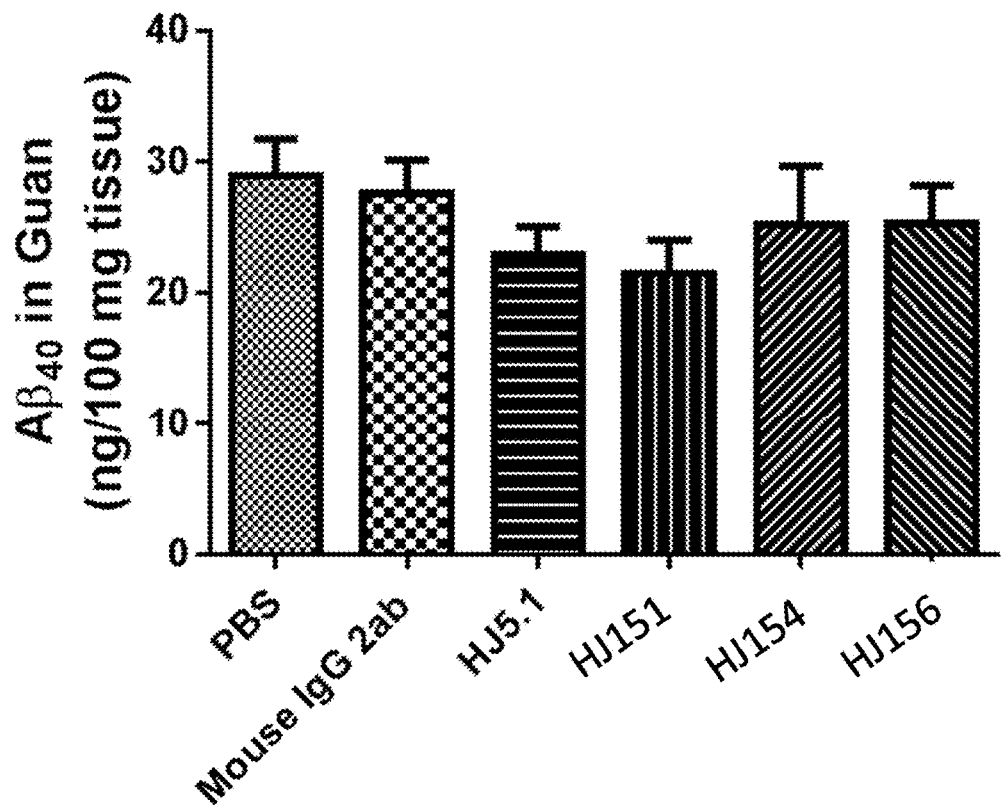
Figure 8D:
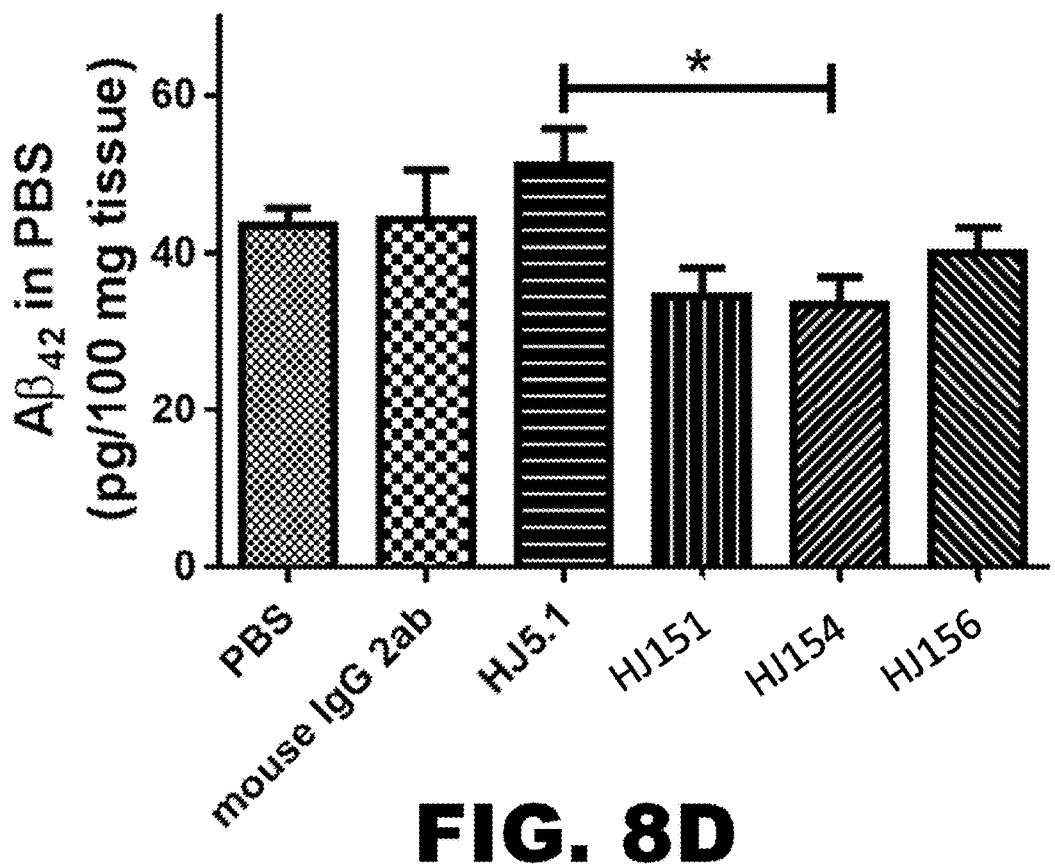
Figure 8E:
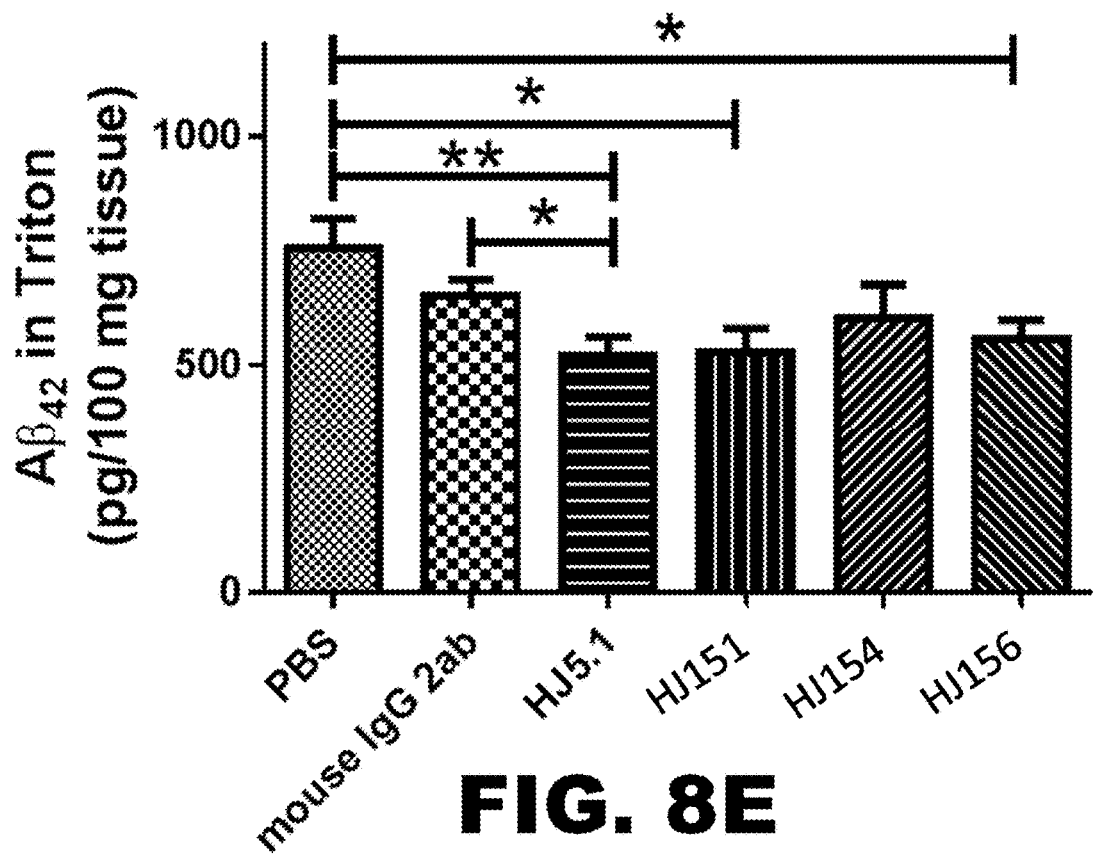
Figure 8F:
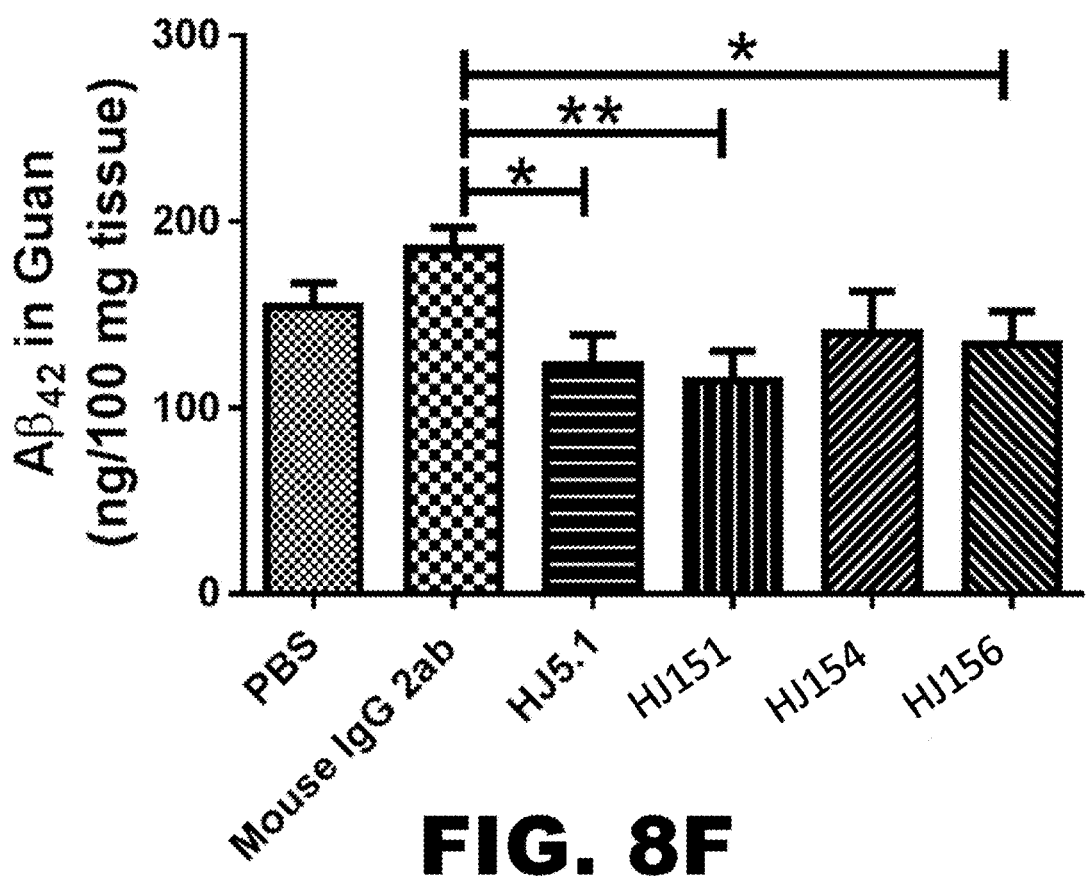

At the age of 3.5-month, the mice were perfused and brain sections were stained for either Aβ plaques using anti-Aβ antibody HJ3.4B or fibrillar plaques using Thioflavine S. The percent of area covered by plaques in the cerebral cortex dorsal to hippocampus was quantified. One-way ANOVA followed by Tukey post-test was used to analyze the data. As shown in FIG. 6 and FIG. 7, there was a statistically significant decrease in the percent area covered by Aβ and fibrillar plaques following ICV infusion of certain anti-ApoE antibodies. The amount of soluble and insoluble Aβ was also quantified in the cerebral cortex dorsal to hippocampus by ELISA. Briefly, cortical tissue was homogenized in PBS, Triton, and 5M guanidine sequentially, and the Aβ levels in each fraction were measured. A statistically significant decrease in insoluble Aβ42 (Triton and guanidine fractions) was observed for HJ151 and HJ156 (FIG. 8).

Example 7

Figure 9:
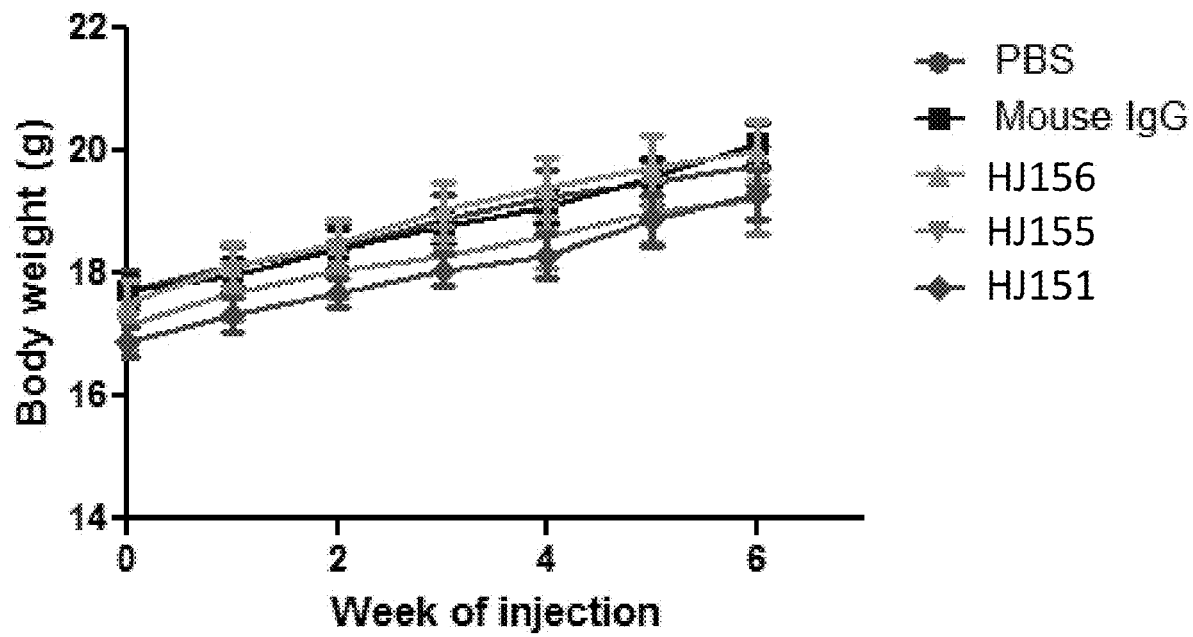
FIG. 9 depicts a graph showing the body weight of APP/PS1-21 E4/E4 mice intraperitoneally injected with anti-ApoE antibodies (1 injection/week for 7 weeks).
Figure 10:
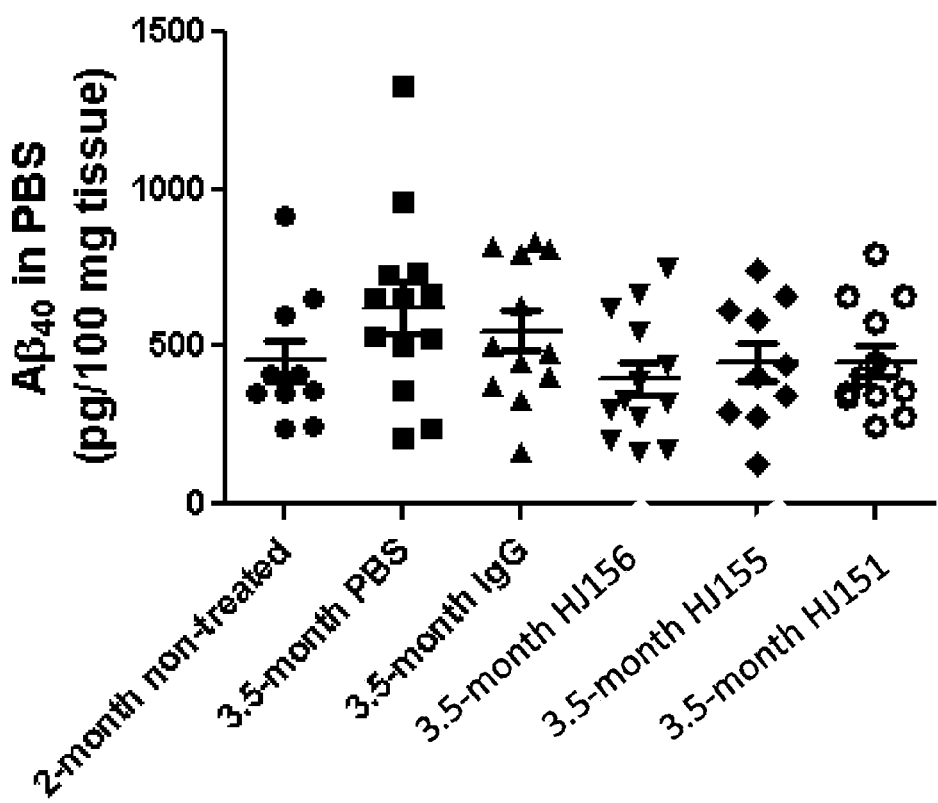
FIG. 10 depicts a graph showing that HJ151, HJ155, and HJ156 do not significantly decrease soluble Aβ40 in the PBS fraction of brain tissue homogenate in APP/PS1-21 E4/E4 mice intraperitoneally injected with anti-ApoE antibodies (1 injection/week for 7 weeks).
Figure 11:
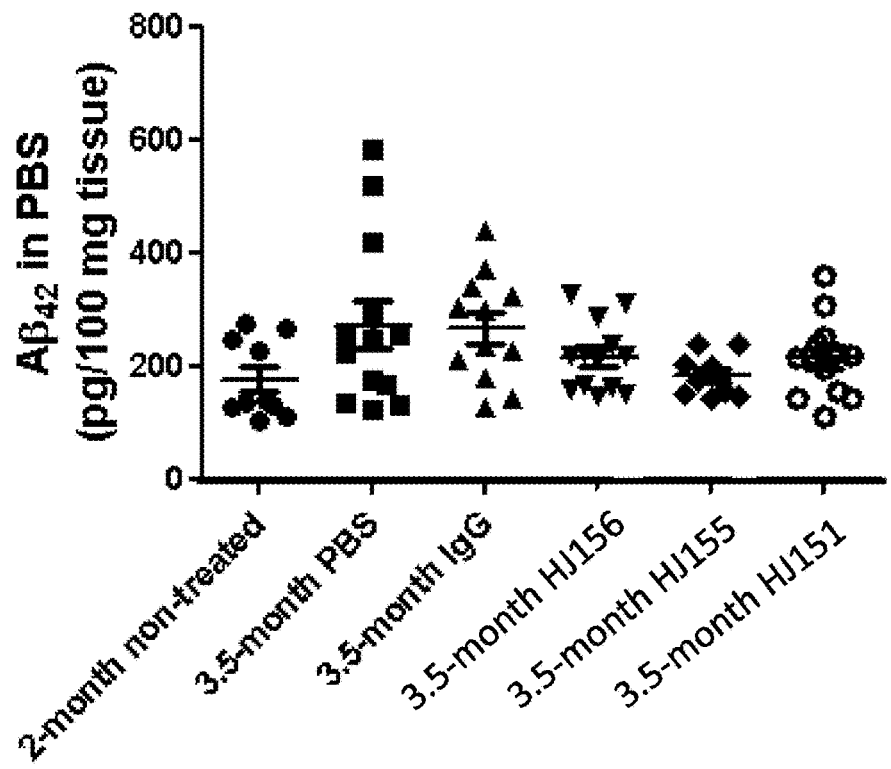
FIG. 11 depicts a graph showing that HJ151, HJ155, and HJ156 do not significantly decrease soluble Aβ42 in the PBS fraction of brain tissue homogenate of APP/PS1-21 E4/E4 mice intraperitoneally injected with anti-ApoE antibodies (1 injection/week for 7 weeks).
Figure 12:
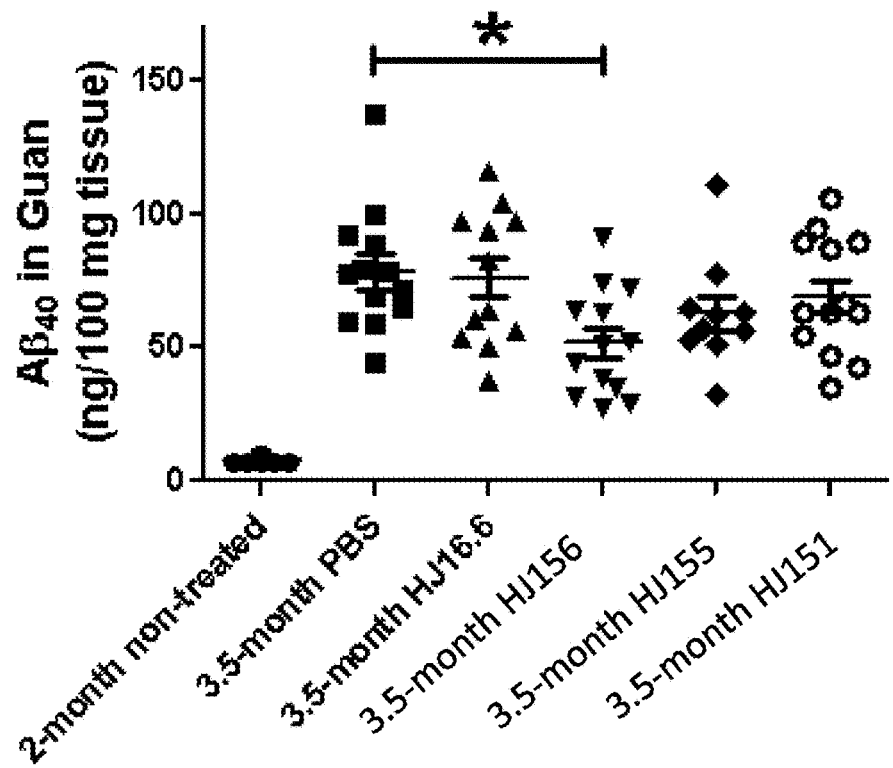
FIG. 12 depicts a graph showing that HJ156 significantly decreases insoluble $A\beta_{40}$ in the 5M guandine fraction of brain tissue homogenate of APP/PS1-21 E4/E4 mice intraperitoneally injected with anti-ApoE antibodies (1 injection/week for 7 weeks). (*$p<0.05$)
Figure 13:
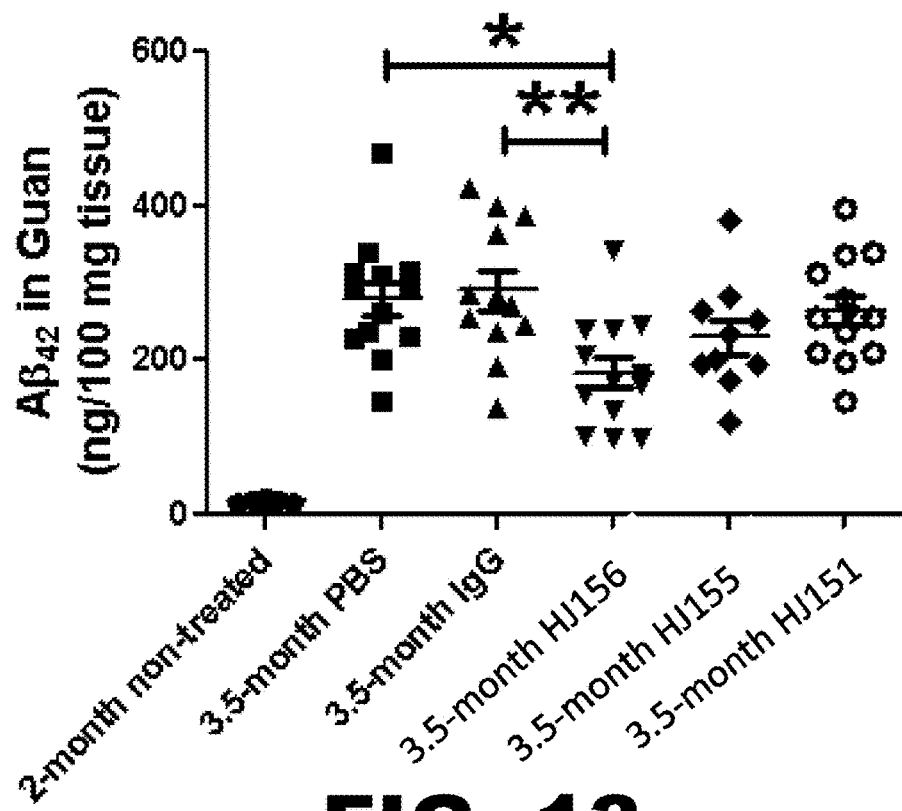
FIG. 13 depicts a graph showing that HJ156 significantly decreases insoluble $A\beta_{42}$ in the 5M guandine fraction of brain tissue homogenate of APP/PS1-21 E4/E4 mice intraperitoneally injected with anti-ApoE antibodies (1 injection/week for 7 weeks). (*$p<0.05$, (**$p<0.01$).

APP/PS1-21 E4/E4 mice received an intraperitoneal injection of PBS (negative control), mouse IgG (negative control), or an anti-apoE antibody (HJ151, HJ155, and HJ156) beginning at 2 months of age (n=10/group). Antibodies were injected once per week at 50 mg/kg. Body weight of each mouse was measured at the time of injection. As shown in FIG. 9, there was no difference in body weight between treatment groups. Three days after the seventh injection, the mice were perfused. The left hem i-brain was fixed in 4% PFA at 4° C. for 48 hrs, then transferred to PBS and stored at 4° C. The right hem i-brain was dissected and frozen for biochemical analysis.

The amount of soluble and insoluble Aβ was quantified in the cerebral cortex dorsal to hippocampus by ELISA. Briefly, cortical tissue was homogenized in PBS and 5M guanidine sequentially, and the Aβ levels in soluble (PBS) and insoluble (guanidine) fractions were measured. As shown in FIG. 10-13, HJ156 significantly decreased insoluble Aβ40 and Aβ42 (p<0.0001) but did not have a statistically significant effect on soluble Aβ. The level of insoluble Aβ40 and 42 were also decreased by HJ155 and HJ151 but the decrease was not significant.

Example 8

APP/PS1-21 E4/E4 mice were injected with an AAV2/8 vector producing anti-ApoE antibodies (HJ151, HJ151Δ, or HJ156) or controls (HJ16.5 and PBS) (n=24/group). The AAV serotype was AAV2/8 and the promoter was a chicken beta actin (CBA) promoter. The injections were done with bilateral intracerebroventricular injections in P0 mice. The HJ151Δ antibody is the HJ151 antibody with a mutation in the Fc domain, which prevents binding to Fc gamma receptors. The antibody HJ16.5 binds to the human protein PLD3 and does not bind to murine PLD3 or other mouse proteins. At the age of 3.5 months, the mice were perfused. The left hemi-brain was fixed in 4% PFA at 4° C. for 48 hrs, then transferred to 30% sucrose and stored at 4° C. The right hemi-brain was dissected and frozen for biochemical analysis.

Figure 14:
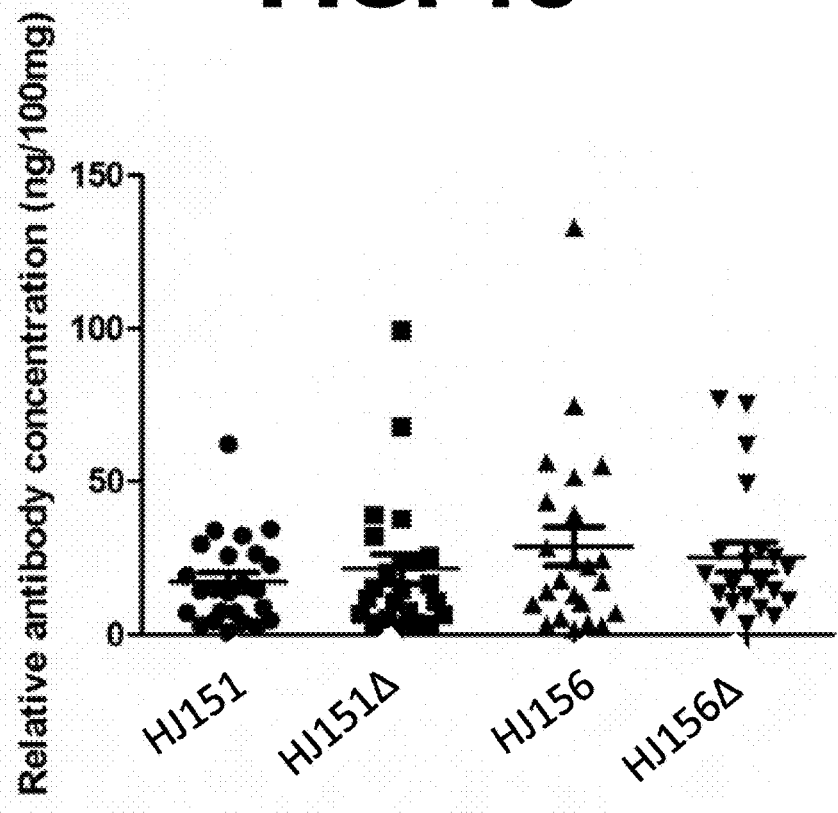
FIG. 14 is a graph depicting relative antibody concentration in the cortex of APPPS1-21/APOE4 mice expressing recombinant (r) HJ151, r HJ151 with D265A mutation (Δ), rHJ156, and rHJ156Δ. APPPS1-21/APOE4 mice were injected at P0 with AAV2/8 that express full length rHJ151 and rHJ156 with or without the D265A mutation. At the age of 3.5 months, antibody concentration in the PBS soluble fraction of cortex was measured by ELISA. The relative level of each antibody was calculated by using its hybridoma-derived, purified antibody as a standard.
Figure 15:
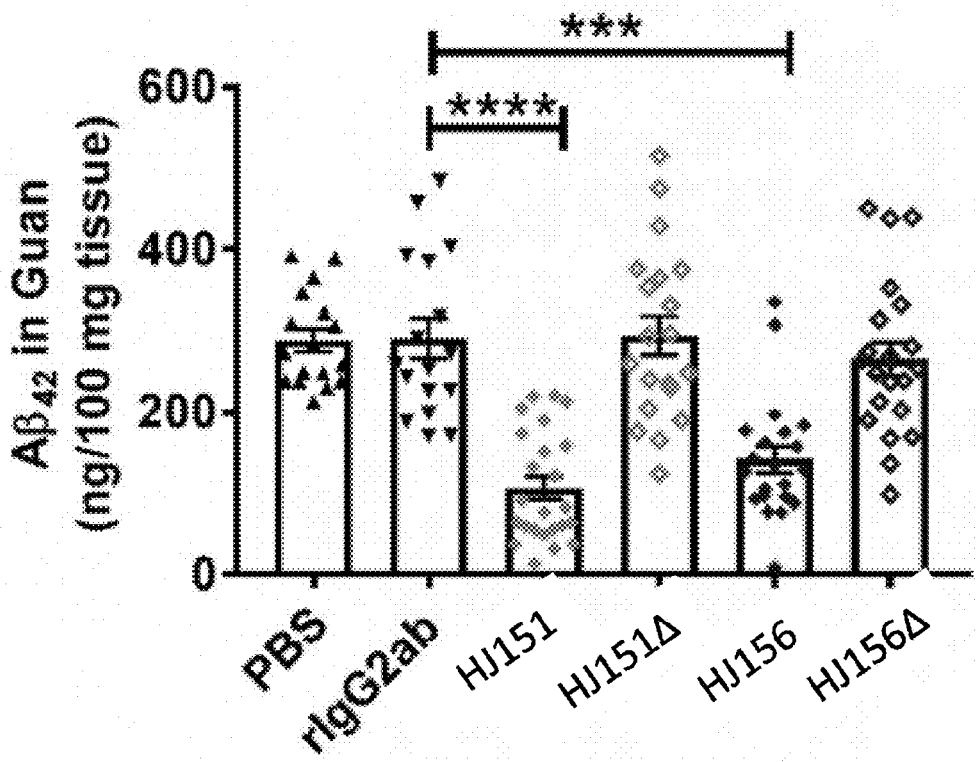
FIG. 15 depicts a graph showing that HJ151 and HJ156 significantly reduce insoluble $A\beta_{42}$ in the guanidine fraction of brain tissue homogenate of APP/PS1-21 E4/E4 mice injected with anti-ApoE antibodies expressed in the brain with the use of an adenoassociated virus (AAV) 2/8 vector. HJ151 and HJ156 with a D265A mutation (HJ151Δ and HJ156Δ) have no effect.
Figure 16:
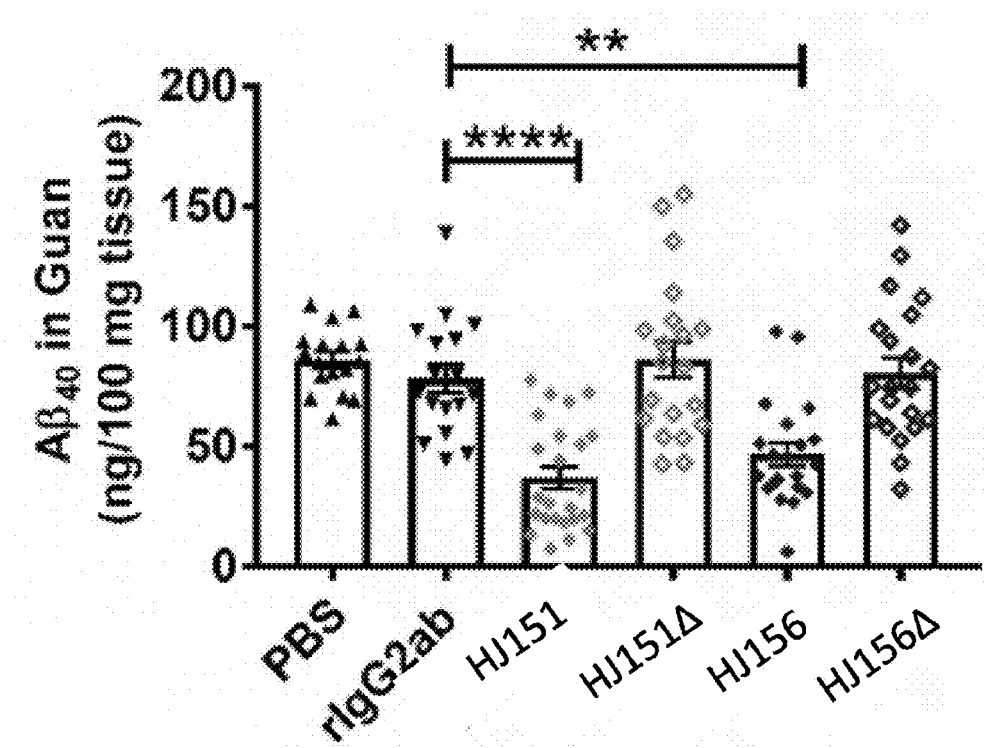
FIG. 16 depicts a graph showing that HJ151 and HJ156 reduce insoluble $A\beta_{40}$ in the guanidine fraction of brain tissue homogenate of APP/PS1-21 E4/E4 mice injected with anti-ApoE antibodies expressed in the brain with the use of an adenoassociated virus (AAV) 2/8 vector. HJ151 and HJ156 with a D265A mutation (HJ151Δ and HJ156Δ) have no effect.
Figure 17A:
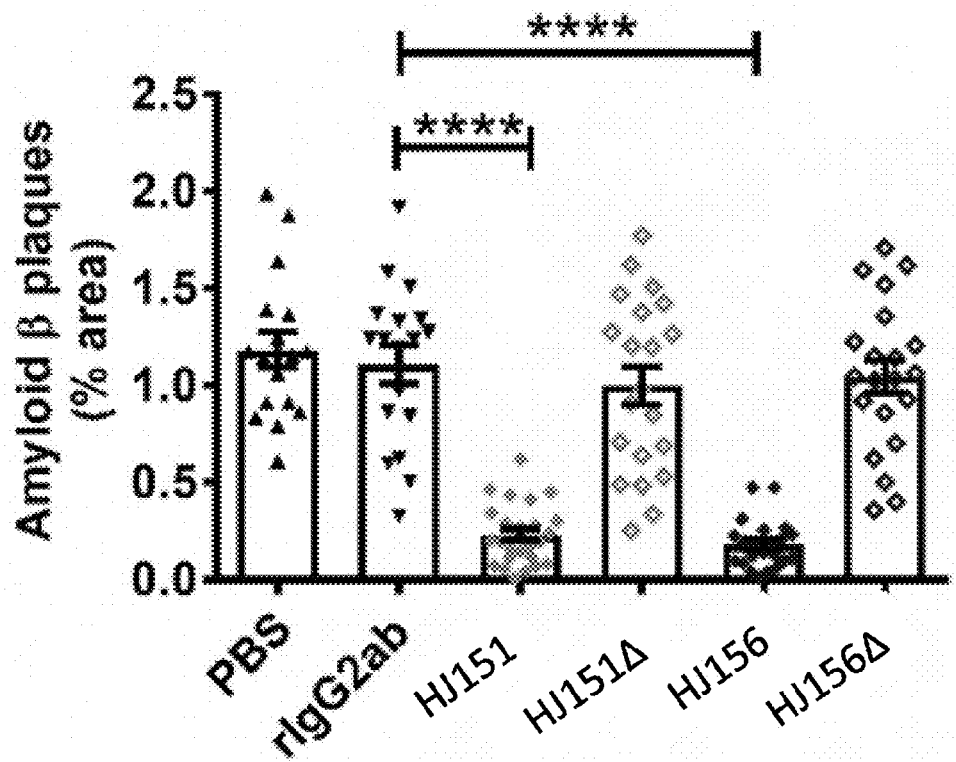
FIG. 17A-B depict graphs showing that HJ151 and HJ156 significantly reduce amyloid β (A) and fibrillar plaque area (B) in brain sections from APP/PS1-21 E4/E4 mice injected with anti-ApoE antibodies expressed in the brain with the use of an adenoassociated virus (AAV) 2/8 vector. HJ151 and HJ156 with a D265A mutation (HJ151Δ and HJ156Δ) have no effect.
Figure 17B:
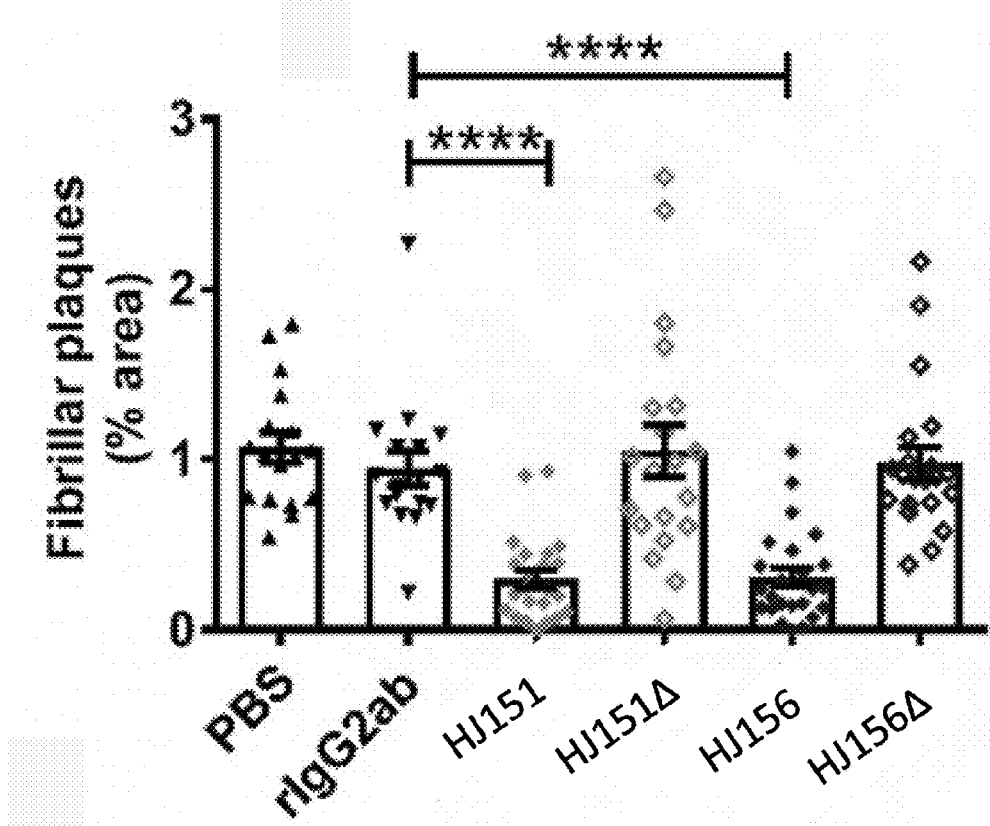
Figure 18A:
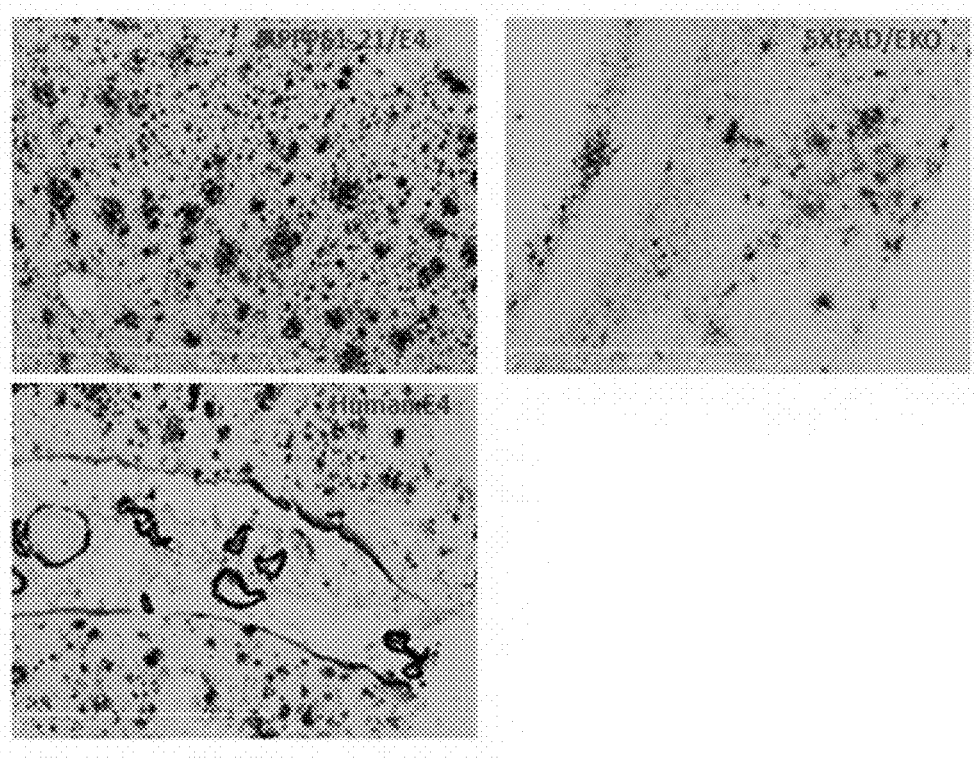
FIG. 18A-G depicts unfixed tissue sections (20 μm thickness) from APPPS1-21/apoE$^{4/4}$ (APPPS1-21/E4), 5XFAD/ apoE knockout (5XFAD/EKO) mice and human apoE$^{4/4}$ (human E4) brains that were stained using biotinylated ("B") antibodies HJ3.4B (A), HJ151B (B), HJ152B (C), HJ153B (D), HJ154B (E), HJ155B (F), and HJ156B (G).
Figure 18B:
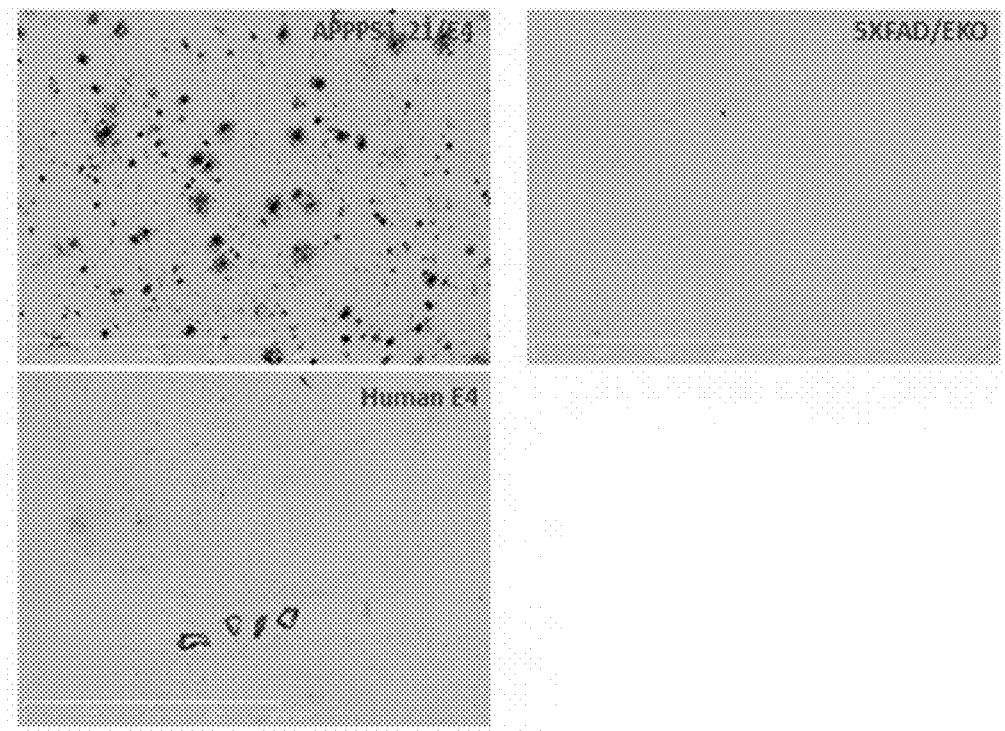
Figure 18C:
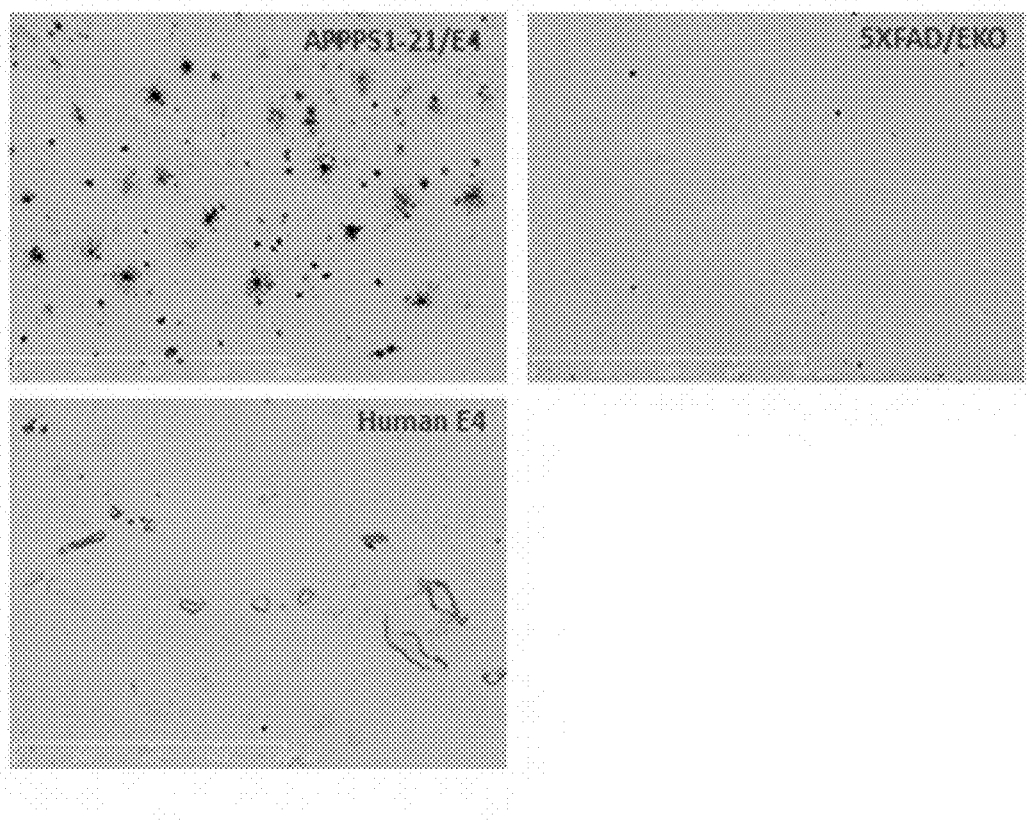
Figure 18D:
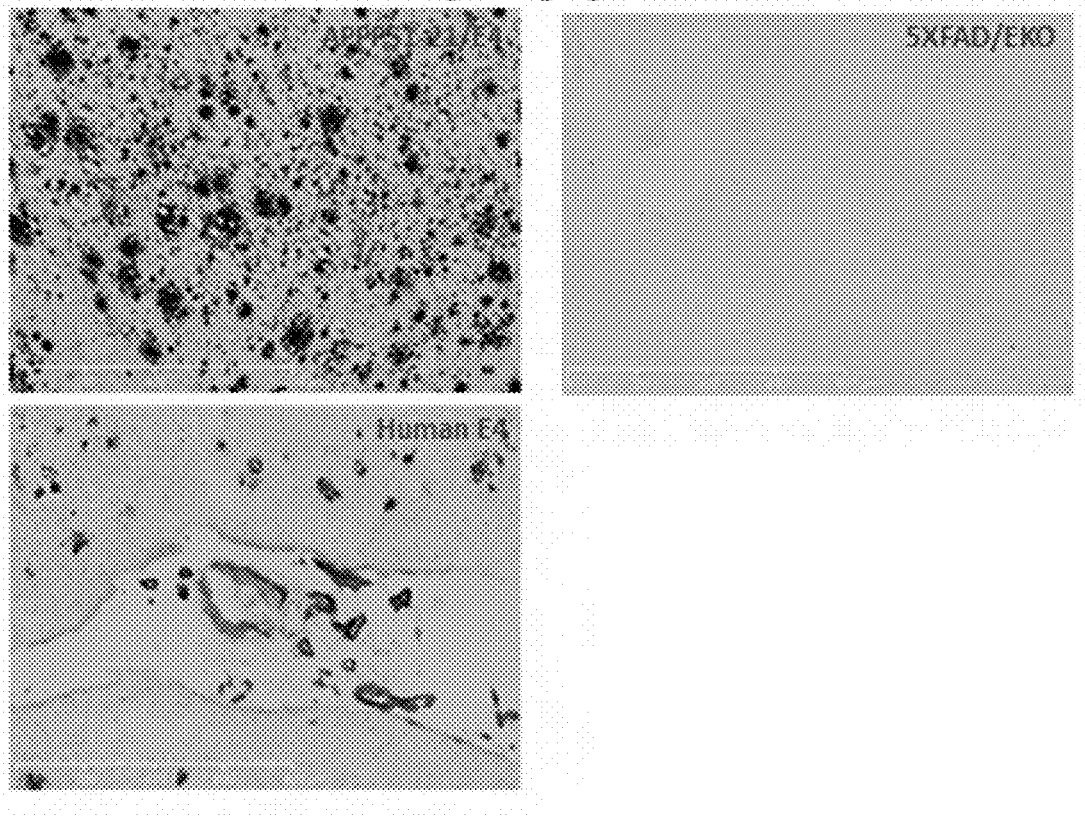
Figure 18E:
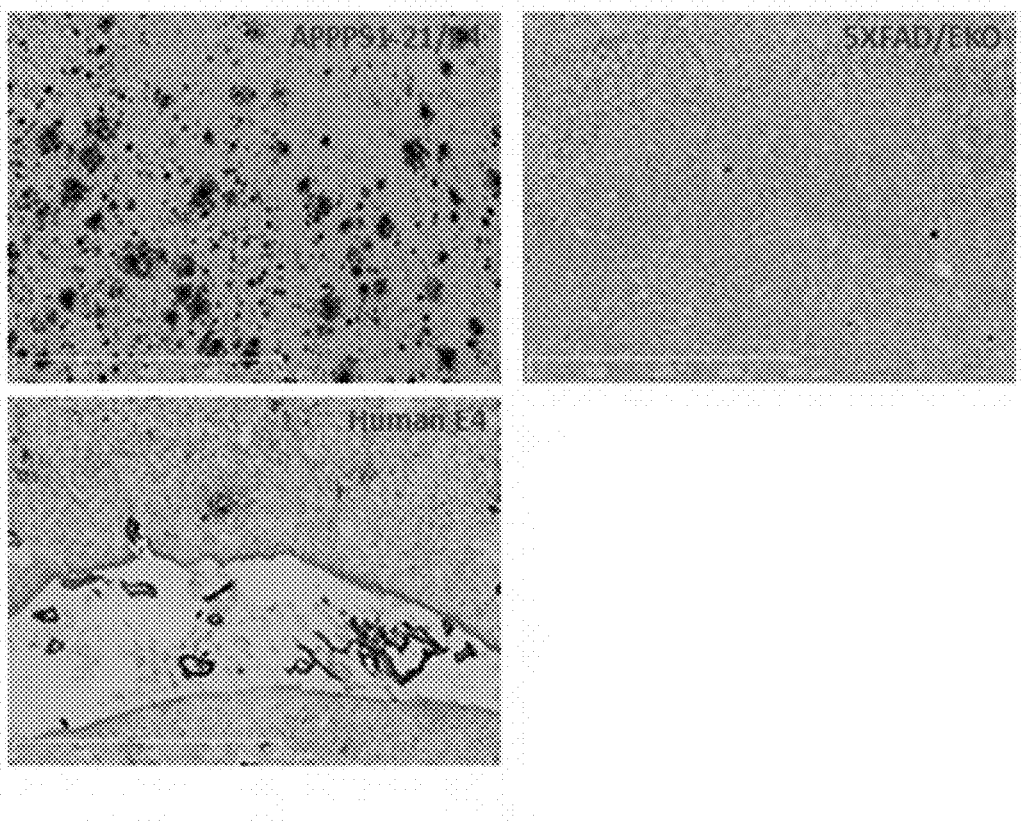
Figure 18F:
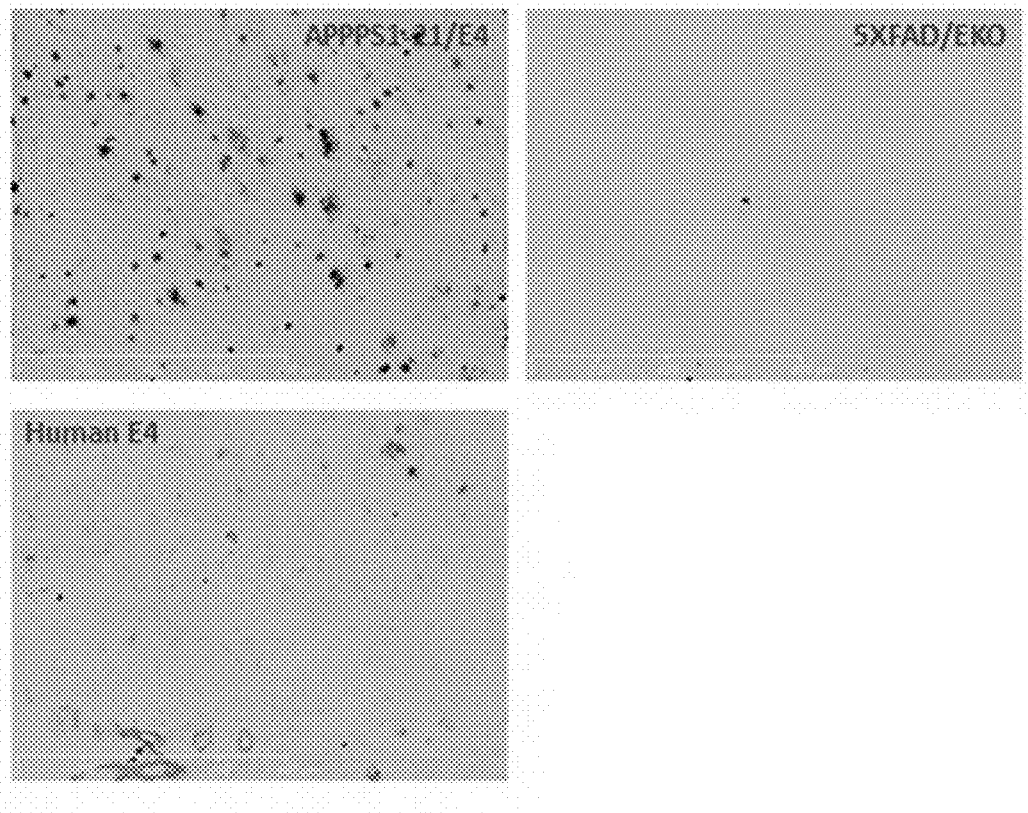
Figure 18G:
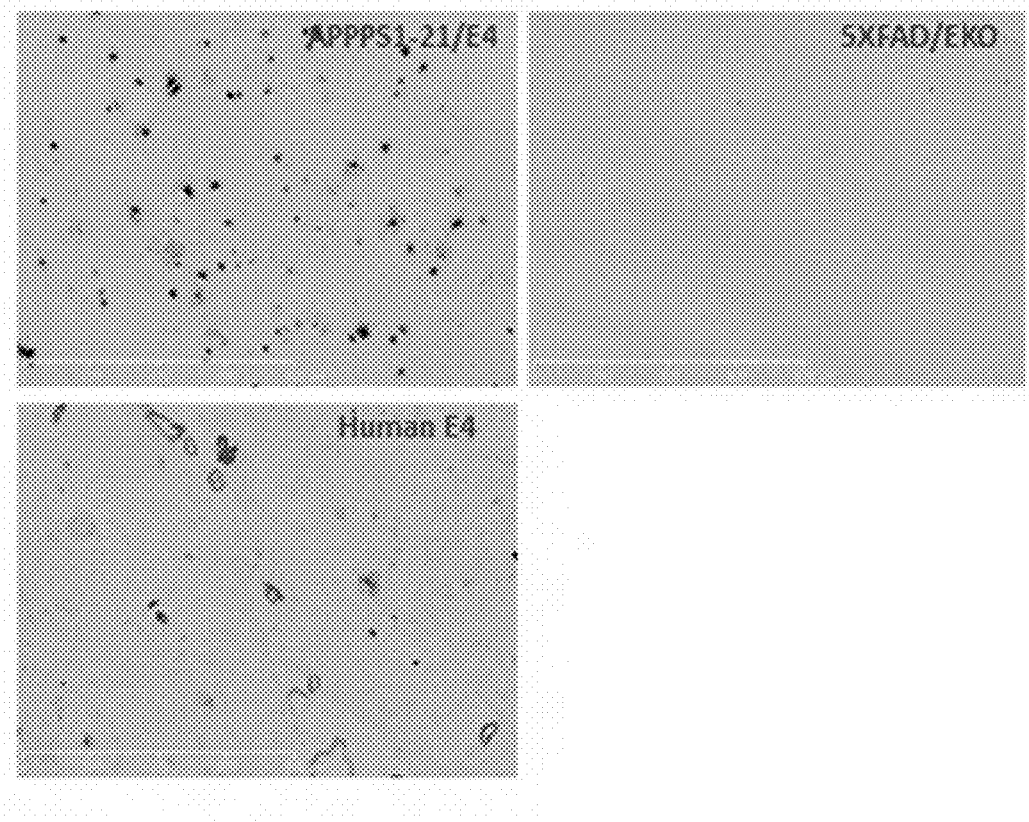

The amount of soluble and insoluble Aβ was quantified in the cerebral cortex dorsal to hippocampus by ELISA. Briefly, cortical tissue was homogenized in PBS and 5M guanidine sequentially, and the Aβ levels in soluble (PBS) and insoluble (guanidine) fractions were measured. As shown in FIGS. 15 and 16, antibodies HJ151 and HJ156 significantly decreased insoluble Aβ40 and Aβ42, whereas HJ151Δ and HJ156Δ had no effect. None of the antibodies had a significant effect of soluble Aβ40 or Aβ42 (not shown). As shown in FIG. 14, relative antibody concentrations in the cortex of APPPS1-21/APOE4 mice expressing recombinant (r) HJ151, r HJ151 with D265A mutation (Δ), rHJ156, and rHJ156Δ were determined by antigen capture ELISA. The relative level of each antibody was calculated by using its hybridoma-derived, purified antibody as a standard. Similar levels of expression were found and no statistical differences between the different antibodies.

Overall, expression of HJ151 and HJ156 by AAV significantly reduced insoluble Aβ40 and Aβ42 in the APP/PS1-21 E4/E4 mouse model. Mutation of Fc effector (D265A) completely abolished the ability of HJ151 to reduce insoluble A. These results indicate clearance of Aβ aggregates by anti-apoE antibody may require an antibody opsonization and phagocytosis step involving microglia mediated Aβ clearance.

Example 9

Unfixed tissue sections (20 μm thickness) from APP/PS1-21 E4/E4 (APPPS1-21/E4), 5XFAD/apoE knockout (5XFAD/EKO) mice and human apoE$^{4/4}$ (human E4) brains from persons who died with amyloid deposition were stained using the biotinylated antibodies HJ3.4B (anti-Aβ), HJ151B, HJ152B, HJ153B, HJ154B, HJ155B, and HJ156B (anti-apoE antibodies). (Note: "B" indicates "biotinylated".) All mice utilized were old enough to have a significant amount of Aβ in the cortex (APPPS1-21/apoE$^{4/4}$, >6 months old; 5XFAD/apoE knockout (5XFAD/EKO), >6 months old). All images in the mice and human sections are from the cortex. The results shown in FIG. 18 demonstrate that HJ3.4B, HJ151B, HJ152B, HJ153B, HJ154B, HJ155B, and HJ156B stain plaques and cerebral amyloid angiopathy in the APP/PS1-21 E4/E4 and human apoE$^{4/4}$ brains. No staining is observed in 5XFAD/EKO brains with anti-apoE specific antibodies.

Example 10

The affinity of several anti-ApoE antibodies for ApoE4 was determined by surface plasmon resonance using a BIAcore T200. Anti-biotin monoclonal mouse antibody was immobilized on a Biacore Series S CM5 sensor chip. Biotinylated recombinant alipidated ApoE4 was then captured on to the chip. Serial dilutions of each antibody were injected at a flow rate of 30 μl/min. Each sample was analyzed, for example, with 3-minute association and 10-minute dissociation. After each injection the chip was regenerated using 3 M MgCl$_2$ or another appropriate buffer. Binding response was corrected by subtracting the response units (RUs) from a flow cell capturing an irrelevant IgG at similar density. A 1:1 Languir model of simultaneous fitting of k$_{on}$ and k$_{off}$ was used for kinetics analysis. The data are shown in Table 2. Recombinant alipidated ApoE4 was either expressed in soluble form in *E. coli* and then purified, or purchased from a commercial supplier.

TABLE 2

| Antibody | k$_{on}$ (1/Ms) | k$_{off}$ (1/s) | KD (M) | Rmax (RU) |
|---|---|---|---|---|
| HJ151 | 1.97E+04 | 1.19E−03 | 6.02E−08 | 77.5 |
| HJ152 | 4.66E+03 | 1.16E−03 | 2.49E−07 | 176 |
| HJ153 | 8.04E+05 | 3.46E−04 | 4.30E−10 | 261.9 |
| HJ154 | 5.16E+05 | 3.48E−04 | 6.75E−10 | 262.9 |
| HJ156 | 2.07E+04 | 4.49E−03 | 2.16E−07 | 78 |
| HJ159 | 1.89E+04 | 7.40E−03 | 3.91E−07 | 71.7 |
| HJ1513 | 6.36E+03 | 8.58E−04 | 1.35E−07 | 226.5 |
| HJ1514 | 1.28E+04 | <1.00E−05 | <7.81E−10 | 43.5 |
| HJ1518 | 4.59E+04 | 9.46E−03 | 2.06E−07 | 56 |
| HJ1526 | 7.88E+03 | 5.28E−03 | 6.70E−07 | 34.7 |

Example 11

ELISA dose response curves were generated for several anti-ApoE antibodies. Briefly, plates were coated overnight with full length recombinant alipidated ApoE2, ApoE3, or ApoE4 (0.5 μg/ml). The following days, plates were washed, blocked and then incubated with an anti-ApoE antibody. A goat, anti-mouse IgG-HRP antibody was used for secondary detection. The data are shown in Table 3. Recombinant alipidated ApoE was either expressed solubly in *E. coli* and then purified, or purchased from a commercial supplier.

TABLE 3

| | Binding EC50s (nM) against ApoE isoforms | | |
|---|---|---|---|
| | IC 50_E2 | IC 50_E3 | IC 50_E4 |
| HJ151 | >1000 | >1000 | 0.44 |
| HJ152 | >1000 | 0.13 | 0.35 |
| HJ153 | 0.02 | 0.02 | 0.03 |
| HJ154 | 0.25 | 0.24 | 0.26 |

TABLE 3-continued

Binding EC50s (nM) against ApoE isoforms

|        | IC 50_E2 | IC 50_E3 | IC 50_E4 |
|--------|----------|----------|----------|
| HJ155  | >1000    | 0.78     | 1.1      |
| HJ156  | >1000    | 1.69     | 0.62     |
| HJ158  | 0.07     | 0.09     | 0.06     |
| HJ159  | >1000    | 1.90     | 0.32     |
| HJ1513 | ~100     | 1.26     | 0.46     |
| HJ1514 | ~100     | 0.23     | 0.04     |
| HJ1518 | >1000    | 0.258    | 0.06     |
| HJ1526 | 0.03     | 0.05     | 0.04     |
| HJ1531 | 0.05     | 0.05     | 0.04     |
| HJ1536 | 0.09     | 0.10     | 0.05     |

Example 12

Figure 19A:
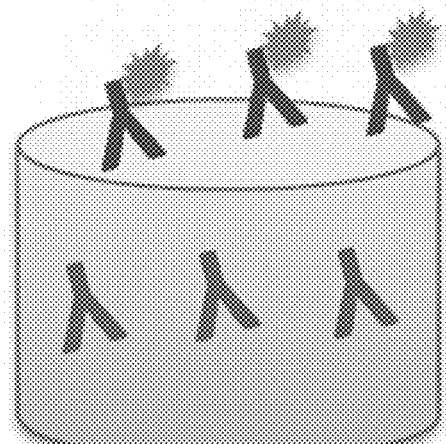
FIG. 19A-D shows antibody detection of ApoE in human plasma lipoprotein particles. (A) shows a schematic of a plasma binding assay used to demonstrate the detection of ApoE in lipoprotein particles from human plasma coated onto an ELISA plate, while (B-D) each show a graph of the results from the binding assay for various antibodies. Detection of ApoE is observed with HJ153, HJ154, HJ1510, HJ1511, HJ1517, HJ1530, and HJ1534.

Anti-ApoE antibodies were assessed for detection of ApoE derived from human plasma lipoprotein by a coated plasma ELISA (FIG. 19A). Human plasma (identified as possessing one or more e4 allele by western blot assay with HJ151 and comprising about 1-5 µM ApoE4) was diluted 100× in PBS and coated onto half-well ELISA microtiter plates overnight at 4° C. Plates were washed extensively in PBS and blocked with 5% BSA/PBS for 1 hour. Antibodies were added to the wells at 400-500 nM starting concentration with 5-fold dilutions thereafter for 1 hour. Binding of antibodies was detected by an anti-mouse IgG secondary conjugated to horse-radish peroxidase (HRP). TMB was the detection substrate with 4N sulfuric acid as the stop solution.

Figure 19B:
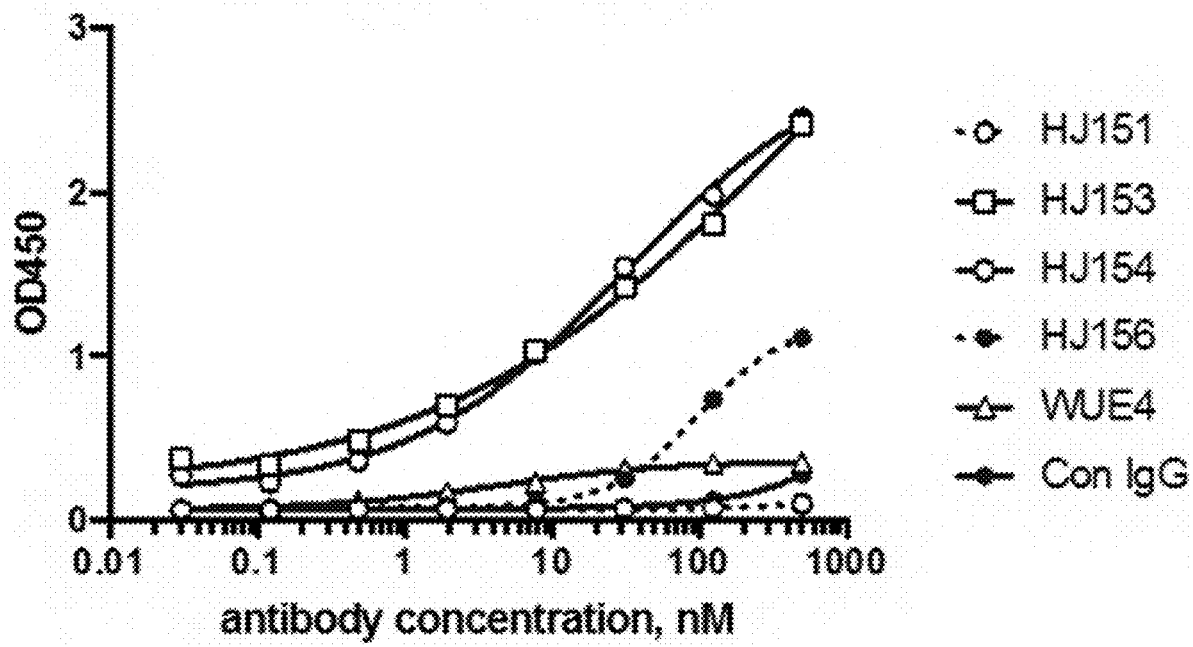
Figure 19C:
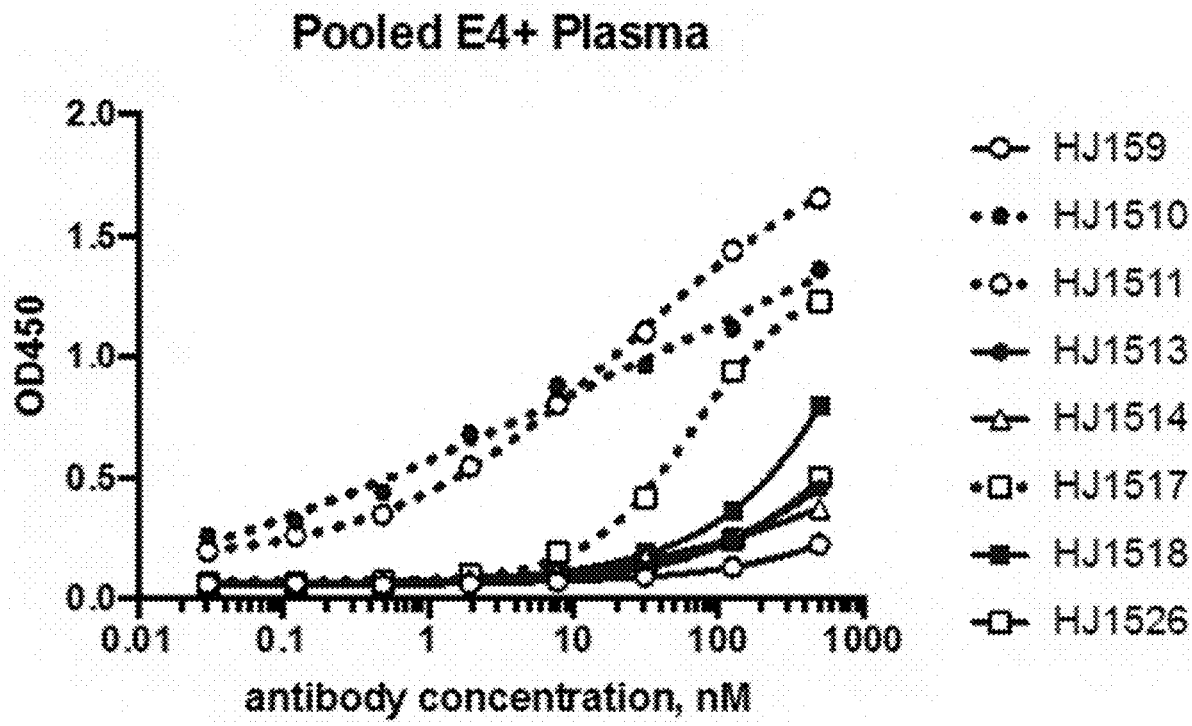
Figure 19D:
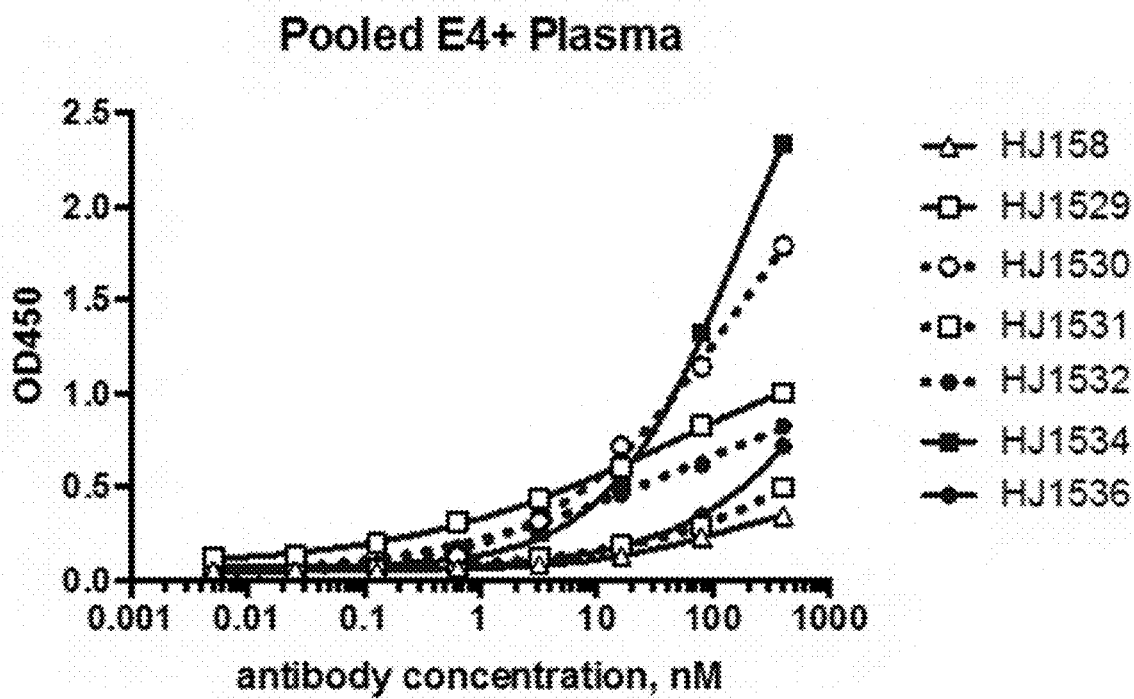

Compared to HJ153 and HJ154, HJ156 demonstrated reduced binding to coated human plasma ApoE (FIG. 19B). A control IgG and a commercially available anti-ApoE antibody, WUE4, showed minimal binding. These data suggest HJ153 and HJ154 robustly detect lipidated ApoE contained in lipoprotein particles from human plasma. FIGS. 19C and D show the binding profiles of other antibodies for coated human plasma. HJ159, HJ1514, HJ1518, HJ1526 (FIG. 19C), HJ158, HJ1531, and HJ1536 (FIG. 19D) did not detect lipidated, plasma ApoE robustly at the highest antibody concentration and minimally at the next dilution downward.

Example 13

Figure 20A:
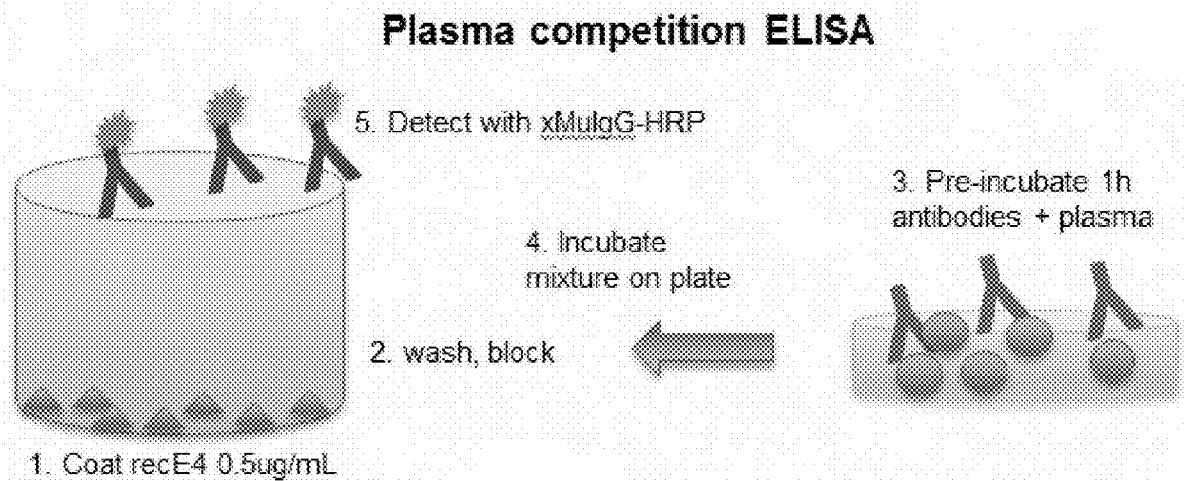
FIG. 20A-C shows antibody detection of ApoE in a competition ELISA. (A) shows a schematic of a plasma competition assay used in assessing preference for antibody binding to coated recombinant alipidated ApoE4 (recApoE; 0.5 ug/mL) after pre-incubation in various dilutions of human plasma, while (B-C) each show a graph of the results from competition ELISA for various antibodies. "x ApoE" is an abbreviation for "anti-ApoE antibody."

Antibodies that failed to detect immobilized human ApoE from plasma were further tested in a competition ELISA to rule out the possibility that coated plasma ApoE epitopes were unavailable for binding due to interaction with the plastic wells (FIG. 20A). Recombinant alipidated ApoE was coated onto half-well ELISA microtiter plates at 0.5 ug/mL in PBS overnight at 4° C. Plates were washed extensively in PBS and blocked with 5% BSA/PBS for 1 hour. HJ153 and antibody clones that did not detect coated human plasma ApoE were pre-incubated in a dilution series of human plasma (comprising about 1-5 µM ApoE4)/5% BSA/PBS (starting dilution 5×, 2-fold thereafter) and either 4 nM or 50 nM of antibody. After 1 hour of pre-incubation, the mixture was added to the blocked plate and incubated for 1 hour. Detection of antibody available for binding to coated alipidated recombinant ApoE4 (not competed off by ApoE in diluted plasma) was with anti-mouse-IgG-HRP and TMB. The reaction was stopped with 4N sulfuric acid.

Figure 20B:
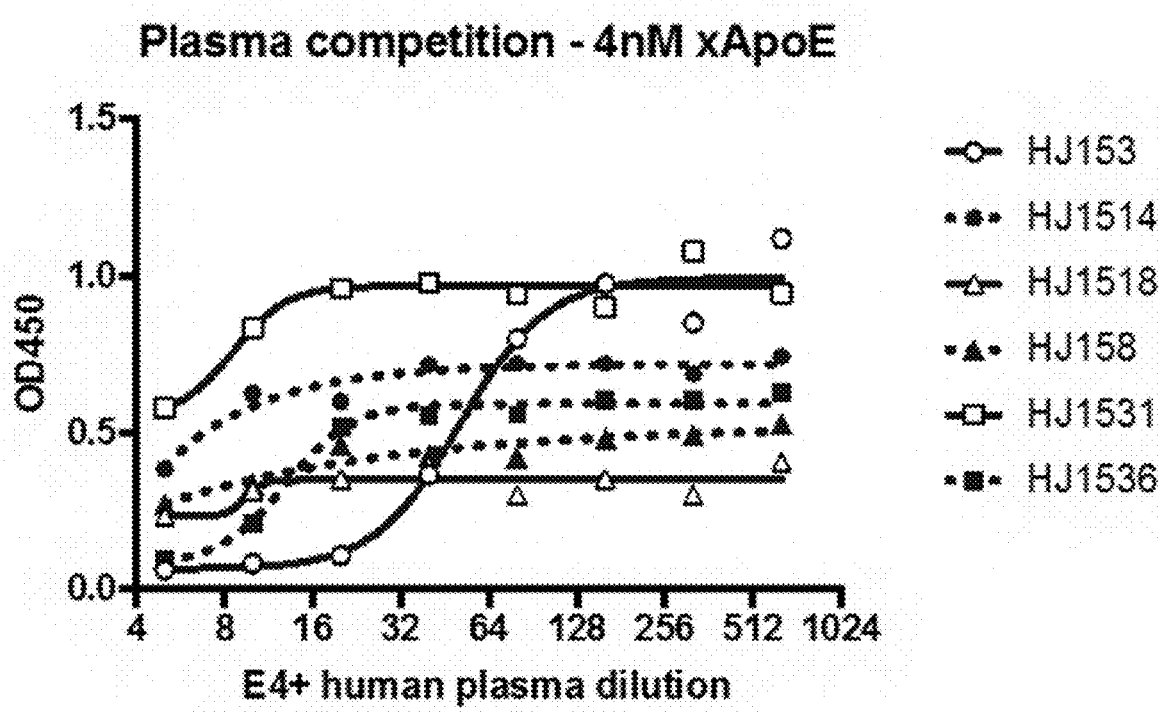
Figure 20C:
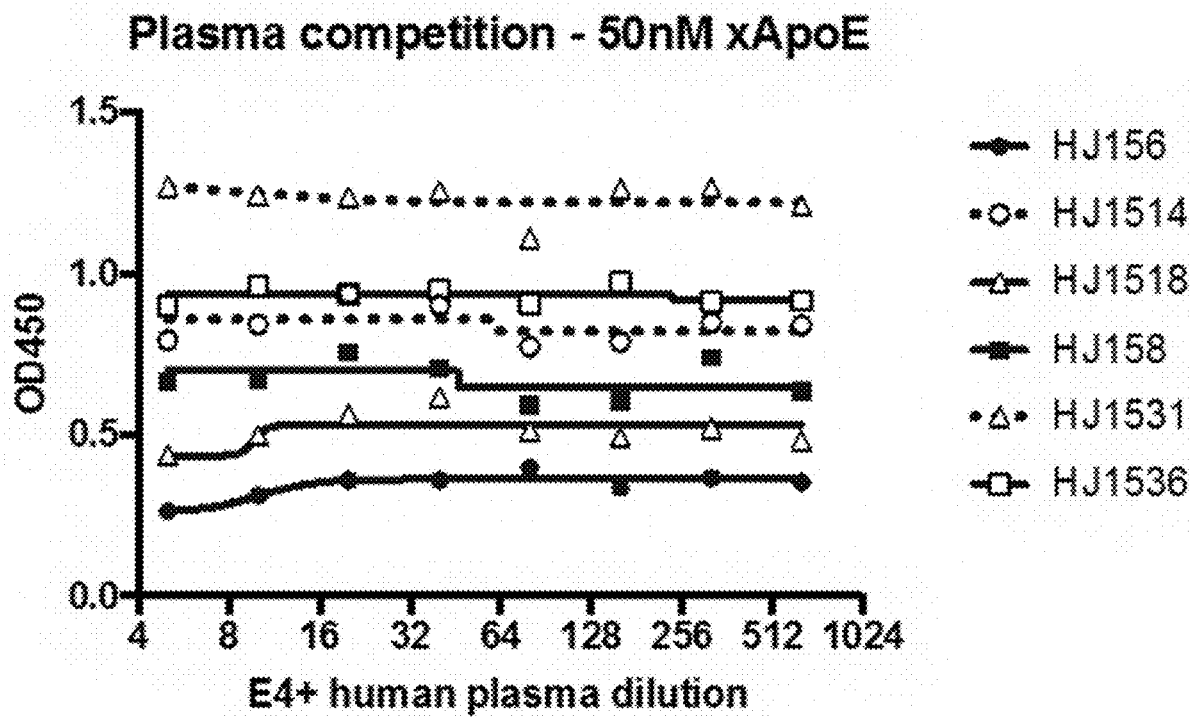
Figure 21A:
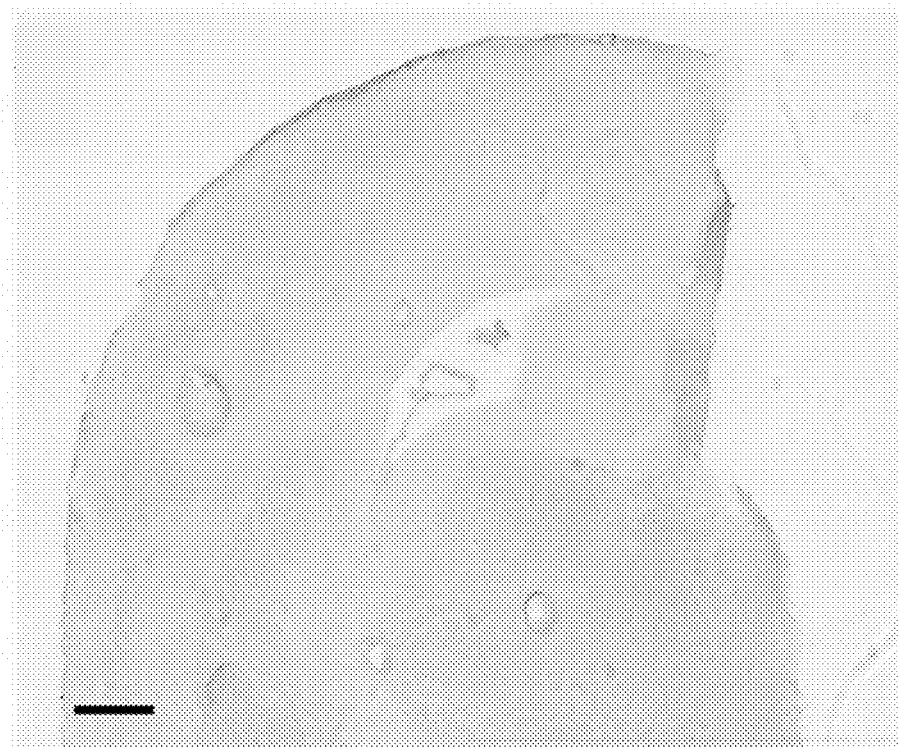
FIG. 21A-D shows images of unfixed frozen brain sections from APP/PS1-21 E2/E2 mice that were immunostained for ApoE with anti-ApoE antibody HJ156B at 20 ug/ml (A,C) or 50 ug/ml (B,D) at two different magnifications. Scale bars, 400 μm.
Figure 21B:
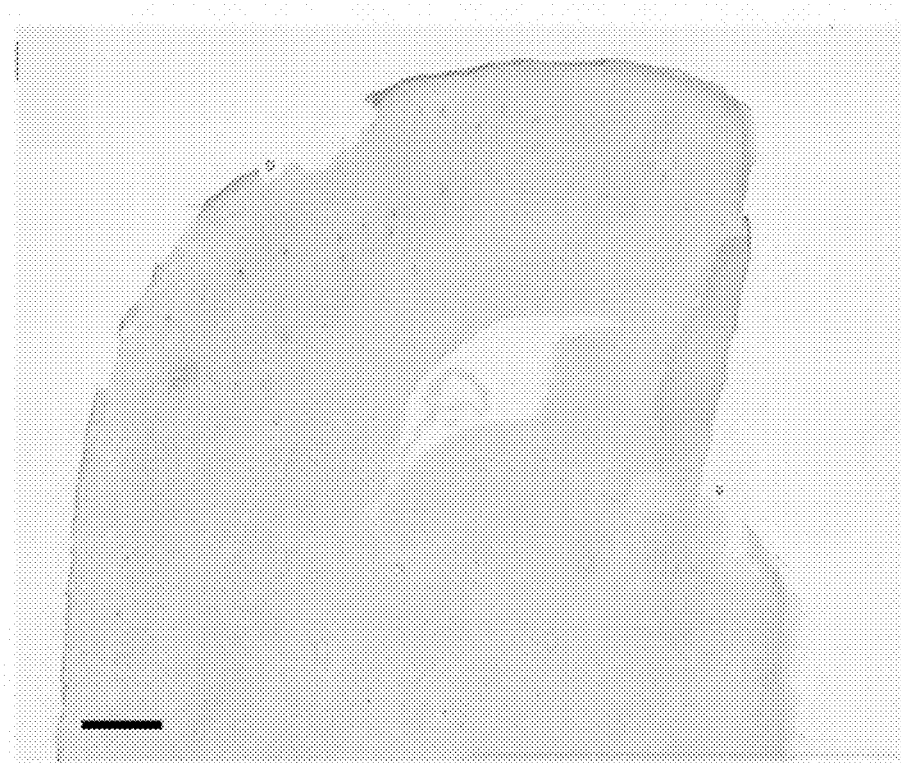
Figure 21C:
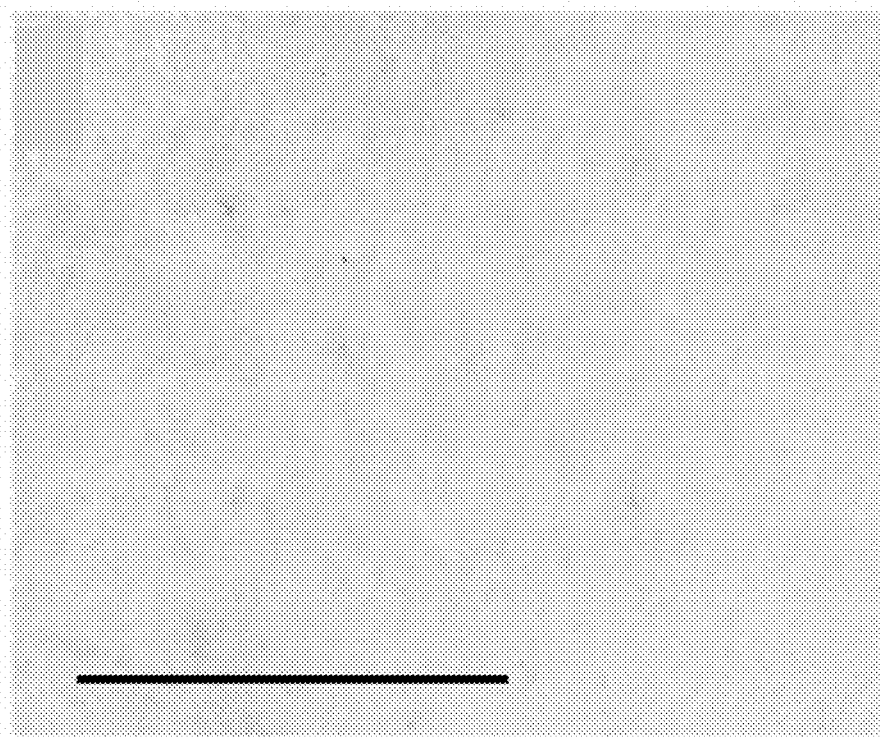
Figure 21D:
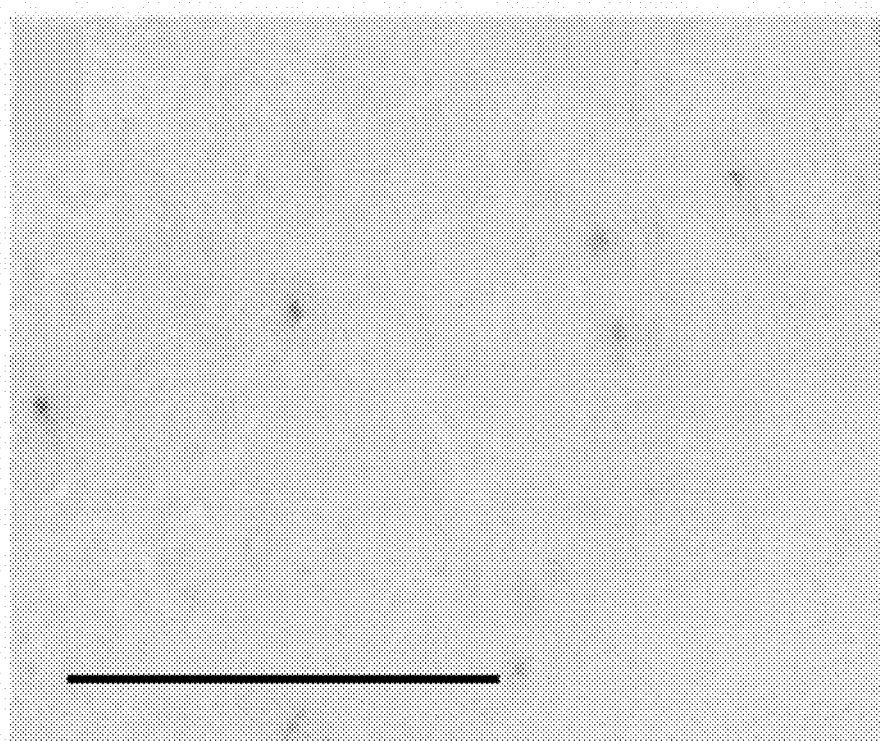
Figure 22A:
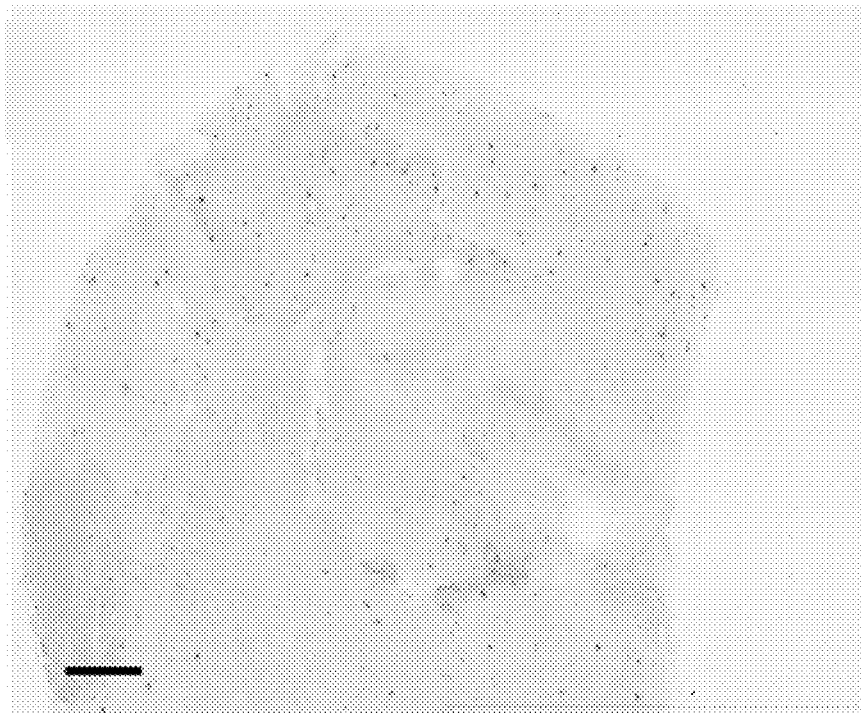
FIG. 22A-D shows images of unfixed frozen brain sections from APP/PS1-21 E3/E3 mice that were immunostained for ApoE with anti-ApoE antibody HJ156B at 20 ug/ml (A,C) or 50 ug/ml (B,D) at two different magnifications. Scale bars, 400 μm.
Figure 22B:
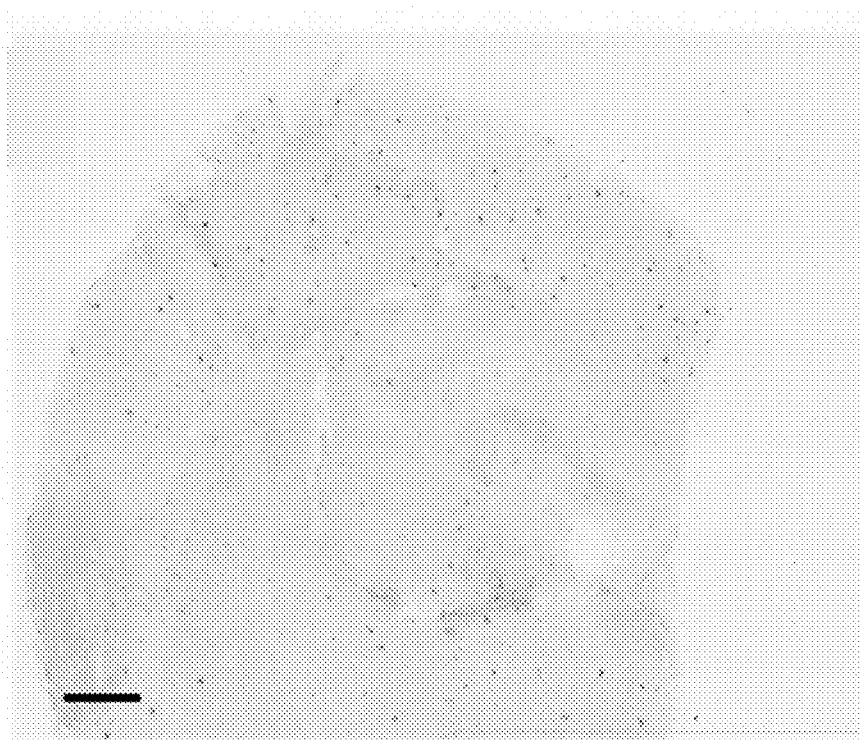
Figure 22C:
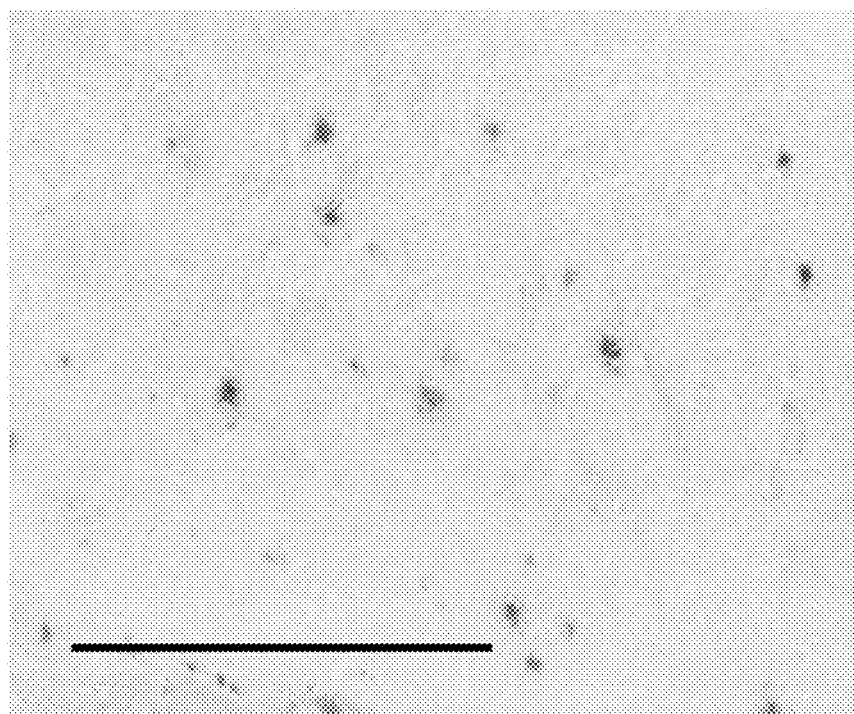
Figure 22D:
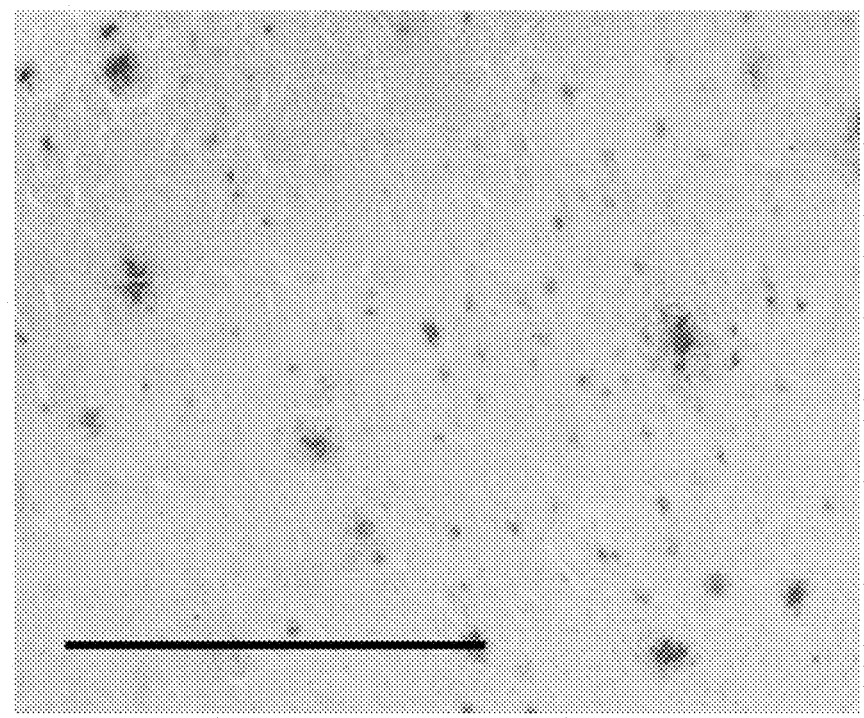
Figure 23A:
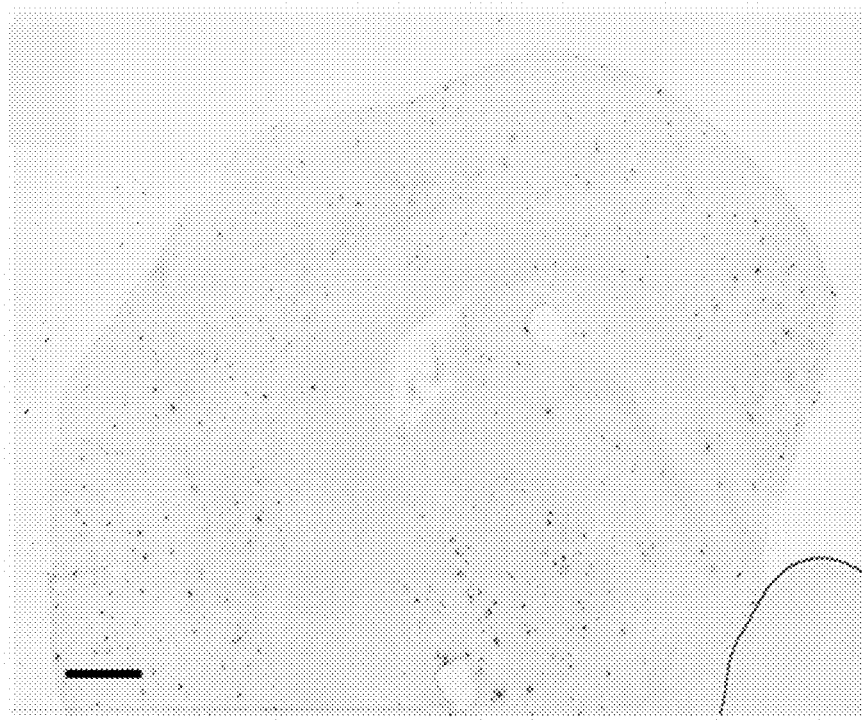
FIG. 23A-D shows images of unfixed frozen brain sections from APP/PS1-21 E4/E4 mice that were immunostained for ApoE with anti-ApoE antibody HJ156B at 20 ug/ml (A,C) or 50 ug/ml (B,D) at two different magnifications. Scale bars, 400 μm.
Figure 23B:
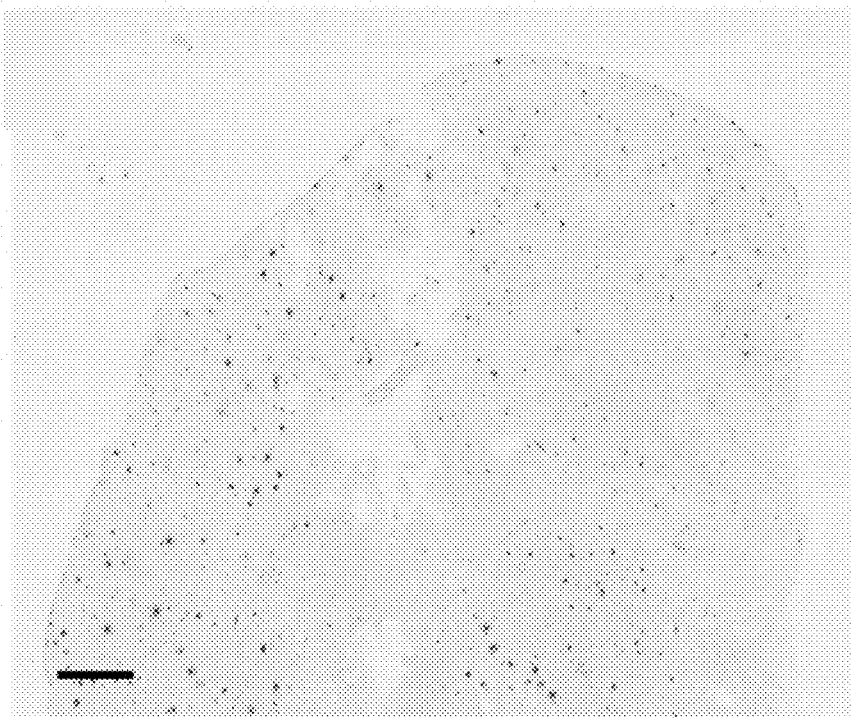
Figure 23C:
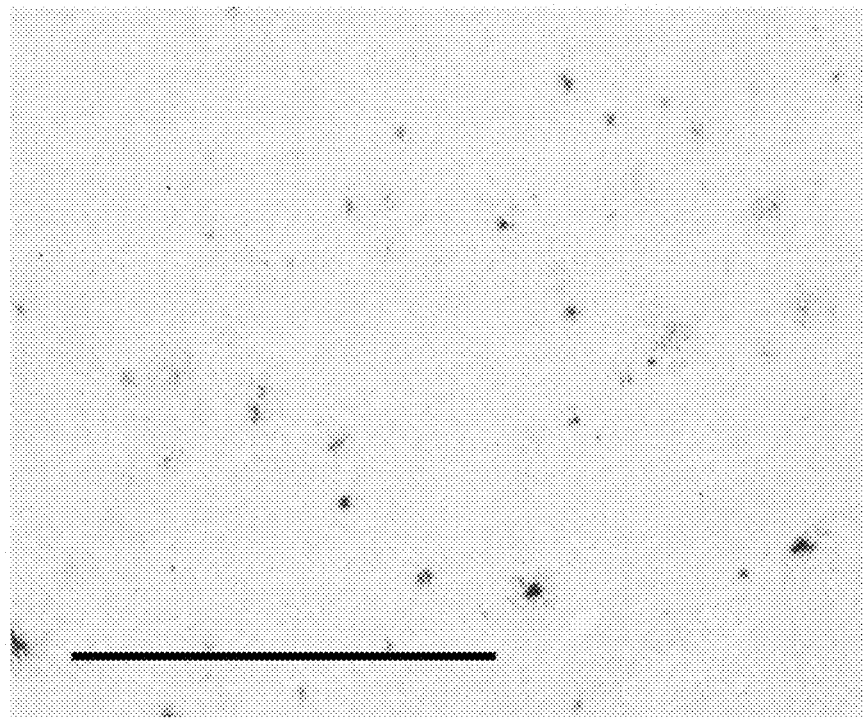
Figure 23D:
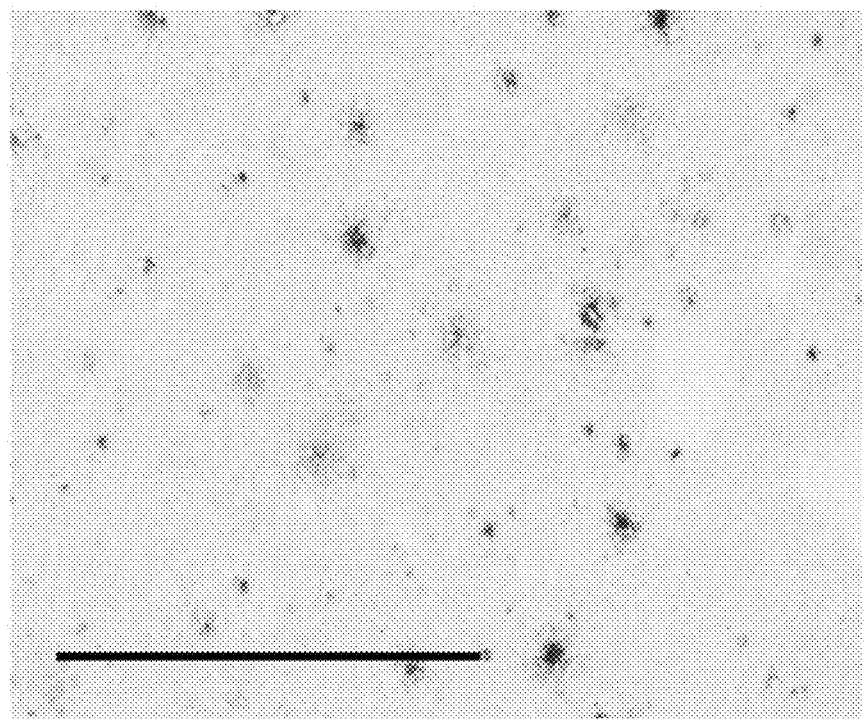
Figure 24A:
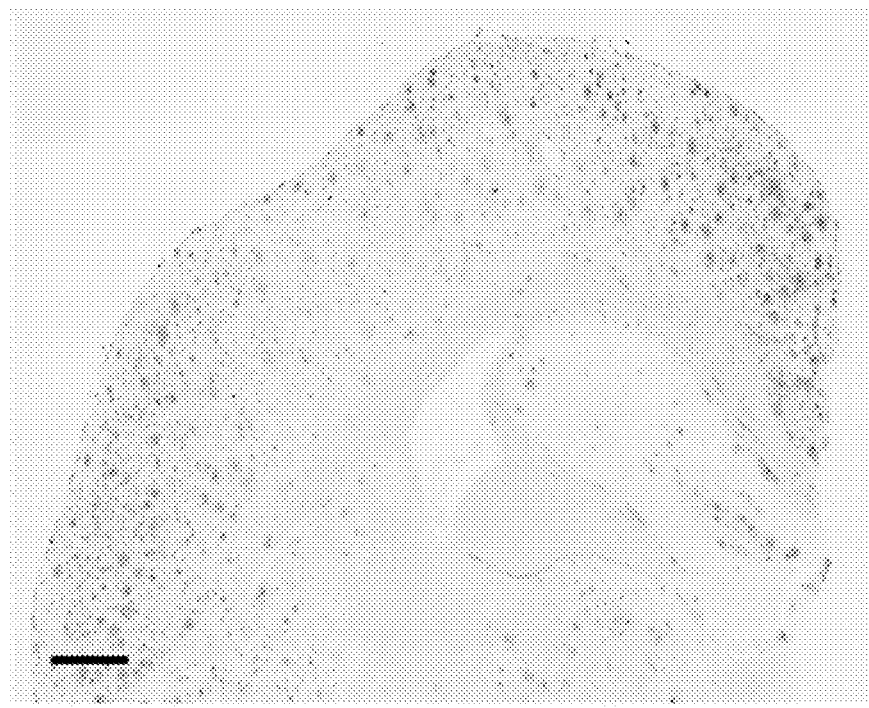
FIG. 24A-D shows images of unfixed frozen brain sections from APP/PS1-21 E4/E4 mice that were immunostained for ApoE with anti-ApoE msIgG/huFc chimeric antibody HJ153 and a biotinylated rabbit anti-human IgG secondary antibody. Primary antibody dilutions of (A) 0.4 μg/mL, (B) 2 μg/mL, (C) 20 μg/mL, and (D) 50 μg/mL were used. Scale bars, 400 μm.
Figure 24B:
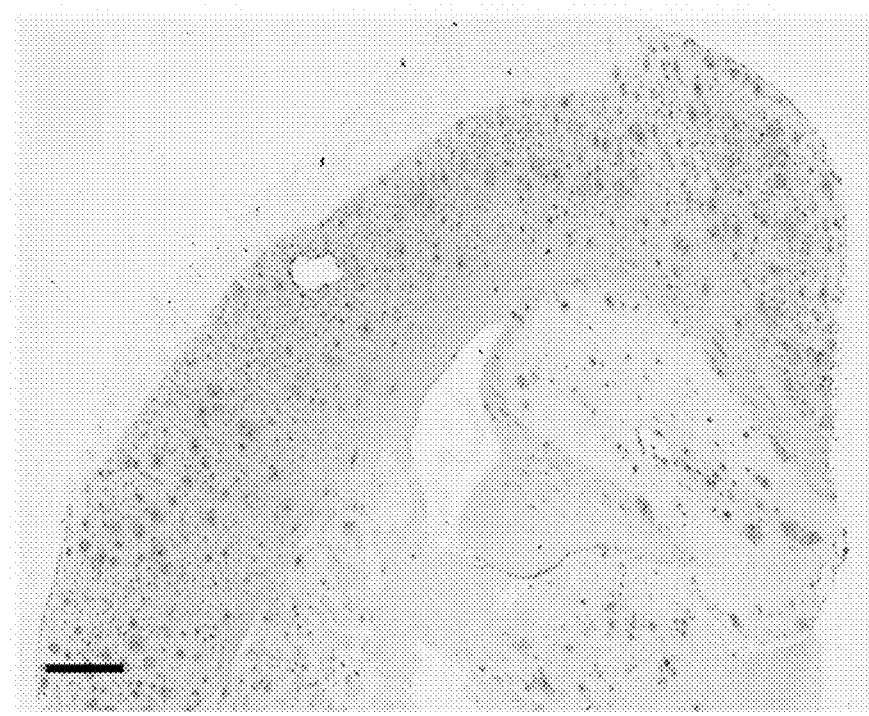
Figure 24C:
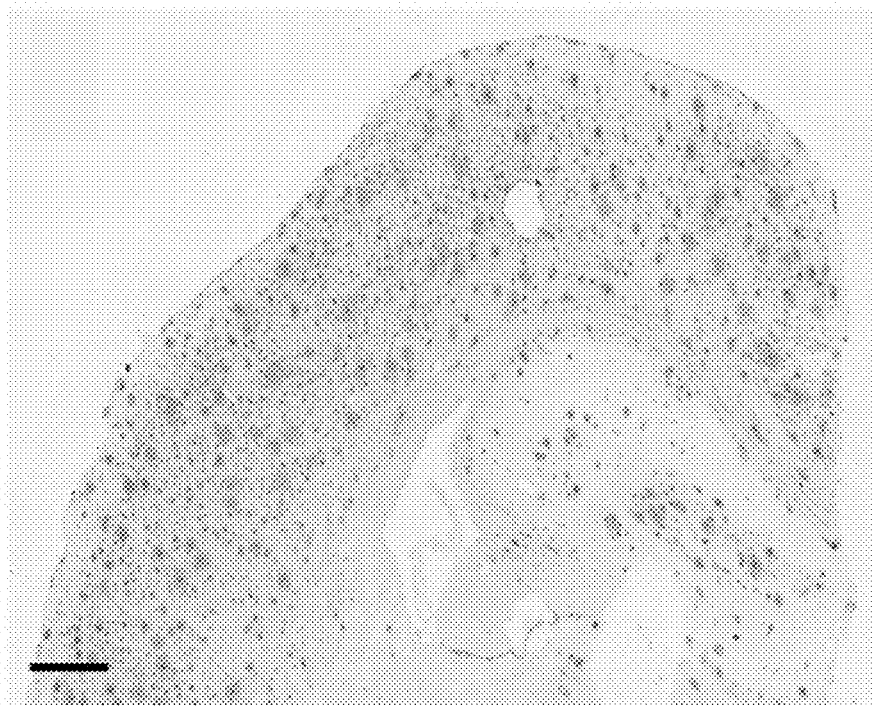
Figure 24D:
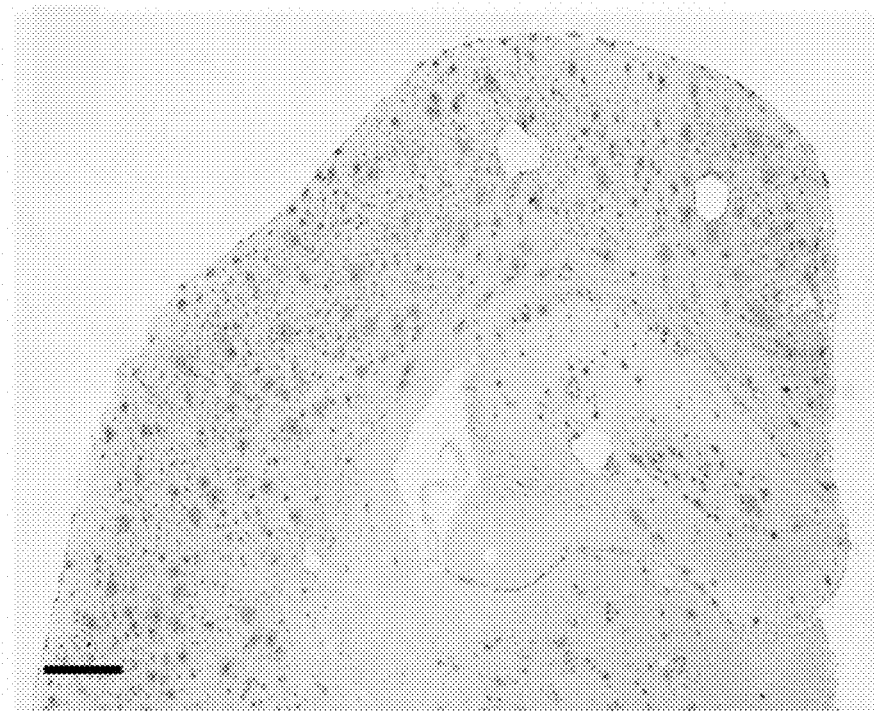
Figure 25A:
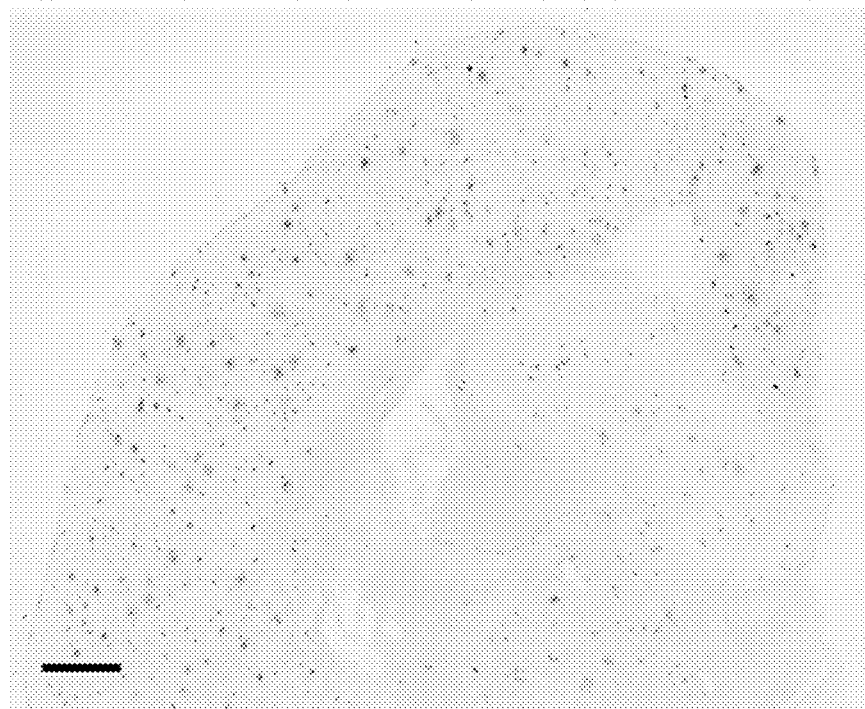
FIG. 25A-D shows images of unfixed frozen brain sections from APP/PS1-21 E4/E4 mice that were immunostained for ApoE with anti-ApoE msIgG/huFc chimeric antibody HJ156 and a biotinylated rabbit anti-human IgG secondary antibody. Primary antibody dilutions of (A) 0.4 μg/mL, (B) 2 μg/mL, (C) 20 μg/mL, and (D) 50 μg/mL were used. Scale bars, 400 μm.
Figure 25B:
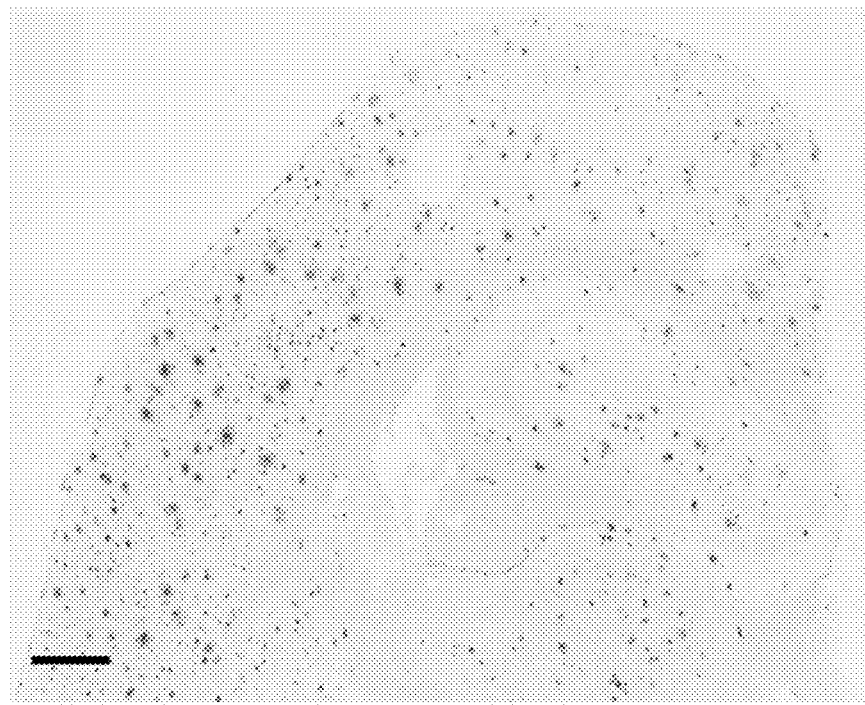
Figure 25C:
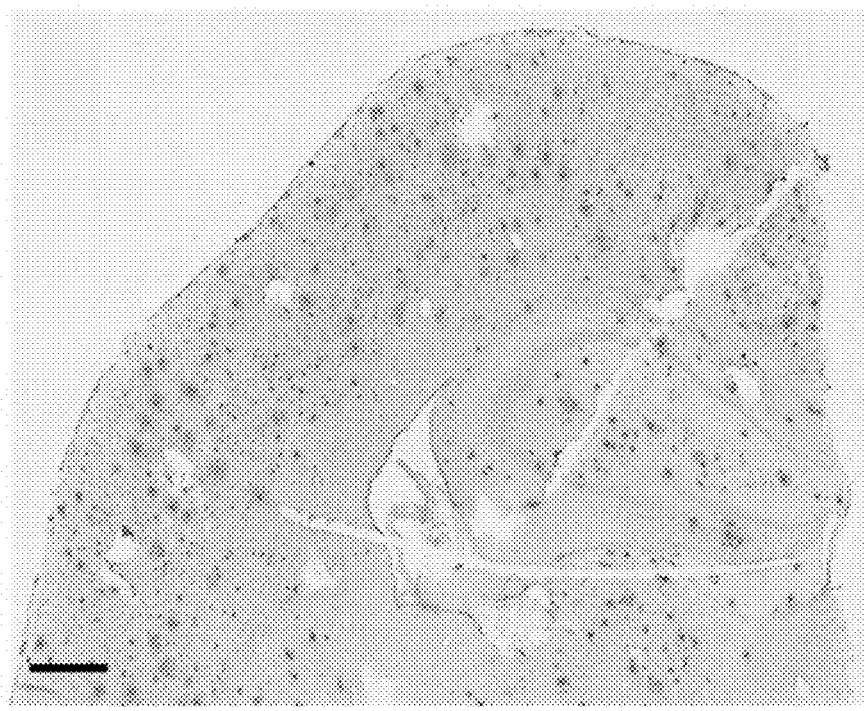
Figure 25D:
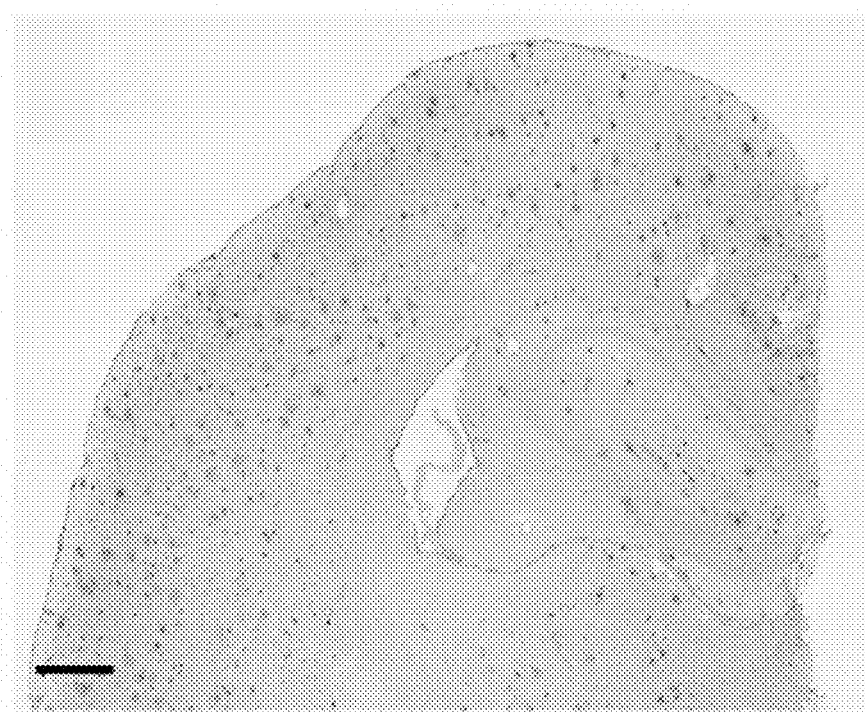
Figure 26A:
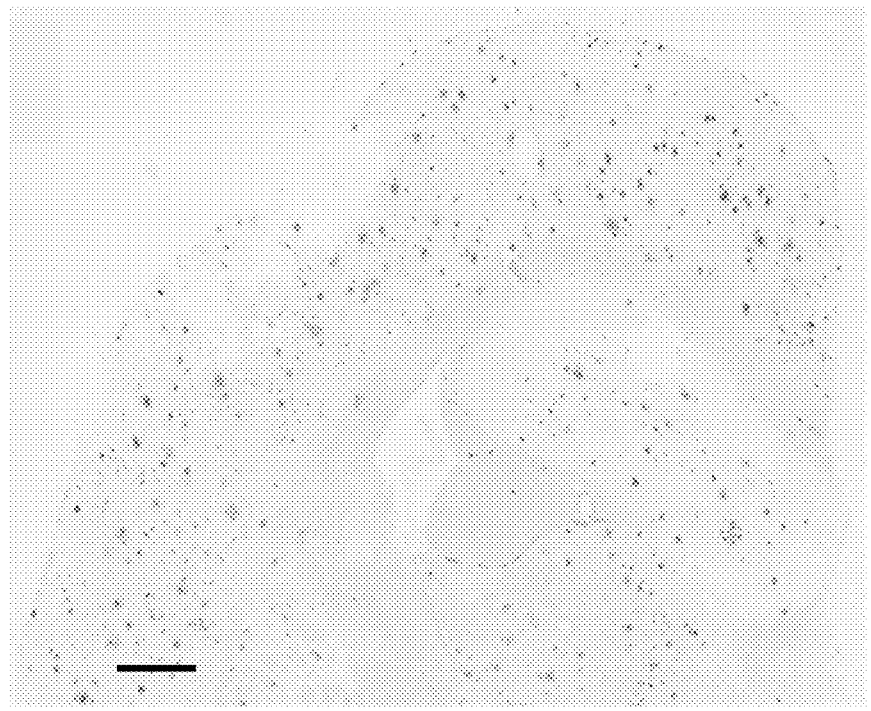
FIG. 26A-D shows images of unfixed frozen brain sections from APP/PS1-21 E4/E4 mice that were immunostained for ApoE with anti-ApoE msIgG/huFc chimeric antibody HJ1514 and a biotinylated rabbit anti-human IgG secondary antibody. Primary antibody dilutions of (A) 0.4 μg/mL, (B) 2 μg/mL, (C) 20 μg/mL, and (D) 50 μg/mL were used. Scale bars, 400 μm.
Figure 26B:
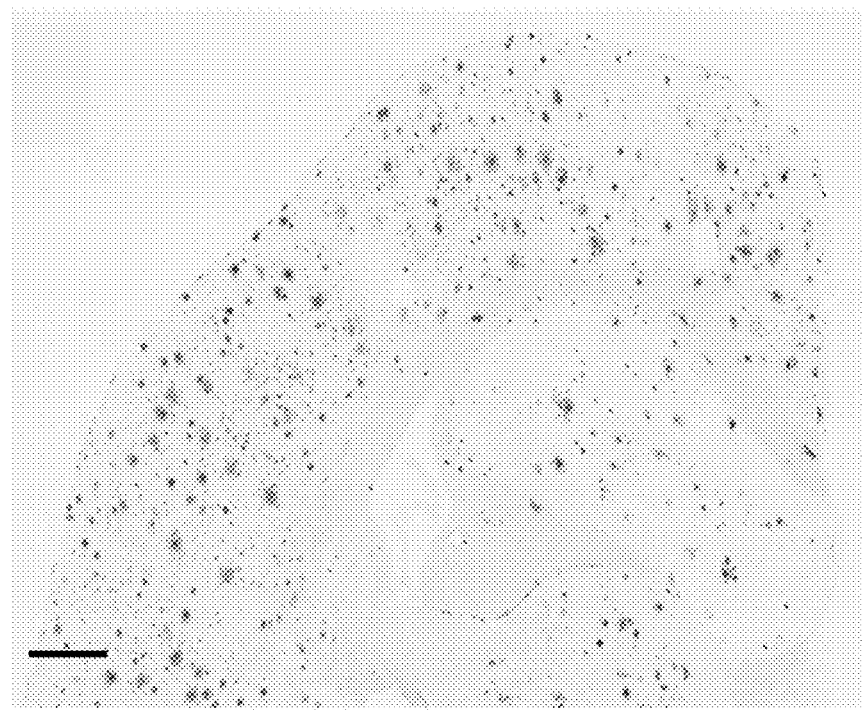
Figure 26C:
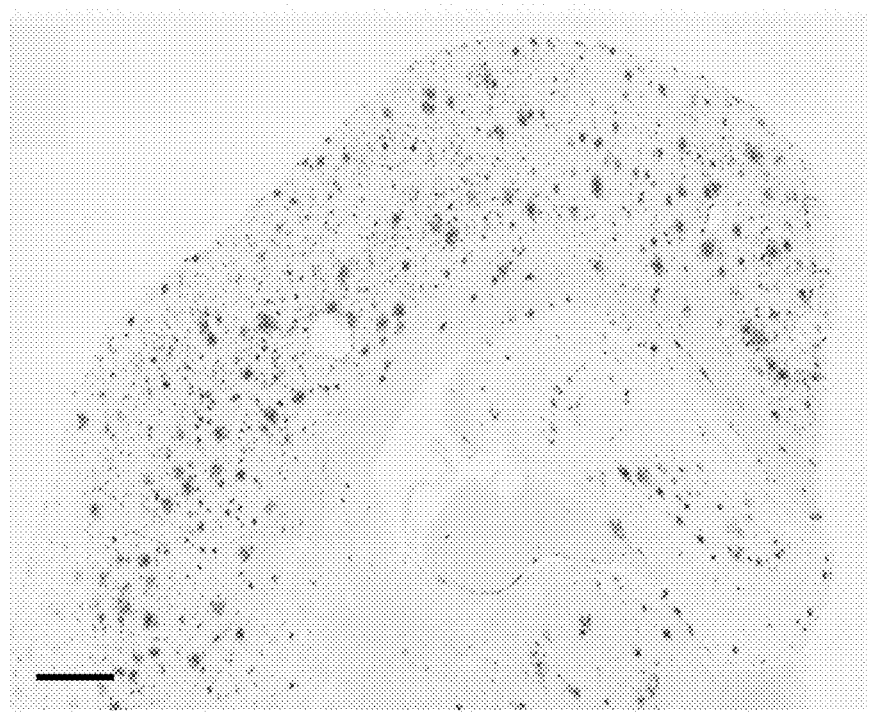
Figure 26D:
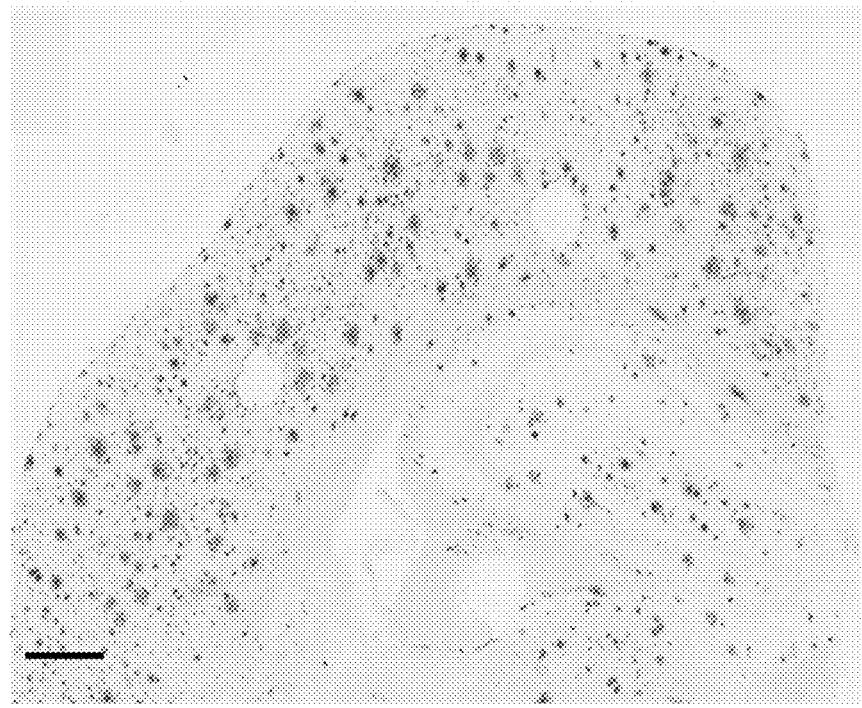
Figure 27A:
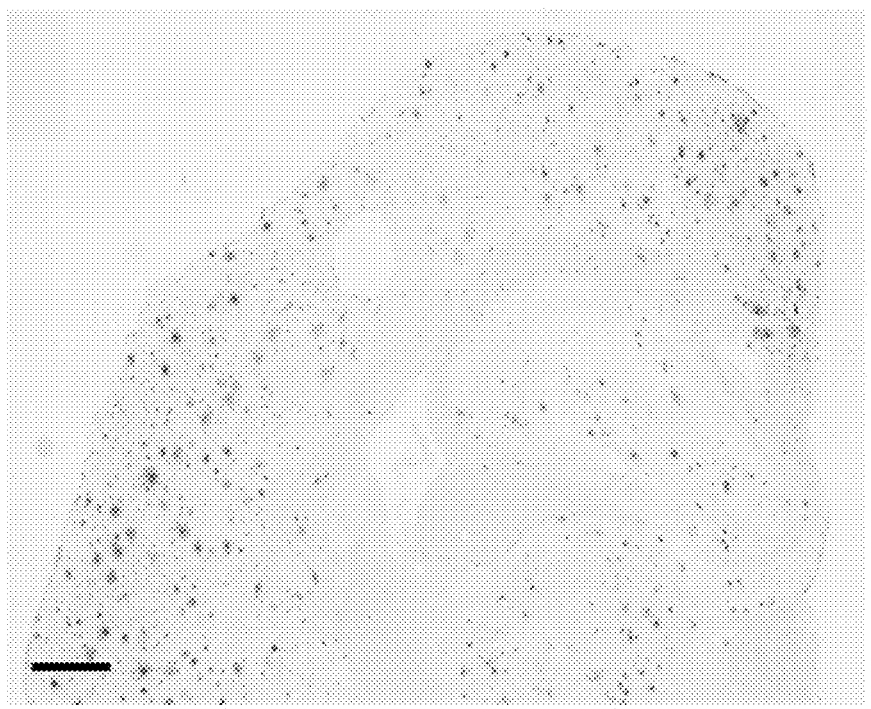
FIG. 27A-D shows images of unfixed frozen brain sections from APP/PS1-21 E4/E4 mice that were immunostained for ApoE with anti-ApoE msIgG/huFc chimeric antibody HJ1518 and a biotinylated rabbit anti-human IgG secondary antibody. Primary antibody dilutions of (A) 0.4 μg/mL, (B) 2 μg/mL, (C) 20 μg/mL, and (D) 50 μg/mL were used. Scale bars, 400 μm.
Figure 27B:
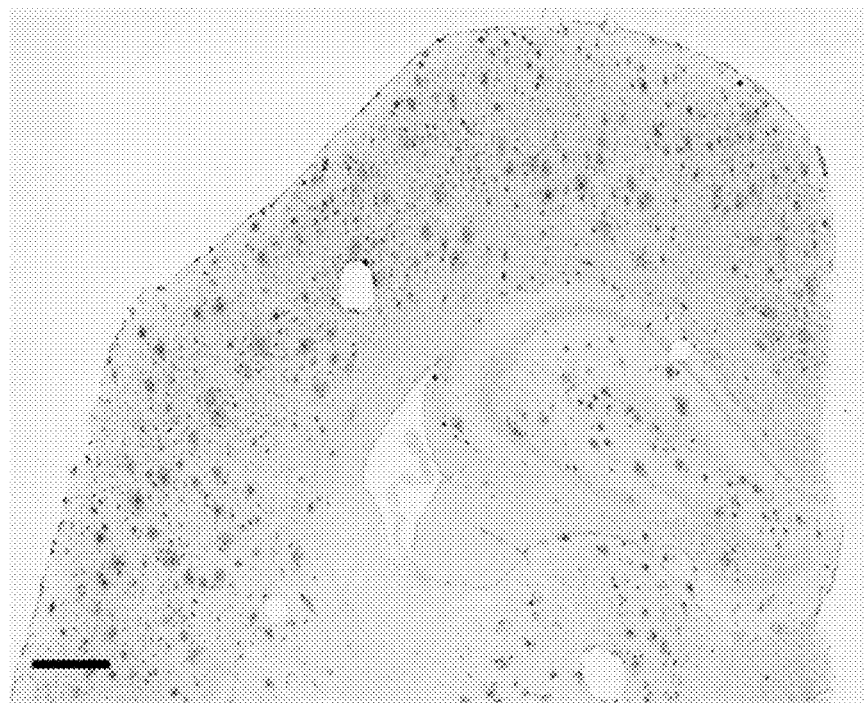
Figure 27C:
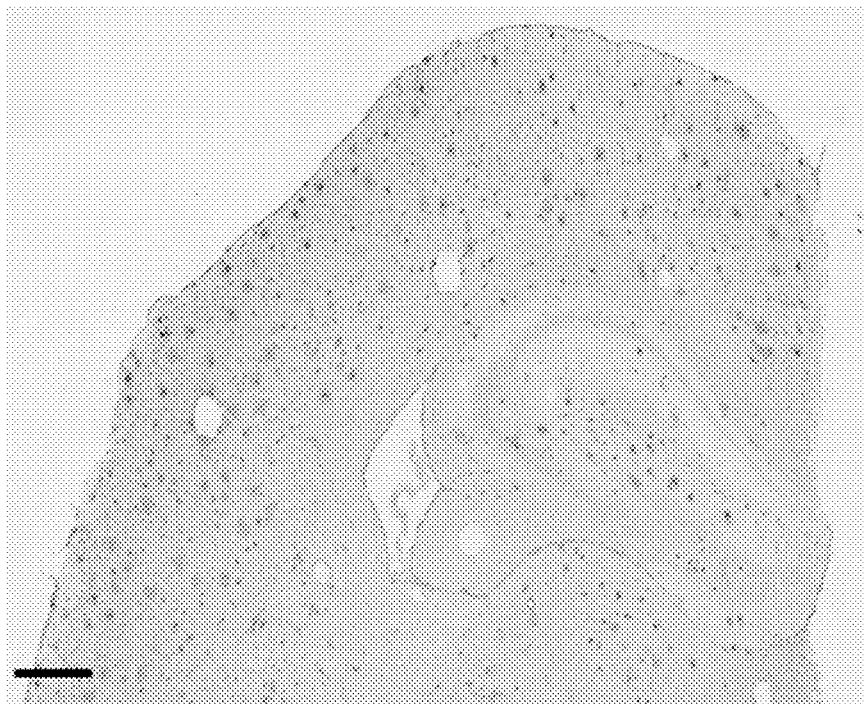
Figure 27D:
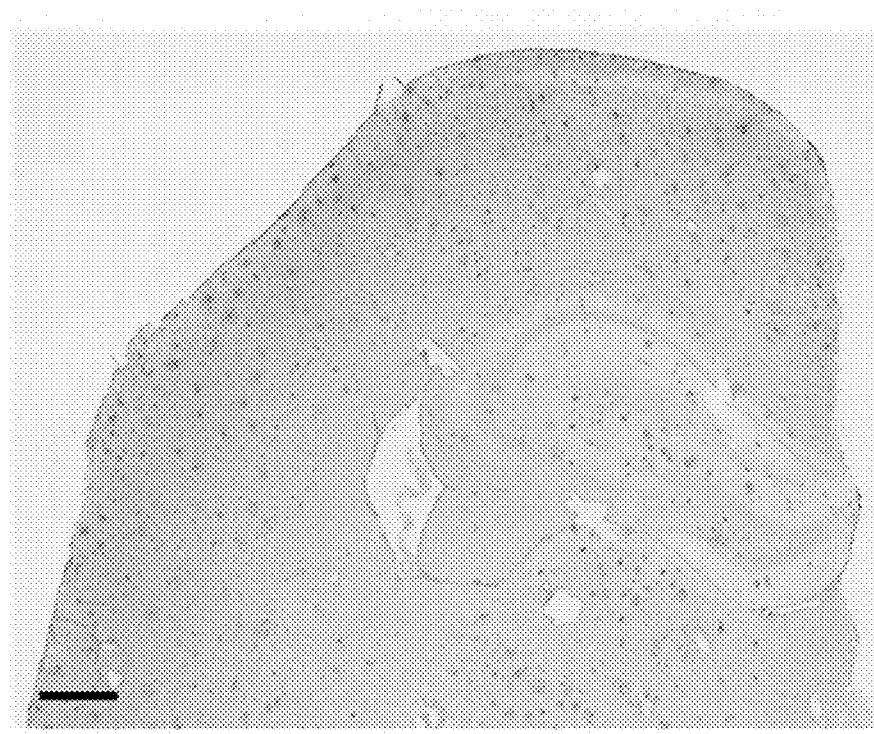
Figure 28A:
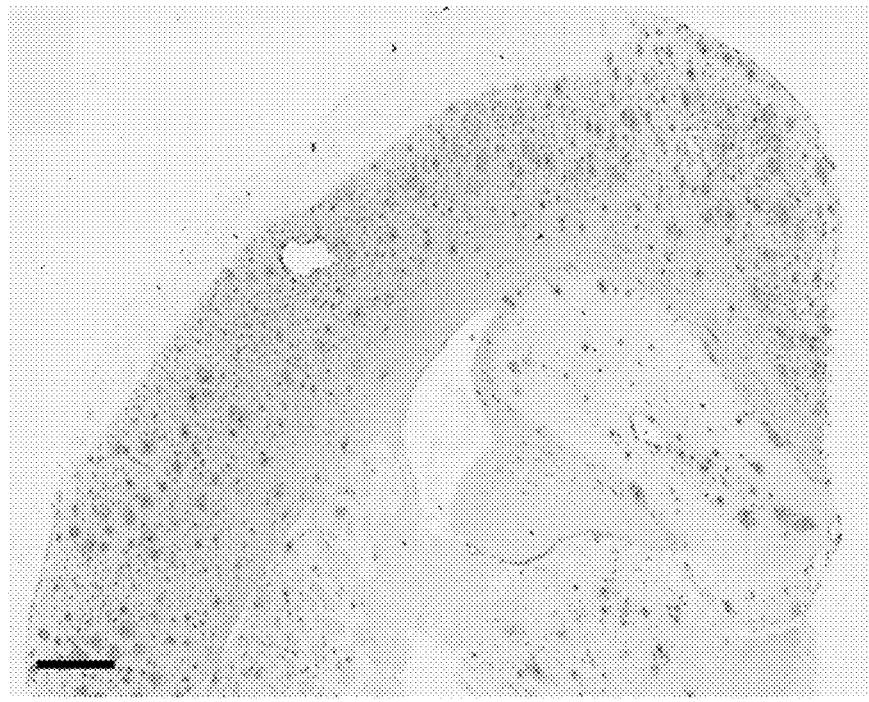
FIG. 28A-D shows images of unfixed frozen brain sections from APP/PS1-21 E4/E4 mice that were immunostained for ApoE with anti-ApoE msIgG/huFc chimeric antibodies at 2 μg/mL—(A) HJ153 chimeric, (B) HJ156 chimeric, (C) HJ1514 chimeric, (D) HJ1518 chimeric. Scale bars, 400 μm.
Figure 28B:
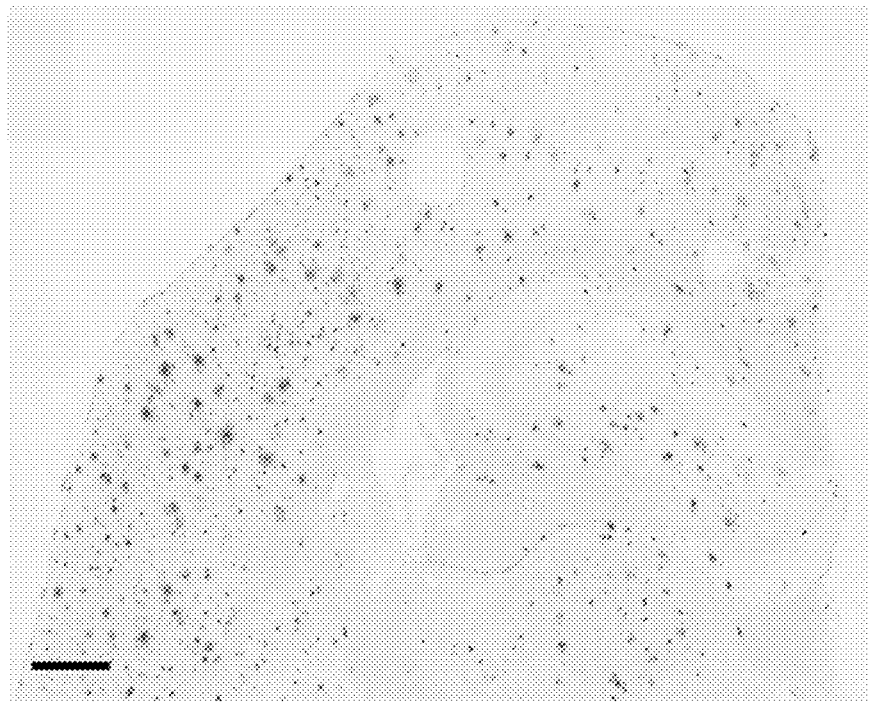
Figure 28C:
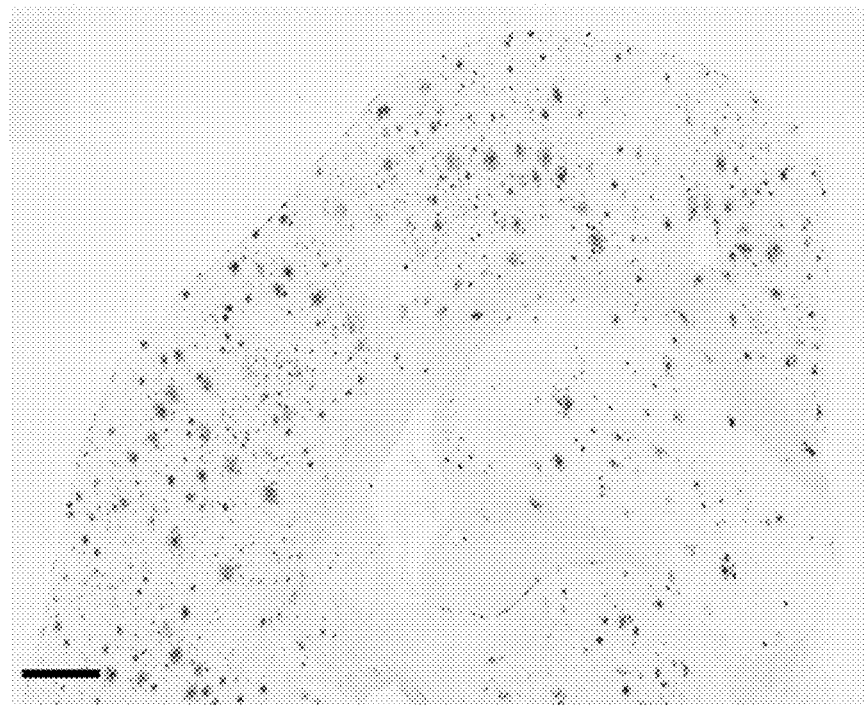
Figure 28D:
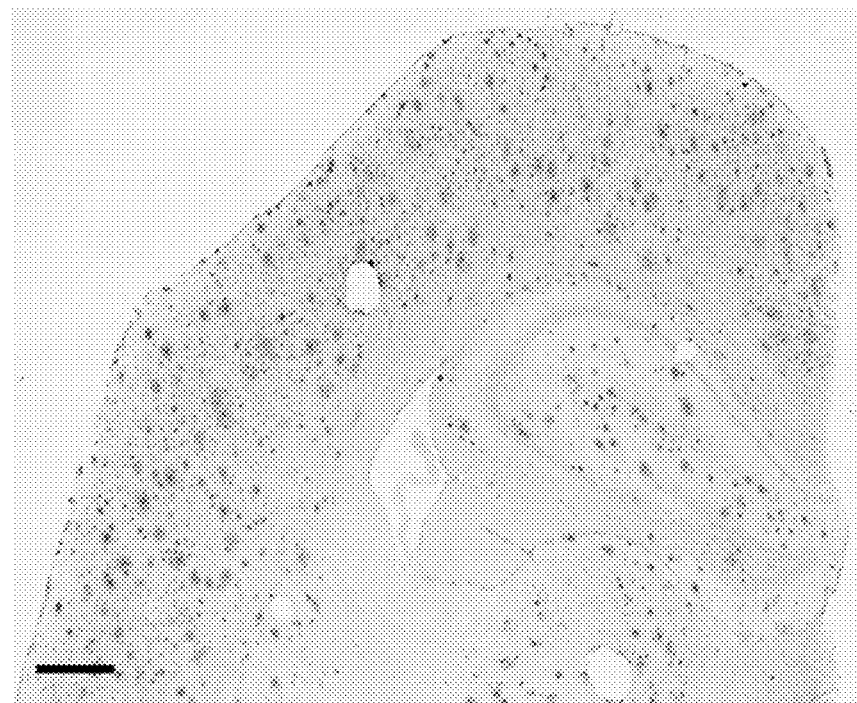

The competition ELISA showed titration of 4 nM HJ153 for binding to coated ApoE4 (FIG. 20B) with increasing plasma dilutions. Antibodies that did not bind plasma in the previous assay did not show titration of binding to coated recombinant alipidated ApoE4 at either 4 nM or 50 nM antibody concentrations. These results suggest that antibodies that do not detect lipidated ApoE in plasma may prefer to bind recombinant alipidated ApoE.

Example 14

Unfixed tissue sections from APP/PS1-21 E2/E2, APP/PS1-21 E3/E3, and APP/PS1-21 E4/E4 mice were stained for ApoE using the biotinylated antibody HJ156 ("HJ156B"). Mice were 9 months old at the time of staining. Section thickness was 20 microns. All mice were perfused transcardially with PBS at 4 degrees C. prior to removal of the brain. The results are shown in FIG. 21-23. All images are from the cortex.

Example 15

Unfixed tissue sections from APP/PS1-21 E4/E4 mice were stained for ApoE using anti-ApoE msIgG/huFc chimeric antibody HJ153, anti-ApoE msIgG/huFc chimeric antibody HJ156, anti-ApoE msIgG/huFc chimeric antibody HJ1514, or anti-ApoE msIgG/huFc chimeric antibody HJ1518. A biotinylated rabbit anti-human IgG antibody was used as the secondary antibody. Mice were 9 months old at the time of staining. Section thickness was 20 microns. All mice were perfused transcardially with PBS at 4 degrees C. prior to removal of the brain. The results are shown in FIG. 24-28. All images are from the cortex.

Example 16

APP/PS1-21 E4/E4 mice received intraperitoneal injections of PBS (negative control), HJ6.6 (IgG negative control), or an anti-apoE antibody (HJ151, HJ155, and HJ156) beginning at 2 months of age (n=10/group). Antibodies were injected once per week at 50 mg/kg until 3.5 months of age. Mice per perfused transcardially with PBS at 4 degrees C. prior to brain removal. Brains were fixed in 4% paraformaldehyde. Sections were cut at 50 microns thickness prior to staining with the indicated reagents.

Figure 29:
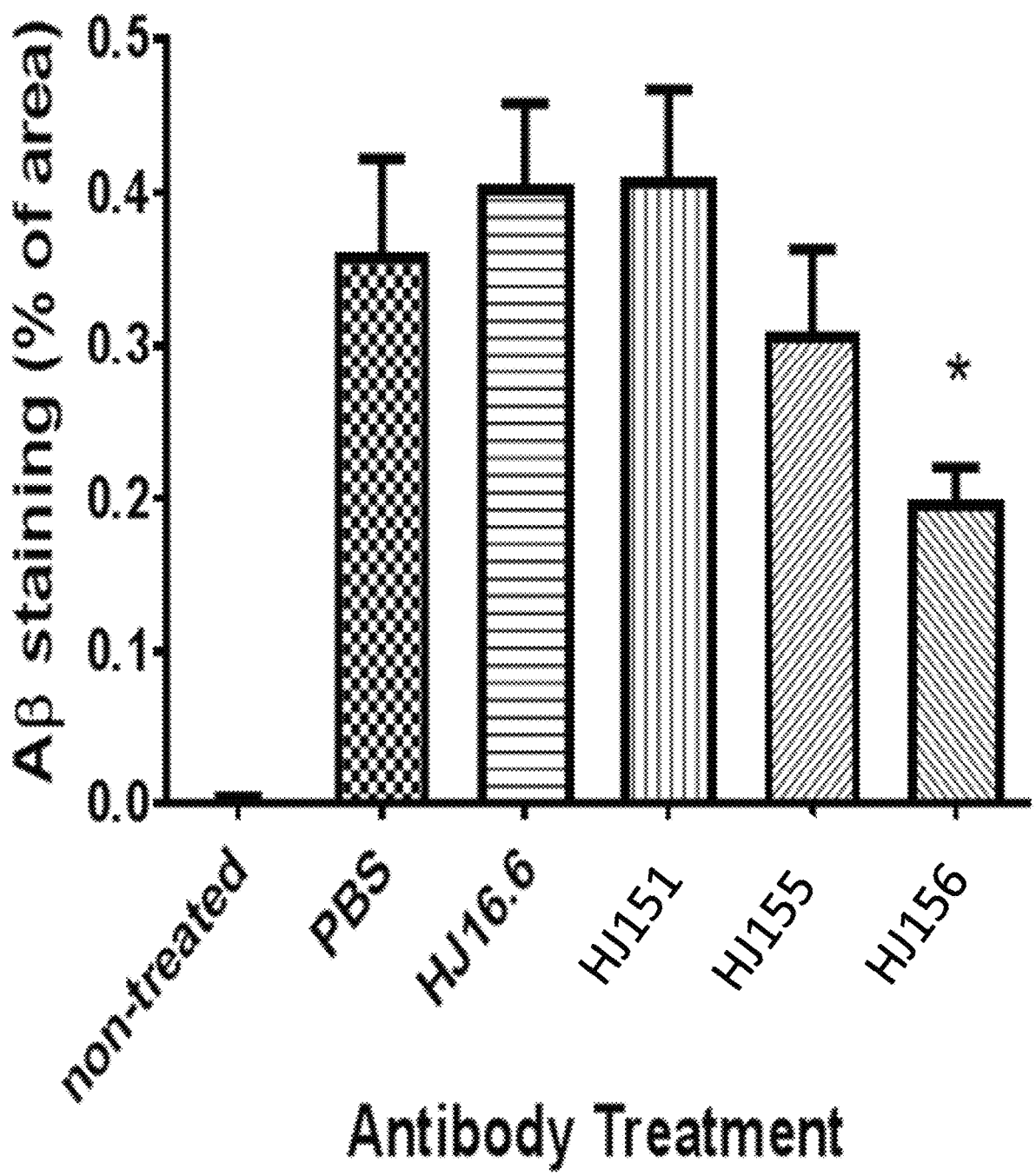
FIG. 29 shows a graph illustrating Aβ deposition, measured as % area Aβ staining, in APP/PS1-21 E4/E4 mice treated with weekly intra-peritoneal (IP) injections of PBS, HJ16.6 (IgG negative control), and the anti-ApoE antibodies HJ151, HJ155, and HJ156 from 2 months of age to 3.5 months of age. All antibodies were administered at 50 mg/kg. Brain sections from 2 month old untreated, and 3.5 month old treated mice were stained with anti-Aβ antibody HJ3.4-biotin. Aβ staining was quantified from cortex, n=10 per group. *p<0.05 compared to PBS and HJ16.6 groups.
Figure 30:
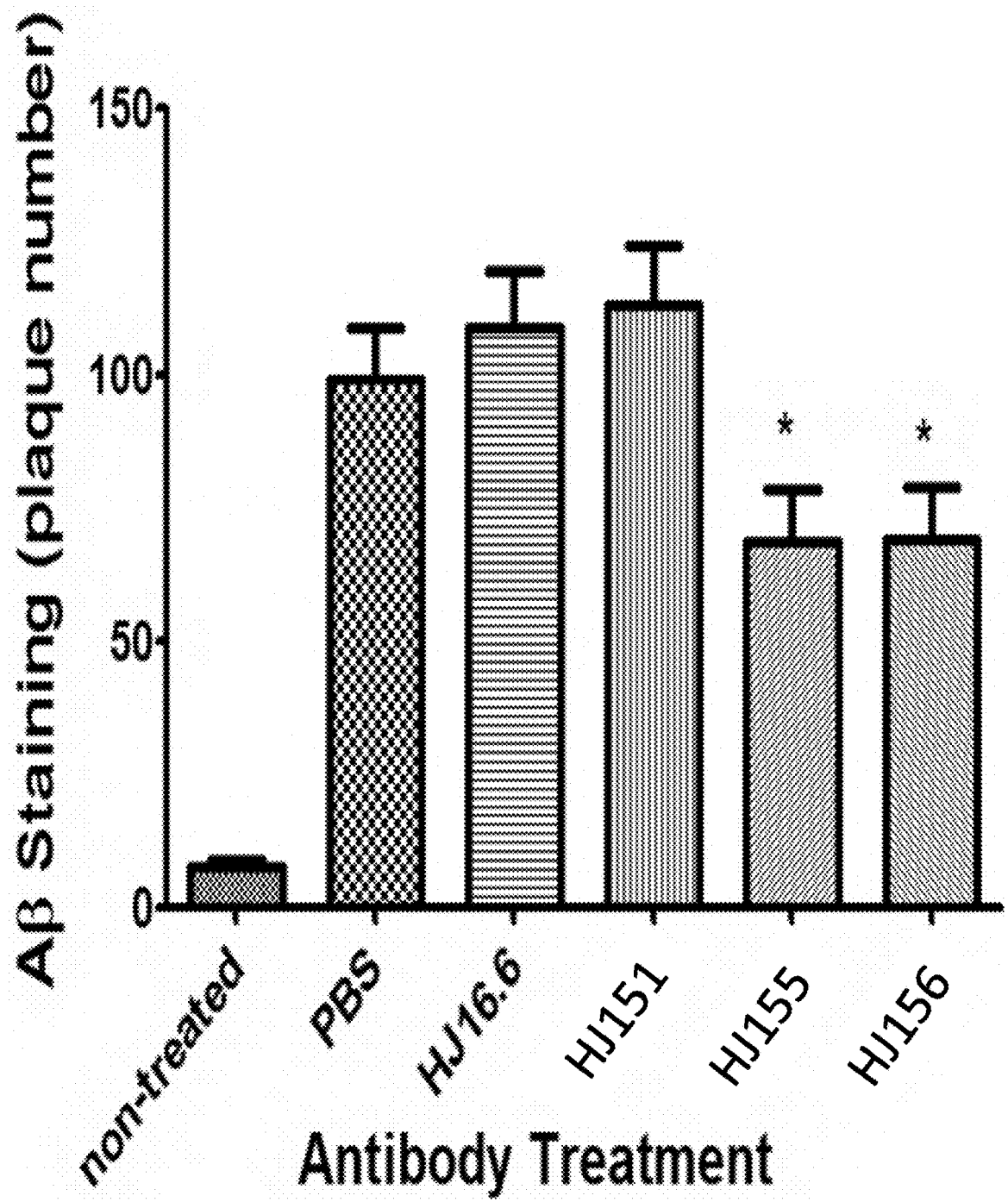
FIG. 30 shows a graph illustrating Aβ plaque number in APP/PS1-21 E4/E4 mice treated with weekly intra-peritoneal (IP) injections of PBS, HJ16.6 (IgG negative control), and the anti-ApoE antibodies HJ151, HJ155, and HJ156 from 2 months of age to 3.5 months of age. All antibodies were administered at 50 mg/kg. Brain sections from 2 month old untreated, and 3.5 month old treated mice were stained with anti-Aβ antibody HJ3.4-biotin. Aβ plaque number, detected by Aβ plaque staining, was quantified from cortex, n=10 per group. *p<0.05 compared to PBS and HJ16.6 groups.
Figure 31:
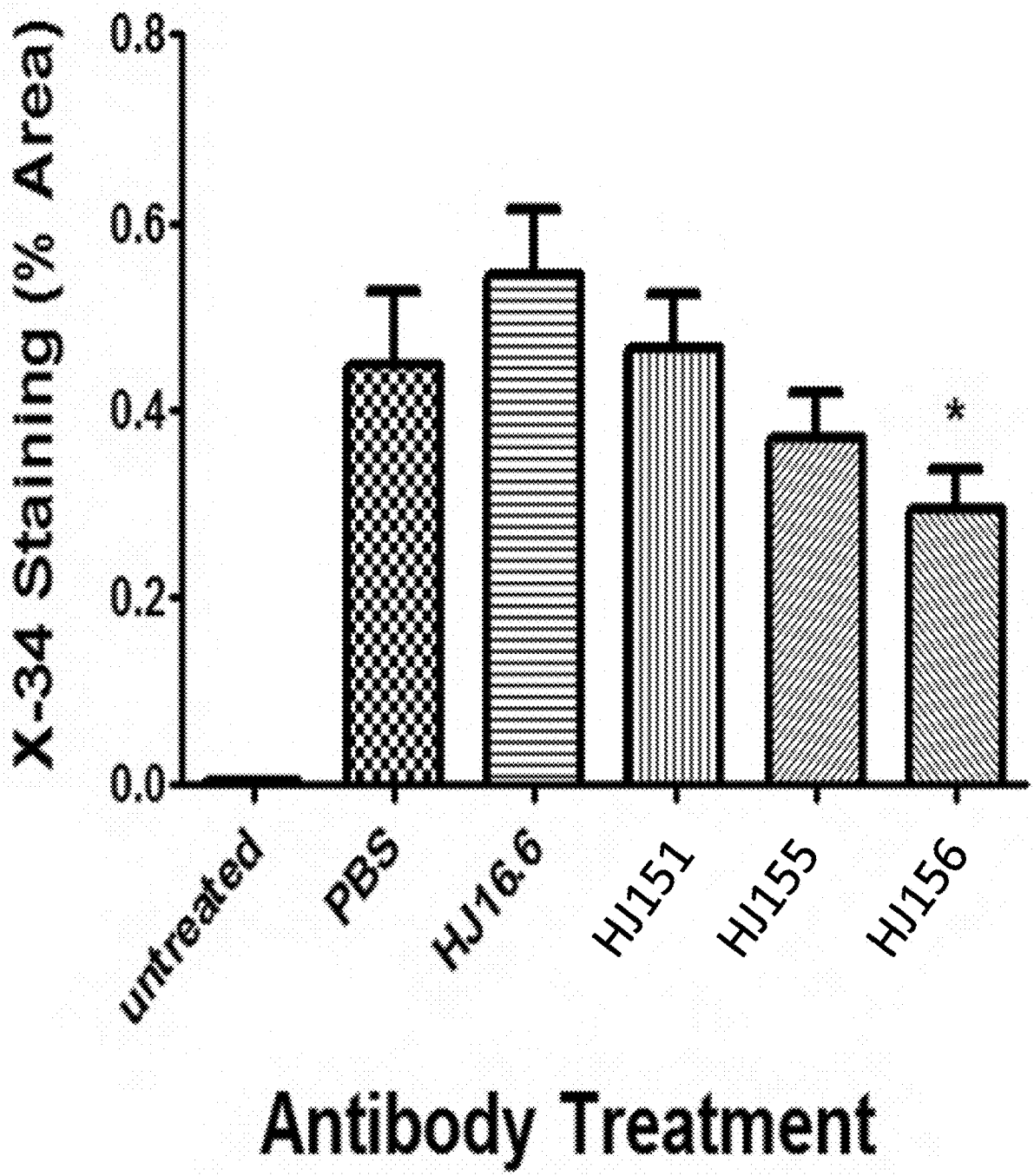
FIG. 31 shows a graph illustrating fibrillar Aβ plaque deposition, measured as % area X-34 staining, in APP/PS1-21 E4/E4 mice treated with weekly intra-peritoneal (IP) injections of PBS, HJ16.6 (IgG negative control), and the anti-ApoE antibodies HJ151, HJ155, and HJ156 from 2 months of age to 3.5 months of age. All antibodies were administered at 50 mg/kg. Brain sections from 2 month old untreated, and 3.5 month old treated mice were stained with X-34, a dye that stains fibrillar plaques. X-34 was quantified from cortex, n=10 per group. *p<0.05 compared to PBS and HJ16.6 groups.
Figure 32:
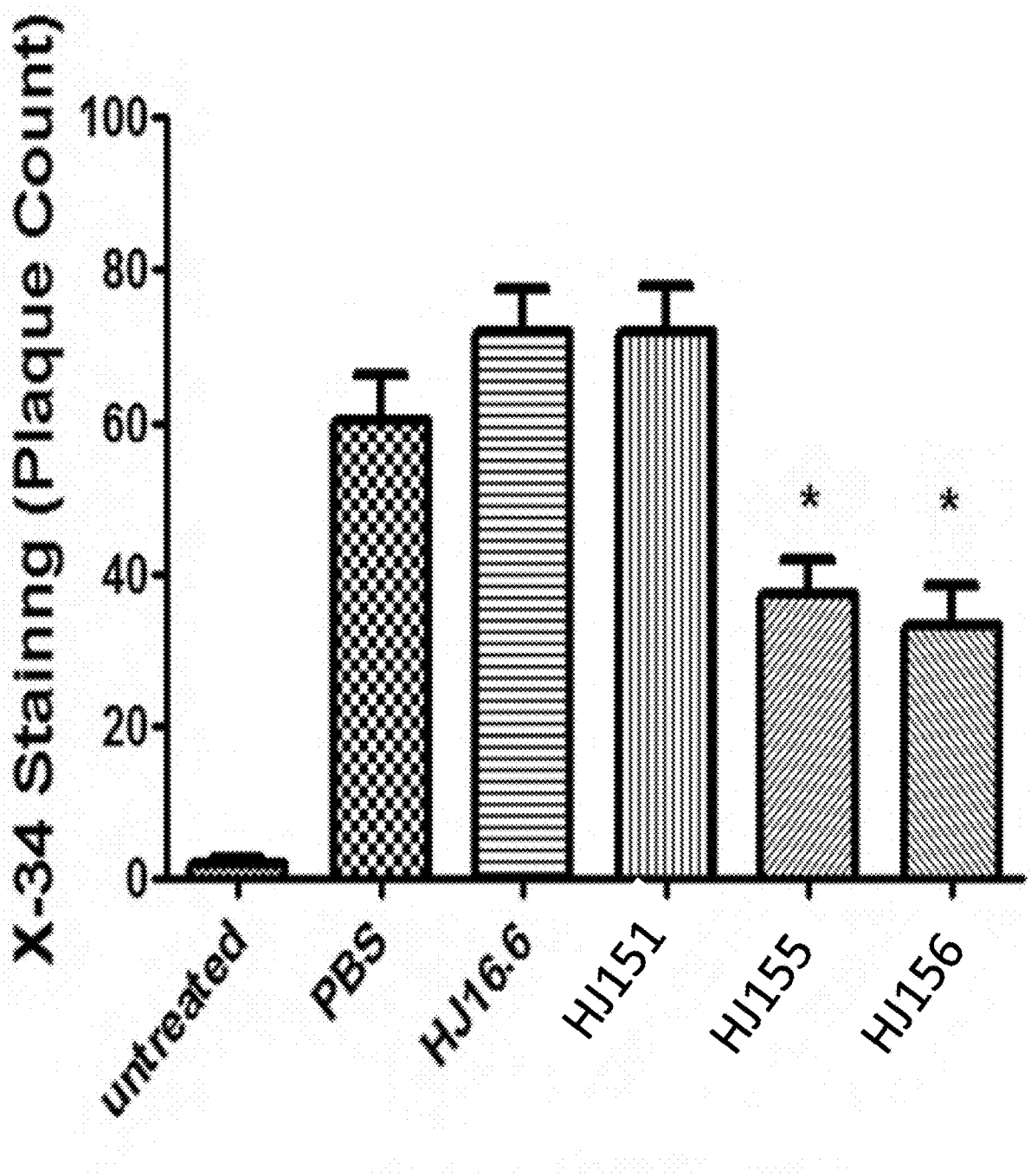
FIG. 32 shows a graph illustrating fibrillar Aβ plaque number in APP/PS1-21 E4/E4 mice treated with weekly intra-peritoneal (IP) injections of PBS, HJ16.6 (IgG negative control), and the anti-ApoE antibodies HJ151, HJ155, and HJ156 from 2 months of age to 3.5 months of age. All antibodies were administered at 50 mg/kg. Brain sections from 2 month old untreated, and 3.5 month old treated mice were stained with X-34, a dye that stains fibrillar plaques.
Figure 33A:
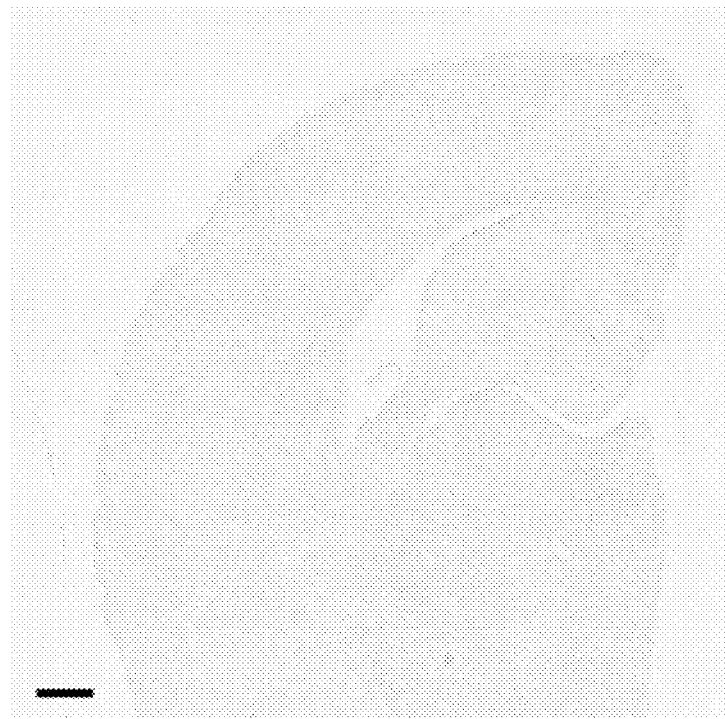
Figure 33B:
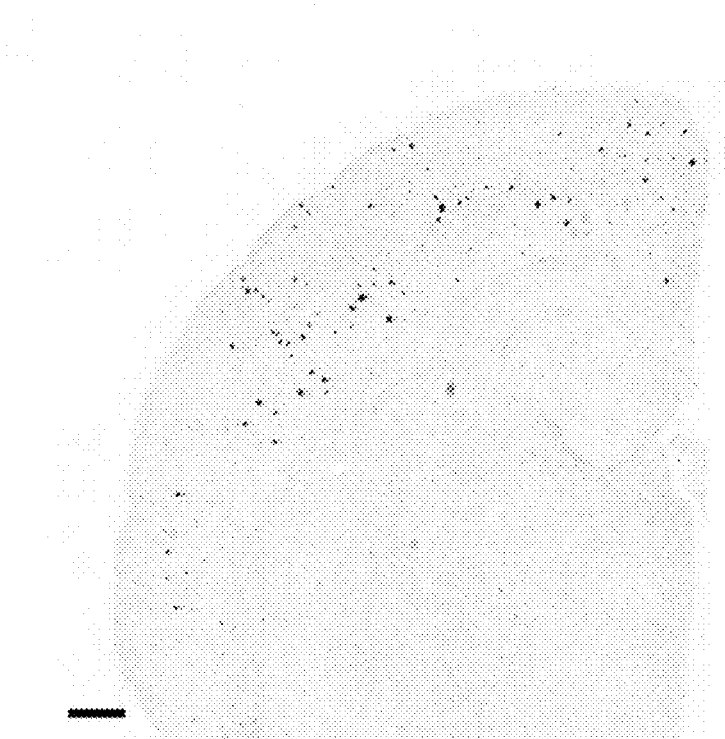
Figure 33C:
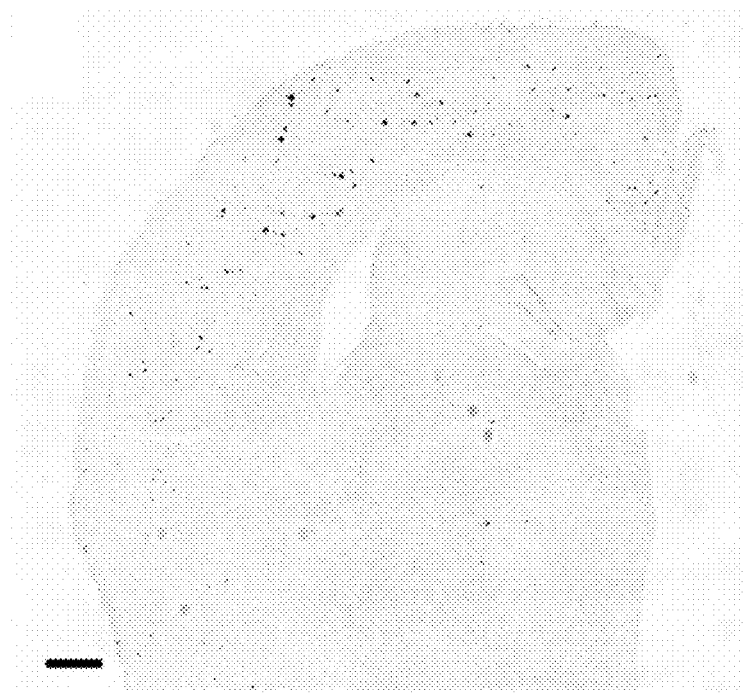
Figure 33D:
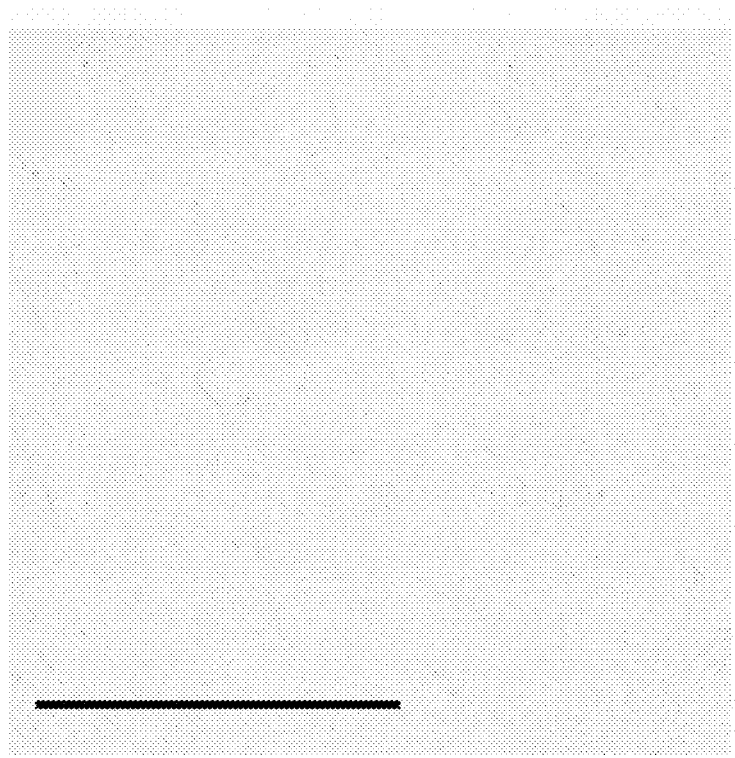
Figure 33E:
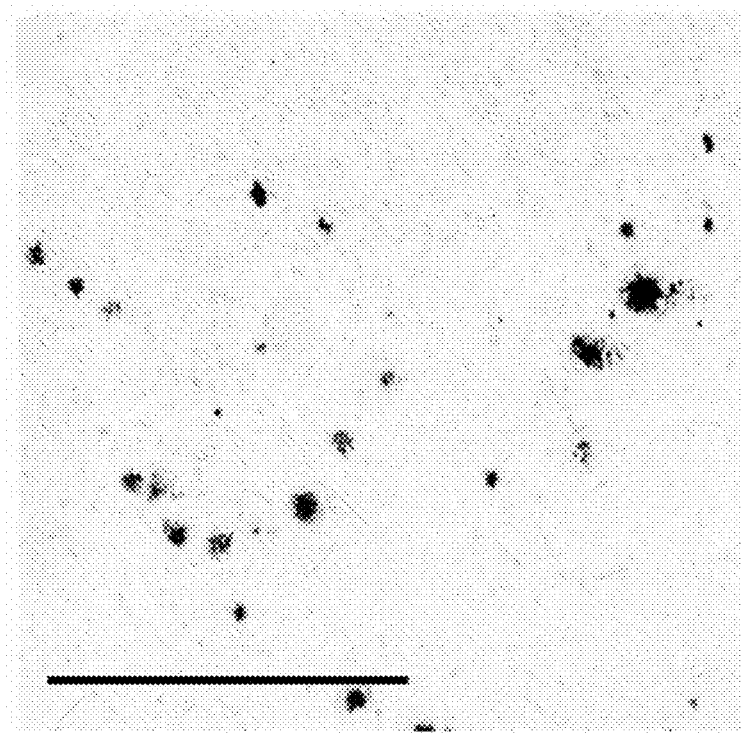
Figure 33F:
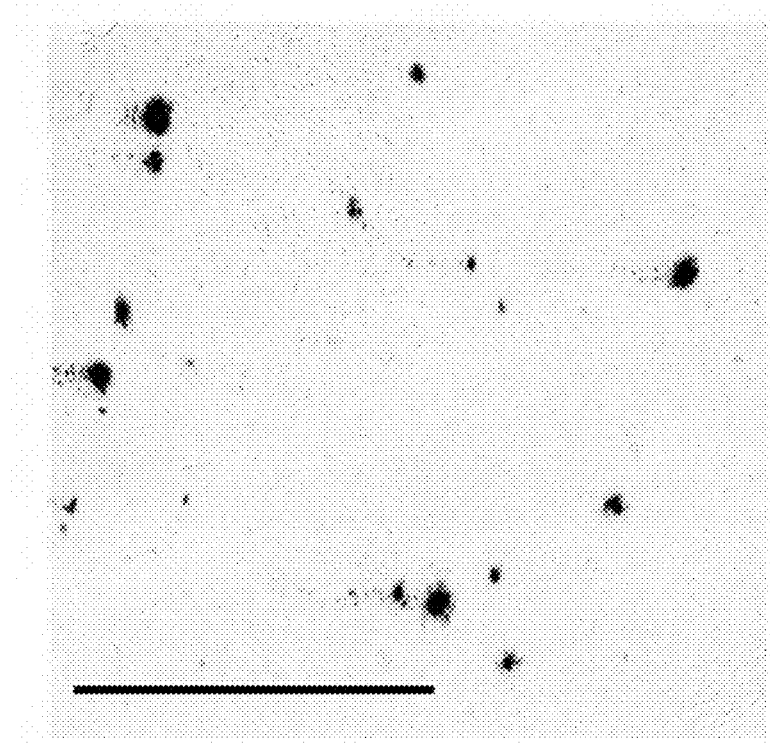
Figure 34A:
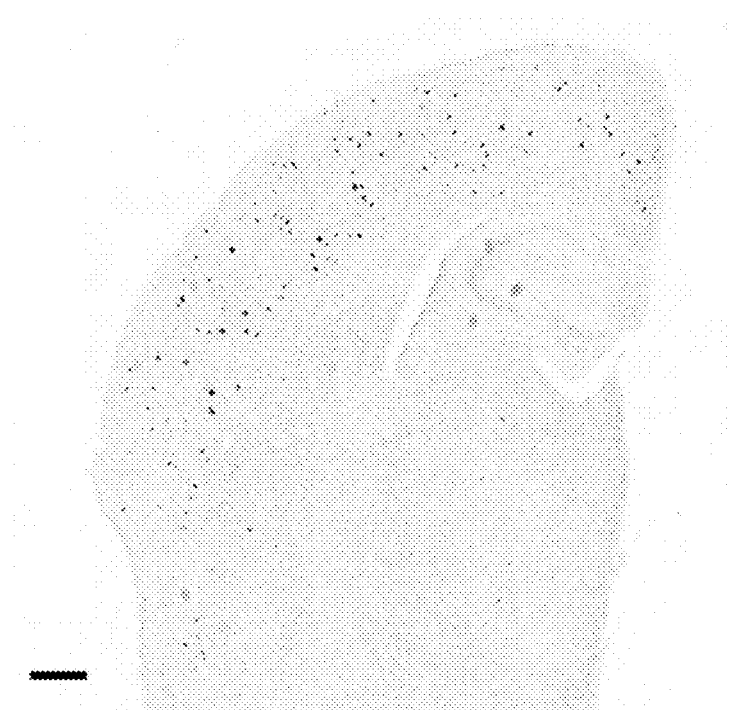
Figure 34B:
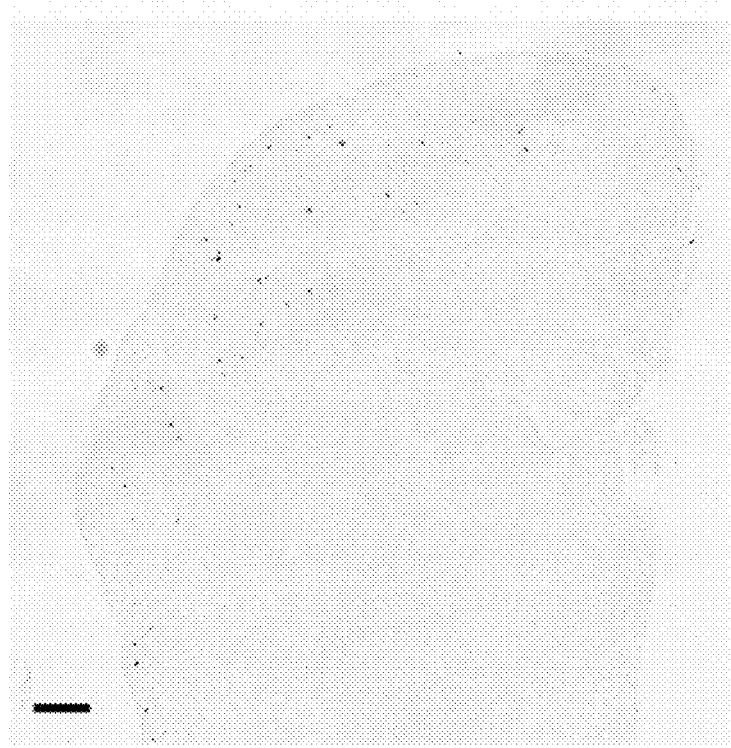
Figure 34C:
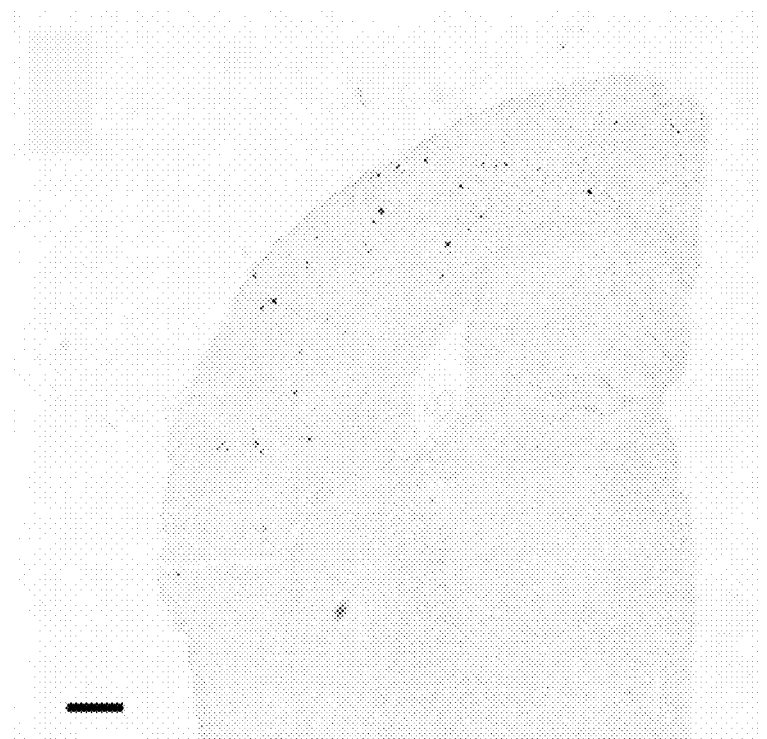
Figure 34D:
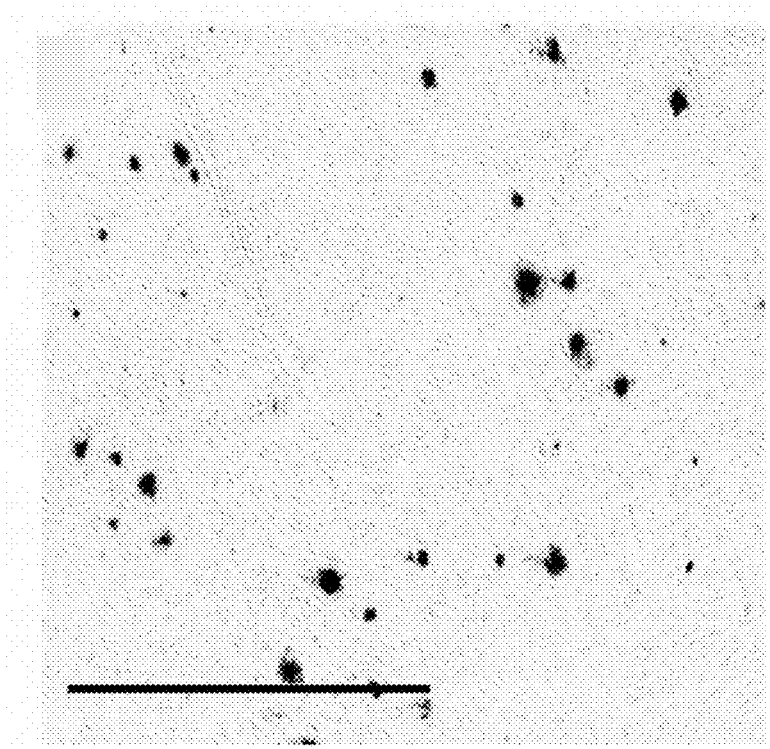
Figure 34E:
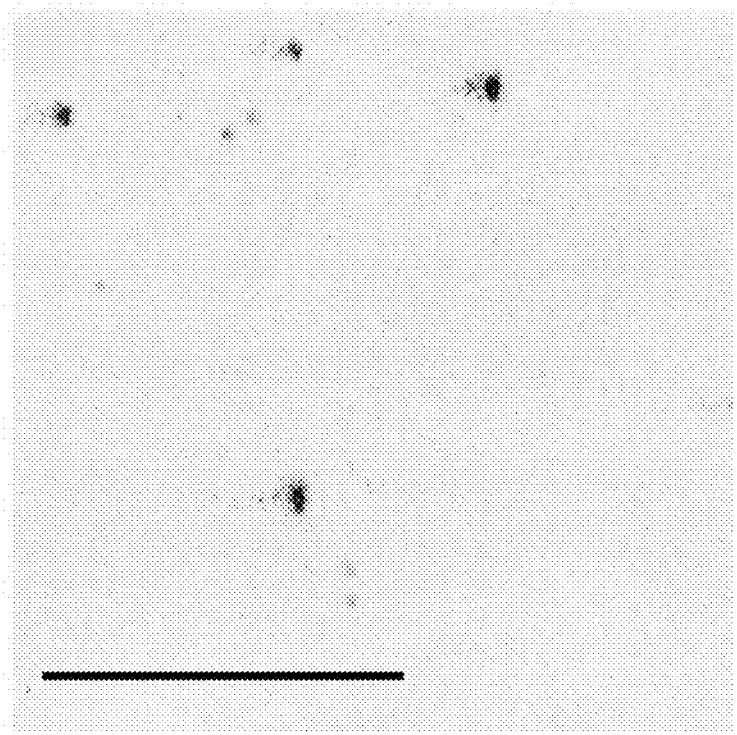
Figure 34F:
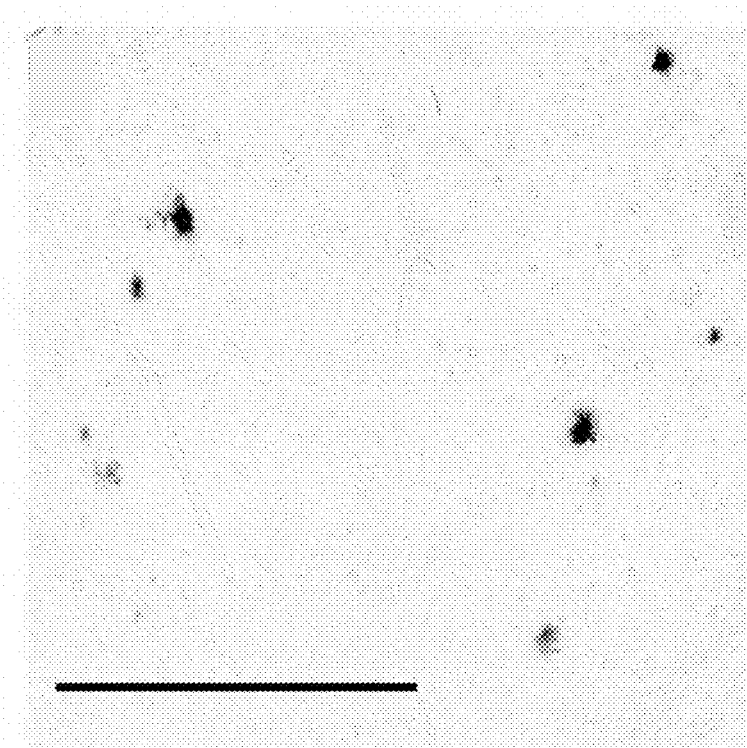
Figure 35A:
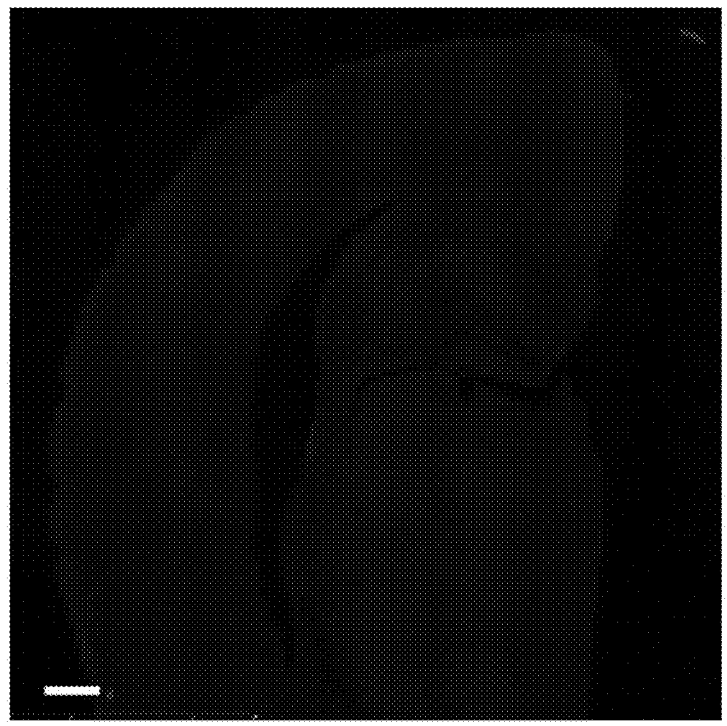
Figure 35B:
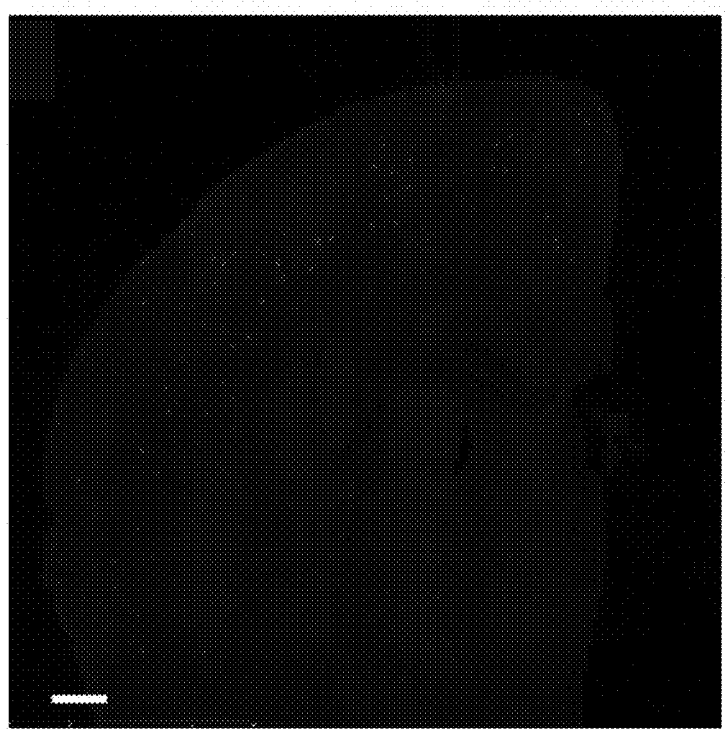
Figure 35C:
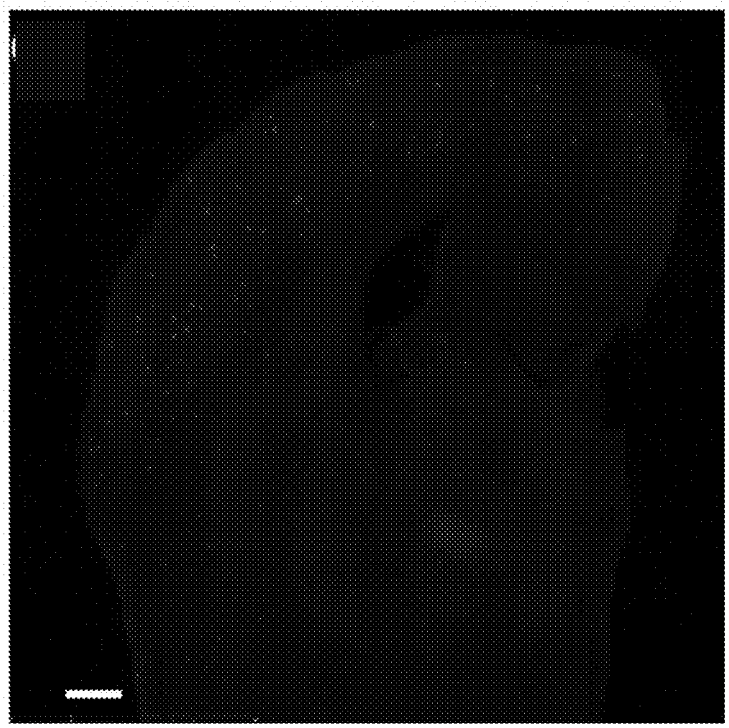
Figure 35D:
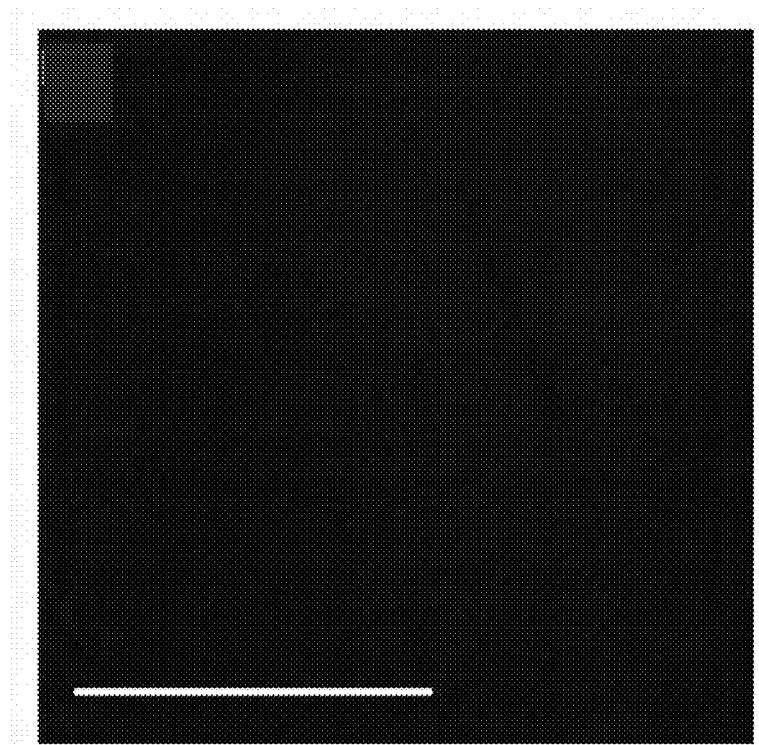
Figure 35E:
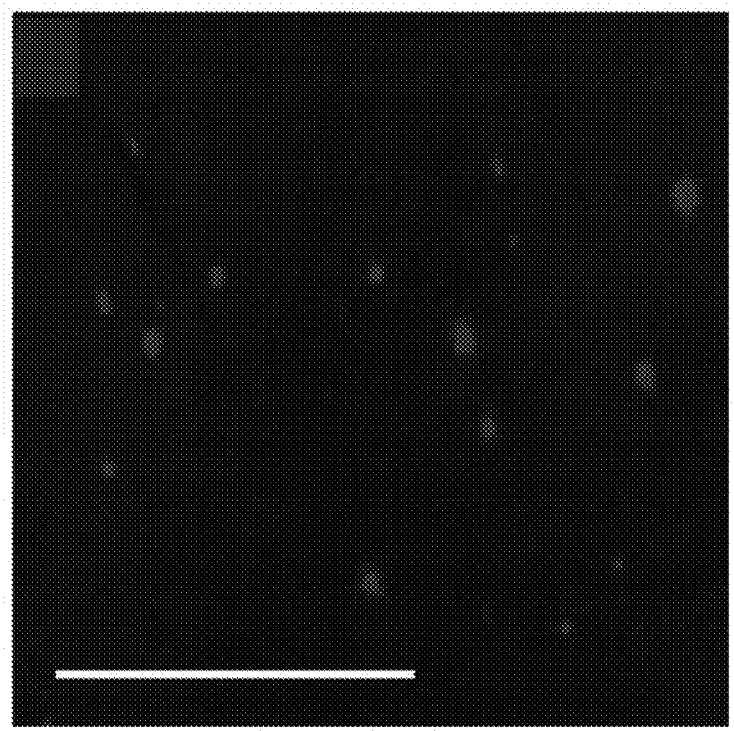
Figure 35F:
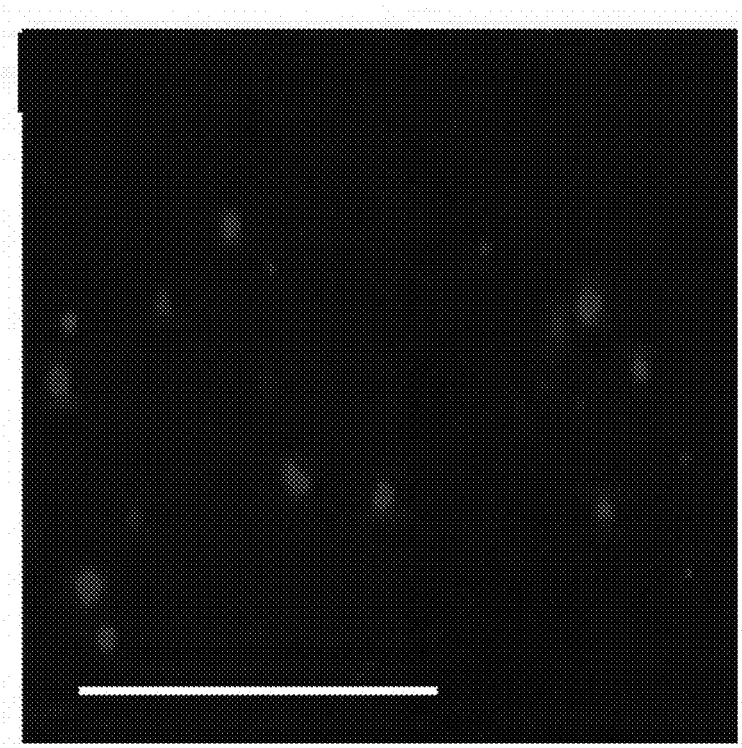
Figure 36A:
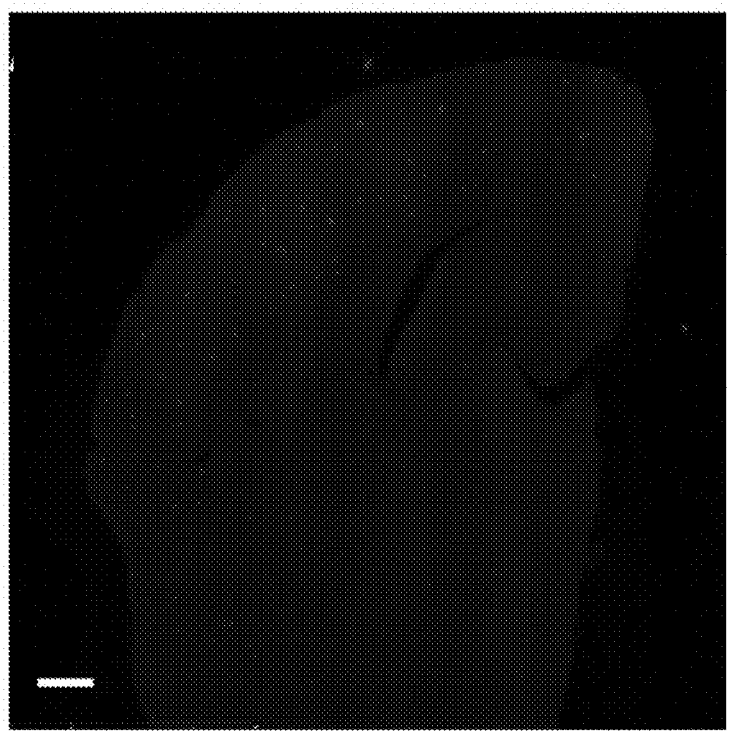
Figure 36B:
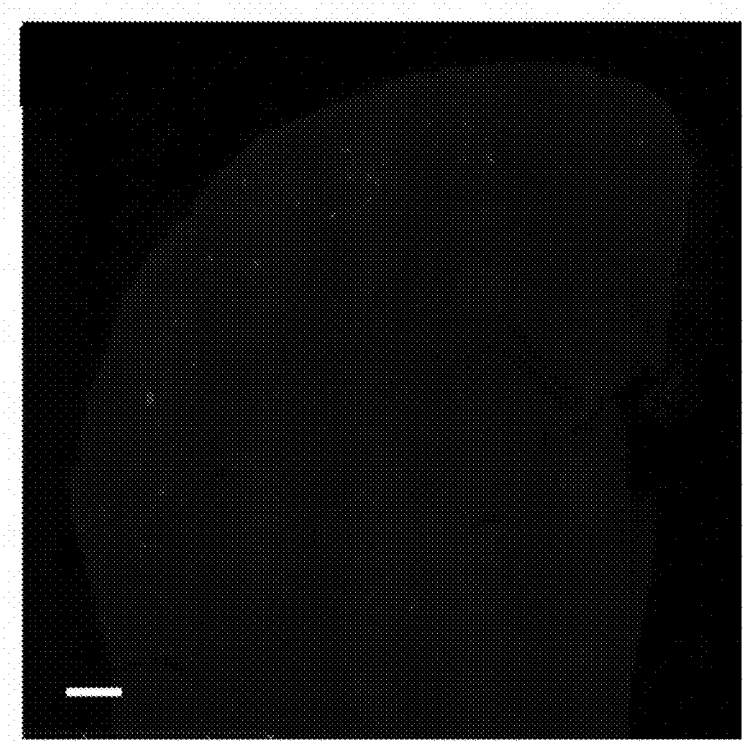
Figure 36C:
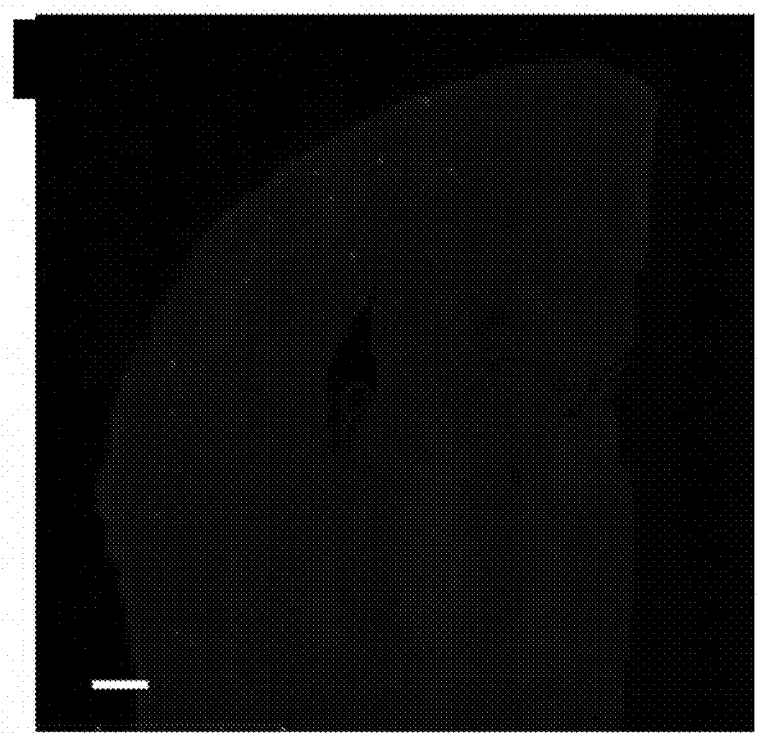
Figure 36D:
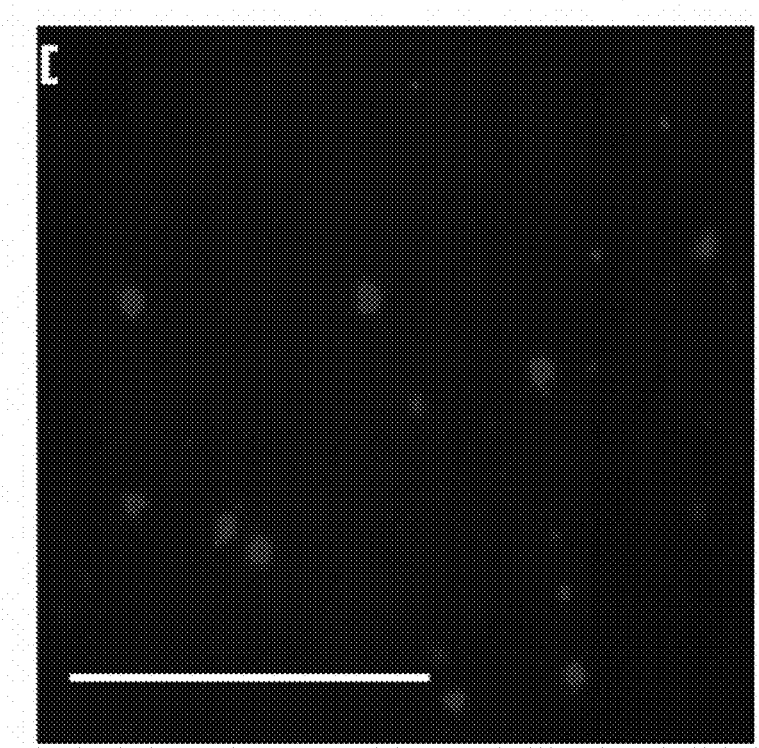
Figure 36E:
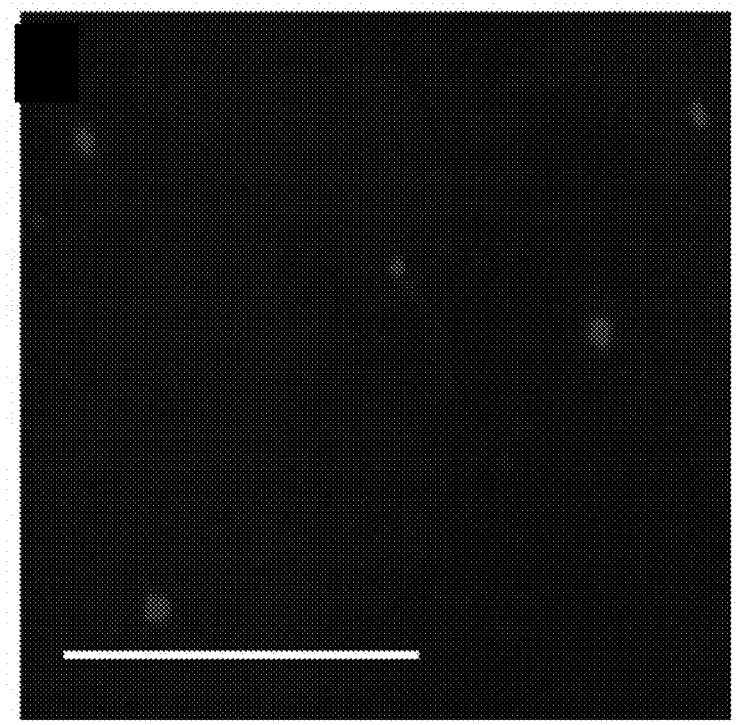
Figure 36F:
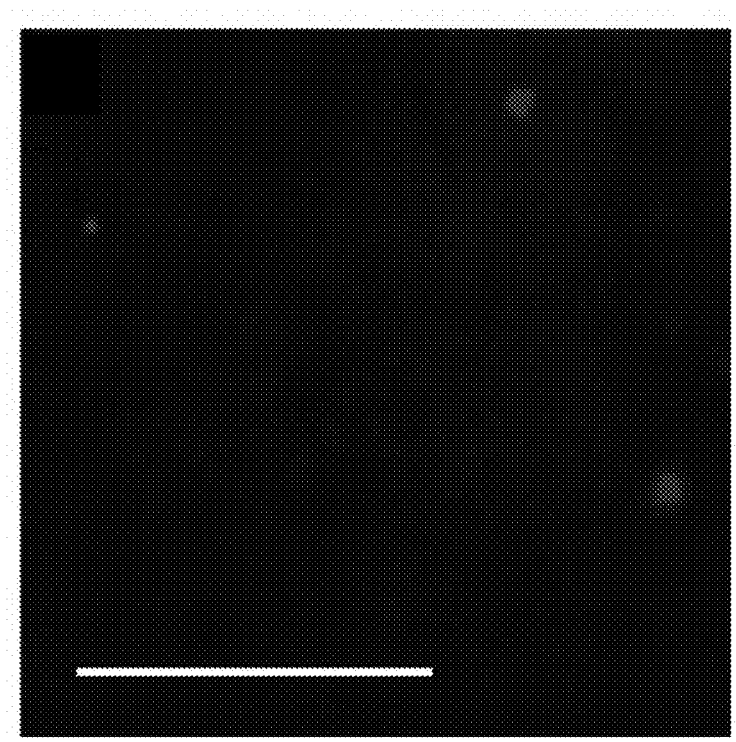

Brain sections from 2 month old untreated and 3.5 month old treated mice were immunostained with anti-Aβ antibody HJ3.4-biotin or stained with X-34 (a dye that stains fibrillar plaques), and staining was quantified from cortex. Treatment of APP/PS1-21 E4/E4 mice with HJ156 leads to a statistically significant reduction in Aβ plaque load, measured either by % area Aβ deposition (FIG. 29) or by plaque number (FIG. 30). Intra-peritoneal administration of HJ155 also resulted in a statistically significant decrease in Aβ plaque number (FIG. 30); a decrease in Aβ deposition (as measured by % area Aβ staining) was also observed, though the decrease was not significant (FIG. 29). Similar reductions in fibrillar Aβ plaque deposition and number were observed by X-34 staining (FIGS. 31 and 32). Representative images from these brain sections are shown in FIG. 33-36.

Example 17

To investigate whether the ability to recognize conformationally distinct forms of ApoE in Aβ plaques results in a more potent plaque reducing antibody, HJ151, HJ153 and HJ156 were further characterized.

Figure 37A:
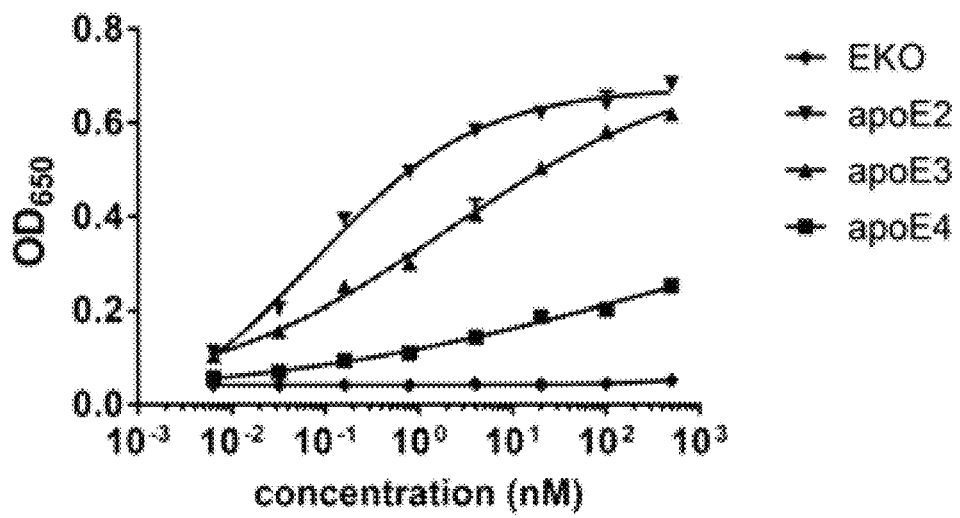
Figure 37B:
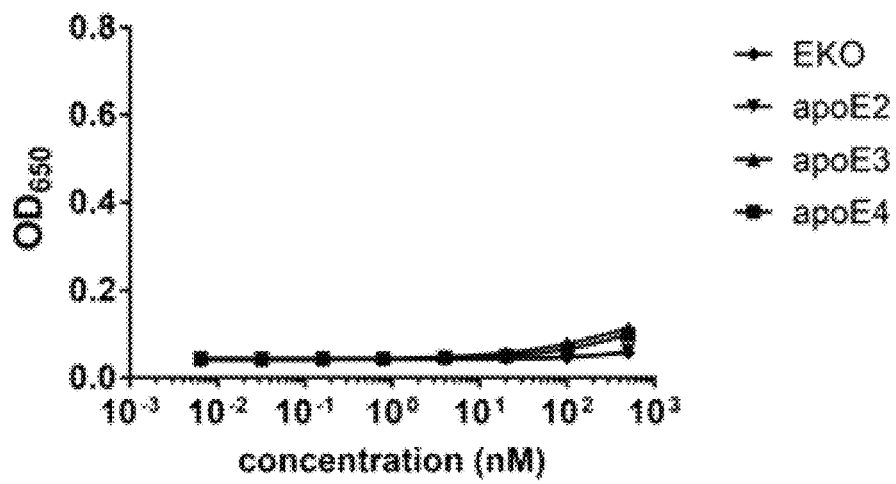
Figure 37C:
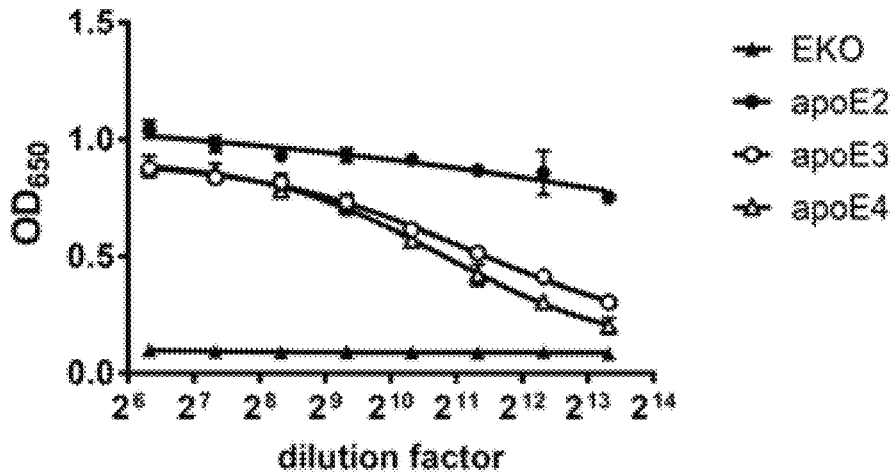
Figure 37D:
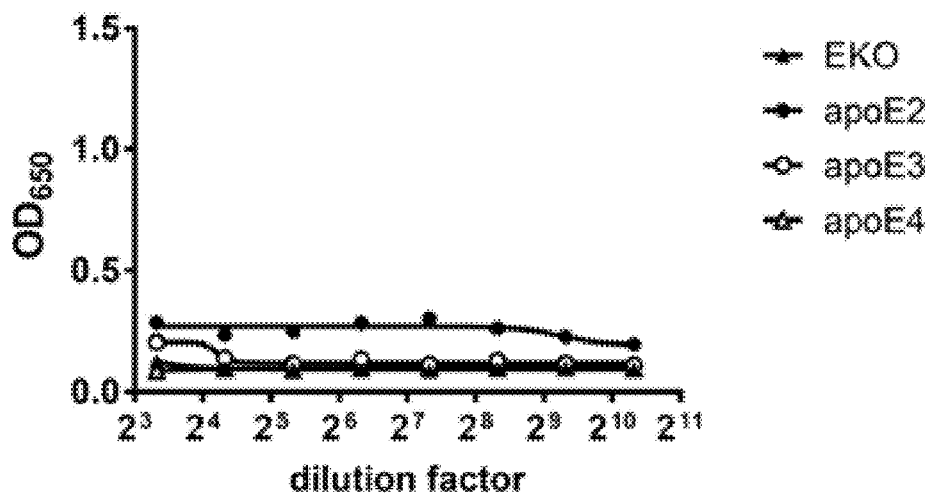
Figure 37E:
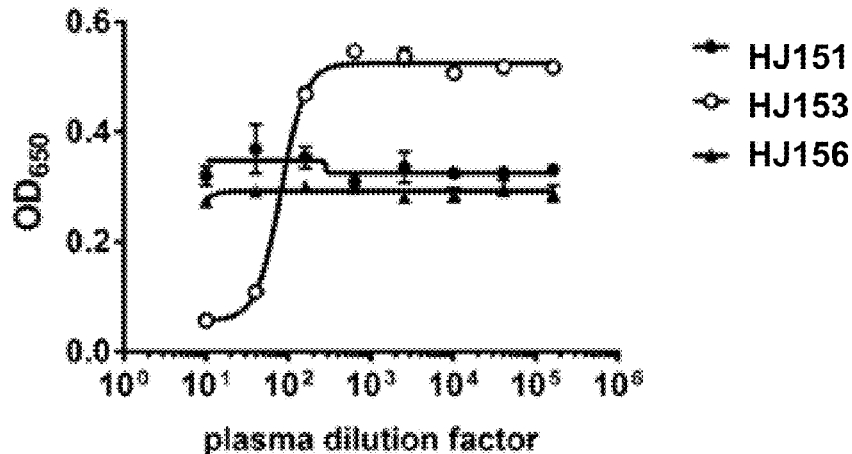

HJ153 or HJ156 were coated onto plates and plasma from ApoE KO (EKO), APOE2, APOE3 and APOE4 mice was loaded (FIG. 37C and FIG. 37D). The results demonstrated that HJ153 bound to lipidated ApoE2, ApoE3 and ApoE4 (FIG. 37C) while HJ156 did not (FIG. 37D). Next, non-lipidated ApoE4 was coated onto the plates and HJ151, HJ153 and HJ156 pre-incubated with serially diluted plasma from APOE4 mice. The results showed that lipidated ApoE was able to compete with the unlipidated ApoE for HJ153, suggesting that HJ153 bound both lipidated and unlipidated forms of ApoE (FIG. 37E). However, the lipidated ApoE was not able to compete for the binding between non lipidated apoE with HJ151 or HJ156, suggesting that HJ151 and HJ156 preferentially bind to non lipidated forms of ApoE (FIG. 37E).

Chimeric versions of HJ153 and HJ156 were also characterized. Plasma from EKO, APOE2, APOE3 and APOE4 KI mice were coated to ELISA plates (with plasma lipoprotein present). Chimeric versions of HJ153 (chi153) and HJ156 (chi156) that contain the binding domains of the mouse IgG antibodies with a human IgG backbone were prepared. Different concentrations of the chimeric antibodies were loaded onto the plates. The chi153 and chi156 that bound to the plate were detected using anti-human IgG (FIG. 37A, FIG. 37B). The results reveal that chi153 was able to bind lipidated ApoE2, ApoE3 and ApoE4 (FIG. 37A) while chi156 did not (FIG. 37B).

Figure 37F:
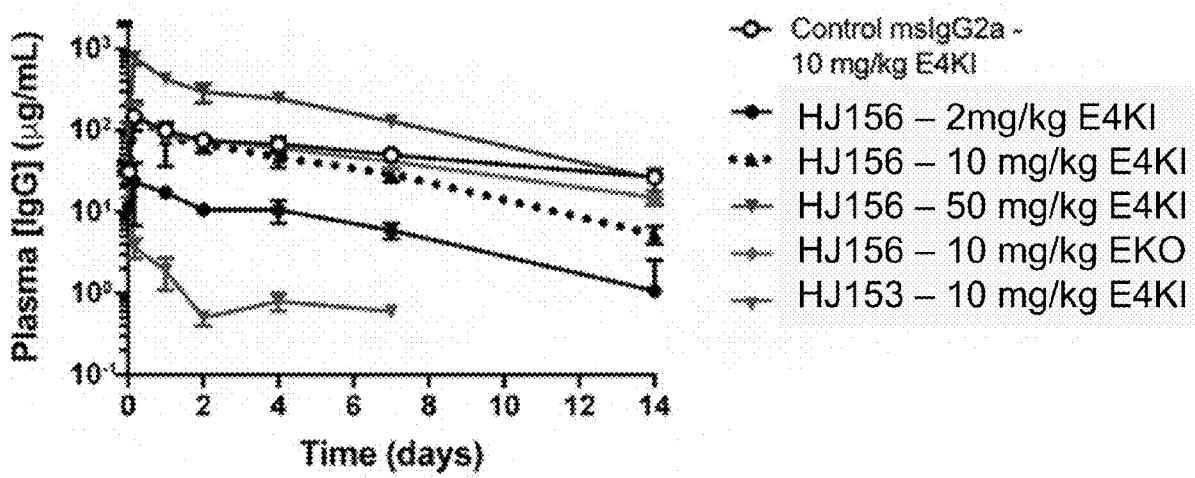

The pharmacokinetic characteristics of HJ153 and HJ156 after IP injection (10 mg/kg body weight) into APOE4 and APOEKO mice (FIG. 37F) were also compared. Plasma HJ153 was below detection limit at time points after 48 hr post-injection while HJ156 was present in the plasma 14 days after injection (FIG. 37F). In summary, our ELISA data suggests that HJ156 preferentially binds to non lipidated ApoE while HJ153 binds to both lipidated and non lipidated ApoE. This is consistent with a likely explanation for the pharmacokinetic characteristics. HJ153 binds to lipidated ApoE which is abundant in the plasma, resulting in a higher clearance rate of HJ153. However, the fact that HJ156 only binds non lipidated ApoE which is low or absent in plasma led to a slower clearance of HJ156 in vivo.

Figure 38A:
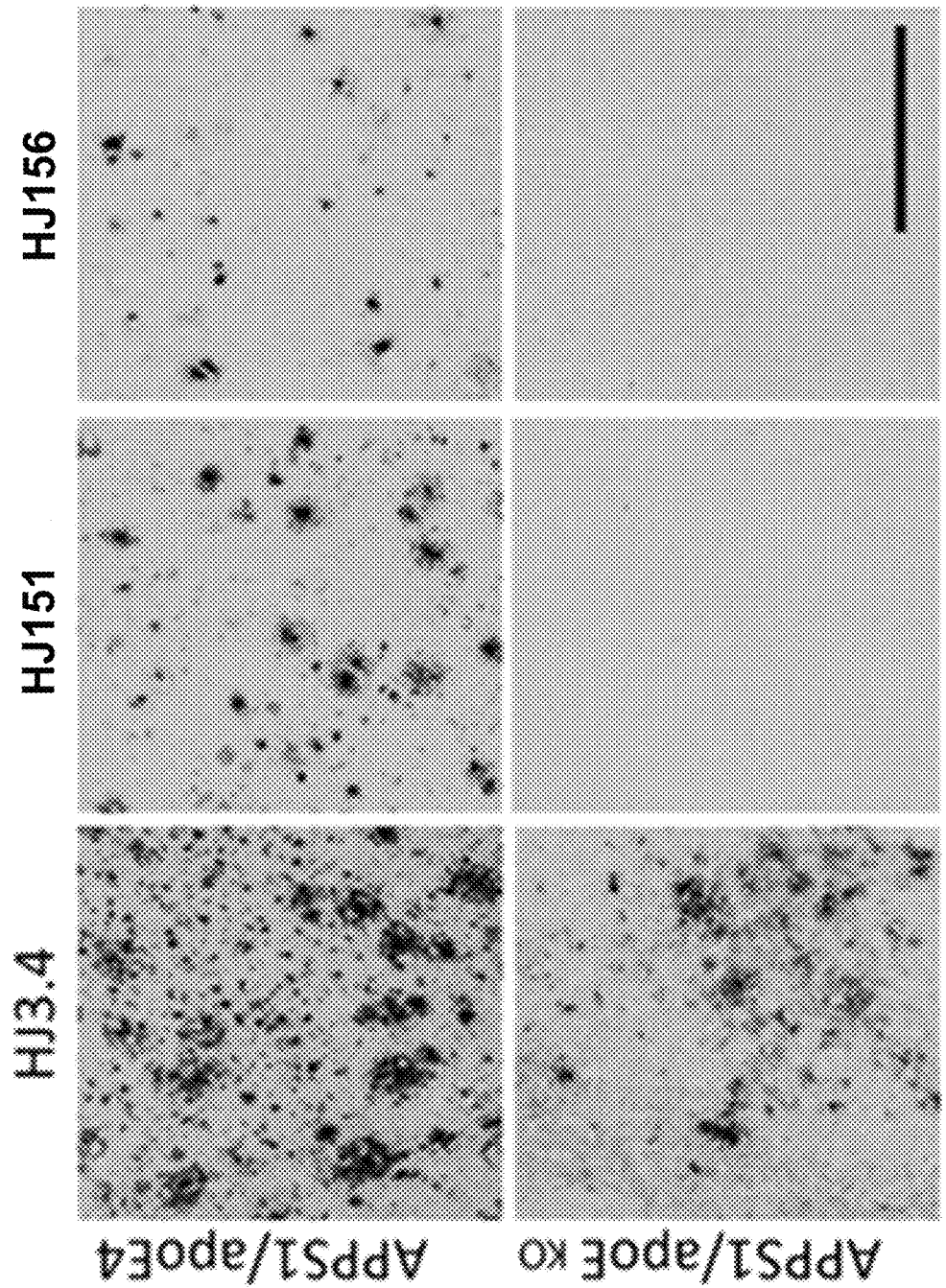
Figure 38B:
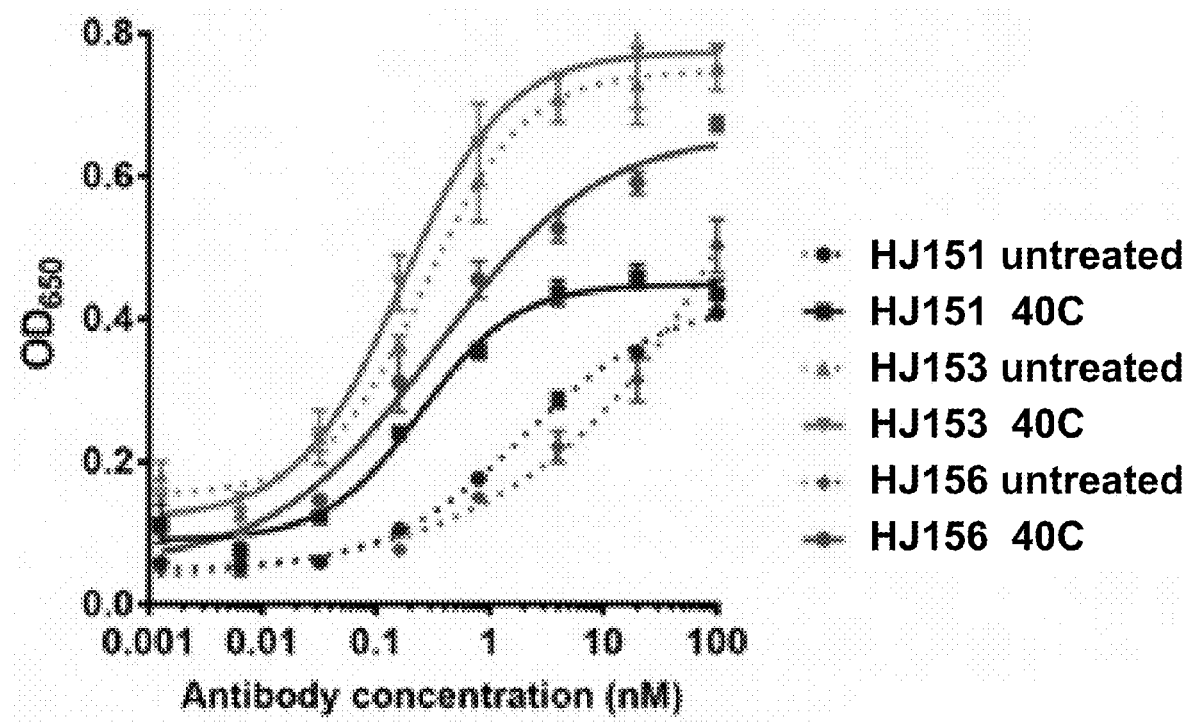
Figure 38C:
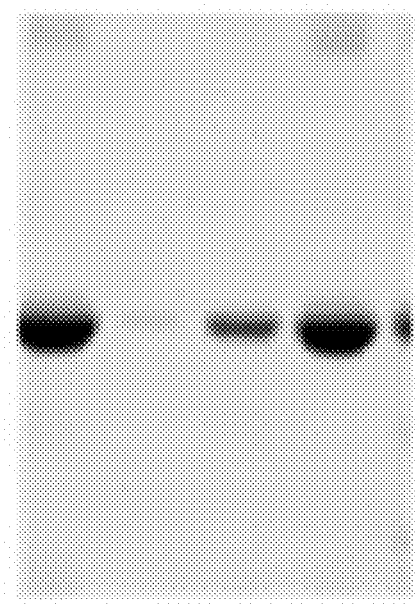
Figure 38D:
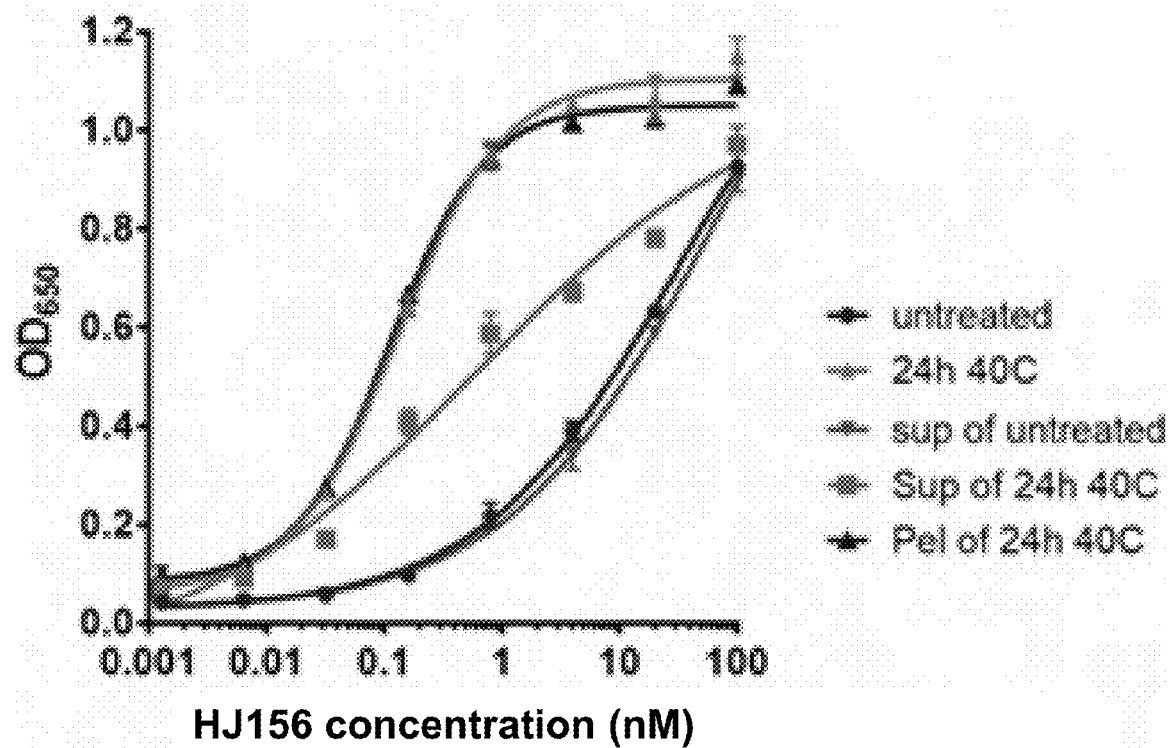
Figure 38E:
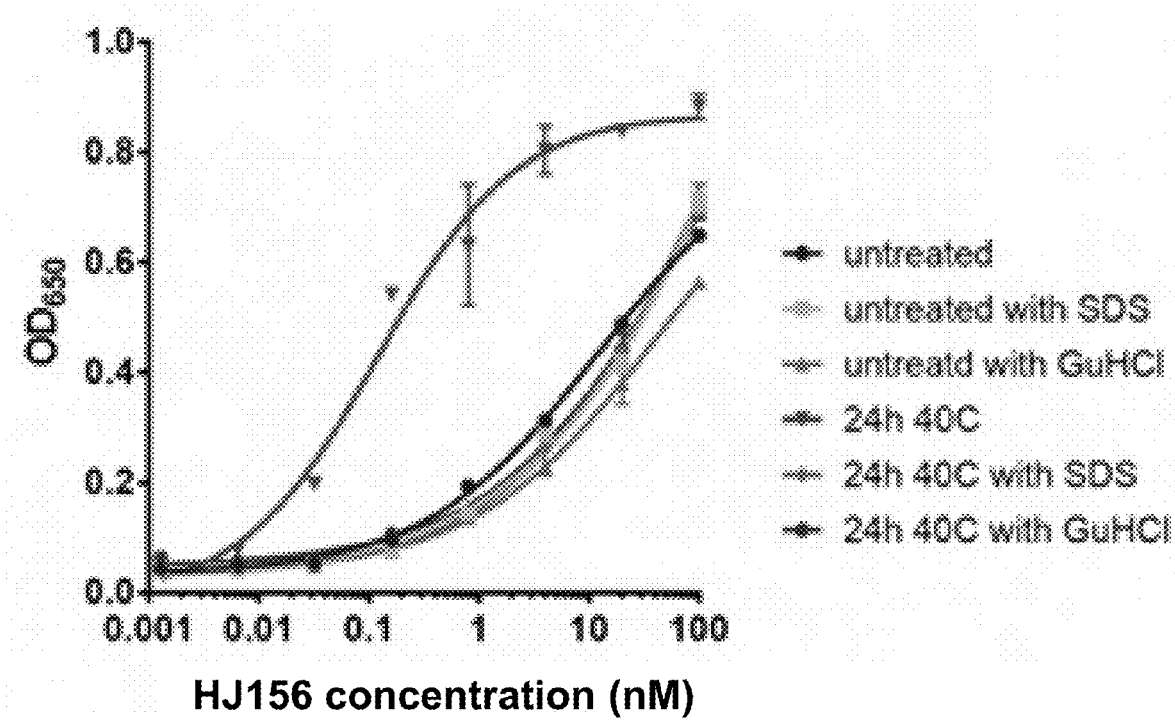

In order to test whether HJ151 and HJ156 bind to some form of ApoE in the brain, unfixed frozen brain sections from APPPS1/APOE4 or APPPS1/EKO mice using HJ151 and HJ156 (FIG. 38A). The presence of Aβ plaques was confirmed with Aβ immunostaining using anti-Aβ antibody HJ3.4 on the sections from the same brain. The results demonstrated that HJ151 and HJ156 were able to bind ApoE in plaques (FIG. 38A). Next, the ability of HJ156 to bind to an aggregated form of ApoE induced by incubation at 40° C. was queried. The binding of untreated ApoE to HJ151, HJ153 or HJ156 was compared to the binding of ApoE incubated at 40° C. to HJ151, HJ153 or HJ156. HJ153 bound to untreated ApoE or ApoE incubated at 40° C. similarly while HJ151 and HJ156 preferentially bound to ApoE incubated at 40° C. (FIG. 38B). It was further confirmed that 40° C. incubation resulted in the formation of aggregates in the pellet fraction after ultracentrifugation at 186,000×g for 1 hr (FIG. 38C). When the ApoE from supernatant or the pellets were coated onto ELISA plates and detected with HJ156, the ApoE from the supernatant showed low binding while the ApoE in the pellet demonstrated high binding (FIG. 38D). The ApoE from the pellet or total incubated ApoE bound with HJ156 to a similar degree (FIG. 38D), suggesting that the HJ156 binding to ApoE species following treatment exposure to 40° C. are the ApoE species in the pellet. Solubilization of the ApoE aggregates reduced their binding to HJ156. Specifically, exposure of the ApoE aggregates to 1% SDS or 4M guanidine was able to eliminate the binding of HJ156 to ApoE aggregates induced by incubation at 40° C. (FIG. 38E). In summary, the data showed that HJ156 preferentially bound to aggregated forms of ApoE as compared to monomeric ApoE. It also bound to ApoE in the plaques in APPPS1 mouse brain sections.

Figure 39A:
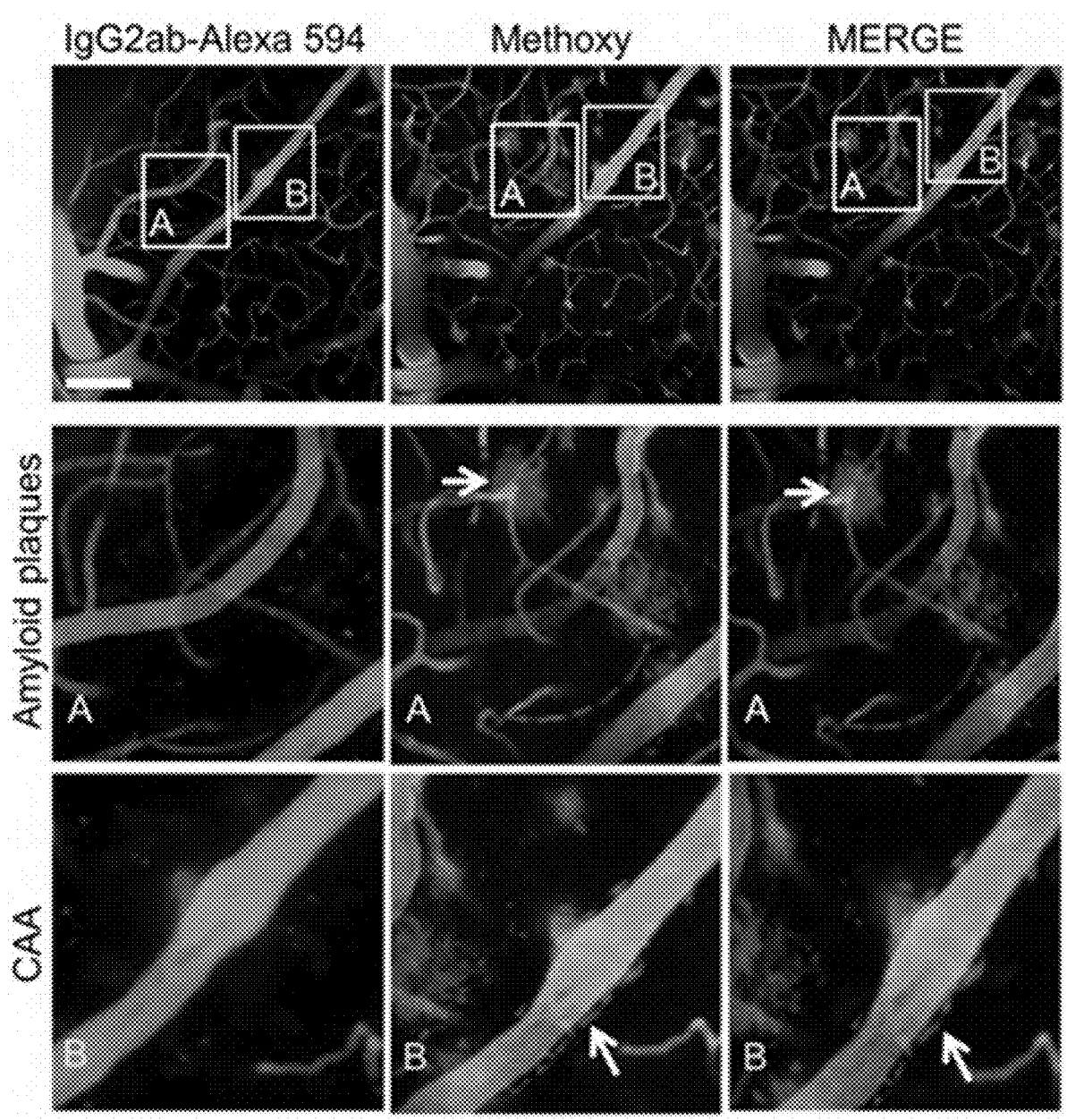
Figure 39B:
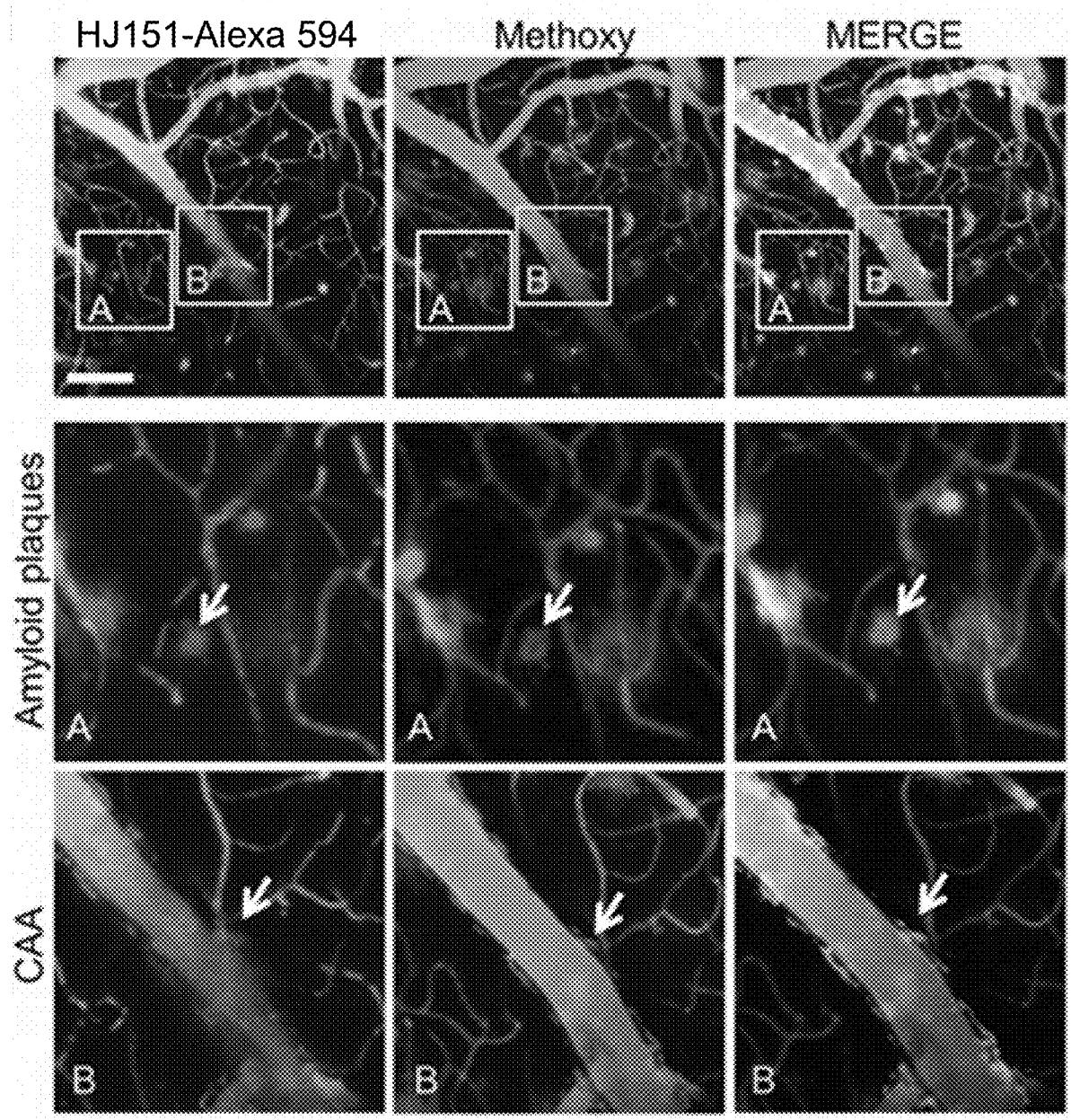
Figure 39C:
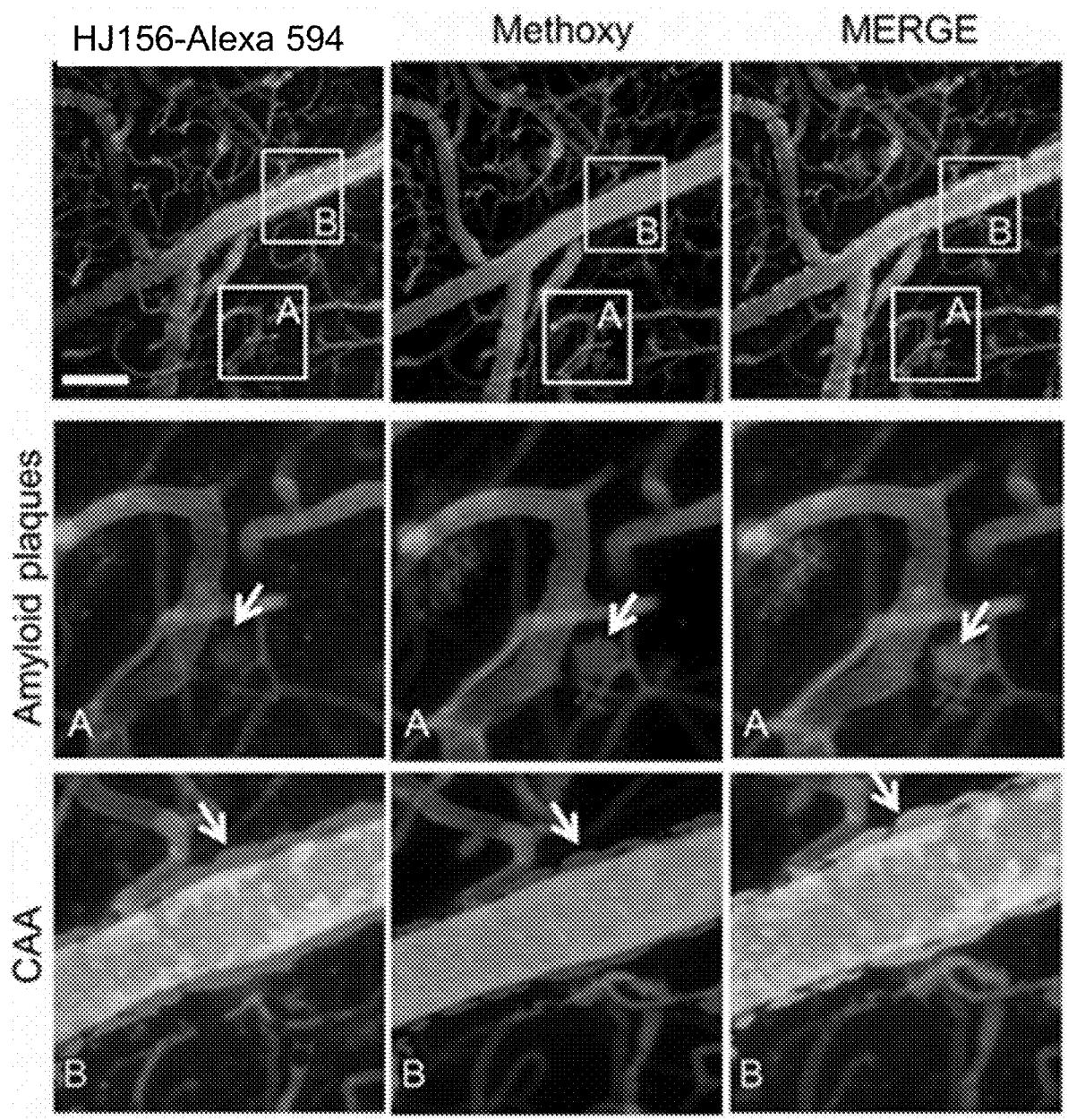
Figure 39D:
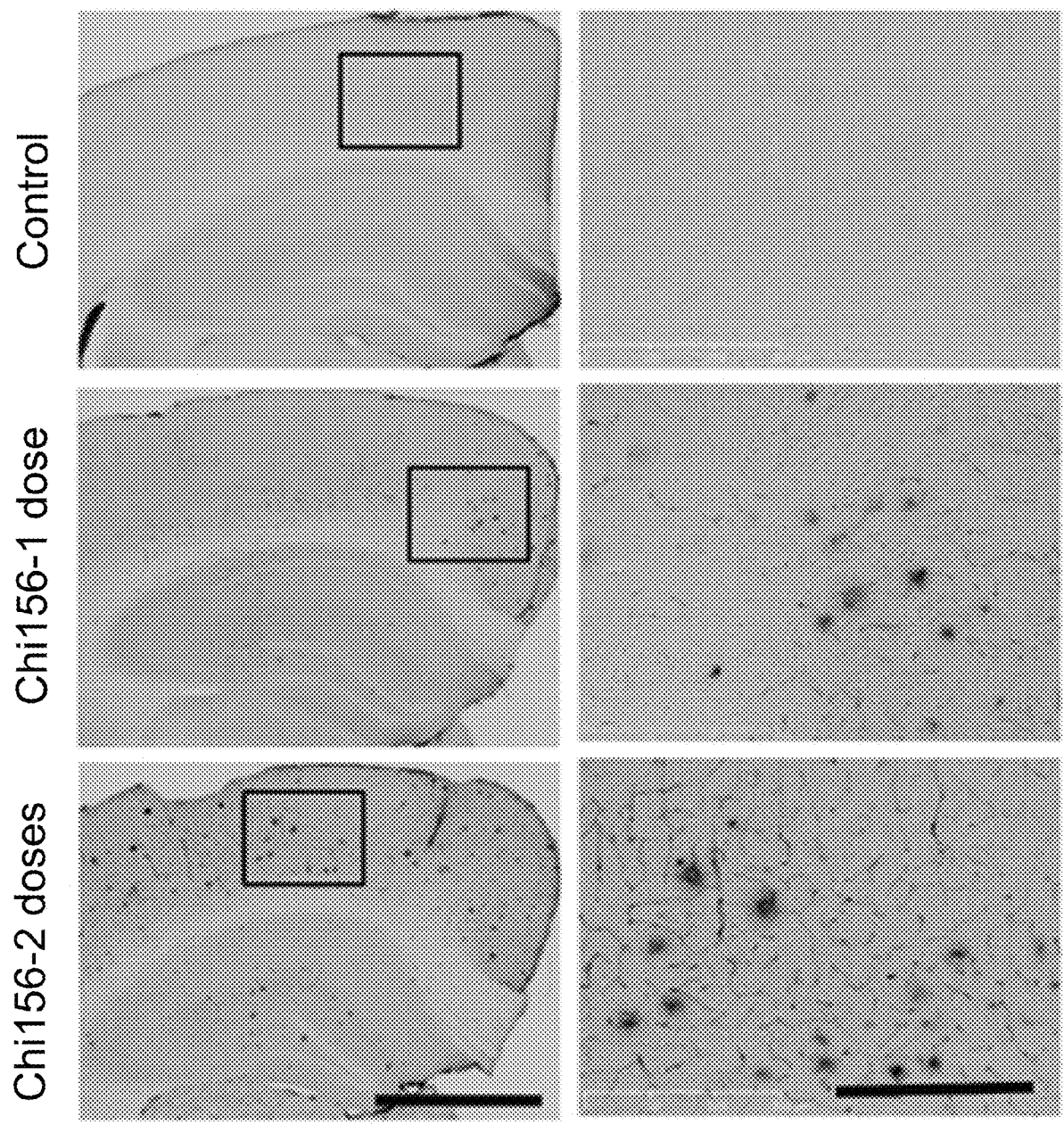

To test whether HJ151 and HJ156 bind to ApoE in the brain of living mice, experiments were performed utilizing in vivo 2-photon microscopy. A control mouse IgG2 antibody, HJ151 and HJ156 were conjugated with Alexa 594 and applied to the surface of the brain (40 µl of 1 mg/ml) of 6 month old APPPS1-21/APOE4 mice. The binding of the antibodies to ApoE was monitored through a cranial window using 2-photon microscopy (FIG. 39A-C). The results demonstrated HJ151 and HJ156 bind ApoE in the amyloid plaques and CAA. To determine whether peripherally administered ApoE antibodies can enter the brain and bind to ApoE, chi156 or control human IgG were IP injected (50 mg/kg body weight) for 1 or 2 doses into the APPPS1-21/APOE4 mice. Two days after the final injection, chi156 was detected bound to plaques in mice that received 1 or 2 injections of the antibody (FIG. 39D). In summary, the data demonstrated that HJ156 was able to enter the brain and bind to ApoE in the Aβ plaques in living animals.

To determine whether HJ151 and HJ156 antibodies can increase activated microglia, CD45+ microglia were quantified relative to the amount of fibrillar plaques after short-term treatment of HJ151 and HJ156 antibodies (4 doses of IP injection every 3 days) in APPPS1-21/APOE4 mice that already had existing plaques at 4 months of age (FIG. 40A, FIG. 41). After acute passive immunization, HJ151 had no effects on the amount of activated microglia while HJ156 significantly increased the CD45+ microglia as compared to the controls (FIG. 40). Effects on microglial activation after acute peripheral injection may be related to antibody efficacy and dose since both of these antibodies can bind to ApoE in plaques.

To determine the dose-range efficacy profile of HJ156, APPPS1-21/APOE4 mice were IP injected with a weekly dose of HJ156 at one of three dose levels (2, 10 and 50 mg/kg) for 2.5 months starting at 2 months of age (mixed gender, n=17-18/group). Control groups received a weekly dose of IgG2ab (50 mg/kg) or anti-Aβ HJ3.4 (50 mg/kg). Three days after the twelfth injection, the mice were deeply anesthetized perfused. The right hemi-brain was dissected the amount of soluble and insoluble Aβ was quantified in the cerebral cortex dorsal to hippocampus by ELISA. Cortical tissue was homogenized in PBS and 5M guanidine sequentially, and the Aβ levels in soluble (PBS) and insoluble (guanidine) fractions were measured. There was a significant dose-dependent effect of HJ156 on reducing insoluble $A\beta_{40}$ and $A\beta_{42}$ levels in the brain (FIG. 42A-B).

Overall, the above data suggests that a key feature of the antibodies disclosed herein for decreasing Aβ plaques is the ability to selectively bind a conformationally altered form of ApoE found in amyloid plaques. Given that non-lipidated ApoE is only a small percentage of total ApoE in vivo, targeting this pool of ApoE may be why no effect is seen on ApoE levels or lipid metabolism. Moreover, it is likely that these antibodies' preferential binding of alipidated ApoE contributes to a longer plasma half-life than as compared to an anti-ApoE antibody that binds to lipidated ApoE (FIG. 37F). This longer half-life would greatly increase the concentration of antibody that can enter the brain and bind to its target.

Example 18

Epitope binding of various anti-ApoE antibodies was evaluated multiple ways. Different sequences of human ApoE were expressed on the surface of yeast by yeast display using different plasmids. Different anti-ApoE antibodies were then assessed to determine binding to the different ApoE sequences by immunofluorescence of the yeast cell surface (Table 4). Because none of the anti-ApoE antibodies tested here recognize murine ApoE, the epitope was further narrowed down by comparison of the murine and human ApoE sequences as shown in Tables 4 and 5. The data in Tables 6 and 7 was generated as follows. DNA constructs containing different regions of ApoE4 with myc tag were transformed into yeast cells. Yeast cells were incubated with HJ15x to detect binding or anti-myc antibody to detect expression. HJ153 was not evaluated in these experiments as it was found to not bind to human ApoE4 expressed in yeast.

TABLE 4

| Antibody | Specificity | Epitope (aa of mature ApoE) |
|---|---|---|
| 151 | E4 | 108-120 |
| 152 | E2, E3, E4 | 150-160 |

TABLE 4-continued

| Antibody | Specificity | Epitope (aa of mature ApoE) |
|---|---|---|
| 153 | E2, E3, E4 | 1-250 |
| 154 | E2, E3, E4 | 130-140 |
| 155 | E2, E3, E4 | 150-160 |
| 156 | E3, E4 | 140-150 |

TABLE 5

| Antibody | Epitope* |
|---|---|
| 151 | 108-120 aa |
| 152 | 150-160 aa |
| 153 | 130-140 aa |
| 154 | 150-160 aa |
| 155 | 140-150 aa |
| 156 | 150-160 aa |

*Numbering based off mature ApoE protein (i.e., lacking the signal peptide).

TABLE 6

| Expression in yeast | ApoE4 amino acids | Approximate region | HJ151 | HJ152 | HJ154 | HJ155 | HJ156 |
|---|---|---|---|---|---|---|---|
| Yes | 1-132 | up to helix 3 | + | − | + | − | − |
| Yes | 1-164 | up to helix 4 | + | + | + | + | + |
| Yes | 1-210 | N terminal domain | + | + | + | + | + |
| Yes | 1-299 | full length | + | + | + | + | + |
| Yes | 24-79 | helix1 + 2 | − | − | − | − | − |
| Yes | 24-125 | helix1 + 2 + 3 | + | − | + | − | − |
| Yes | 24-164 | helix1 + 2 + 3 + 4 | + | + | + | + | + |
| Low | 54-164 | helix2 + 3 + 4 | + | + | + | + | + |
| No | 88-164 | helix3 + 4 | | | | | |
| No | 132-164 | LDLR binding | | | | | |
| No | 132-210 | post helix 3 | | | | | |
| Yes | 164-210 | intermediate domain | − | − | − | − | − |
| Yes | 210-299 | C-terminal domain | − | − | − | − | − |

TABLE 7

| Expression in yeast | ApoE4 amino acids | Approximate region | HJ159 | HJ1513 | HJ1514 | HJ1518 | HJ1526 |
|---|---|---|---|---|---|---|---|
| Yes | 1-132 | up to helix 3 | − | − | − | − | + |
| Yes | 1-164 | up to helix 4 | + | + | + | + | + |
| Yes | 1-210 | N terminal domain | + | + | + | + | + |
| Yes | 1-299 | full length | + | + | + | + | + |
| Yes | 24-79 | helix1 + 2 | − | − | − | − | − |
| Yes | 24-125 | helix1 + 2 + 3 | − | − | − | − | + |
| Yes | 24-164 | helix1 + 2 + 3 + 4 | + | + | + | + | + |
| Low | 54-164 | helix2 + 3 + 4 | + | + | + | + | + |
| No | 88-164 | helix3 + 4 | | | | | |
| No | 132-164 | LDLR binding | | | | | |
| No | 132-210 | post helix 3 | | | | | |
| Yes | 164-210 | intermediate domain | − | − | − | − | − |
| Yes | 210-299 | C-terminal domain | − | − | − | − | − |

Example 19

Clearance (CL) is a pharmacokinetic parameter that describes the efficiency of irreversible elimination of a drug from systemic circulation, expressed as volume of blood/plasma/serum cleared of drug per unit time. Anti-ApoE antibodies that bind to lipidated ApoE in the plasma exhibit high clearance due to very high concentrations of lipidated ApoE present in circulation. In contrast, antibodies that specifically bind alipidated ApoE would be expected to exhibit low clearance and other pharmacokinetic properties that are similar to an isotype control antibody that does not bind to antigen. For such antibodies the clearance would not be dose-dependent.

Prior to the present disclosure, antibodies that have the ability to preferentially bind alipidated ApoE over lipidated ApoE were not known. The inventors have surprisingly found certain antibodies that preferentially bind alipidated ApoE over lipidated ApoE. Moreover, certain antibodies were found to bind with greater affinity to aggregated ApoE than to non-aggregated ApoE. The aggregated ApoE can be prepared by oxidation and/or heat treatment of ApoE (e.g., recombinant ApoE). The aggregated ApoE can be separated from the non-aggregated from by ultracentrifugation (at least 186,000 g).

Mice were administered antibody via intraperitoneal injections at the indicated doses and submandibular bleeds were performed at 30 minutes, 4 hours, 1 day, 2 days, 4 days, and 7 days. Anti-ApoE drug levels were determined in the sampled plasma by an ELISA assay using recombinant apoE4 as a capture antigen for HJ156 or human Her2 protein for the control IgG antibody (anti-Her2). Clearance values were calculated based on overall pharmacokinetics for the antibodies over the entire time course of the experiment.

TABLE 8

Plasma antibody clearance values for HJ156 at various doses in APOE4KI and APOEKO mice.

| Antibody | Dose (mg/kg) | Mouse | CL (mL/day/kg) |
| --- | --- | --- | --- |
| control mouse IgG | 10 | ApoE4 knock-in | 9.4 |
| HJ156 | 2 | ApoE4 knock-in | 20 |
| HJ156 | 10 | ApoE4 knock-in | 19 |
| HJ156 | 50 | ApoE4 knock-in | 20 |
| HJ156 | 10 | ApoE4 knock-out | 13 |

What is claimed is:

1. An isolated anti-ApoE antibody comprising (a) a light chain variable region comprising CDRL1 of SEQ ID NO: 51, CDRL2 of SEQ ID NO: 24, and CDRL3 of SEQ ID NO: 25; and (b) a heavy chain variable region comprising CDRH1 of SEQ ID NO: 52, CDRH2 of SEQ ID NO: 53, and CDRH3 of SEQ ID NO: 54.

2. The isolated antibody of claim 1, wherein the amino acid sequence of the light chain variable region is SEQ ID NO: 11.

3. The isolated antibody of claim 1, wherein the amino acid sequence of the heavy chain variable region is SEQ ID NO: 12.

4. The isolated antibody of claim 1, wherein the framework region of each variable region has at least 75% sequence identity with a human framework region sequence.

5. The isolated antibody of claim 1, wherein the isolated antibody further comprises one or more constant regions, or a portion of a constant region, that has at least 90% sequence identity with human constant region sequence.

6. The isolated antibody of claim 1, wherein the antibody is a monoclonal antibody or an antibody fragment.

7. The isolated antibody of claim 1, wherein the antibody is a monoclonal antibody.

8. The isolated antibody of claim 1, wherein the isolated antibody further comprises a constant region, or a portion of a constant region, that has at least 90% sequence identity with human constant region sequence.

\* \* \* \* \*

SEQUENCE LISTING

```
<160> NUMBER OF SEQ ID NOS: 126

<210> SEQ ID NO 1
<211> LENGTH: 113
<212> TYPE: PRT
<213> ORGANISM: Artificial Sequence
<220> FEATURE:
<223> OTHER INFORMATION: SYNTHESIZED

<400> SEQUENCE: 1

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Val His Ser
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Cys Thr Phe Gly Gly Gly Thr Lys Leu Glu Ile Lys
            100                 105                 110

Arg

<210> SEQ ID NO 2
<211> LENGTH: 111
<212> TYPE: PRT
<213> ORGANISM: Artificial Sequence
<220> FEATURE:
<223> OTHER INFORMATION: SYNTHESIZED

<400> SEQUENCE: 2

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Thr Asp Tyr
            20                  25                  30

Glu Met His Trp Val Lys Gln Thr Pro Val His Gly Leu Glu Trp Ile
        35                  40                  45
```

```
Gly Val Ile Asp Pro Glu Lys Gly Gly Thr Ala Tyr Asn Gln Lys Phe
 50                  55                  60

Lys Gly Lys Ala Ile Leu Thr Ala Asp Lys Ser Ser Thr Ala Tyr
 65                  70                  75                  80

Met Asp Leu Arg Ser Leu Thr Ser Glu Asp Ser Ala Val Tyr Tyr Cys
                 85                  90                  95

Leu Lys Asp Ser Trp Gly Gln Gly Thr Thr Leu Thr Val Ser Ser
                100                 105                 110
```

<210> SEQ ID NO 3
<211> LENGTH: 114
<212> TYPE: PRT
<213> ORGANISM: Artificial Sequence
<220> FEATURE:
<223> OTHER INFORMATION: SYNTHESIZED

<400> SEQUENCE: 3

```
Asp Ile Val Met Ser Gln Ser Pro Ser Ser Leu Ala Val Ser Ala Gly
  1               5                  10                  15

Glu Lys Val Thr Met Ser Cys Lys Ser Ser Gln Ser Leu Leu Asn Ser
                 20                  25                  30

Arg Thr Arg Lys His Phe Leu Ala Trp Tyr Gln Gln Lys Pro Gly Gln
             35                  40                  45

Ser Pro Lys Val Leu Ile Tyr Trp Ala Ser Ser Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Gln Ala Glu Asp Leu Ala Val Tyr Tyr Cys Lys Gln
                 85                  90                  95

Ser Cys Asn Leu Pro Trp Thr Phe Gly Gly Gly Thr Lys Leu Glu Ile
                100                 105                 110

Lys Arg
```

<210> SEQ ID NO 4
<211> LENGTH: 114
<212> TYPE: PRT
<213> ORGANISM: Artificial Sequence
<220> FEATURE:
<223> OTHER INFORMATION: SYNTHESIZED

<400> SEQUENCE: 4

```
Glu Val Lys Leu Glu Glu Ser Gly Gly Gly Leu Val Gln Pro Gly Gly
  1               5                  10                  15

Ser Met Lys Leu Ser Cys Ala Ala Ser Gly Phe Ser Phe Ser Asp Ala
                 20                  25                  30

Trp Met Asp Trp Val Arg Gln Ser Pro Glu Lys Gly Leu Glu Trp Val
             35                  40                  45

Ala Glu Ile Arg Asn Lys Ala Asp Asn His Ala Thr Phe Tyr Ala Glu
 50                  55                  60

Ser Val Lys Gly Arg Phe Thr Ile Ser Arg Asp Asp Ser Lys Ser Ser
 65                  70                  75                  80

Val Tyr Leu Gln Met Asn Ser Leu Arg Ala Glu Asp Ser Gly Ile Tyr
                 85                  90                  95

Tyr Cys Leu Leu Trp Asp Tyr Trp Gly Gln Gly Thr Thr Leu Thr Val
                100                 105                 110

Ser Ser
```

```
<210> SEQ ID NO 5
<211> LENGTH: 107
<212> TYPE: PRT
<213> ORGANISM: Artificial Sequence
<220> FEATURE:
<223> OTHER INFORMATION: SYNTHESIZED

<400> SEQUENCE: 5

Gln Ile Val Leu Thr Gln Ser Pro Ala Ile Met Ser Ala Ser Pro Gly
1               5                   10                  15

Glu Lys Val Thr Ile Ser Cys Ser Ala Ser Ser Val Thr Tyr Met
            20                  25                  30

Tyr Trp Tyr Gln Gln Lys Pro Gly Ala Ser Pro Lys Ser Trp Ile Tyr
        35                  40                  45

Arg Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Phe Gln Ser Tyr Pro Leu Thr
                85                  90                  95

Phe Gly Ala Gly Thr Lys Leu Glu Leu Lys Arg
            100                 105

<210> SEQ ID NO 6
<211> LENGTH: 118
<212> TYPE: PRT
<213> ORGANISM: Artificial Sequence
<220> FEATURE:
<223> OTHER INFORMATION: SYNTHESIZED

<400> SEQUENCE: 6

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Arg Gly Leu Glu Trp Ile
        35                  40                  45

Gly Glu Ile Asp Pro Ser Asp Gly Phe Thr Tyr Asn Asn Gln Asn Phe
    50                  55                  60

Lys Asp Lys Ser Thr Leu Thr Val Asp Arg Ser Ser Gly Thr Ala Tyr
65                  70                  75                  80

Leu Gln Leu Ser Ser Leu Thr Ser Glu Asp Ser Ala Val Tyr Tyr Cys
                85                  90                  95

Ala Gly Ser Leu Gly Arg Ile Gly Leu Ala Tyr Trp Gly His Gly Thr
            100                 105                 110

Leu Val Thr Val Ser Ala
        115

<210> SEQ ID NO 7
<211> LENGTH: 107
<212> TYPE: PRT
<213> ORGANISM: Artificial Sequence
<220> FEATURE:
<223> OTHER INFORMATION: SYNTHESIZED

<400> SEQUENCE: 7

Gln Ile Val Leu Thr Gln Ser Pro Ala Ile Met Ser Ala Ser Pro Gly
1               5                   10                  15

Glu Lys Val Thr Met Ser Cys Ser Ala Ser Ser Val Ser Asn Met
            20                  25                  30
```

```
Tyr Trp Tyr Gln Gln Lys Pro Gly Ser Ser Pro Lys Ser Trp Ile Tyr
         35                  40                  45

Arg Thr Ser Asn Leu Ala Ser Gly Val Pro Ala Arg Phe Ser Gly Ser
 50                  55                  60

Gly Ser Gly Thr Ser Tyr Ser Leu Thr Ile Ser Asn Met Glu Ala Glu
 65                  70                  75                  80

Asp Ala Ala Thr Tyr Tyr Cys Gln His Tyr Gln Asn Tyr Pro Leu Thr
                 85                  90                  95

Phe Gly Ala Gly Thr Lys Leu Glu Leu Lys Arg
            100                 105
```

<210> SEQ ID NO 8
<211> LENGTH: 118
<212> TYPE: PRT
<213> ORGANISM: Artificial Sequence
<220> FEATURE:
<223> OTHER INFORMATION: SYNTHESIZED

<400> SEQUENCE: 8

```
Gln Val Gln Leu Gln Gln Pro Gly Thr Glu Phe Val Met Ser Gly Ala
 1               5                  10                  15

Ser Val Met Leu Ser Cys Lys Ala Ser Gly Tyr Ile Phe Thr Asn Tyr
                 20                  25                  30

Trp Leu His Trp Val Lys Gln Arg Pro Gly His Gly Leu Glu Trp Ile
             35                  40                  45

Gly Glu Ile Asp Pro Ser Asp Ser Tyr Ser Ile Cys Asn Asp Asn Phe
 50                  55                  60

Lys Gly Lys Ser Thr Leu Thr Val Asp Lys Ser Ser Ser Thr Ala Tyr
 65                  70                  75                  80

Met Gln Leu Ser Ser Leu Thr Ser Glu Asp Ser Ala Val Tyr Tyr Cys
                 85                  90                  95

Ala Gly Ser Leu Gly Arg Val Gly Leu Ala Tyr Trp Gly Gln Gly Thr
            100                 105                 110

Leu Val Thr Val Ser Thr
        115
```

<210> SEQ ID NO 9
<211> LENGTH: 113
<212> TYPE: PRT
<213> ORGANISM: Artificial Sequence
<220> FEATURE:
<223> OTHER INFORMATION: SYNTHESIZED

<400> SEQUENCE: 9

```
Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Ser Ile Val His Ser
                 20                  25                  30

Asn Gly Asn Thr Tyr Leu Glu Trp Tyr Leu Gln Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95
```

```
Ser His Val Pro Tyr Thr Phe Gly Gly Gly Thr Lys Leu Glu Ile Lys
                100                 105                 110

Arg

<210> SEQ ID NO 10
<211> LENGTH: 118
<212> TYPE: PRT
<213> ORGANISM: Artificial Sequence
<220> FEATURE:
<223> OTHER INFORMATION: SYNTHESIZED

<400> SEQUENCE: 10

Arg Val Gln Leu Gln Gln Ser Gly Pro Gly Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Arg Gln Arg Pro Gly Gln Gly Leu Glu Trp Ile
        35                  40                  45

Gly Trp Ile Phe Pro Gly Ser Gly Ile Thr Tyr Tyr Asn Glu Lys Phe
    50                  55                  60

Lys Gly Lys Ala Thr Leu Thr Val Asp Arg Ser Ser Thr Ala Tyr
65                  70                  75                  80

Met Leu Leu Ser Ser Leu Thr Ser Glu Asp Ser Ala Val Tyr Phe Cys
                85                  90                  95

Ala Arg Tyr Ala Tyr Gly Ser Pro Phe Ala Tyr Trp Gly Gln Gly Thr
                100                 105                 110

Leu Val Thr Val Ser Ala
        115

<210> SEQ ID NO 11
<211> LENGTH: 113
<212> TYPE: PRT
<213> ORGANISM: Artificial Sequence
<220> FEATURE:
<223> OTHER INFORMATION: SYNTHESIZED

<400> SEQUENCE: 11

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Ile His Ser
            20                  25                  30

Asn Gly Asn Thr Tyr Leu Glu Trp Phe Leu Gln Arg Pro Gly Gln Ser
        35                  40                  45

Pro Glu Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
                100                 105                 110

Arg

<210> SEQ ID NO 12
<211> LENGTH: 118
<212> TYPE: PRT
<213> ORGANISM: Artificial Sequence
<220> FEATURE:
<223> OTHER INFORMATION: SYNTHESIZED
```

<400> SEQUENCE: 12

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ile Phe Thr Asp Tyr
            20                  25                  30

Tyr Ile Asn Trp Val Lys Arg Pro Gly Gln Gly Leu Glu Trp Ile
        35                  40                  45

Gly Trp Ile Phe Pro Gly Ser Gly Val Ser Tyr Asn Glu Gln Phe
    50                  55                  60

Lys Gly Lys Ala Thr Leu Thr Val Asp Lys Pro Ser Asn Thr Ala Tyr
65                  70                  75                  80

Ile Phe Leu Ser Arg Leu Thr Ser Glu Asp Ser Ala Val Tyr Phe Cys
                85                  90                  95

Ala Arg Tyr Tyr Ser Ser Ser Pro Phe Ala Tyr Trp Gly Gln Gly Thr
                100                 105                 110

Leu Val Thr Val Ser Ala
        115

<210> SEQ ID NO 13
<211> LENGTH: 113
<212> TYPE: PRT
<213> ORGANISM: Artificial Sequence
<220> FEATURE:
<223> OTHER INFORMATION: SYNTHESIZED

<400> SEQUENCE: 13

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val Tyr Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Tyr Phe Thr Leu Lys Ile
65                  70                  75                  80

Ser Arg Val Glu Ala Glu Asp Leu Gly Ile Tyr Tyr Cys Phe Gln Gly
                85                  90                  95

Ser His Val Pro Tyr Thr Phe Gly Gly Gly Thr Lys Leu Glu Ile Lys
                100                 105                 110

Arg

<210> SEQ ID NO 14
<211> LENGTH: 118
<212> TYPE: PRT
<213> ORGANISM: Artificial Sequence
<220> FEATURE:
<223> OTHER INFORMATION: SYNTHESIZED

<400> SEQUENCE: 14

Gln Val Gln Leu Gln Gln Ser Gly Pro Asp Leu Val Lys Pro Gly Ala
1               5                   10                  15

Ser Val Lys Ile Ser Cys Lys Ala Ser Gly Tyr Thr Phe Ile Asp Tyr
            20                  25                  30

Tyr Ile Asn Trp Ala Lys Gln Arg Pro Gly Gln Gly Leu Glu Trp Ile
        35                  40                  45

```
Gly Trp Ile Phe Pro Gly Ser Gly Ser Thr Tyr Tyr Asn Glu Lys Phe
        50                  55                  60

Lys Gly Lys Ala Thr Leu Thr Val Asp Lys Ser Ser Ser Thr Ala Tyr
65                  70                  75                  80

Met Phe Leu Ser Ser Leu Thr Ser Glu Asp Ser Ala Val Phe Phe Cys
                85                  90                  95

Ala Arg Tyr Tyr Gly Ser Ser Pro Phe Ala Tyr Trp Gly Gln Gly Thr
                100                 105                 110

Leu Val Thr Val Ser Ala
        115

<210> SEQ ID NO 15
<211> LENGTH: 113
<212> TYPE: PRT
<213> ORGANISM: Artificial Sequence
<220> FEATURE:
<223> OTHER INFORMATION: SYNTHESIZED

<400> SEQUENCE: 15

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Ile His Ser
            20                  25                  30

Asn Gly Asn Thr Tyr Leu Glu Trp Phe Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
                100                 105                 110

Arg

<210> SEQ ID NO 16
<211> LENGTH: 118
<212> TYPE: PRT
<213> ORGANISM: Artificial Sequence
<220> FEATURE:
<223> OTHER INFORMATION: SYNTHESIZED

<400> SEQUENCE: 16

Gln Ile Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Asn Trp Val Arg Gln Arg Pro Gly Gln Gly Leu Glu Trp Ile
        35                  40                  45

Gly Trp Ile Tyr Pro Glu Ser Phe Asn Thr Tyr Asn Glu Lys Phe
        50                  55                  60

Lys Gly Lys Ala Thr Leu Thr Val Asp Thr Ser Ser Asn Thr Ala Tyr
65                  70                  75                  80

Met Gln Leu Ser Ser Leu Thr Ser Glu Asp Ser Ala Val Tyr Phe Cys
                85                  90                  95
```

```
Ala Arg Tyr Tyr Val Ser Ser Pro Phe Ala Tyr Trp Gly Gln Gly Thr
            100                 105                 110

Leu Val Thr Val Ser Ala
        115

<210> SEQ ID NO 17
<211> LENGTH: 114
<212> TYPE: PRT
<213> ORGANISM: Artificial Sequence
<220> FEATURE:
<223> OTHER INFORMATION: SYNTHESIZED

<400> SEQUENCE: 17

Asp Ile Val Met Ser Gln Ser Pro Ser Ser Leu Ala Val Ser Ala Gly
1               5                   10                  15

Glu Lys Val Thr Met Thr Cys Lys Ser Ser Gln Ser Leu Leu Asn Ser
            20                  25                  30

Arg Thr Arg Lys Asn Phe Leu Thr Trp Tyr Arg Gln Lys Pro Gly Gln
        35                  40                  45

Ser Pro Lys Pro Leu Ile Tyr Trp Ala Ser Ser Arg Glu Ser Gly Val
    50                  55                  60

Pro Asp Arg Phe Ala Gly Ser Gly Ser Gly Thr Asp Phe Thr Leu Thr
65                  70                  75                  80

Ile Ser Ser Val Gln Ala Glu Asp Leu Ala Val Tyr Tyr Cys Lys Gln
                85                  90                  95

Ser Tyr Asn Leu Pro Trp Thr Phe Gly Gly Gly Thr Lys Leu Glu Ile
            100                 105                 110

Lys Arg

<210> SEQ ID NO 18
<211> LENGTH: 114
<212> TYPE: PRT
<213> ORGANISM: Artificial Sequence
<220> FEATURE:
<223> OTHER INFORMATION: SYNTHESIZED

<400> SEQUENCE: 18

Glu Val Asn Leu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Asn Lys Ala Asp Asn His Ala Thr Tyr Tyr Ala Glu
    50                  55                  60

Ser Val Lys Gly Arg Phe Thr Ile Ser Arg Asp Ser Lys Ser Ser
65                  70                  75                  80

Val Tyr Leu Gln Met Asn Ser Leu Arg Thr Glu Asp Thr Gly Ile Tyr
                85                  90                  95

Tyr Cys Val Leu Trp Asp Tyr Trp Gly Gln Gly Thr Thr Leu Thr Val
            100                 105                 110

Ser Ser

<210> SEQ ID NO 19
<211> LENGTH: 113
<212> TYPE: PRT
<213> ORGANISM: Artificial Sequence
<220> FEATURE:
<223> OTHER INFORMATION: SYNTHESIZED
```

```
<400> SEQUENCE: 19

Asp Val Leu Met Thr Gln Ser Pro Leu Ser Leu Pro Val Ser Leu Gly
1               5                   10                  15

Asp Gln Ala Ser Ile Ser Cys Arg Ser Ser Gln Ser Ile Val His Arg
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Arg
            100                 105                 110

Arg

<210> SEQ ID NO 20
<211> LENGTH: 118
<212> TYPE: PRT
<213> ORGANISM: Artificial Sequence
<220> FEATURE:
<223> OTHER INFORMATION: SYNTHESIZED

<400> SEQUENCE: 20

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Ser Asp Tyr
            20                  25                  30

Tyr Ile Asn Trp Val Lys Gln Arg Pro Gly Gln Gly Leu Glu Trp Ile
        35                  40                  45

Gly Trp Ile Phe Pro Gly Ser Gly Ser Ser Tyr Tyr Asn Glu Lys Phe
    50                  55                  60

Lys Gly Lys Ala Thr Leu Thr Val Asp Lys Ser Ser Arg Thr Ala Tyr
65              70                  75                  80

Met Leu Leu Ser Ser Leu Thr Ser Glu Asp Ser Ala Val Tyr Phe Cys
                85                  90                  95

Ala Arg Tyr Tyr Gly Ser Ser Pro Phe Ala Tyr Trp Gly Gln Gly Thr
            100                 105                 110

Leu Val Thr Val Ser Thr
            115

<210> SEQ ID NO 21
<211> LENGTH: 108
<212> TYPE: PRT
<213> ORGANISM: Artificial Sequence
<220> FEATURE:
<223> OTHER INFORMATION: SYNTHESIZED

<400> SEQUENCE: 21

Glu Ile Val Leu Thr Gln Ser Pro Ala Leu Met Ala Ala Ser Pro Gly
1               5                   10                  15

Glu Lys Val Thr Ile Thr Cys Ser Val Ser Ser Ser Ile Ser Ser Ser
            20                  25                  30

Asn Leu His Trp Phe Gln Gln Lys Ser Glu Thr Ser Pro Lys Pro Trp
        35                  40                  45
```

```
Ile Phe Gly Thr Ser Tyr Leu Ala Ser Gly Val Pro Val Arg Phe Ser
 50                  55                  60

Gly Ser Gly Ser Gly Thr Ser Tyr Ser Leu Thr Ile Ser Ser Met Glu
 65                  70                  75                  80

Ala Glu Asp Ala Ala Thr Tyr Tyr Cys Gln Gln Trp Asn Ser Tyr Pro
                 85                  90                  95

Leu Thr Phe Gly Ala Gly Thr Lys Leu Glu Leu Arg
            100                 105
```

<210> SEQ ID NO 22
<211> LENGTH: 123
<212> TYPE: PRT
<213> ORGANISM: Artificial Sequence
<220> FEATURE:
<223> OTHER INFORMATION: SYNTHESIZED

<400> SEQUENCE: 22

```
Gln Val Gln Leu Gln Gln Pro Gly Thr Ala Leu Val Lys Pro Gly Ala
1               5                  10                  15

Ser Val Lys Leu Ser Cys Lys Ser Gly Tyr Thr Phe Thr Asp Tyr
             20                  25                  30

Trp Val His Trp Val Lys Gln Arg Pro Gly Gln Gly Leu Glu Trp Ile
             35                  40                  45

Gly Asn Ile Asn Pro Arg Asn Gly Gly Ile Asn Tyr Asn Glu Asn Phe
 50                  55                  60

Lys Gly Lys Ala Ile Leu Thr Val Asp Arg Ser Phe Ser Ile Ala Tyr
 65                  70                  75                  80

Met Gln Leu Asn Ser Leu Thr Ser Glu Asp Ser Ala Val Tyr Tyr Cys
                 85                  90                  95

Ala Arg Pro Gly Ala Thr Val Val His Arg Thr Pro Trp Phe Ala His
            100                 105                 110

Trp Gly Gln Gly Thr Leu Val Thr Val Ser Ala
            115                 120
```

<210> SEQ ID NO 23
<211> LENGTH: 16
<212> TYPE: PRT
<213> ORGANISM: Artificial Sequence
<220> FEATURE:
<223> OTHER INFORMATION: SYNTHESIZED

<400> SEQUENCE: 23

```
Arg Ser Ser Gln Thr Ile Val His Ser Asp Gly Asn Thr Tyr Leu Glu
1               5                  10                  15
```

<210> SEQ ID NO 24
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 24

```
Lys Val Ser Asn Arg Phe Ser
1               5
```

<210> SEQ ID NO 25
<211> LENGTH: 9
<212> TYPE: PRT
<213> ORGANISM: Artificial Sequence
<220> FEATURE:
<223> OTHER INFORMATION: SYNTHESIZED

```
<400> SEQUENCE: 25

Phe Gln Gly Ser His Val Pro Tyr Thr
1               5

<210> SEQ ID NO 26
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 26

Gly Tyr Thr Phe Thr Asp Tyr Glu Met His
1               5                   10

<210> SEQ ID NO 27
<211> LENGTH: 17
<212> TYPE: PRT
<213> ORGANISM: Artificial Sequence
<220> FEATURE:
<223> OTHER INFORMATION: SYNTHESIZED

<400> SEQUENCE: 27

Val Ile Asp Pro Glu Lys Gly Gly Thr Ala Tyr Asn Gln Lys Phe Lys
1               5                   10                  15

Gly

<210> SEQ ID NO 28
<211> LENGTH: 4
<212> TYPE: PRT
<213> ORGANISM: Artificial Sequence
<220> FEATURE:
<223> OTHER INFORMATION: SYNTHESIZED

<400> SEQUENCE: 28

Leu Lys Asp Ser
1

<210> SEQ ID NO 29
<211> LENGTH: 17
<212> TYPE: PRT
<213> ORGANISM: Artificial Sequence
<220> FEATURE:
<223> OTHER INFORMATION: SYNTHESIZED

<400> SEQUENCE: 29

Lys Ser Ser Gln Ser Leu Leu Asn Ser Arg Thr Arg Lys His Phe Leu
1               5                   10                  15

Ala

<210> SEQ ID NO 30
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 30

Trp Ala Ser Ser Arg Glu Ser
1               5

<210> SEQ ID NO 31
<211> LENGTH: 9
<212> TYPE: PRT
<213> ORGANISM: Artificial Sequence
```

```
<220> FEATURE:
<223> OTHER INFORMATION: SYNTHESIZED

<400> SEQUENCE: 31

Lys Gln Ser Cys Asn Leu Pro Trp Thr
1               5

<210> SEQ ID NO 32
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 32

Gly Phe Ser Phe Ser Asp Ala Trp Met Asp
1               5                   10

<210> SEQ ID NO 33
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 33

Glu Ile Arg Asn Lys Ala Asp Asn His Ala Thr Phe Tyr Ala Glu Ser
1               5                   10                  15

Val Lys Gly

<210> SEQ ID NO 34
<211> LENGTH: 5
<212> TYPE: PRT
<213> ORGANISM: Artificial Sequence
<220> FEATURE:
<223> OTHER INFORMATION: SYNTHESIZED

<400> SEQUENCE: 34

Leu Leu Trp Asp Tyr
1               5

<210> SEQ ID NO 35
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 35

Ser Ala Ser Ser Ser Val Thr Tyr Met Tyr
1               5                   10

<210> SEQ ID NO 36
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 36

Arg Thr Ser Asn Leu Ala Ser
1               5

<210> SEQ ID NO 37
<211> LENGTH: 9
<212> TYPE: PRT
```

```
<213> ORGANISM: Artificial Sequence
<220> FEATURE:
<223> OTHER INFORMATION: SYNTHESIZED

<400> SEQUENCE: 37

Gln Gln Phe Gln Ser Tyr Pro Leu Thr
1               5

<210> SEQ ID NO 38
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 38

Gly Tyr Thr Phe Thr Ser Tyr Trp Met His
1               5                   10

<210> SEQ ID NO 39
<211> LENGTH: 17
<212> TYPE: PRT
<213> ORGANISM: Artificial Sequence
<220> FEATURE:
<223> OTHER INFORMATION: SYNTHESIZED

<400> SEQUENCE: 39

Glu Ile Asp Pro Ser Asp Gly Phe Thr Tyr Asn Asn Gln Asn Phe Lys
1               5                   10                  15
Asp

<210> SEQ ID NO 40
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 40

Ala Gly Ser Leu Gly Arg Ile Gly Leu Ala Tyr
1               5                   10

<210> SEQ ID NO 41
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 41

Ser Ala Ser Ser Ser Val Ser Asn Met Tyr
1               5                   10

<210> SEQ ID NO 42
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 42

Arg Thr Ser Asn Leu Ala Ser
1               5
```

```
<210> SEQ ID NO 43
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 43

Gln His Tyr Gln Asn Tyr Pro Leu Thr
1               5

<210> SEQ ID NO 44
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 44

Gly Tyr Ile Phe Thr Asn Tyr Trp Leu His
1               5                   10

<210> SEQ ID NO 45
<211> LENGTH: 17
<212> TYPE: PRT
<213> ORGANISM: Artificial Sequence
<220> FEATURE:
<223> OTHER INFORMATION: SYNTHESIZED

<400> SEQUENCE: 45

Glu Ile Asp Pro Ser Asp Ser Tyr Ser Ile Cys Asn Asp Asn Phe Lys
1               5                   10                  15

Gly

<210> SEQ ID NO 46
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 46

Ala Gly Ser Leu Gly Arg Val Gly Leu Ala Tyr
1               5                   10

<210> SEQ ID NO 47
<211> LENGTH: 16
<212> TYPE: PRT
<213> ORGANISM: Artificial Sequence
<220> FEATURE:
<223> OTHER INFORMATION: SYNTHESIZED

<400> SEQUENCE: 47

Arg Ser Ser Gln Ser Ile Val His Ser Asn Gly Asn Thr Tyr Leu Glu
1               5                   10                  15

<210> SEQ ID NO 48
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 48

Gly Tyr Thr Phe Thr Asp Tyr Tyr Ile Asn
1               5                   10
```

```
<210> SEQ ID NO 49
<211> LENGTH: 17
<212> TYPE: PRT
<213> ORGANISM: Artificial Sequence
<220> FEATURE:
<223> OTHER INFORMATION: SYNTHESIZED

<400> SEQUENCE: 49

Trp Ile Phe Pro Gly Ser Gly Ile Thr Tyr Tyr Asn Glu Lys Phe Lys
1               5                   10                  15
Gly

<210> SEQ ID NO 50
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 50

Ala Arg Tyr Ala Tyr Gly Ser Pro Phe Ala Tyr
1               5                   10

<210> SEQ ID NO 51
<211> LENGTH: 16
<212> TYPE: PRT
<213> ORGANISM: Artificial Sequence
<220> FEATURE:
<223> OTHER INFORMATION: SYNTHESIZED

<400> SEQUENCE: 51

Arg Ser Ser Gln Asn Ile Ile His Ser Asn Gly Asn Thr Tyr Leu Glu
1               5                   10                  15

<210> SEQ ID NO 52
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 52

Gly Tyr Ile Phe Thr Asp Tyr Tyr Ile Asn
1               5                   10

<210> SEQ ID NO 53
<211> LENGTH: 17
<212> TYPE: PRT
<213> ORGANISM: Artificial Sequence
<220> FEATURE:
<223> OTHER INFORMATION: SYNTHESIZED

<400> SEQUENCE: 53

Trp Ile Phe Pro Gly Ser Gly Val Ser Tyr Tyr Asn Glu Gln Phe Lys
1               5                   10                  15
Gly

<210> SEQ ID NO 54
<211> LENGTH: 11
<212> TYPE: PRT
<213> ORGANISM: Artificial Sequence
<220> FEATURE:
<223> OTHER INFORMATION: SYNTHESIZED
```

```
<400> SEQUENCE: 54

Ala Arg Tyr Tyr Ser Ser Ser Pro Phe Ala Tyr
1               5                   10

<210> SEQ ID NO 55
<211> LENGTH: 16
<212> TYPE: PRT
<213> ORGANISM: Artificial Sequence
<220> FEATURE:
<223> OTHER INFORMATION: SYNTHESIZED

<400> SEQUENCE: 55

Arg Ser Ser Gln Asn Ile Val Tyr Ser Asn Gly Asn Thr Tyr Leu Glu
1               5                   10                  15

<210> SEQ ID NO 56
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 56

Gly Tyr Thr Phe Ile Asp Tyr Tyr Ile Asn
1               5                   10

<210> SEQ ID NO 57
<211> LENGTH: 17
<212> TYPE: PRT
<213> ORGANISM: Artificial Sequence
<220> FEATURE:
<223> OTHER INFORMATION: SYNTHESIZED

<400> SEQUENCE: 57

Trp Ile Phe Pro Gly Ser Gly Ser Thr Tyr Tyr Asn Glu Lys Phe Lys
1               5                   10                  15

Gly

<210> SEQ ID NO 58
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 58

Ala Arg Tyr Tyr Gly Ser Ser Pro Phe Ala Tyr
1               5                   10

<210> SEQ ID NO 59
<211> LENGTH: 16
<212> TYPE: PRT
<213> ORGANISM: Artificial Sequence
<220> FEATURE:
<223> OTHER INFORMATION: SYNTHESIZED

<400> SEQUENCE: 59

Arg Ser Ser Gln Asn Ile Ile His Ser Asn Gly Asn Thr Tyr Leu Glu
1               5                   10                  15

<210> SEQ ID NO 60
<211> LENGTH: 10
<212> TYPE: PRT
<213> ORGANISM: Artificial Sequence
<220> FEATURE:
<223> OTHER INFORMATION: SYNTHESIZED
```

```
<400> SEQUENCE: 60

Gly Tyr Thr Phe Thr Asp Tyr Tyr Ile Asn
1               5                   10

<210> SEQ ID NO 61
<211> LENGTH: 17
<212> TYPE: PRT
<213> ORGANISM: Artificial Sequence
<220> FEATURE:
<223> OTHER INFORMATION: SYNTHESIZED

<400> SEQUENCE: 61

Trp Ile Tyr Pro Glu Ser Phe Asn Thr Tyr Tyr Asn Glu Lys Phe Lys
1               5                   10                  15

Gly

<210> SEQ ID NO 62
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 62

Ala Arg Tyr Tyr Val Ser Ser Pro Phe Ala Tyr
1               5                   10

<210> SEQ ID NO 63
<211> LENGTH: 17
<212> TYPE: PRT
<213> ORGANISM: Artificial Sequence
<220> FEATURE:
<223> OTHER INFORMATION: SYNTHESIZED

<400> SEQUENCE: 63

Lys Ser Ser Gln Ser Leu Leu Asn Ser Arg Thr Arg Lys Asn Phe Leu
1               5                   10                  15

Thr

<210> SEQ ID NO 64
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 64

Lys Gln Ser Tyr Asn Leu Pro Trp Thr
1               5

<210> SEQ ID NO 65
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 65

Gly Phe Thr Phe Ser Asp Ala Trp Met Asp
1               5                   10

<210> SEQ ID NO 66
<211> LENGTH: 19
<212> TYPE: PRT
<213> ORGANISM: Artificial Sequence
```

```
<220> FEATURE:
<223> OTHER INFORMATION: SYNTHESIZED

<400> SEQUENCE: 66

Glu Ile Arg Asn Lys Ala Asp Asn His Ala Thr Tyr Tyr Ala Glu Ser
1               5                   10                  15

Val Lys Gly

<210> SEQ ID NO 67
<211> LENGTH: 5
<212> TYPE: PRT
<213> ORGANISM: Artificial Sequence
<220> FEATURE:
<223> OTHER INFORMATION: SYNTHESIZED

<400> SEQUENCE: 67

Val Leu Trp Asp Tyr
1               5

<210> SEQ ID NO 68
<211> LENGTH: 16
<212> TYPE: PRT
<213> ORGANISM: Artificial Sequence
<220> FEATURE:
<223> OTHER INFORMATION: SYNTHESIZED

<400> SEQUENCE: 68

Arg Ser Ser Gln Ser Ile Val His Arg Asn Gly Asn Thr Tyr Leu Glu
1               5                   10                  15

<210> SEQ ID NO 69
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 69

Gly Tyr Thr Phe Ser Asp Tyr Tyr Ile Asn
1               5                   10

<210> SEQ ID NO 70
<211> LENGTH: 17
<212> TYPE: PRT
<213> ORGANISM: Artificial Sequence
<220> FEATURE:
<223> OTHER INFORMATION: SYNTHESIZED

<400> SEQUENCE: 70

Trp Ile Phe Pro Gly Ser Gly Ser Ser Tyr Tyr Asn Glu Lys Phe Lys
1               5                   10                  15

Gly

<210> SEQ ID NO 71
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 71

Ala Arg Tyr Tyr Gly Ser Ser Pro Phe Ala Tyr
1               5                   10
```

```
<210> SEQ ID NO 72
<211> LENGTH: 12
<212> TYPE: PRT
<213> ORGANISM: Artificial Sequence
<220> FEATURE:
<223> OTHER INFORMATION: SYNTHESIZED

<400> SEQUENCE: 72

Ser Val Ser Ser Ser Ile Ser Ser Ser Asn Leu His
1               5                   10

<210> SEQ ID NO 73
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 73

Gly Thr Ser Tyr Leu Ala Ser
1               5

<210> SEQ ID NO 74
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 74

Gln Gln Trp Asn Ser Tyr Pro Leu Thr
1               5

<210> SEQ ID NO 75
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 75

Gly Tyr Thr Phe Thr Asp Tyr Trp Val His
1               5                   10

<210> SEQ ID NO 76
<211> LENGTH: 17
<212> TYPE: PRT
<213> ORGANISM: Artificial Sequence
<220> FEATURE:
<223> OTHER INFORMATION: SYNTHESIZED

<400> SEQUENCE: 76

Asn Ile Asn Pro Arg Asn Gly Gly Ile Asn Tyr Asn Glu Asn Phe Lys
1               5                   10                  15

Gly

<210> SEQ ID NO 77
<211> LENGTH: 12
<212> TYPE: PRT
<213> ORGANISM: Artificial Sequence
<220> FEATURE:
<223> OTHER INFORMATION: SYNTHESIZED

<400> SEQUENCE: 77

Ala Arg Pro Gly Ala Thr Val Val His Arg Thr Pro
1               5                   10
```

```
<210> SEQ ID NO 78
<211> LENGTH: 16
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (5)..(5)
<223> OTHER INFORMATION: Xaa = Ser, Thr, Asn, or Gln
<220> FEATURE:
<221> NAME/KEY: MISC_FEATURE
<222> LOCATION: (7)..(7)
<223> OTHER INFORMATION: Xaa = Ala, Ile, Leu, Met, Phe, Trp, Tyr, or Val
<220> FEATURE:
<221> NAME/KEY: MISC_FEATURE
<222> LOCATION: (8)..(8)
<223> OTHER INFORMATION: Xaa = Ala, Ile, Leu, Met, Phe, Trp, Tyr, Val,
      Arg, His, or Lys
<220> FEATURE:
<221> NAME/KEY: MISC_FEATURE
<222> LOCATION: (9)..(9)
<223> OTHER INFORMATION: Xaa = Ser, Thr, Asn, Gln, Arg ,His, or Lys

<400> SEQUENCE: 78

Arg Ser Ser Gln Xaa Ile Xaa Xaa Xaa Asn Gly Asn Thr Tyr Leu Glu
1               5                   10                  15

<210> SEQ ID NO 79
<211> LENGTH: 16
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (5)..(5)
<223> OTHER INFORMATION: Xaa = Ser or Asn
<220> FEATURE:
<221> NAME/KEY: MISC_FEATURE
<222> LOCATION: (7)..(7)
<223> OTHER INFORMATION: Xaa = Ile or Val
<220> FEATURE:
<221> NAME/KEY: MISC_FEATURE
<222> LOCATION: (8)..(8)
<223> OTHER INFORMATION: Xaa = Tyr or His
<220> FEATURE:
<221> NAME/KEY: MISC_FEATURE
<222> LOCATION: (9)..(9)
<223> OTHER INFORMATION: Xaa = Ser or Arg

<400> SEQUENCE: 79

Arg Ser Ser Gln Xaa Ile Xaa Xaa Xaa Asn Gly Asn Thr Tyr Leu Glu
1               5                   10                  15

<210> SEQ ID NO 80
<211> LENGTH: 10
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (3)..(3)
<223> OTHER INFORMATION: Xaa = Ala, Ile, Leu, Met, Phe, Trp, Tyr, Val,
      Ser, Thr, Asn or Gln
<220> FEATURE:
<221> NAME/KEY: MISC_FEATURE
<222> LOCATION: (5)..(5)
<223> OTHER INFORMATION: Xaa = Ala, Ile, Leu, Met, Phe, Trp, Tyr, Val,
      Ser, Thr, Asn or Gln
```

```
<400> SEQUENCE: 80

Gly Tyr Xaa Phe Xaa Asp Tyr Tyr Ile Asn
1               5                   10

<210> SEQ ID NO 81
<211> LENGTH: 10
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (3)..(3)
<223> OTHER INFORMATION: Xaa = Ile or Thr
<220> FEATURE:
<221> NAME/KEY: MISC_FEATURE
<222> LOCATION: (5)..(5)
<223> OTHER INFORMATION: Xaa = Ile, Ser or Thr

<400> SEQUENCE: 81

Gly Tyr Xaa Phe Xaa Asp Tyr Tyr Ile Asn
1               5                   10

<210> SEQ ID NO 82
<211> LENGTH: 17
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (3)..(3)
<223> OTHER INFORMATION: Xaa = Ala, Ile, Leu, Met, Phe, Trp, Tyr or Val
<220> FEATURE:
<221> NAME/KEY: MISC_FEATURE
<222> LOCATION: (5)..(5)
<223> OTHER INFORMATION: Xaa = Asp, Glu, or Gly
<220> FEATURE:
<221> NAME/KEY: MISC_FEATURE
<222> LOCATION: (7)..(7)
<223> OTHER INFORMATION: Xaa = Gly, Ala, Ile, Leu, Met, Phe, Trp, Tyr,
      or Val
<220> FEATURE:
<221> NAME/KEY: MISC_FEATURE
<222> LOCATION: (8)..(8)
<223> OTHER INFORMATION: Xaa = Ala, Ile, Leu, Met, Phe, Trp, Tyr, Val,
      Ser, Thr, Asn, or Gln
<220> FEATURE:
<221> NAME/KEY: MISC_FEATURE
<222> LOCATION: (9)..(9)
<223> OTHER INFORMATION: Xaa = Ser,Thr, Asn, or Gln
<220> FEATURE:
<221> NAME/KEY: MISC_FEATURE
<222> LOCATION: (14)..(14)
<223> OTHER INFORMATION: Xaa = Arg, His, Lys, Ser, Thr, Asn, or Gln

<400> SEQUENCE: 82

Trp Ile Xaa Pro Xaa Ser Xaa Xaa Xaa Tyr Tyr Asn Glu Xaa Phe Lys
1               5                   10                  15

Gly

<210> SEQ ID NO 83
<211> LENGTH: 17
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (3)..(3)
<223> OTHER INFORMATION: Xaa = Tyr or Phe
```

```
<220> FEATURE:
<221> NAME/KEY: MISC_FEATURE
<222> LOCATION: (5)..(5)
<223> OTHER INFORMATION: Xaa = Glu or Gly
<220> FEATURE:
<221> NAME/KEY: MISC_FEATURE
<222> LOCATION: (7)..(7)
<223> OTHER INFORMATION: Xaa = Phe or Gly
<220> FEATURE:
<221> NAME/KEY: MISC_FEATURE
<222> LOCATION: (8)..(8)
<223> OTHER INFORMATION: Xaa = Ile, Val, Asn, or Ser
<220> FEATURE:
<221> NAME/KEY: MISC_FEATURE
<222> LOCATION: (9)..(9)
<223> OTHER INFORMATION: Xaa = Ser or Thr
<220> FEATURE:
<221> NAME/KEY: MISC_FEATURE
<222> LOCATION: (14)..(14)
<223> OTHER INFORMATION: Xaa = Gln or Lys

<400> SEQUENCE: 83

Trp Ile Xaa Pro Xaa Ser Xaa Xaa Xaa Tyr Tyr Asn Glu Xaa Phe Lys
 1               5                  10                  15

Gly

<210> SEQ ID NO 84
<211> LENGTH: 11
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (4)..(4)
<223> OTHER INFORMATION: Xaa = Ala, Ile, Leu, Met, Phe, Trp, Tyr, or Val
<220> FEATURE:
<221> NAME/KEY: MISC_FEATURE
<222> LOCATION: (5)..(5)
<223> OTHER INFORMATION: Xaa = Ala, Ile, Leu, Met, Phe, Trp, Tyr, Val,
      Ser, Thr, Asn, Gln, or Gly
<220> FEATURE:
<221> NAME/KEY: MISC_FEATURE
<222> LOCATION: (6)..(6)
<223> OTHER INFORMATION: Xaa = Ser, Thr, Asn, Gln, or Gly

<400> SEQUENCE: 84

Ala Arg Tyr Xaa Xaa Xaa Ser Pro Phe Ala Tyr
 1               5                  10

<210> SEQ ID NO 85
<211> LENGTH: 11
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (4)..(4)
<223> OTHER INFORMATION: Xaa = Ala or Tyr
<220> FEATURE:
<221> NAME/KEY: MISC_FEATURE
<222> LOCATION: (5)..(5)
<223> OTHER INFORMATION: Xaa = Gly, Val, Ser, or Tyr
<220> FEATURE:
<221> NAME/KEY: MISC_FEATURE
<222> LOCATION: (6)..(6)
<223> OTHER INFORMATION: Xaa = Gly or Ser

<400> SEQUENCE: 85

Ala Arg Tyr Xaa Xaa Xaa Ser Pro Phe Ala Tyr
 1               5                  10
```

```
<210> SEQ ID NO 86
<211> LENGTH: 17
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (14)..(14)
<223> OTHER INFORMATION: Xaa = Ser, Thr, Asn, Gln, Arg, His, or Lys
<220> FEATURE:
<221> NAME/KEY: MISC_FEATURE
<222> LOCATION: (17)..(17)
<223> OTHER INFORMATION: Xaa = Ser, Thr, Asn, Gln, Ala, Ile, Leu, Met,
      Phe, Trp, Tyr, Val, Asp, or Glu

<400> SEQUENCE: 86

Lys Ser Ser Gln Ser Leu Leu Asn Ser Arg Thr Arg Lys Xaa Phe Leu
1               5                   10                  15

Xaa

<210> SEQ ID NO 87
<211> LENGTH: 17
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (14)..(14)
<223> OTHER INFORMATION: Xaa = His or Asn
<220> FEATURE:
<221> NAME/KEY: MISC_FEATURE
<222> LOCATION: (17)..(17)
<223> OTHER INFORMATION: Xaa = Thr or Ala

<400> SEQUENCE: 87

Lys Ser Ser Gln Ser Leu Leu Asn Ser Arg Thr Arg Lys Xaa Phe Leu
1               5                   10                  15

Xaa

<210> SEQ ID NO 88
<211> LENGTH: 9
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (4)..(4)
<223> OTHER INFORMATION: Xaa = Cys, Ala, Ile, Leu, Met, Phe, Trp, Tyr,
      or Val

<400> SEQUENCE: 88

Lys Gln Ser Xaa Asn Leu Pro Trp Thr
1               5

<210> SEQ ID NO 89
<211> LENGTH: 9
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (4)..(4)
<223> OTHER INFORMATION: Xaa = Cys or Tyr
```

```
<400> SEQUENCE: 89

Lys Gln Ser Xaa Asn Leu Pro Trp Thr
1               5

<210> SEQ ID NO 90
<211> LENGTH: 10
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (3)..(3)
<223> OTHER INFORMATION: Xaa = Ser, Thr, Asn, or Gln

<400> SEQUENCE: 90

Gly Phe Xaa Phe Ser Asp Ala Trp Met Asp
1               5                   10

<210> SEQ ID NO 91
<211> LENGTH: 10
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (3)..(3)
<223> OTHER INFORMATION: Xaa = Ser or Thr

<400> SEQUENCE: 91

Gly Phe Xaa Phe Ser Asp Ala Trp Met Asp
1               5                   10

<210> SEQ ID NO 92
<211> LENGTH: 19
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (12)..(12)
<223> OTHER INFORMATION: Xaa = Ala, Ile, Leu, Met, Phe, Trp, Tyr, or Val

<400> SEQUENCE: 92

Glu Ile Arg Asn Lys Ala Asp Asn His Ala Thr Xaa Tyr Ala Glu Ser
1               5                   10                  15

Val Lys Gly

<210> SEQ ID NO 93
<211> LENGTH: 19
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (12)..(12)
<223> OTHER INFORMATION: Xaa = Phe or Tyr

<400> SEQUENCE: 93

Glu Ile Arg Asn Lys Ala Asp Asn His Ala Thr Xaa Tyr Ala Glu Ser
1               5                   10                  15

Val Lys Gly
```

```
<210> SEQ ID NO 94
<211> LENGTH: 5
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (1)..(1)
<223> OTHER INFORMATION: Xaa = Ala, Ile, Leu, Met, Phe, Trp, Tyr, or Val

<400> SEQUENCE: 94

Xaa Leu Trp Asp Tyr
1               5

<210> SEQ ID NO 95
<211> LENGTH: 5
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (1)..(1)
<223> OTHER INFORMATION: Xaa = Leu or Val

<400> SEQUENCE: 95

Xaa Leu Trp Asp Tyr
1               5

<210> SEQ ID NO 96
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 96

Phe Gln Gly Ser His Val Pro Cys Thr
1               5

<210> SEQ ID NO 97
<211> LENGTH: 113
<212> TYPE: PRT
<213> ORGANISM: Artificial Sequence
<220> FEATURE:
<223> OTHER INFORMATION: SYNTHESIZED

<400> SEQUENCE: 97

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ile
            20                  25                  30

Asn Gly Asn Thr Tyr Leu His Trp Ser Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Asn
                85                  90                  95

Thr His Leu Pro Leu Thr Phe Gly Ala Gly Thr Lys Leu Glu Leu Lys
            100                 105                 110

Arg
```

```
<210> SEQ ID NO 98
<211> LENGTH: 118
<212> TYPE: PRT
<213> ORGANISM: Artificial Sequence
<220> FEATURE:
<223> OTHER INFORMATION: SYNTHESIZED

<400> SEQUENCE: 98

Glu Val Gln Leu Met Glu Ser Gly Gly Asp Leu Val Lys Pro Gly Gly
1               5                   10                  15

Ser Leu Glu Leu Ser Cys Thr Val Ser Gly Phe Thr Phe Asn Asn Tyr
            20                  25                  30

Ala Met Ser Trp Ile Arg Gln Thr Pro Glu Lys Arg Leu Glu Trp Val
        35                  40                  45

Ala Thr Ile Ser Asp Gly Gly Thr Asn Thr Tyr Phe Pro Asp Asn Val
    50                  55                  60

Lys Gly Arg Phe Thr Ile Ser Arg Asp Asn Ala Lys Ser Asn Leu Tyr
65                  70                  75                  80

Leu Gln Met Ser His Leu Gln Ser Glu Asp Thr Ala Met Tyr Tyr Cys
                85                  90                  95

Ala Arg Glu Gly Arg Gly Thr Trp Phe Ala Tyr Trp Gly Gln Gly Thr
            100                 105                 110

Leu Val Thr Val Ser Ala
        115

<210> SEQ ID NO 99
<211> LENGTH: 16
<212> TYPE: PRT
<213> ORGANISM: Artificial Sequence
<220> FEATURE:
<223> OTHER INFORMATION: SYNTHESIZED

<400> SEQUENCE: 99

Arg Ser Ser Gln Ser Leu Val His Ile Asn Gly Asn Thr Tyr Leu His
1               5                   10                  15

<210> SEQ ID NO 100
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 100

Lys Val Ser Asn Arg Phe Ser
1               5

<210> SEQ ID NO 101
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 101

Ser Gln Asn Thr His Leu Pro Leu Thr
1               5

<210> SEQ ID NO 102
<211> LENGTH: 10
<212> TYPE: PRT
<213> ORGANISM: Artificial Sequence
<220> FEATURE:
<223> OTHER INFORMATION: SYNTHESIZED
```

```
<400> SEQUENCE: 102

Gly Phe Thr Phe Asn Asn Tyr Ala Met Ser
1               5                   10

<210> SEQ ID NO 103
<211> LENGTH: 17
<212> TYPE: PRT
<213> ORGANISM: Artificial Sequence
<220> FEATURE:
<223> OTHER INFORMATION: SYNTHESIZED

<400> SEQUENCE: 103

Thr Ile Ser Asp Gly Gly Thr Asn Thr Tyr Phe Pro Asp Asn Val Lys
1               5                   10                  15
Gly

<210> SEQ ID NO 104
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 104

Ala Arg Glu Gly Arg Gly Thr Trp Phe Ala Tyr
1               5                   10

<210> SEQ ID NO 105
<211> LENGTH: 11
<212> TYPE: PRT
<213> ORGANISM: Artificial Sequence
<220> FEATURE:
<223> OTHER INFORMATION: SYNTHESIZED

<400> SEQUENCE: 105

His Ala Ser Gln Asn Ile Asn Ile Trp Leu Ser
1               5                   10

<210> SEQ ID NO 106
<211> LENGTH: 7
<212> TYPE: PRT
<213> ORGANISM: Artificial Sequence
<220> FEATURE:
<223> OTHER INFORMATION: SYNTHESIZED

<400> SEQUENCE: 106

Lys Ala Ser Asn Leu His Thr
1               5

<210> SEQ ID NO 107
<211> LENGTH: 9
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (4)..(4)
<223> OTHER INFORMATION: Xaa = Ser, Thr, Asn, Gln, Arg, His, or Lys

<400> SEQUENCE: 107

Gln Gln Gly Xaa Ser Tyr Pro Leu Thr
1               5
```

```
<210> SEQ ID NO 108
<211> LENGTH: 9
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (4)..(4)
<223> OTHER INFORMATION: Xaa = Gln or His

<400> SEQUENCE: 108

Gln Gln Gly Xaa Ser Tyr Pro Leu Thr
1               5

<210> SEQ ID NO 109
<211> LENGTH: 10
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (6)..(6)
<223> OTHER INFORMATION: Xaa = Ser, Thr, Asn, Gln, Ala, Val, Ile, Leu,
      Met, Phe, Tyr, or Trp

<400> SEQUENCE: 109

Gly Phe Ser Phe Asn Xaa Tyr Ala Met Asn
1               5                   10

<210> SEQ ID NO 110
<211> LENGTH: 10
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (6)..(6)
<223> OTHER INFORMATION: Xaa = Ile or Thr

<400> SEQUENCE: 110

Gly Phe Ser Phe Asn Xaa Tyr Ala Met Asn
1               5                   10

<210> SEQ ID NO 111
<211> LENGTH: 19
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (4)..(4)
<223> OTHER INFORMATION: Xaa = Ser, Thr, Asn, or Gln
<220> FEATURE:
<221> NAME/KEY: MISC_FEATURE
<222> LOCATION: (6)..(6)
<223> OTHER INFORMATION: Xaa = Ser, Thr, Asn, or Gln
<220> FEATURE:
<221> NAME/KEY: MISC_FEATURE
<222> LOCATION: (8)..(8)
<223> OTHER INFORMATION: Xaa = Ser, Thr, Asn, Gln, Asp, or Glu

<400> SEQUENCE: 111

Arg Ile Arg Xaa Lys Xaa Asn Xaa Tyr Ala Thr Phe Tyr Ala Asp Ser
1               5                   10                  15

Val Lys Asp
```

```
<210> SEQ ID NO 112
<211> LENGTH: 19
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (4)..(4)
<223> OTHER INFORMATION: Xaa = Asn or Ser
<220> FEATURE:
<221> NAME/KEY: MISC_FEATURE
<222> LOCATION: (6)..(6)
<223> OTHER INFORMATION: Xaa = Ser or Thr
<220> FEATURE:
<221> NAME/KEY: MISC_FEATURE
<222> LOCATION: (8)..(8)
<223> OTHER INFORMATION: Xaa = Asn or Asp

<400> SEQUENCE: 112

Arg Ile Arg Xaa Lys Xaa Asn Xaa Tyr Ala Thr Phe Tyr Ala Asp Ser
1               5                   10                  15

Val Lys Asp

<210> SEQ ID NO 113
<211> LENGTH: 10
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (1)..(1)
<223> OTHER INFORMATION: Xaa = Ala, Val, Ile, Leu, Met, Phe, Tyr, or Trp
<220> FEATURE:
<221> NAME/KEY: MISC_FEATURE
<222> LOCATION: (7)..(7)
<223> OTHER INFORMATION: Xaa = Ser, Thr, Asn, Gln, Ala, Val, Ile, Leu,
      Met, Phe, Tyr, or Trp
<220> FEATURE:
<221> NAME/KEY: MISC_FEATURE
<222> LOCATION: (8)..(8)
<223> OTHER INFORMATION: Xaa = Ala, Val, Ile, Leu, Met, Phe, Tyr, or Trp

<400> SEQUENCE: 113

Xaa Ser Pro Tyr Asp Gly Xaa Xaa Ala Tyr
1               5                   10

<210> SEQ ID NO 114
<211> LENGTH: 10
<212> TYPE: PRT
<213> ORGANISM: Artificial Sequence
<220> FEATURE:
<223> OTHER INFORMATION: SYNTHESIZED
<220> FEATURE:
<221> NAME/KEY: MISC_FEATURE
<222> LOCATION: (1)..(1)
<223> OTHER INFORMATION: Xaa = Val or Ala
<220> FEATURE:
<221> NAME/KEY: MISC_FEATURE
<222> LOCATION: (7)..(7)
<223> OTHER INFORMATION: Xaa = Ala or Ser
<220> FEATURE:
<221> NAME/KEY: MISC_FEATURE
<222> LOCATION: (8)..(8)
<223> OTHER INFORMATION: Xaa = Leu or Phe

<400> SEQUENCE: 114

Xaa Ser Pro Tyr Asp Gly Xaa Xaa Ala Tyr
1               5                   10
```

<210> SEQ ID NO 115
<211> LENGTH: 108
<212> TYPE: PRT
<213> ORGANISM: Artificial Sequence
<220> FEATURE:
<223> OTHER INFORMATION: SYNTHESIZED

<400> SEQUENCE: 115

```
Asp Ile Gln Met Asn Gln Ser Pro Ser Ser Leu Phe Ala Ser Leu Gly
1               5                   10                  15

Asp Thr Ile Thr Ile Thr Cys His Ala Ser Gln Asn Ile Asn Val Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Thr Gly Val Ser Ser Arg Phe Ser Gly
    50                  55                  60

Ser Gly Ser Gly Thr Asp Phe Thr Leu Thr Ile Asn Asn Leu Gln Pro
65                  70                  75                  80

Glu Asp Ile Ala Thr Tyr Tyr Cys Gln Gln Gly Gln Ser Tyr Pro Leu
                85                  90                  95

Thr Phe Gly Ala Gly Thr Lys Leu Glu Leu Lys Arg
            100                 105
```

<210> SEQ ID NO 116
<211> LENGTH: 119
<212> TYPE: PRT
<213> ORGANISM: Artificial Sequence
<220> FEATURE:
<223> OTHER INFORMATION: SYNTHESIZED

<400> SEQUENCE: 116

```
Glu Val Gln Phe Val Glu Ser Gly Gly Gly Leu Val Gln Pro Lys Gly
1               5                   10                  15

Ser Leu Lys Leu Ser Cys Ala Ala Ser Gly Phe Ser Phe Asn Ile Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asp Tyr Ala Thr Phe Tyr Ala Asp
    50                  55                  60

Ser Val Lys Asp Arg Phe Thr Ile Ser Arg Asp Asp Ser Glu Ser Met
65                  70                  75                  80

Leu Tyr Leu Gln Met Asn Asn Leu Lys Ile Glu Asp Thr Ala Met Tyr
                85                  90                  95

Tyr Cys Val Ser Pro Tyr Asp Gly Ala Leu Ala Tyr Trp Gly Gln Gly
            100                 105                 110

Thr Ser Val Thr Val Ser Ser
        115
```

<210> SEQ ID NO 117
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 117

```
Gln Gln Gly Gln Ser Tyr Pro Leu Thr
1               5
```

<210> SEQ ID NO 118
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 118

Gly Phe Ser Phe Asn Ile Tyr Ala Met Asn
1               5                   10

<210> SEQ ID NO 119
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 119

Arg Ile Arg Ser Lys Ser Asn Asp Tyr Ala Thr Phe Tyr Ala Asp Ser
1               5                   10                  15

Val Lys Asp

<210> SEQ ID NO 120
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 120

Val Ser Pro Tyr Asp Gly Ala Leu Ala Tyr
1               5                   10

<210> SEQ ID NO 121
<211> LENGTH: 108
<212> TYPE: PRT
<213> ORGANISM: Artificial Sequence
<220> FEATURE:
<223> OTHER INFORMATION: SYNTHESIZED

<400> SEQUENCE: 121

Asp Ile Gln Met Asn Gln Ser Pro Ser Ser Leu Ser Ala Ser Leu Gly
1               5                   10                  15

Asp Thr Ile Thr Ile Thr Cys His Ala Ser Gln Asn Ile Asn Ile Trp
            20                  25                  30

Leu Ser Trp Tyr Gln Gln Lys Pro Gly Asn Ile Pro Lys Leu Leu Ile
        35                  40                  45

Tyr Lys Ala Ser Asn Leu His Thr Gly Val Pro Ser Arg Phe Ser Gly
    50                  55                  60

Ser Gly Ser Gly Thr Gly Phe Thr Leu Thr Ile Ser Ser Leu Gln Pro
65                  70                  75                  80

Glu Asp Ile Ala Thr Tyr Tyr Cys Gln Gln His Ser Tyr Pro Leu
                85                  90                  95

Thr Phe Gly Gly Gly Thr Lys Leu Glu Ile Lys Arg
            100                 105

<210> SEQ ID NO 122
<211> LENGTH: 119
<212> TYPE: PRT
<213> ORGANISM: Artificial Sequence
<220> FEATURE:
<223> OTHER INFORMATION: SYNTHESIZED

<400> SEQUENCE: 122

Glu Val Gln Phe Val Glu Ser Gly Gly Gly Leu Val Gln Pro Lys Gly
1               5                   10                  15

Ser Leu Lys Leu Ser Cys Glu Val Ser Gly Phe Ser Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Asn Lys Thr Asn Asn Tyr Ala Thr Phe Tyr Ala Asp
    50                  55                  60

Ser Val Lys Asp Arg Phe Thr Ile Ser Arg Asp Asp Ser Lys Asn Thr
65                  70                  75                  80

Leu Tyr Leu Gln Met Asn Asn Leu Lys Ala Glu Asp Thr Ala Met Tyr
                85                  90                  95

Phe Cys Ala Ser Pro Tyr Asp Gly Ser Phe Ala Tyr Trp Gly Gln Gly
            100                 105                 110

Thr Leu Val Thr Val Ser Ala
        115

<210> SEQ ID NO 123
<211> LENGTH: 9
<212> TYPE: PRT
<213> ORGANISM: Artificial Sequence
<220> FEATURE:
<223> OTHER INFORMATION: SYNTHESIZED

<400> SEQUENCE: 123

Gln Gln Gly His Ser Tyr Pro Leu Thr
1               5

<210> SEQ ID NO 124
<211> LENGTH: 10
<212> TYPE: PRT
<213> ORGANISM: Artificial Sequence
<220> FEATURE:
<223> OTHER INFORMATION: SYNTHESIZED

<400> SEQUENCE: 124

Gly Phe Ser Phe Asn Thr Tyr Ala Met Asn
1               5                   10

<210> SEQ ID NO 125
<211> LENGTH: 19
<212> TYPE: PRT
<213> ORGANISM: Artificial Sequence
<220> FEATURE:
<223> OTHER INFORMATION: SYNTHESIZED

<400> SEQUENCE: 125

Arg Ile Arg Asn Lys Thr Asn Asn Tyr Ala Thr Phe Tyr Ala Asp Ser
1               5                   10                  15

Val Lys Asp

<210> SEQ ID NO 126
<211> LENGTH: 10
<212> TYPE: PRT
<213> ORGANISM: Artificial Sequence
<220> FEATURE:
<223> OTHER INFORMATION: SYNTHESIZED

```
<400> SEQUENCE: 126

Ala Ser Pro Tyr Asp Gly Ser Phe Ala Tyr
1               5                   10
```